United States Patent [19]
Kluender et al.

[11] Patent Number: 6,166,082
[45] Date of Patent: Dec. 26, 2000

[54] SUBSTITUTED 5-BIARYLPENTANOIC ACIDS AND DERIVATIVES AS MATRIX METALLOPROTEASE INHIBITORS

[75] Inventors: Harold Clinton Eugene Kluender, Trumbull, Conn.; Guenter Hans Heinz Herbert Benz, Velbert, Germany; David Ross Brittelli, Branford, Conn.; William Harrison Bullock, Hamden, Conn.; Kerry Jeanne Combs, Wallingford, Conn.; Brian Richard Dixon, Woodbridge, Conn.; Stephan Schneider, Wuppertal, Germany; Jill Elizabeth Wood, Hamden, Conn.; Michael Christopher VanZandt, New Haven, Conn.; Donald John Wolanin; Scott M. Wilhelm, both of Orange, Conn.

[73] Assignee: Bayer Corporation, Pittsburgh, Pa.

[21] Appl. No.: 09/057,679

[22] Filed: Apr. 9, 1998

Related U.S. Application Data

[63] Continuation of application No. 08/539,409, Nov. 6, 1995, Pat. No. 5,789,434, which is a continuation-in-part of application No. 08/339,846, Nov. 15, 1994, abandoned.

[51] Int. Cl.[7] ........................ A61K 31/19; A61K 31/235; A61K 31/38; C07C 59/74; C07D 409/00

[52] U.S. Cl. .......................... 514/570; 514/545; 514/448; 514/422; 514/423; 562/459; 560/51; 549/70; 548/527; 548/530; 548/531

[58] Field of Search ............................. 562/459; 560/51; 514/545, 570, 448, 422, 423; 549/70; 548/527, 530, 531

[56] References Cited

U.S. PATENT DOCUMENTS

| | | | |
|---|---|---|---|
| 3,182,061 | 5/1965 | Goldschmidt | 260/520 |
| 3,624,142 | 11/1971 | Shen et al. | 260/515 A |
| 3,652,646 | 3/1972 | Leigh et al. | 260/473 G |
| 3,707,549 | 12/1972 | Mills | 260/470 |
| 3,749,750 | 7/1973 | Wei | 260/470 |
| 3,754,021 | 8/1973 | Shen et al. | 260/515 A |
| 3,784,701 | 1/1974 | Tomcufcik et al. | 424/317 |
| 3,867,434 | 2/1975 | Diamond | 260/515 A |
| 3,876,800 | 4/1975 | Krausz et al. | 424/317 |
| 3,882,174 | 5/1975 | Seeger et al. | 260/558 R |
| 3,917,846 | 11/1975 | Diamond et al. | 424/317 |
| 3,962,228 | 6/1976 | Wei et al. | 260/243 C |
| 3,993,683 | 11/1976 | Nickl et al. | 260/470 |
| 3,997,589 | 12/1976 | Seeger et al. | 260/469 |
| 4,008,323 | 2/1977 | Cousse et al. | 424/250 |
| 4,021,479 | 5/1977 | Seeger et al. | 260/520 B |
| 4,049,823 | 9/1977 | Schacht et al. | 424/308 |
| 4,058,558 | 11/1977 | Cousse et al. | 260/515 |
| 4,151,302 | 4/1979 | Gante et al. | 424/317 |
| 4,168,385 | 9/1979 | Trust et al. | 560/56 |
| 4,219,668 | 8/1980 | Chiccarelli | 562/469 |
| 4,247,466 | 1/1981 | Chiccarelli | 260/343.6 |
| 4,271,191 | 6/1981 | Mazoyer | 424/317 |

(List continued on next page.)

FOREIGN PATENT DOCUMENTS

| | | |
|---|---|---|
| 667498 | 11/1965 | Belgium . |
| 0180290 | 5/1986 | European Pat. Off. . |
| 0275024 | 7/1988 | European Pat. Off. . |
| 0465879 | 1/1992 | European Pat. Off. . |
| 0488682 | 6/1992 | European Pat. Off. . |
| 2104632 | 5/1972 | France . |
| 2503140 | 10/1982 | France . |
| 2854475 | 7/1980 | Germany . |
| 60-209539 | 10/1985 | Japan . |
| 61-200963 | 9/1986 | Japan . |
| 61-200964 | 9/1986 | Japan . |
| 62-132825 | 6/1987 | Japan . |
| 63-88168 | 4/1988 | Japan . |
| 4128262 | 4/1992 | Japan . |
| 6234754 | 8/1994 | Japan . |
| 1565616 | 4/1980 | United Kingdom . |
| 99/18079 | 4/1999 | WIPO . |

OTHER PUBLICATIONS

Chiccarelli et al., "Disposition and Metabolism of Fenbufen in several Laboratory Animals", Arzneim.–Forsch./Drug Res., 30(I): 707–715 (1980).

Child et al., "A New Non–steroidal Anti–inflammatory Analgesic: γ–Oxo (1,1'–biphenyl)–4–butanoic Acid (Fenbufen)", Arzneim.–Forsch./Drug Res., 30(I): 695–702 (1980).

(List continued on next page.)

*Primary Examiner*—Deborah C. Lambkin

[57] ABSTRACT

Inhibitors for matrix metalloproteases, pharmaceutical compositions containing them, and a process for using them to treat a variety of physiological conditions. The compounds of the invention have the generalized formula $$(T)_xA—B—D—E—G$$

wherein A and B are aryl or heteroaryl rings; each T is a substituent group; x is 0, 1, or 2; the group D represents

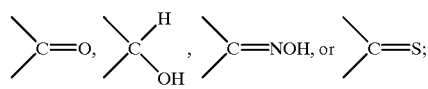

the group E represents a three carbon chain bearing one to three substituent groups which are independent or are involved in ring formation, possible structures being shown in the text and claims; and the group G represents —M,

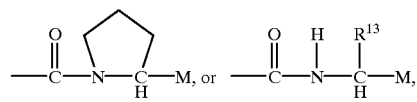

in which M represents —$CO_2H$, —$CON(R^{11})_2$, or —$CO_2R^{12}$; and $R^{13}$ represents any of the side chains of the 19 noncyclic naturally occurring amino acids, and include pharmaceutically acceptable salts thereof.

18 Claims, 3 Drawing Sheets

U.S. PATENT DOCUMENTS

| | | | |
|---|---|---|---|
| 4,304,788 | 12/1981 | Edge | 424/308 |
| 4,310,544 | 1/1982 | Edge | 424/308 |
| 4,472,316 | 9/1984 | Sota et al. | 260/455 R |
| 4,577,025 | 3/1986 | Arai et al. | 546/198 |
| 4,594,197 | 6/1986 | Tomisawa et al. | 558/255 |
| 4,683,331 | 7/1987 | Kuchar et al. | 562/459 |
| 4,933,367 | 6/1990 | Wolff et al. | 514/570 |
| 4,937,243 | 6/1990 | Markwell et al. | 514/237.8 |
| 5,098,613 | 3/1992 | Bollinger et al. | 260/413 |
| 5,109,000 | 4/1992 | Markwell et al. | 514/237.8 |
| 5,124,322 | 6/1992 | Hughes | 514/183 |
| 5,177,204 | 1/1993 | Kuchar et al. | 544/126 |
| 5,217,996 | 6/1993 | Ksander | 514/533 |
| 5,250,552 | 10/1993 | Boschelli et al. | 514/376 |
| 5,273,990 | 12/1993 | De Lombaert | 514/381 |
| 5,462,954 | 10/1995 | Baker et al. | 514/381 |
| 5,473,100 | 12/1995 | Isomura et al. | 562/26 |
| 5,525,629 | 6/1996 | Crimmin et al. | 514/542 |
| 5,591,891 | 1/1997 | Fourmie-Zaluski et al. | 567/426 |
| 5,629,343 | 5/1997 | Hagmann et al. | 514/513 |
| 5,648,524 | 7/1997 | Wang et al. | 562/426 |
| 5,658,944 | 8/1997 | Chapman, Jr. et al. | 514/478 |
| 5,668,176 | 9/1997 | Bagley et al. | 514/569 |
| 5,714,515 | 2/1998 | Bunger | 514/557 |
| 5,736,559 | 4/1998 | Himmelsbach et al. | 514/330 |
| 5,760,276 | 6/1998 | Beard et al. | 560/102 |
| 5,776,977 | 7/1998 | Naik et al. | 514/532 |
| 5,789,434 | 8/1998 | Kluender et al. | 514/414 |

OTHER PUBLICATIONS

Child et al., "Fenbufen, a New Anti–Inflammatory Analgesic: Synthesis and Structure–Activity Relationships of Analogs", J. Pharma. Sci., 66(4): 466–476 (1977).

Cousse et al., "Synthèse, structure et activité hypocholestéoléminate d'une série d'acides γ–aryl, γ–oxo butyriques substitués et dérieés", Eur. J. Med. Chem., 22: 45–57 (1987).

Curran, W. V. and Ross, A., "6–Phenyl–4, 5–dihydro–3(2H)–pyridazinones. A Series of Hypotensive Agents", J. Med. Chem., 17(3): 273–281 (1974).

El–Hashash et al., "Reactions of 3,5–Disubstituted–2–Furanone with Amines, Grignard Reagents, Toluene and Xylene", Indian Journal of Heterocyclic Chemistry, 5: 231–232 (1996).

Fournel et al., "Differential induction profile of drug–metabolizing enzymes after treatment with hypolipidemic agents", Xenobiotica, 17(4): 445–457 (1987).

Kameo et al., "studies on Antirheumatic Agents: 3–Benzoylpropionic Acid Derivatives", Chem. Pharm. Bull., 36(6): 2050–2060 (1988).

Kameo et al., "Studies on Hypolipidemic Agents. IV. 3–[4–(Phenylthio)benzoyl] propionic Acids Derivatives", Chem.Pharm. Bull., 37(5): 1260–1267 (1989).

Kawashima et al., "Structure–Activity Studies of 3–Benzoylpropionic Acid Derivatives Suppressing Adjuvant Arthritis", Chem. Pharm. Bull., 40(3): 774–777 (1992).

Kuchar et al., "Quantitiative Relations Between Structure and Anti Inflammatory Activity of Ayloxoalkanoic Acids", Collection Czechoslovak Chem.Commun., 53: 1862–1872 (1988).

Sammour et al., "Akylation of Aromatic Hydrocarbons with β–Aroylacrylic Acids", J. Prakt.Chemie, 314(5–6): 906–914 (1972).

Takeshita et al., "Immunopharmacological Studies of New 3–Benzoyl–4–Mercaptobutyric Acid Derivatives. II Immunosuppressive Effects", Drugs Exptl.Clin.Res., XIV(5): 311–318 (1988).

Tomisawa et al., "Studies on Hypolipidemic Agents. II. 3–(4–Phenoxybenzoyl)–propionic Acid Derivatives", Chem. Pharm. Bull., 33(6) 2386–2394 (1985).

Weizmann et al.,"A New Method for the Synthesis of β–Phenyl–Naphthalene Derivatives", Chemistry and Industry, pp. 402–404 (Jun. 8, 1940).

Chem.Abstr. Accession No. 108: 131724k. Tamam, et al., "Alkylation of indole with β–aroylacrylic acids and some studies on the alkylated products", Egypt J. Chem., 28(4): 341–351 (1986).

Chem.Abstr. Accession No. 108: 112129d. Tamam, et al., "Alkylation of indole with β–aroylacrylic acids and some studies on the alkylated products", J. Chem. Soc. Pak., 9(1): 1–10 (1987).

Chem.Abstr. Accession No. 108: 31304. Kuchar, et al., "Metabolic Model and QSAR of Long–acting Anti–inflammatory Arylaliphatic Acids", (1987).

Chem. Abst., 30: 7729$^3$ (1936), Farbenind, I. G., "Compounds having capillary action".

Chem.Abstr., Accession No. 119: 270810a (1993). Kaender, G., "Preparation of biaryl substituted 4–amino–butyric acids amides".

Chem.Abstr., Accession No. 120: 164483g (1994). De Lombaert, S., "Preparation of (phosphonomethyl)aminoalkanoases as neutral endopeptidase inhibitors".

Chem.Abstr., Accession No. 120: 245512t (1994). De Lombaert, S., "Preparation of tetrazolylalkylaminomethylphosphonates as neutral endopeptidase inhibitors".

SUBSTITUTED 5-BIARYLPENTANOIC ACIDS AND DERIVATIVES AS MATRIX METALLOPROTEASE INHIBITORS

This application is a continuation of application Ser. No. 08/539,409, filed Nov. 6, 1995 and now U.S. Pat. No. 5,789,434, which was a Continuation-in-Part of application Ser. No. 08/339,846, filed Nov. 15, 1994, abandoned, which are hereby incorporated by reference.

FIELD

This invention relates to enzyme inhibitors, and more particularly, to novel 4-biarylbutyric or 5-biarylpentanoic acid compounds or derivatives thereof useful for inhibiting matrix metalloproteases.

BACKGROUND

The matrix metalloproteases (aka. matrix metalloendoproteinases or MMPs) are a family of zinc endoproteinases which include, but are not limited to, interstitial collagenase (aka. MMP-1), stromelysin (aka. proteoglycanase, transin, or MMP-3), geiatinase A (aka. 72 kDa-gelatinase or MMP-2) and gelatinase B (aka. 95 kDa-gelatinase or MMP-9). These MMPs are secreted by a variety of cells including fibroblasts and chondrocytes, along with natural proteinatious inhibitors known as TIMPs (Tissue Inhibitor of MetalloProteinase).

All of these MMPs are capable of destroying a variety of connective tissue components of articular cartilage or basement membranes. Each MMP is secreted as an inactive proenzyme which must be cleaved in a subsequent step before it is able to exert its own proteolytic activity. In addition to the matrix destroying effect, certain of these MMPs such as MMP-3 have been implemented as the in vivo activator for other MMPs such as MMP-1 and MMP-9 (A. Ho, H. Nagase, Arch Biochem Biophys., 267, 211–16 (1988); Y. Ogata, J. J. Enghild, H. Nagase, J. Biol. Chem., 267, 3581–84 (1992)). Thus, a cascade of proteolytic activity can be initiated by an excess of MMP-3. It follows that specific MMP-3 inhibitors should limit the activity of other MMPs that are not directly inhibited by such inhibitors.

It has also been reported that MMP-3 can cleave and thereby inactivate the endogenous inhibitors of other proteinases such as elastase (P. G. Winyard, Z. Zhang, K. Chidwick, D. R. Blake, R. W. Carrell G., Murphy, FEBS Letts., 279, 1, 91–94 (1991)). Inhibitors if MMP-3 could thus influence the activity of other destructive proteinases by modifying the level of their endogenous inhibitors.

A number of diseases are thought to be mediated by excess or undesired matrix-destroying metalloprotease activity or by an imbalance in the ratio of the MMPs to the TIMPs. These include: a) osteoarthritis (Woessner, et al., J. Biochelogical Chem., 259(6), 3633–3638 (1984); J. Rheumatol., 10, 852–860 (1883)), b) rheumatoid arthritis (D. E. Mullins, et al., Biochim. Biophys. Acta, 695, 117–214 (1983); Arthritis and Rheumatism, 20, 1231–1239 (1977); Arthritis and Rheumatism, 34, 1076–1105 (1991)), c) septic arthritis (R. J. Williams, et al., Arthr. Rheum., 33, 533–41 (1990)), d) tumor metastasis (R. Reich, et al., Cancer Res., 48, 3307–3312 (1988), and L. M. Matrisian, et al., Proc. Nat'l. Acad. Sci., USA, 83, 9413–7 (1986)), e) periodontal diseases (C. M. Overall, et al., J. Periodontal Res., 22, 81–88 (1987)), f) corneal ulceration (F. R. Burns, et al., Invest. Opthalmol., 30, 1569–1575 (1989)), g) proteinuria (W. H. Baricos, et al., Biochem. J., 254, 609–612 (1988)), h) coronary thrombosis from atherosclerotic plaque rupture (A. M. Henney, et al., Proc. Nat'l. Acad. Sci. USA, 88, 8154–8158 (1991)), i) aneurysmal aortic disease (N. Vine and J. T. Powell, Clin. Sci., 81, 233–9 (1991)), j) birth control (J. F. Woessner, et al., Steroids, 54, 491–499 (1989)), k) dystrophobic epidermnolysis bullosa (A. Kronberger, et al., J. Invest. Dermatol., 79, 208–211 (1982)), and l) degenerative cartilage loss following traumatic joint injury, conditions leading to inflammatory responses, osteopenias mediated by MMP activity, tempero mandibular joint disease, demyelating diseases of the nervous system, etc. (J. Neurochem., 50, 688–694 (1988)).

The need for new therapies is especially important in the case of arthritic diseases. The primary disabling effect of oeteoarthritis (OA), rheumatoid arthritis (RA) and septic arthritis is the progressive loss of articular cartilage and thereby normal joint function. No marketed pharmaceutical agent is able to prevent or slow this cartilage loss, although nonsteroidal antiinflammatory drugs (NSAIDs) have been given to control pain and swelling. The end result of these diseases is total loss of joint function which is only treatable by joint replacement surgery. MMP inhibitors are expected to halt or reverse the progression of cartilage loss and obviate or delay surgical intervention.

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiment with various types of proteases have shown that the matrix metalloproteases play a dominant role in these processes in particular gelatinases A and B (MMP-2 and MMP-9, respectively). For an overview of this field see Biochimica et Biophysica Acta 695 (1983), 177–214; Eur. Respir. J. 7 (1994), 2062–2072; Critical Reviews in Oral Biology and Medicine 4 (1993), 197–250.

Furthermore, it could be shown that inhibition of degradation of extracellular matrix by the native matrix metalloprotease inhibitor TIMP-2 (a protein) arrests cancer growth (Cancer Res. 52, 701–708, 1992) and that TIMP-2 inhibits tumor-induced angiogenesis in experimental systems (Science 248, 1408–1410, 1990). For a review see Annals of the New York Academy of Sciences 1994, 222–232. It was furthermore demonstrated that the synthetic matrix metalloprotease inhibitor batimastat when given intraperitoneally inhibits human colon tumor growth and spread in an orthotopic model in nude mice (Cancer Res. 54, 4726–4728, 1994) and prolongs the survival of mice bearing human ovarian carcinoma xenografts (Cancer Res. 53, 2087–2091, 1993). The use of this and related compounds has been described in WO-A-9321942.

There are several patents and patent applications claiming the use of metalloproteinase inhibitors for the retardation of metastatic cancer, promoting tumor regression, inhibiting cancer cell proliferation, slowing or preventing of cartilage loss associated with osteoarthritis or for treatment of other diseases as noted above (e.g. WO-A-9519965, WO-A-9519956, WO-A-9519957, WO-A-9519961, WO-A-9321942, WO-A-9321942, WO-9421625, U.S. Pat. No. 4,599,361; U.S. Pat. No. 5,190,937; EP 0574 758 A1, published Dec. 22, 1993; EP 026 436 A1 published Aug. 3, 1988; and EP 0520 573 A1, published Dec. 30, 1992). The preferred compounds of these patents have peptide backbones with a zinc complexing group (hydroxamic acid, thiol, carboxylic acid or phosphinic acid) at one end and a variety of sidechains, both those found in the natural amino acids as well as those with more novel functional groups. Such small peptides are often poorly absorbed, exhibiting low oral bioavailability. They are also subject to rapid proteolytic metabolism, thus having short half lives. As an example, batimastat, the compound described in WO-A-9321942, can only be given intraperitoneally.

Certain 3-biphenoylpropanoic and 4-biaryloylbutanoic acids are described in the literature as anti-inflammatory, anti-platelet aggregation, anti-phlogistic, anti-proliferative, hypolipidemic, antirheumatic, analgesic, and hypocholesterolemic agents. In none of these examples is a reference made to MMP inhibition as a mechanism for the claimed therapeutic effect. Certain related compounds are also used as intermediates in the preparation of liquid crystals.

Specifically U.S. Pat. No. 3,784,701 claims certain substituted benzoylpropionic acids to treat inflammation and pain. These compounds include 3-biphenoylpropanoic acid (aka fenbufen) shown below.

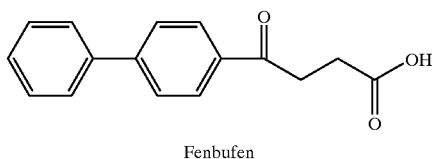

Fenbufen

R. G. Child, et al., J. Pharm. Sci., 66, 466–476 (1977) describes structure-activity relationships of several analogs of fenbufen. These include several compounds in which the biphenyl ring system is substituted or the propanoic acid portion is substituted with phenyl, halogen, hydroxyl or methyl, or the carboxylic acid or carbonyl functions are converted to a variety of derivatives. No compounds are described which contain a 4'-substituted biphenyl and a substituted propanoic acid portion combined in one molecule. The phenyl (compounds XLIV and LXXVII) and methyl (compound XLVIII) substituted compounds shown below were described as inactive.

XLVIII

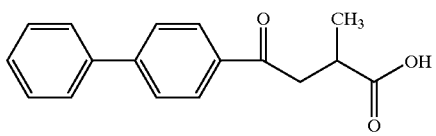

XLIX

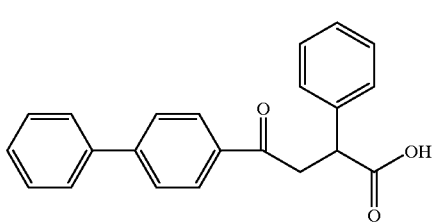

LXXVII

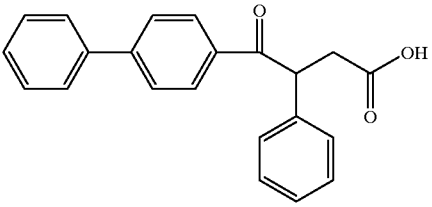

K. K. Kameo, et al., Chem. Pharm. Bull., 36, 2050–2060 and JP patent 62132825 describe certain substituted 3-biphenoylpropionic acid derivatives and analogs thereof including the following. Various compounds with other substituents on the propionic acid portion are described, but they do not contain biphenyl residues.

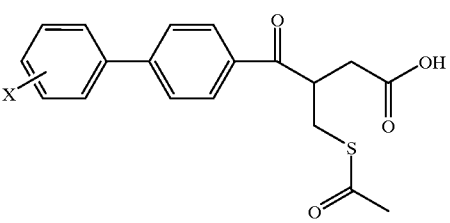

X = H, 4'-Br, 4'-Cl, 4'-CH3 and 2'-Br

H. Cousse, et al., Eur. J. Med. Chem., 22, 45–57 (1987) describe the following methyl and methylene substituted 3-biphenoyl-propanoic and -propenoic acids. The corresponding compounds in which the carbonyl is replaced with either CHOH or CH$_2$ are also described.

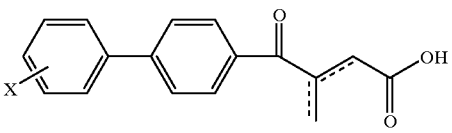

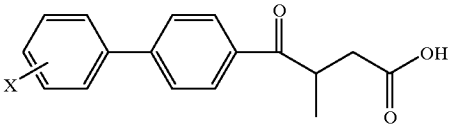

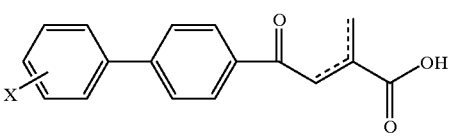

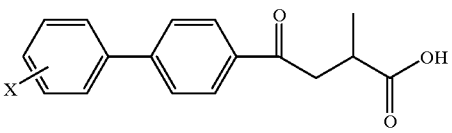

X = H, Cl, Br, CH3O, F and NH$_2$

German Patent Application No. 19 57 750 of Tomae also describes certain of the above methylene substituted biphenoylpropanoic acids.

M. A. El-Hashsh, et al., Revue Roum. Chim., 23, 1581–1588 (1978) describe products derived from b-aroyl-acrylic acid epoxides including the following biphenyl compound. No compounds substituted on the biphenyl portion are described.

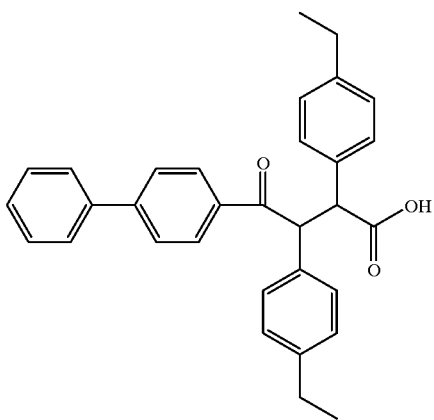

T. Kitamura, et al., Japanese Patent Application No. 84-65795 840404 describes certain biphenyl compounds used as intermediates for the production of liquid crystals including the following. The biphenyl is not substituted in these intermediates.

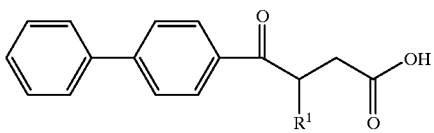

$R^1$ = alkyl of 1–10 carbons

German Patent No. 28 54 475 uses the following compound as an intermediate. The biphenyl group is not substituted.

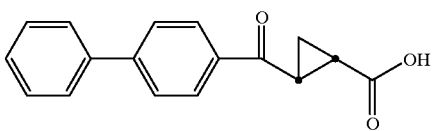

A. Sammou, et al., Egypt J. Chem., 15, 311–327 (1972) and J. Couquelet, et al., Bull. Soc. Chim. Fr., 9, 3196–9 (1971) describe certain dialkylamino substituted biphenoyl-propanoic acids including the following. In no case is the biphenyl group substituted.

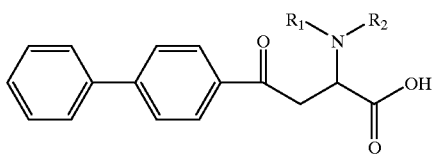

$R_1, R_2$ = alkyl, benzyl, H
and morpholine ring together with the Nitrogen

It would be desirable to have effective MMP inhibitors which possess improved bioavailablity and biological stability relative to the peptide-based compounds of the prior art, and which can be optimized for use against particular target MMPs. Such compounds are the subject of the present application.

SUMMARY

This invention relates to compounds having matrix metalloprotease inhibitory activity and the generalized formula:

$$(T)_x A—B—D—E—G. \quad (I)$$

In the above generalized formula (I), $(T)_x A$ represents a substituted or unsubstituted aromatic 6-membered ring or heteroaromatic 5–6 membered ring containing 1–2 atoms of N, O, or S. T represents one or more substituent groups, the subscript x represents the number of such substituent groups, and A represents the aromatic or heteroaromatic ring, designated as the A ring or A unit. When N is employed in conjunction with either S or O in the A ring, these heteroatoms are separated by at least one carbon atom.

The substituent group(s) T are independently selected from the group consisting of halogen; alkyl; haloalkyl; alkenyl; alkynyl; —$(CH_2)_p Q$ in which p is 0 or an integer of 1–4; and -alkenyl-Q in which the alkenyl moiety comprises 2–4 carbons. Q in the latter two groups is selected from the group consisting of aryl, heteroaryl, —CN, —CHO, —$NO_2$, —$CO_2R^2$, —$OCOR^2$, —$SOR^3$, —$SO_2R^3$, —$CON(R^2)_2$, —$SO_2N(R^2)_2$, —$COR^2$, —$N(R^2)_2$, —$N(R^2)COR^2$, —$N(R^2)CO_2R^3$, —$N(R^2)CON(R^2)_2$, —$CHN_4$, —$OR^4$, and —$SR^4$. In these formulae $R^2$ represents H, alkyl, aryl, heteroaryl, arylalkyl, or heteroaryl-alkyl; R3 represents alkyl, aryl, heteroaryl, arylalkyl, or heteroaryl-alkyl; and R4 represents H, alkyl, aryl, heteroaryl, arylalkyl, heteroaryl-alkyl, alkenyl, alkynyl, haloalkyl, acyl, or alkyleneoxy or polyalkyleneoxy terminated with H, alkyl, or phenyl. Unsaturation in a moiety which is attached to Q or which is part of Q is separated from any N, O, or S of Q by at least one carbon atom. The A ring may be unsubstituted or may carry up to 2 substituents T. Accordingly, the subscript x is 0, 1, or 2.

In the generalized formula (I), B represents an aromatic 6-membered ring or a heteroaromatic 5–6 membered ring containing 1–2 atoms of N, O, or S. It is referred to as the B ring or B unit. When N is employed in conjunction with either S or O in the B ring, these heteroatoms are separated by at least one carbon atom.

In the generalized formula (I), D represents

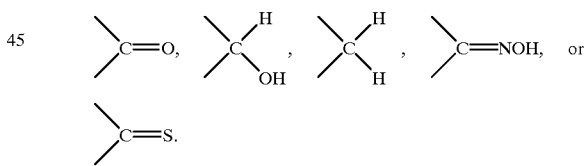

In the generalized formula (1), E represents a chain of n carbon atoms bearing m substituents $R^6$, in which the $R^6$ groups are independent substituents, or constitute spiro or nonspiro rings. Rings may be formed in two ways: a) two groups $R^6$ are joined, and taken together with the chain atom(s) to which the two R6 group(s) are attached, and any intervening chain atoms, constitute a 3–7 membered ring, or b) one group $R^6$ is joined to the chain on which this one group $R^6$ resides, and taken together with the chain atom(s) to which the $R^6$ group is attached, and any intervening chain atoms, constitutes a 3–7 membered ring. The number n of carbon atoms in the chain is 2 or 3, and the number m of $R^6$ substituents is an integer of 1–3. The number of carbons in the totality of $R^6$ groups is at least two.

Each group $R^6$ is independently selected from the group consisting of:

alkyl, provided that if the A unit is phenyl, the B unit is phenylene, m is 1, and n is 2, then x is 1 or 2;

aryl, provided that if said A unit is phenyl, said B unit is phenylene, said aryl group is phenyl, n is 2, and m is 1 or 2, then x is 1 or 2;

heteroaryl;

arylalkyl;

heteroaryl-alkyl;

alkenyl;

aryl-substituted alkenyl;

heteraryl-substituted alkenyl;

alkynyl;

aryl-substituted alkynyl;

heteroaryl-substituted alkynyl;

—(CH$_2$)$_t$R$^7$, wherein t is 0 or an integer of 1–5 and R$^7$ is selected from the group consisting of:

N-phthalimidoyl;

N-(1,2-naphthalenedicarboximidoyl);

N-(2,3-naphthalenedicarboximidoyl);

N-(1,8-naphthalenedicarboximidoyl);

N-indoloyl;

N-(2-pyrrolodinonyl);

N-succinimidoyl;

N-maleimidoyl;

3-hydantoinyl;

1,2,4-urazolyl;

amido;

urethane;

urea; and nonaromatic substituted or unsubstituted heterocycles containing and connected through a N atom, and comprising one additional O or S; and amino;

and corresponding heteroaryl moieties in which the aryl portion of an aryl-containing R$^7$ group comprises 4–9 carbons and at least one N, O, or S heteroatom, but with the proviso that when R$^7$ is a nonaromatic heterocycle or an amino group, and t is 0, m is 1, and n is 2, then x is 1 or 2; and —(CH$_2$)$_v$ZR$^8$ in which v is 0 or an integer of 1–4, Z represents

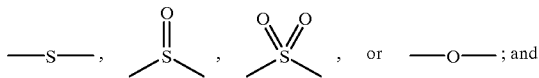

R$^8$ is selected from the group consisting of:

alkyl;

aryl;

heteroaryl;

arylalkyl;

heteroaryl-alkyl; and

—C(O)R$^9$ in which R$^9$ represents alkyl of at least two carbons, aryl, heteroaryl, arylalkyl, or heteroaryl-alkyl;

and with the further provisos that when R$^8$ is —C(O)R$^9$, Z is S or O;

when Z is O, R$^8$ may also be alkyleneoxy or poly-alkyleneoxy terminated with H, alkyl, or phenyl; and when said A unit is phenyl, said B unit is phenylene, m is 1, n is 2, and v is 0, then x is 1 or 2; and trialkylsilyl-substituted alkyl.

Furthermore, aryl or heteroaryl portions of any of the T or R$^6$ groups optionally may bear up to two substituents selected from the group consisting of —(CH$_2$)$_y$C(R$^{11}$)(R$^{12}$)OH, —(CH$_2$)$_y$OR$^{11}$, —(CH$_2$)$_y$SR$^{11}$, —(CH$_2$)$_y$S(O)R$^{11}$, —(CH$_2$)$_y$S(O)$_2$R$^{11}$, —(CH$_2$)$_y$SO$_2$N(R$^{11}$)$_2$, —(CH$_2$)$_y$N(R$^{11}$)$_2$, —(CH$_2$)$_y$N(R$^{11}$)COR$^{12}$, —OC(R$^{11}$)$_2$O— in which both oxygen atoms are connected to the aryl ring, —(CH$_2$)$_y$COR$^{11}$, —(CH$_2$)$_y$CON(R$^{11}$)$_2$, —(CH$_2$)$_y$CO$_2$R$^{11}$, —(CH$_2$)$_y$OCOR$^{11}$, -halogen, —CHO, —CF$_3$, —NO$_2$, —CN, and —R$^{12}$, in which y is 0–4; R$^{11}$ represents H or lower alkyl; and R$^{12}$ represents lower alkyl.

In the generalized formula (I), G represents —PO$_3$H$_2$, —M,

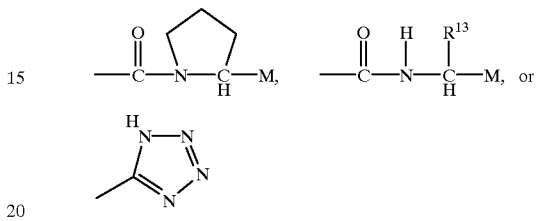

in which M represents —CO$_2$H, —CON(R$^{11}$)$_2$, or —CO$_2$R$^{12}$, and R$^{13}$ represents any of the side chains of the 19 noncyclic naturally occurring amino acids. Pharmaceutically acceptable salts of these compounds are also within the scope of the invention.

In most related reference compounds of the prior art, the biphenyl portion of the molecule is unsubstituted, and the propanoic or butanoic acid portion is either unsubstituted or has a single methyl or phenyl group. Presence of the larger phenyl group has been reported to cause prior art compounds to be inactive as anti-inflammatory analgesic agents. See, for example, R. G. Child, et al., J. Pharm. Sci., 66, 466–476 (1977) By contrast, it has now been found that compounds which exhibit potent MMP inhibitory activity contain a substituent of significant size on the propanoic or butanoic portion of the molecule. The biphenyl portions of the best MMP inhibitors also preferably contain a substituent on the 4' position, although when the propanoic or butanoic portions are optimally substituted, the unsubstituted biphenyl compounds of the invention have sufficient activity to be considered realistic drug candidates.

In addition to the above-described compounds, the invention also relates to pharmaceutical compositions having matrix metalloprotease inhibitory activity, which compositions comprise a compound of the invention as described above and in more detail in the detailed description below, and a pharmaceutically acceptable carrier.

The invention also relates to a method of treating a human to achieve an effect, in which the effect is: alleviation of osteoarthritis, rheumatoid arthritis, septic arthritis, periodontal disease, corneal ulceration, proteinuria, aneurysmal aortic disease, dystrophobic epidermolysis bullosa, conditions leading to inflammatory responses, osteopenias mediated by MMP activity, tempero mandibular joint disease, or demyelating diseases of the nervous system; retardation of tumor metastasis or degenerative cartilage loss following traumatic joint injury; reduction of coronary thrombosis from atherosclerotic plaque rupture; or improved birth control; the method comprising administering an amount of a compound of the invention as described above, and in more detail in the detailed description below, which is effective to inhibit the activity of at least one matrix metailoprotease, resulting in achievement of the desired effect.

DESCRIPTION OF THE DRAWINGS

The invention will be better understood from a consideration of the following detailed description, taken in conjunction with the drawings, in which.

DETAILED DESCRIPTION

Figure 1:
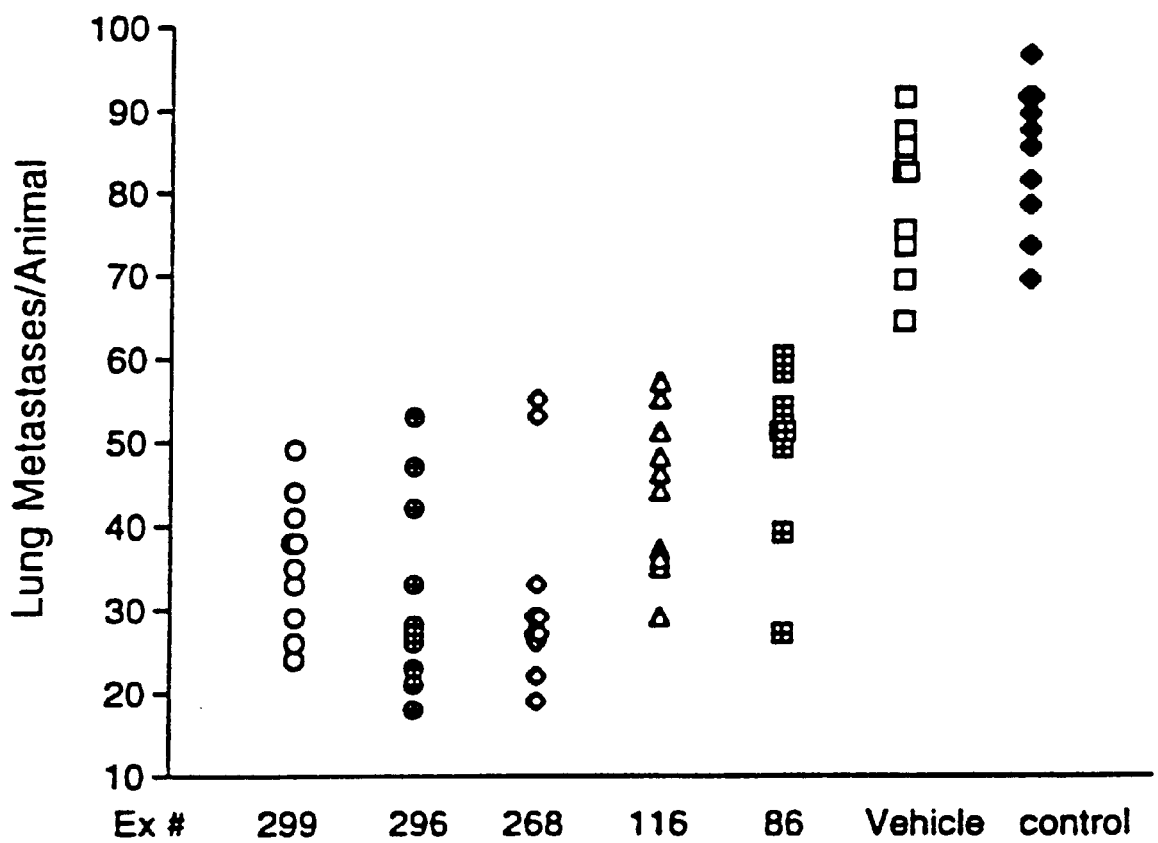
FIG. 1 is a graph which shows the inhibition of B16.F10 experimental metastasis in male BDF1 mice by invention compounds at 40 mg/kg (po)

More particularly, the compounds of the present invention are materials having matrix metalloprotease inhibitory activity and the generalized formula:

in which $(T)_xA$ represents a substituted or unsubstituted aromatic or heteroaromatic moiety selected from the group consisting of:

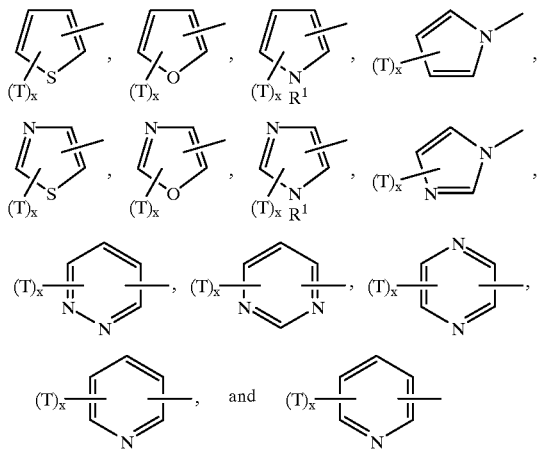

in which $R^1$ represents H or alkyl of 1–3 carbons.

In these structures, the aromatic ring is referred to as the A ring or A unit, and each T represents a substituent group, referred to as a T group or T unit. Substituent groups T are independently selected from the group consisting of: the halogens —F, —Cl, —Br, and —I; alkyl of 1–10 carbons; haloalkyl of 1–10 carbons; alkenyl of 2–10 carbons; alkynyl of 2–10 carbons; —$(CH_2)_pQ$ in which p is 0 or an integer 1–4, and -alkenyl-Q in which the alkenyl moiety comprises 2–4 carbons. Q in each of the latter two groups is selected from the group consisting of aryl of 6–10 carbons; heteroaryl comprising 4–9 carbons and at least one N, O, or S heteroatom; —CN; —CHO; —$NO_2$; —$CO_2R^2$; —$OCOR^2$; —$SOR^3$; —$SO_2R^3$; —$CON(R^2)_2$; —$SO_2N(R^2)_2$; —C(O)$R^2$; —$N(R^2)_2$; —$N(R^2)COR^2$; —$N(R^2)CO_2R^3$; —$N(R^2)CON(R^2)_2$; —$CHN_4$; —$OR^4$; and —$SR^4$. The groups $R^2$, $R^3$, and $R^4$ are defined as follows.

$R^2$ represents H; alkyl of 1–6 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons.

$R^3$ represents alkyl of 1–4 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the allcyl portion contains 1–4 carbons.

$R^4$ represents H; alkyl of 1–12 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; heteroaryl-alkyl in which the heteroaryl portion comprises 4–9 carbons and at least one N, O, or S heteroatom and the alkyl portion contains 1–4 carbons; alkenyl of 2–12 carbons; alkynyl of 2–12 carbons; —$(C_qH_{2q}O)_rR^5$ in which q is 1–3, r is 1–3, and $R^5$ is H provided q is greater than 1, or $R^5$ is alkyl of 1–4 carbons, or phenyl; —$(CH_2)_sX$ in which s is 2–3 and X is halogen; or —$C(O)R^2$.

Any unsaturation in a moiety which is attached to Q or which is part of Q is separated from any N, O, or S of Q by at least one carbon atom, and the number of substituents, designated x, is 0, 1, or 2.

In the generalized formula (I), B represents an aromatic or heteroaromatic ring selected from the group consisting of:

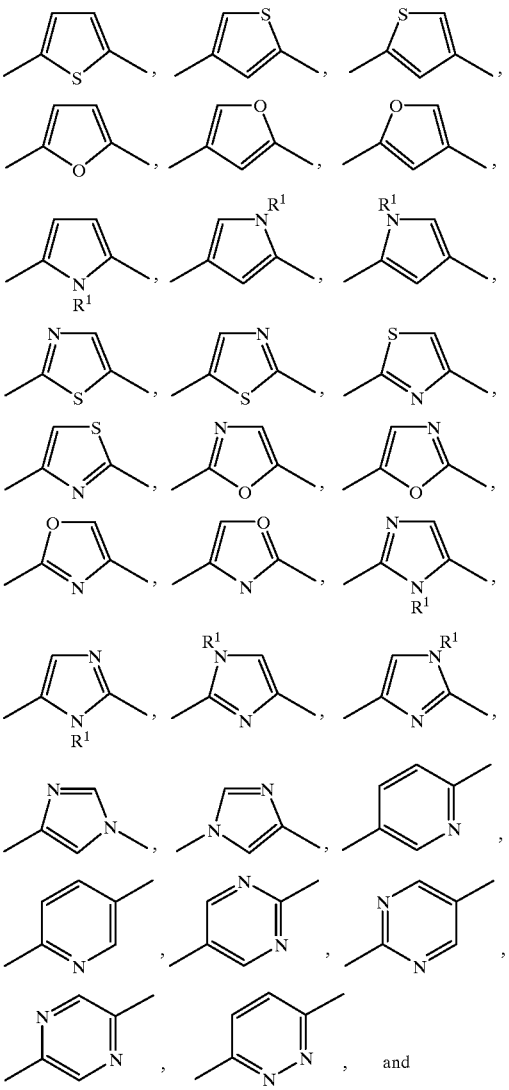

-continued

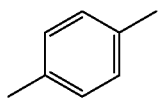

in which R¹ is defined as above These rings are referred to as the B ring or B unit.

In the generalized formula (I), D represents the moieties

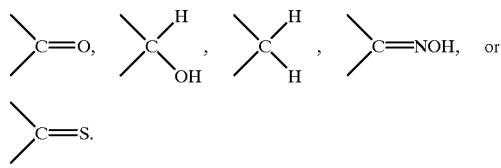

In the generalized formula (I), E represents a chain of n carbon atoms bearing m substituents $R^6$, referred to as $R^6$ groups or $R^6$ units. The $R^6$ groups are independent substituents, or constitute spiro or nonspiro rings. Rings may be formed in two ways: a) two groups $R^6$ are joined, and taken together with the chain atom(s) to which the two R6 group(s) are attached, and any intervening chain atoms, constitute a 3–7 membered ring, or b) one group $R^6$ is joined to the chain on which this one group $R^6$ resides, and taken together with the chain atom(s) to which the $R^6$ group is attached, and any intervening chain atoms, constitutes a 3–7 membered ring. The number n of carbon atoms in the chain is 2 or 3, and the number m of $R^6$ substituents is an integer of 1–3. The number of carbons in the totality of $R^6$ groups is at least two.

Each group $R^6$ is independently selected from the group consisting of the substituents listed below as items 1)–14).

1) An $R^6$ group may be alkyl of 1–10 carbons, provided that if the A unit is phenyl, the B unit is phenylene, m is 1, n is 2, and the alkyl group is located on the alpha carbon relative to the D unit, then x is 1 or 2.
2) An $R^6$ group may be aryl of 6–10 carbons, provided that if the A unit is phenyl, the B unit is phenylene, the aryl group is phenyl, n is 2, and m is 1 or 2, then x is 1 or 2.
3) An $R^6$ group may be heteroaryl comprising 4–9 carbons and at least one N, O, or S heteroatom.
4) An $R^6$ group may be arylalkyl in which the aryl portion contains 6–10 carbons and the alkyl portion contains 1–8 carbons.
5) An $R^6$ group may be heteroaryl-alkyl in which the heteroaryl portion comprises 4–9 carbons and at least one N, O, or S heteroatom, and the alkyl portion contains 1–8 carbons;
6) An $R^6$ group may be alkenyl of 2–10 carbons.
7) An $R^6$ group may be aryl-alkenyl in which the aryl portion contains 6–10 carbons and the alkenyl portion contains 2–5 carbons.
8) An $R^6$ group may be heteroaryl-alkenyl in which the heteroaryl portion comprises 4–9 carbons and at least one N, O, or S heteroatom and the alkenyl portion contains 2–5 carbons;
9) An $R^6$ group may be alkynyl of 2–10 carbons.
10) An $R^6$ group may be aryl-alkynyl in which the aryl portion contains 6–10 carbons and the alkynyl portion contains 2–5 carbons.
11) An $R^6$ group may be heteroaryl-alkynyl in which the heteroaryl portion comprises 4–9 carbons and at least one N, O, or S heteroatom and the alkynyl portion contains 2–5 carbons.
12) An $R^6$ group may be —$(CH_2)_tR^7$ in which t is 0 or an integer of 1–5 and $R^7$ is selected from the group consisting of

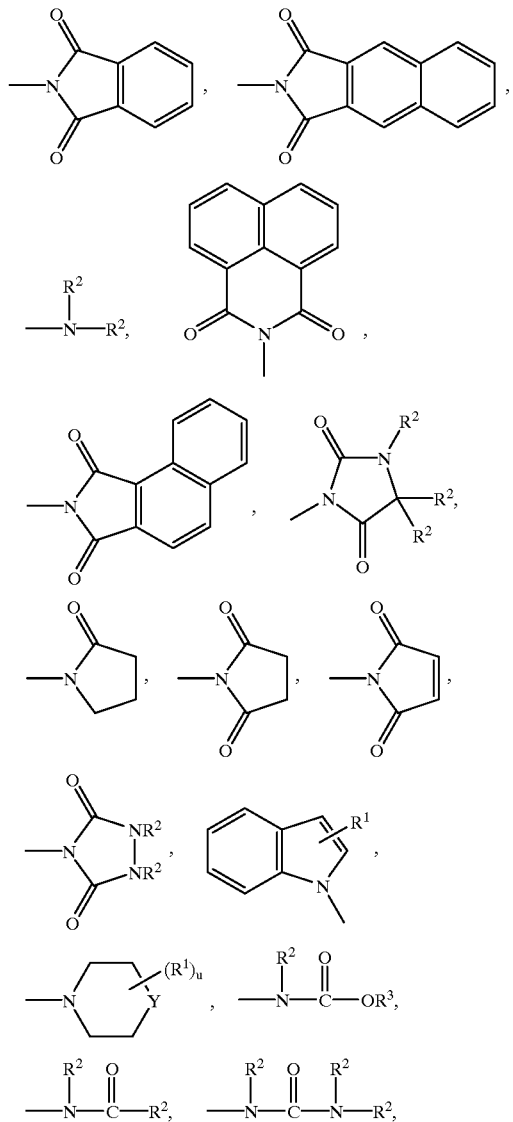

as well as corresponding heteroaryl moieties in which the aryl portion of an aryl-containing $R^7$ group comprises 4–9 carbons and at least one N, O, or S heteroatom. In such R7 groups, Y represents O or S; $R^1$, $R^2$, and $R^3$ are as defined above; and u is 0, 1, or 2; provided that when $R^7$ is

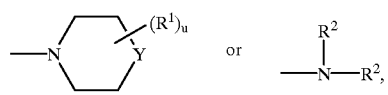

and the A unit is phenyl, the B unit is phenylene, m is 1, n is 2, and t is 0, then x is 1 or 2.
13) An $R^6$ group may be —$(CH_2)_vZR^8$ in which v is 0 or an integer of 1 to 4; Z represents —S—, —S(O)—, —SO$_2$—, or —O—; and R$^8$ is selected from the group consisting of: alkyl of 1 to 12 carbons; aryl of 6 to 10 carbons;

heteroaryl comprising 4–9 carbons and at least one N, O, or S heteroatom; arylalkyl in which the aryl portion contains 6 to 12 carbons and the alkyl portion contains 1 to 4 carbons; heteroaryl-alkyl in which the aryl portion comprises 4–9 carbons and at least one N, O, or S heteroatom and the alkyl portion contains 1–4 carbons; —C(O)R$^9$ in which R$^9$ represents alkyl of 2–6 carbons, aryl of 6–10 carbons, heteroaryl comprising 4–9 carbons and at least one N, O, or S heteroatom, or arylalkyl in which the aryl portion contains 6–10 carbons or is heteroaryl comprising 4–9 carbons and at least one N, O, or S heteroatom, and the alkyl portion contains 1–4 carbons, with the provisos that when R$^8$ is —C(O)R$^9$, Z is —S— or —O—;

when Z is —O—, R$^8$ may also be —(C$_q$H$_{2q}$O)$_r$R$^5$ in which q, r, and R$^5$ are as defined above; and when the A unit is phenyl, the B unit is phenylene, m is 1, n is 2, and v is 0, then x is 1 or 2; and 14) An R$^6$ group may be —(CH$_2$)$_w$SiR$^{10}$$_3$ in which w is an integer of 1 to 3, and R$^{10}$ represents alkyl of 1 to 2 carbons.

In addition, aryl or heteroaryl portions of any of the T or R$^6$ groups optionally may bear up to two substituents selected from the group consisting of —(CH$_2$)$_y$C(R$^{11}$)(R$^{12}$)OH, —(CH$_2$)$_y$OR$^{11}$, —(CH$_2$)$_y$SR$^{11}$, —(CH$_2$)$_y$S(O)R$^{11}$, —(CH$_2$)$_y$S(O)$_2$R$^{11}$, —(CH$_2$)$_y$SO$_2$N(R$^{11}$)$_2$, —(CH$_2$)$_y$N(R$^{11}$)$_2$, —(CH$_2$)$_y$N(R$^{11}$)COR$^{12}$, —OC(R$^{11}$)$_2$O— in which both oxygen atoms are connected to the aryl ring, —(CH$_2$)$_y$COR$^{11}$, —(CH$_2$)$_y$CON(R$^{11}$)$_2$, —(CH$_2$)$_y$CO$_2$R$^{11}$, —(CH$_2$)$_y$OCOR$^{11}$, -halogen, —CHO, —CF$_3$, —NO$_2$, —CN, and —R$^{12}$, in which y is 0–4; R$^{11}$ represents H or alkyl of 1–4 carbons; and R$^{12}$ represents alkyl of 1–4 carbons.

In the generalized formula (I), G represents —PO$_3$H$_2$, —M,

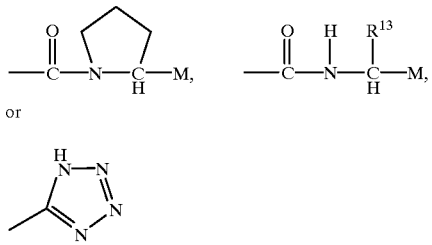

in which M represents —CO$_2$H, —CON(R$^{11}$)$_2$, or —CO$_2$R$^{12}$, and

R$^{13}$ represents any of the side chains of the 19 noncyclic naturally occurring amino acids. Pharmaceutically acceptable salts of the compounds falling within the generalized formula (I) are also within the invention.

In the compounds of the invention, the following are preferred.

The substituent group T is preferably halogen, or an ether OR$^4$ wherein R$^4$ is preferably alkyl of 1–12 carbons or arylalkyl in which the aryl portion is 6–10 carbons and the alkyl portion contains 1–4 carbons. Most preferably, T is halogen, and when T is OR$^4$, R$^4$ is alkyl of 1–6 carbons, or benzyl.

The subscript x, which defines the number of T substituents, is preferably 1 or 2, most preferably 1, and this substituent is on the 4-position of ring A.

The A ring is preferably a phenyl or thiophene ring, most preferably phenyl.

The B ring is preferably a 1,4-phenylene or 2,5-thiophene ring, most preferably 1,4-phenylene.

The D unit is most preferably a carbonyl group.

The group R6 is preferably:

1) arylalkyl wherein the aryl portion contains 6–10 carbons and the alkyl portion contains 1–8 carbons;

2) —(CH$_2$)$_t$R$^7$ wherein t is 0 or an integer of 1–5 and R$^7$ is an imidoyl group containing an aromatic residue; or 3) —(CH$_2$)$_v$ZR$^8$ wherein v is 0 or an integer of 1–4, Z is S or O, and R$^8$ is aryl of 6–10 carbons or arylalkyl wherein the aryl portion contains 6 to 12 carbons and the alkyl portion contains 1 to 4 carbons.

The group R6 is most preferably the following, and in these, any aromatic moiety is preferably substituted:

1) arylalkyl wherein the aryl portion is phenyl and the alkyl portion contains 1–4 carbons;

2) —(CH$_2$)$_t$R$^7$ wherein t is an integer of 1–3, and R$^7$ is N-phthalimidoyl, N-(1,2-naphthalenedicarboximidoyl), N-(2,3-naphthalenedicarboximidoyl), or N-(1,8-naphthalenedicarboximidoyl); or 3) —(CH$_2$)$_v$ZR$^8$ wherein v is an integer of 1–3, Z is S, and R$^8$ is phenyl.

The G unit is most preferably a carboxylic acid group.

It is to be understood that as used herein, the term "alkyl" means straight, branched, cyclic, and polycyclic materials. The term "haloalkyl" means partially or fully halogenated alkyl groups such as —(CH$_2$)$_2$Cl, —CF$_3$ and —C$_6$F$_{13}$, for example.

The B ring of generalized formula (I) is a substituted or unsubstituted aromatic or heteroaromatic ring, in which any substituents are groups which do not cause the molecule to fail to fit the active site of the target enzyme, or disrupt the relative conformations of the A and B rings, such that they would be detrimental. Such groups may be moieties such as lower alkyl, lower alkoxy, CN, NO$_2$, halogen, etc., but are not to be limited to such groups.

In one of its embodiments, the invention relates to compounds of generalized formula (I) in which at least one of the units A, B, T, and R$^6$ comprises a heteroaromatic ring. Preferred heteroaromatic ring-containing compounds are those in which the heteroaryl groups are heteroaryl of 4–9 carbons comprising a 5–6 membered heteroaromatic ring containing O, S, or NR$^1$ when the ring is 5-membered, and N when said ring is 6-membered. Particularly preferred heteroaromatic ring-containing compounds are those in which at least one of the A and B units comprises a thiophene ring. When A unit is thiophene, it is preferably connected to B unit at position 2 and carries one substituent group T on position 5. When B Unit is thiophene, it is preferably connected through positions 2 and 5 to D and A units respectively.

In the generalized formula (I), the A and B rings are preferably phenyl and phenylene, respectively, the A ring preferably bears at least one substituent group T preferably located on the position furthest from the position of the A ring which is connected to the B ring, the D unit is preferably a carbonyl group, and the G unit is preferably a carboxyl group.

In another embodiment, the invention relates to compounds of generalized formula (I), in the E unit of which n is 2 and m is 1. These compounds thus possess two carbon atoms between the D unit and the G unit, and carry one substituent on this two-carbon chain.

In another of its embodiments, the invention relates to compounds of generalized formula (I) in which the A ring is a substituted or unsubstituted phenyl group, the B ring is p-phenylene, and aryl portions of any aryl-containing T and $R^6$ moieties contain only carbon in the rings. These compounds thus contain no heteroaromatic rings.

In another of its embodiments, the invention relates to compounds of generalized formula (I) in which m is 1 and $R^6$ is an independent substituent. These compounds are materials which contain only a single substituent $R^6$ on the E unit, and this substituent in not involved in a ring. Preferred compounds within this subset have the formula

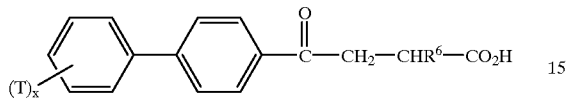

in which x is 1 or 2, and one substituent group T is located on the 4-position of the A ring, relative to the point of attachment between the A and B rings. Substituent group T of this subset is preferably the halogens —Cl, —Br or I or is an ether —$OR^4$. Most preferred compounds contain only one substituent T on the 4-position of the A ring relative to the attachment to B ring.

Preferred compounds of general formula (I) in which $R^6$ is —$(CH_2)_tR^7$ have t as an integer of 1–5. Preferred compounds of general formula (I) in which $R^6$ is —$(CH_2)_vZR^8$ have v as an integer of 1–4 and Z as —S— or —O—. Preferred compounds of general formula (I) in which $R^6$ is alkyl contain 4 or more carbons in said alkyl and those in which $R^6$ is arylalkyl contain 2–3 carbons in the alkyl portion of said arylalkyl.

In another of its embodiments, the invention relates to compounds of generalized formula (I) in which the number of substituents m on the E unit is 2 or 3; and when m is 2, both groups $R^6$ are independent substituents, or together constitute a spiro ring, or one group $R^6$ is an independent substituent and the other constitutes a spiro ring; and when m is 3, two groups $R^6$ are independent substituents and one group $R^6$ constitutes a ring, or two groups R6 constitute a ring and one group R6 is an independent substituent, or three groups R6 are independent substituents. This subset therefore contains compounds in which the E unit is di- or trisubstituted, and in the disubstituted case any rings formed by one or both $R^6$ groups are spiro rings, and in the trisubstituted case, the $R^6$ groups may form either spiro or nonspiro rings.

In another of its embodiments, the invention relates to compounds of generalized formula (I) in which the number of substituents m on the E unit is 1 or 2; and when m is 1, the group $R^6$ constitutes a nonspiro ring; and when m is 2, both groups $R^6$ together constitute a nonspiro ring or one group R6 is an independent substituent and the other constitutes a nonspiro ring. This subset therefore contains compounds in which the E unit carries one or two substituents $R^6$, and at least one of these substituents is involved in a nonspiro ring.

More particularly, representative compounds of generalized formula (I) in which one or more of the substituent groups $R^6$ are involved in formation of nonspiro rings have E units of the following structures:

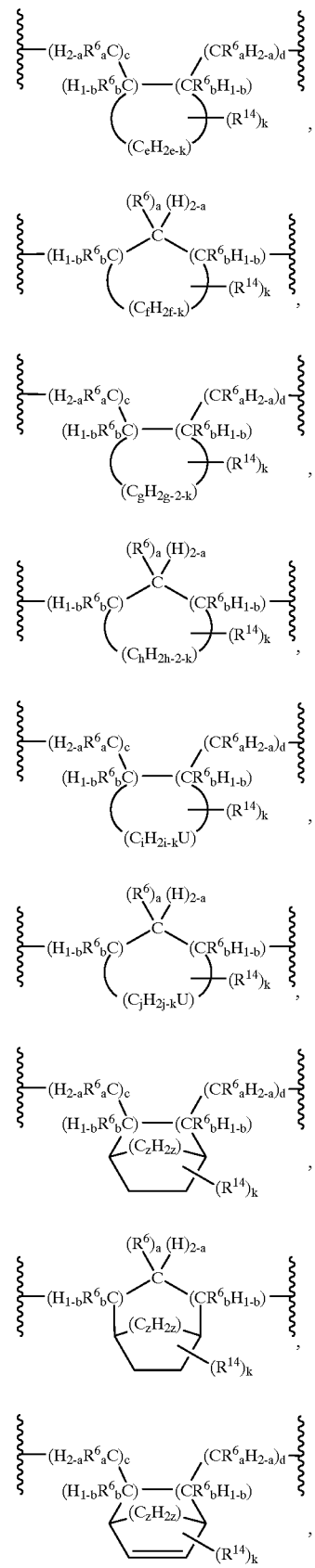

and

-continued

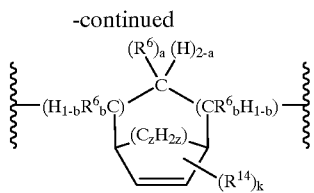

in which a is 0, 1, or 2; b is 0 or 1; c is 0 or 1; d is 0 or 1; c+d is 0 or 1; e is 1–5; f is 1–4; g is 3–5; h is 2–4; i is 0–4; j is 0–3; k is 0–2; the total number of groups $R^6$ is 0, 1, or 2; U represents O, S, or $NR^1$; and z is 1 or 2; Each group $R^{14}$ is independently selected from the group consisting of: alkyl of 1–9 carbons; arylalkyl in which the alkyl portion contains 1–7 carbons and the aryl portion contains 6–10 carbons; alkenyl of 2–9 carbons; aryl-substituted alkenyl in which the alkenyl portion contains 2–4 carbons and the aryl portion contains 6–10 carbons; alkynyl of 2–9 carbons; aryl-substituted alkynyl in which the alkynyl portion contains 2–4 carbons and the aryl portion contains 6–10 carbons; aryl of 6–10 carbons; —$COR^2$; —$CO_2R^3$; —$CON(R^2)_2$, —$(CH_2)_tR^7$ in which t is 0 or an integer of 1–4; and —$(CH_2)_vZR^8$ in which v is 0 or an integer of 1 to 3, and Z represents —S— or —O—. $R^1$, $R^7$, and $R^8$ have been defined above.

Preferred compounds of generalized formula (I) in which one or more of the substituent groups $R^6$ are involved in formation of nonspiro rings have E units of the following structures:

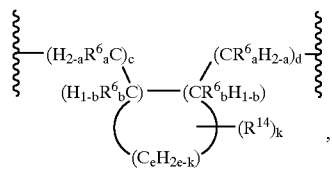

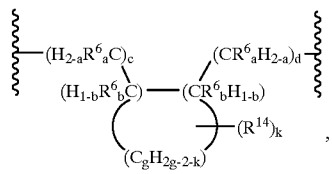

and

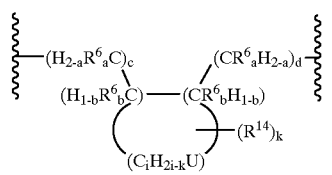

in which a, b, c, d, (c+d), e, g, i, k, the total number of groups $R^6$, U, and $R^{14}$ are as defined above.

The more preferred compounds of generalized formula (I) in which one or more of the substituent groups $R^6$ are involved in formation of nonspiro rings have the formula

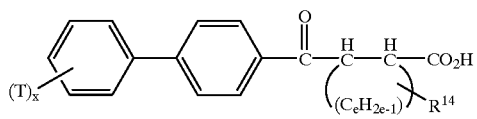

in which the subscript x is 1 or 2; one substituent T is located on the 4-position of the A ring, relative to the point of attachment between the A and B rings; e is 2 or 3; and $R^{14}$ is as defined above.

The invention also relates to certain intermediates useful in the synthesis of some of the claimed inhibitors. These intermediates are compounds having the generalized formula

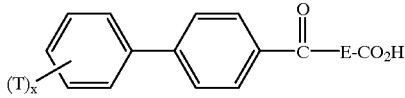

in which E represents

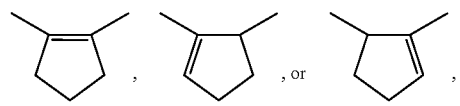

T represents a substituent group, and x is 1 or 2.

Those skilled in the art will appreciate that many of the compounds of the invention exist in enantiomeric or diastereomeric forms, and that it is understood by the art that such stereoisomers generally exhibit different activities in biological systems. This invention encompasses all possible stereoisomers which possess inhibitory activity against an MMP, regardless of their stereoisomeric designations, as well as mixtures of stereoisomers in which at least one member possesses inhibitory activity.

The most preferred compounds of the present invention are as indicated and named in the list below:

196 4-[4-(4-chlorophenyl)phenyl]-4-oxo-2-(phenylthiomethyl)butanoic acid
197 4-[4-(4-chlorophenyl)phenyl]-4-oxo-2S-(phenylthiomethyl)butanoic acid
198 4-[4-(4-chlorophenyl)phenyl]-4-oxo-2R-(phenylthiomethyl)butanoic acid
114 4-[4-(4-chlorophenyl)phenyl]-4-oxo-2-(3-phenylpropyl)butanoic acid
115 4-[4-(4-chlorophenyl)phenyl]-4-oxo-2R-(3-phenylpropyl)butanoic acid
116 4-[4-(4-chlorophenyl)phenyl]-4-oxo-2S-(3-phenylpropyl)butanoic acid
144 4-[4-(4-chlorophenyl)phenyl]-4-oxo-2-[2-(3-N,N-diethylcarbamoyl)phenyl]butanoic acid
145 4-[4-(4-chlorophenyl)phenyl]-4-oxo-2S-[2-(3-N,N-diethylcarbamoyl)phenyl]butanoic acid
146 4-[4-(4-chlorophenyl)phenyl]-4-oxo-2R-[2-(3-N,N-diethylcarbamoyl)phenyl]butanoic acid
85 4-[4-(4-pentyloxyphenyl)phenyl]-4-oxo-2-(3-phenylpropyl)butanoic acid
86 4-[4-(4-pentyloxyphenyl)phenyl]-4-oxo-2S-(3-phenylpropyl)butanoic acid
87 4-[4-(4-pentyloxyphenyl)phenyl]-4-oxo-2R-(3-phenylpropyl)butanoic acid
99 4-[4-(4-benzyloxyphenyl)phenyl]-4-oxo-2-(3-phenylpropyl)butanoic acid
100 4-[4-(4-benzyloxyphenyl)phenyl]-4-oxo-2S-(3-phenylpropyl)butanoic acid
101 4-[4-(4-benzyloxyphenyl)phenyl]-4-oxo-2R-(3-phenylpropyl)butanoic acid
267 4-[4-(4-chlorophenyl)phenyl]-4-oxo-2-(2-phthalimidoethyl)butanoic acid
268 4-[4-(4-chlorophenyl)phenyl]-4-oxo-2S-(2-phthalimidoethyl)butanoic acid
269 4-[4-(4-chlorophenyl)phenyl]-4-oxo-2R-(2-phthalimidoethyl)butanoic acid
294 trans-5-[4-(4-chlorophenyl)phenylcarbonyl]-trans-2-phenylthiocyclopentanecarboxylic acid 296 (1S,2R,5S)-trans-5-[4-(4-chlorophenyl)
  phenylcarbonyl]-trans-2-
  phenylthiocyclopentanecarboxylic acid
297 (1R,2S,5R)-trans-5-[4-(4-chlorophenyl)
  phenylcarbonyl]-trans-2-
  phenylthiocyclopentanecarboxylic acid
298 trans-5-[4-(4-chlorophenyl)phenylcarbonyl]-cis-2-(2-
  methoxycarbonylphenylthio)cyclopentanecarboxylic acid
299 (1S,2S,5S)-trans-5-[4-(4-chlorophenyl)
  phenylcarbonyl]-cis-2-(2-methoxycarbonylphenylthio)
  cyclopentanecarboxylic acid
300 (1R,2R,5R)-trans-5-[4-(4-chlorophenyl)
  phenylcarbonyl]-cis-2-(2-methoxycarbonylphenylthio)
  cyclopentanecarboxylic acid
360 trans-5-[4-(4-chlorophenyl)phenylcarbonyl]-trans-2-
  phthalimidomethylcyclopentanecarboxylic acid
361 (1S,2R,5S)-trans-5-[4-(4-chlorophenyl)
  phenylcarbonyl]-trans-2-
  phthalimidomethylcydopentanecarboxylic add
362 (1R,2S,5R)-trans-5-[4-(4-chlorophenyl)
  phenylcarbonyl]-trans-2-
  phthalimidomethylcyclopentanecarboxylic acid General Preparative Methods:

The compounds of the invention may be prepared by use of known chemical reactions and procedures. Nevertheless, the following general preparative methods are presented to aid the reader in synthesizing the inhibitors, with more detailed particular examples being presented below in the experimental section describing the working examples.

All variable groups of these methods are as described in the generic description if they are not specifically defined below. The variable subscript n is independently defined for each method. When a variable group with a given symbol (i.e. $R^6$ or T) is used more than once in a given structure, it is to be understood that each of these groups may be independently varied within the range of definitions for that symbol. As defined above, the compounds of the invention contain as the E unit a chain of 2 or 3 carbon atoms bearing 1 to 3 substituents $R^6$ which are not defined as H. By contrast, it is to be noted that in the general method schemes below, the $R^6$ groups are used as if their definition includes H, to show where such $R^6$ groups may exist in the structures, and for ease in drawing. No change in the definition of $R^6$ is intended by this non-standard usage, however. Thus, only for purposes of the general method schemes below, $R^6$ may be H in addition to the moieties set forth in the definition of $R^6$. The ultimate compounds contain 1 to 3 non-hydrogen groups $R^6$.

General Method A—The compounds of this invention in which the rings A and B are substituted phenyl and phenylene respectively are conveniently prepared by use of a Friedel-Crafts reaction of a substituted biphenyl II with an activated acyl-containing intermediate such as the succinic or glutaric anhydride derivative III or acid chloride IV in the presence of a Lewis acid catalyst such as aluminum trichloride in an aprotic solvent such as 1,1,2,2-tetrachloroethane. The well known Friedel-Crafts reaction can be accomplished with use of many alternative solvents and acid catalysts as described by E. Berliner, *Org. React.*, 5, 229 (1949) and H. Heaney, *Comp. Org. Synth.*, 2, 733 (1991).

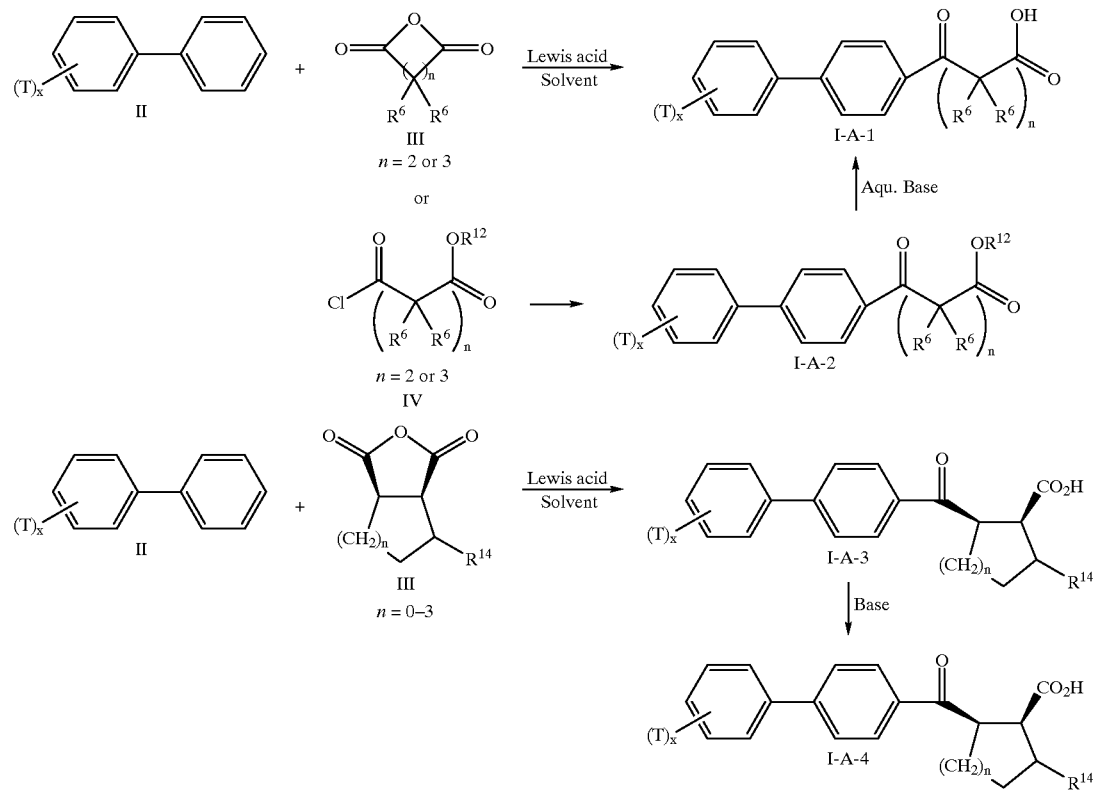

If the anhydride III is monosubstituted or multiply-substituted in an unsymmetrical way, the raw product I-A often exists as a mixture of isomers via attack of the anhydride from either of the two carbonyls. The resultant isomers can be separated into pure forms by crystallization or chromatography using standard methods known to those skilled in the art.

When they are not commercially available, the succinic anhydrides III can be prepared via a Stobbe Condensation of a dialkyl succinate with an aldehyde or ketone (resulting in side chain $R^6$), followed by catalytic hydrogenation, hydrolysis of a hemiester intermediate to a diacid and then conversion to the anhydride III by reaction with acetyl chloride or acetic anhydride. Alternatively, the hemiester intermediate is converted by treatment with thionyl chloride or oxalyl chloride to the acid chloride IV. For a review of the Stobbe condensation, including lists of suitable solvents and bases see W. S. Johnson and G. H. Daub, Org. React., 6, 1 (1951). This method, as applied to the preparation of III ($R^6$=H, isobutyl and H, n-pentyl), has been described by D. Wolanin, et al., U.S. Pat. No. 4,771,038, Sep. 13, 1988.

Method A is especially useful for the preparation of cyclic compounds such as I-A-3 in which two $R^6$ groups are connected in a methylene chain to form a 3–7 member ring. Small ring (3–5 member) anhydrides are readily available only as cis isomers which yield cis invention compounds I-A-3. The trans compounds I-A-4 are then prepared by treatment of I-A-3 with a base such as DBU in THF.

The substituted four member ring starting material anhydrides such as III-A-1 are formed in a photochemical 2+2 reaction as shown below. This method is especially useful for the preparation of compounds in which $R^{14}$ is acetoxy or acetoxymethylene. After the subsequent Friedel-Crafts reaction the acetate can be removed by basic hydrolysis and the carboxyl protected by conversion to 2-(trimethylsilyl)ethyl ester. The resultant intermediate with $R^{14}$=CH$_2$OH can be converted to invention compounds with other $R^{14}$ groups by using procedures described in General Method K.

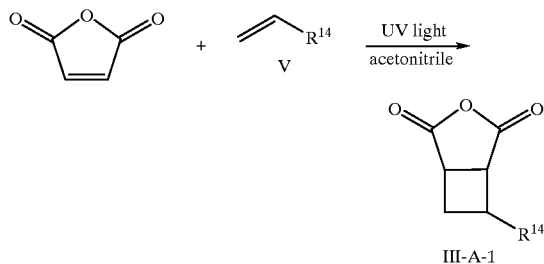

The Friedel Crafts method is also useful when double bonds are found either between C-2 and C-3 of a succinoyl chain (from maleic anhydride or 1-cyclopentene-1,2-dicarboxylic anhydride, for example) or when a double bond is found in a side chain, such as in the use of itaconic anhydride as starting material to yield products in which two $R^6$ groups as found on one chain carbon together form an exomethylene (=CH$_2$) group. Subsequent uses of these compounds are described in Methods D and E.

General Method B—Alternatively the compounds I can be prepared via a reaction sequence involving monoalkylation of a dialkyl malonate VI with an alkyl halide to form intermediate VII, followed by alkylation with a halomethyl biphenyl ketone VIII to yield intermediate IX. Compounds of structure IX are then hydrolyzed with aqueous base and then heated to decarboxylate the malonic acid intermediate and yield I-B-2 (Method B-1). By using one equivalent of aqueous base the esters I-B-2 with $R^{12}$ as alkyl are obtained, and using more than two equivalents of base the acid compounds ($R^{12}$=H) are obtained. Optionally, heat is not used and the diacid or acid-ester I-B-1 is obtained. Alternatively, the diester intermediate IX can be heated with a strong acid such as concentrated hydrochloric acid in acetic acid in a sealed tube at about 110° C. for about 24 hr to yield I-B-2 ($R^{12}$=H).

Alternatively, the reaction of VI with VIII can be conducted before that with the alkyl halide to yield the same IX (Method B-2).

Intermediates VIII are formed from biphenyls II in a Friedel-Craft reaction with haloacetyl halides such as bromoacetyl bromide or chloroacetyl chloride. Alternatively, the biphenyl can be reacted with acetyl chloride or acetic anhydride and the resultant product halogenated with, for example, bromine to yield intermediates VIII (X=Br).

Method B has the advantage of yielding single regio isomers when Method A yields mixtures. Method B is especially useful when the side chains $R^6$ contain aromatic or heteroaromatic rings that may participate in intramolecular acylation reactions to give side products if Method A were to be used. This method is also very useful when the $R^6$ group adjacent to the carboxyl of the final compound contains heteroatoms such as oxygen, sulfur, or nitrogen, or more complex functions such as imide rings.

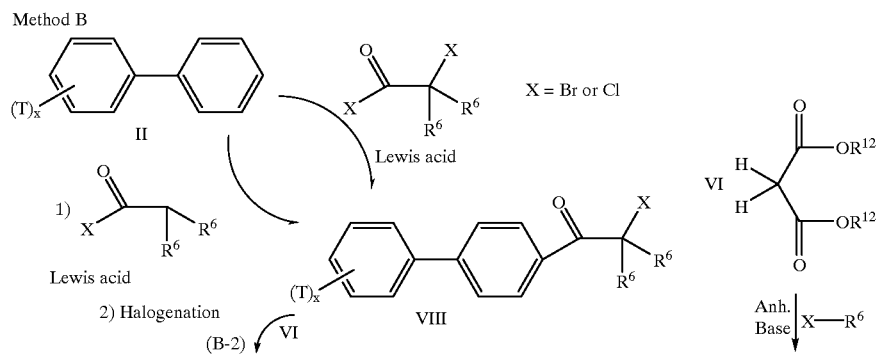

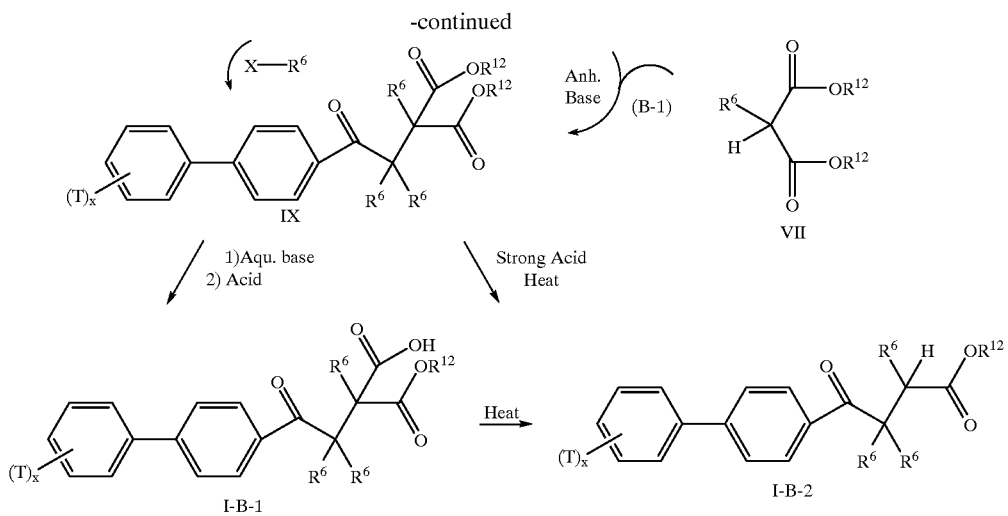

General Method C—Especially useful is the use of chiral HPLC to separate the enantiomers of racemic product mixtures (see, for example, D. Arlt, B. Boemer, R Grosser and W. Lange, *Angew. Chem. Int. Ed. Engl.* 30 (1991) No. 12). The compounds of this invention are prepared as pure enantiomers by use of a chiral auxiliary route—see, for example: D. A. Evans, Aldrichimica Acta, 15(2), 23 (1982) and other similar references known to one skilled in the art.

C-1. Acid halide X is reacted with the lithium salt of chiral auxiliary XI (R is often isopropyl or benzyl) to yield intermediate XII, which in turn is akylated at low temperatures (typically under −50° C.) with halo-tert-butylacetyl compound XIII to yield pure isomer XIV. The use of opposite chirality XI yields opposite chirality XIV. Conversion of XIV to the enantiomerically pure diacid XV is accomplished by treatment with lithium hydroxide/hydrogen peroxide in THF/water, followed by acids such as trifluoroacetic acid. The compound XV is then converted to enantiomerically pure anhydride III-A by treatment with acetyl chloride. The use of a Friedel-Crafts reaction as in method A then converts III-A to I-C-1.

C-2. Biphenyl starting material II may also first be reacted in a Friedel-Crafts reaction as earlier described with succinic anhydride followed by Fisher esterification with a lower alcohol such as methanol in the presence of a strong acid such as sulfuric acid to form acyl derivative I-C-2. The carbonyl group of this material is then blocked as a ketal such as that formed by treatment with 1,2-bistrimethyl-silyloxyethane in the presence of a catalyst such as trimethyl-silyltriflate in a suitable solvent. Many other ketal derivatives and reaction conditions familiar to those skilled in the art can also be used in this step. Basic hydrolysis of the ester followed by reaction of the resultant I-C-3 with XI in the presence of an amide coupling agent such as 1-(3-dimethylaminopropyl)-3-ethylcarbodiimide yields amide I-C-4. Reaction of this chiral amide with an alkylating agent such as alkyl or arylalkyl triflate or halide yields enantiomerically enriched product I-C-5 which can be converted to final product I-C-6 by treatment with a weak base such as lithium hydroxide/hydrogen peroxide and then acid. These deblocking steps can be conducted in either order.

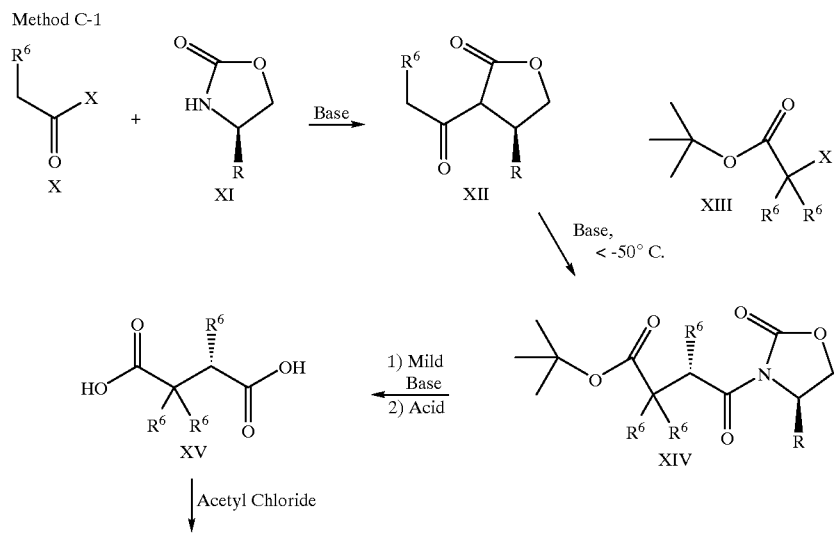

Method C-1

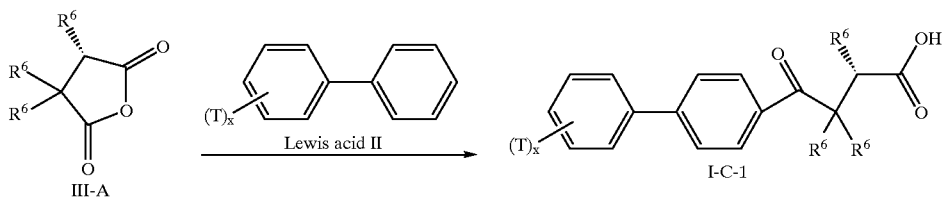

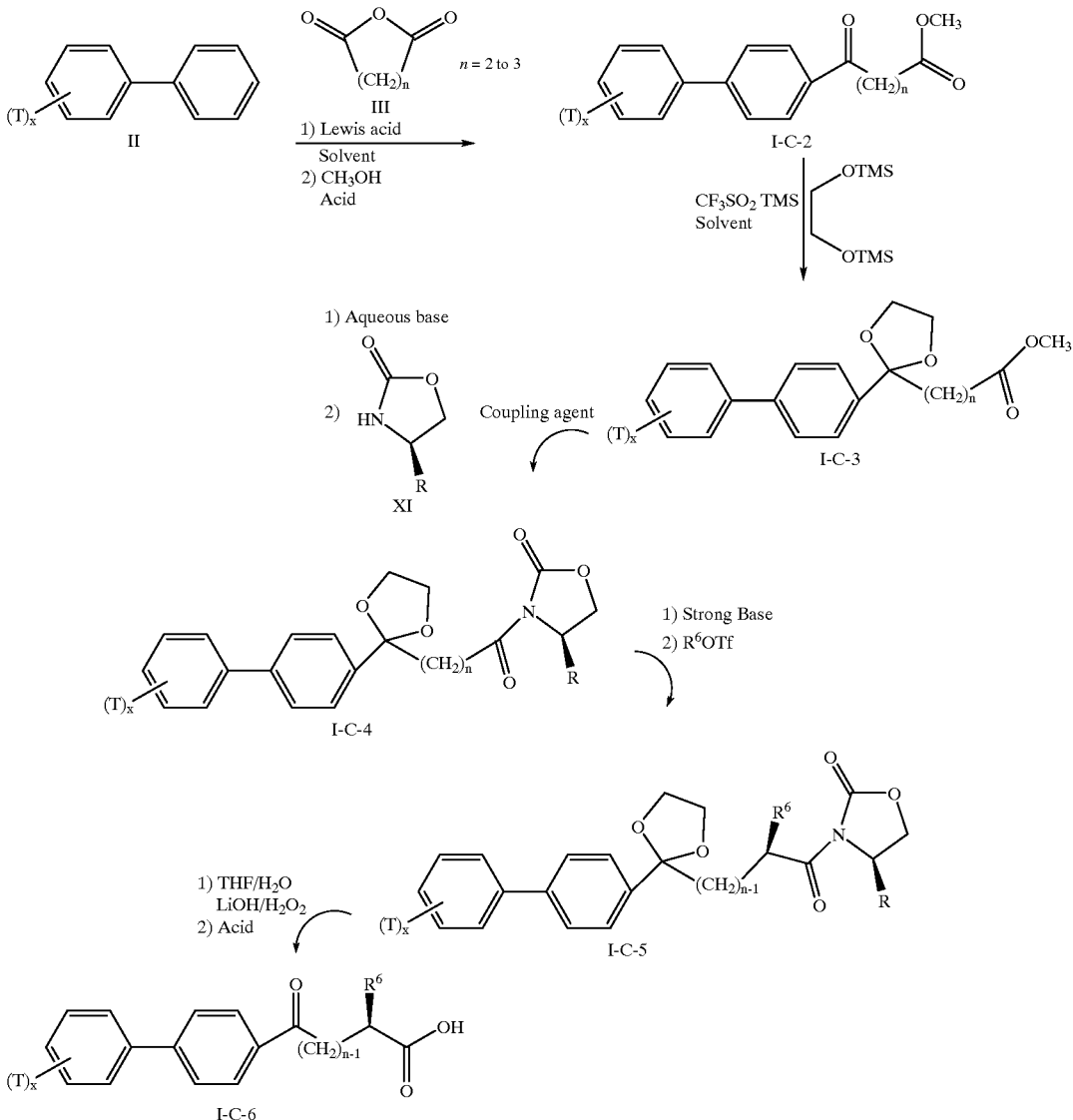

General Method D—Compounds in which $R^6$ are alkyl- or aryl- or heteroaryl- or acyl- or heteroarylcarbonyl-thiomethylene are prepared by methods analogous to those described in the patent WO 90/05719. Thus substituted itaconic anhydride XVI (n=1) is reacted under Friedel-Crafts conditions to yield acid I-D-1 which can be separated by chromatography or crystallization from small amounts of isomeric I-D-5. Alternatively, I-D-5 are obtained by reaction of invention compounds I-D-4 (from any of Methods A through C) with formaldehyde in the presence of a base.

Compounds I-D-1 or I-D-5 are then reacted with a mercapto derivative XVII or XVIII in the presence of a catalyst such as Potassium carbonate, ethyldiisobutylamine, tetrabutylammonium fluoride or free radical initiators such as azobisisobutyronitrile (AIBN) in a solvent such as dimethylformamide or tetrahydrofuran to yield invention compounds I-D-2, I-D-3, I-D-6 or I-D-7.

Method D

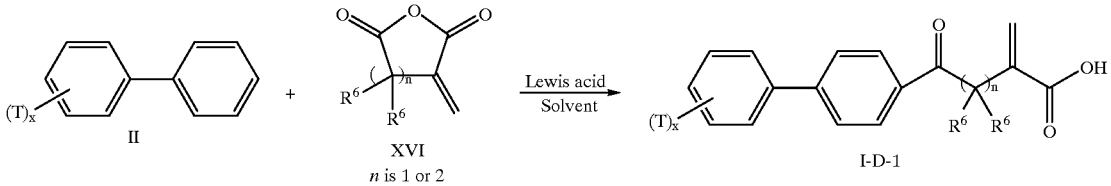

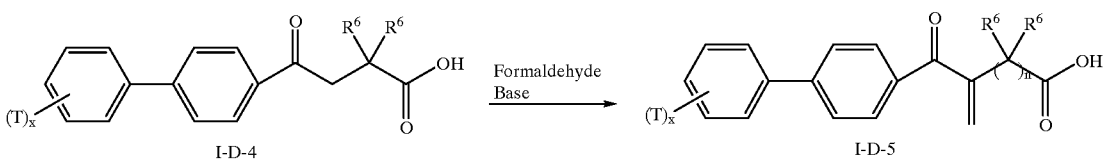

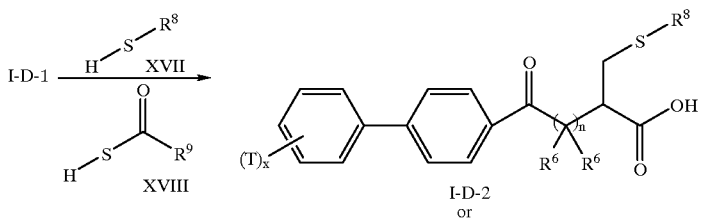

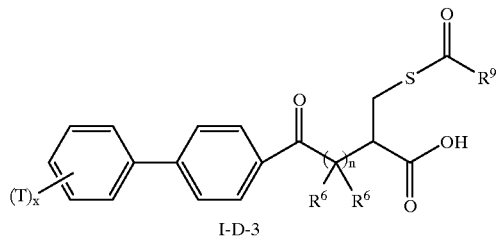

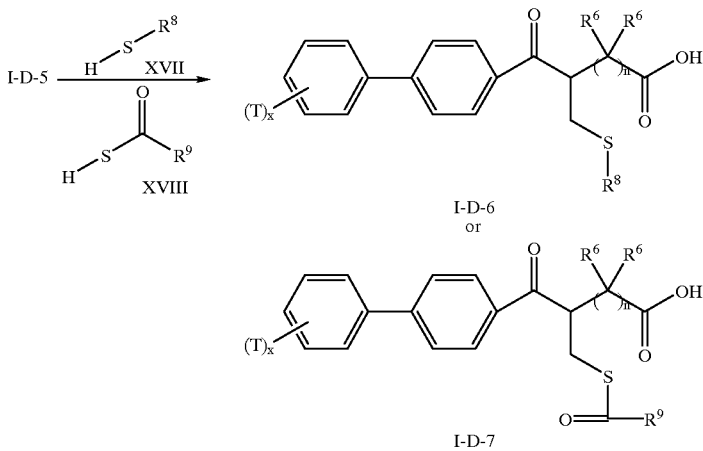

General Method E—Reaction of optionally substituted maleic anhydride XIX under Friedel-Crafts conditions with II yields invention compound I-E-1, which in turn is reacted with either of mercapto derivatives XVII or XVIII to yield invention compounds I-E-2 or I-E-3 or with substituted amine XX to yield invention compounds I-E-4. Esterification of I-E-1 (R6=H) with $CH_3I$/DBU followed by reagent XXI and AgF and then basic hydrolysis yields pyrrolidine invention compound I-E-5. R14 can be various alkyl or arylalkyl including benzyl. Reaction of the intermediate ester (from step 2) with benzyloxycarbonyl chloride in THF at reflux followed by hydrolysis yields invention compounds in which $R^{14}$ is benzyloxycarbonyl.

Method E

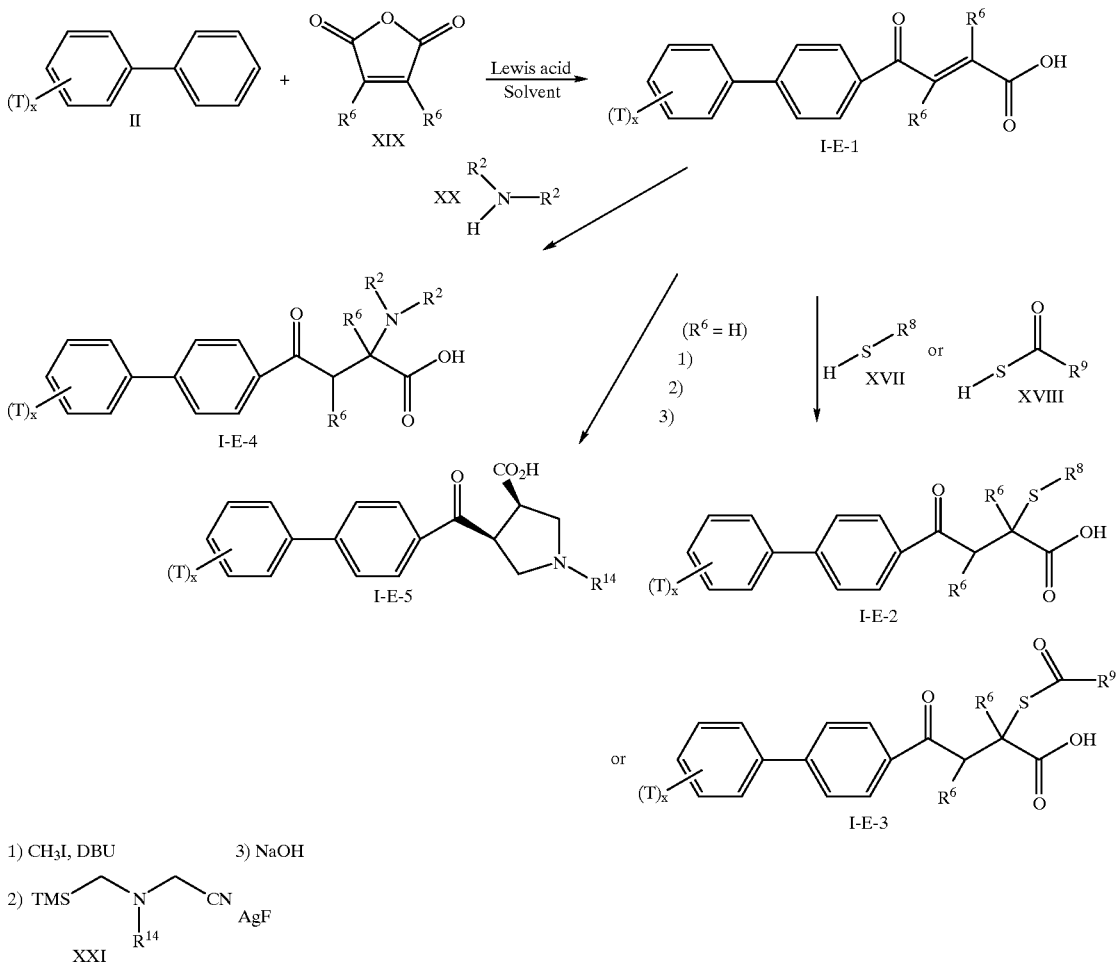

1) CH₃I, DBU  3) NaOH

2) TMS—N(R¹⁴)—CN, AgF
XXI

General Method F—Biaryl compounds such as those of this application may also be prepared by Suzuki or Stille cross-coupling reactions of aryl or heteroaryl metallic compounds in which the metal is zinc, tin, magnesium, lithium, boron, silicon, copper, cadmium or the like with an aryl or heteroaryl halide or triflate (trifluoromethane-sulfonate) or the like. In the equation below either Met or X is the metal and the other is the halide or triflate. Pd(com) is a soluble complex of palladium such as tetrakis(triphenylphosphine)-palladium(0) or bis-(triphenylphos-phine)-palladium(II) chloride. These methods are well known to those skilled in the art. See, for example, A. Suzuki, Pure Appl. Chem., 66, 213–222 (1994); A. Suzuki, Pure Appl. Chem., 63, 419–422 (1991); and V. Farina and G. Roth, "Metal-Organic Chemistry" Volume 5 (Chapter 1), 1994 (in press).

The starting materials XXIII (B=1,4-phenylene) are readily formed using methods analogous to those of methods A, B or C but using a halobenzene rather than a biphenyl as starting material. When desired, the materials in which X is halo can be converted to those in which X is metal by reactions well known to those skilled in the art such as treatment of a bromo intermediate with hexamethylditin and palladium tetrakistriphenylphosphine in toluene at reflux to yield the trimethyltin intermediate. The starting materials XXIII (B=heteroaryl) are most conveniently prepared by method C but using readily available heteroaryl rather than biphenyl starting materials. The intermediates XXII are either commercial or easily prepared from commercial materials by methods well known to those skilled in the art.

These general methods are useful for the preparation of compounds for which Friedel-Crafts reactions such as those of Methods A, B, C, D or E would lead to mixtures with various biaryl acylation patterns. Method F is also especially useful for the preparation of products in which the aryl groups A or B contain one or more heteroatoms (heteroaryls) such as those compounds that contain thiophene, furan, pyridine, pyrrole, oxazole, thiazole, pyrimidine or pyrazine rings or the like instead of phenyls.

Method F

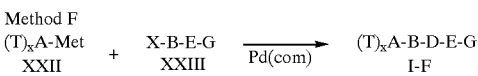

T, x, A, B, E and G as in Structure I
Met =Metal and X=Halide or Triflate
or
Met=Halid or Triflate and X=Metal General Method C—When the R⁶ groups of method F form together a 4–7 member carbocyclic ring as in Intermediate XXV below, the double bond can be moved out of conjugation with the ketone group by treatment with two equivalents of a strong base such as lithium diisopropylamide or lithium hexamethylsilylamnide or the like followed by acid quench to yield compounds with the structure XXVI. Reaction of XXVI with mercapto derivatives using methods analogous to those of General Method D then leads to cyclic compounds I-G-1 or I-G-2.

lowed by dehydration with triphenylphosphine/diethyl azodicarboxylate (DEAD) in a suitable solvent such as THF at reflux to yield XXIX. Hydrolysis of the ester with aqueous base followed by amide formation with $R^{12}ONHR^{12}$ (R is lower alkyl, but usually $CH_3$) in the presence of a coupling agent such as dicyclohexyldiimide (DCC) yields XXX. Other acyl activating groups well known to those skilled in the art such as acid chlorides or mixed anhydrides could be

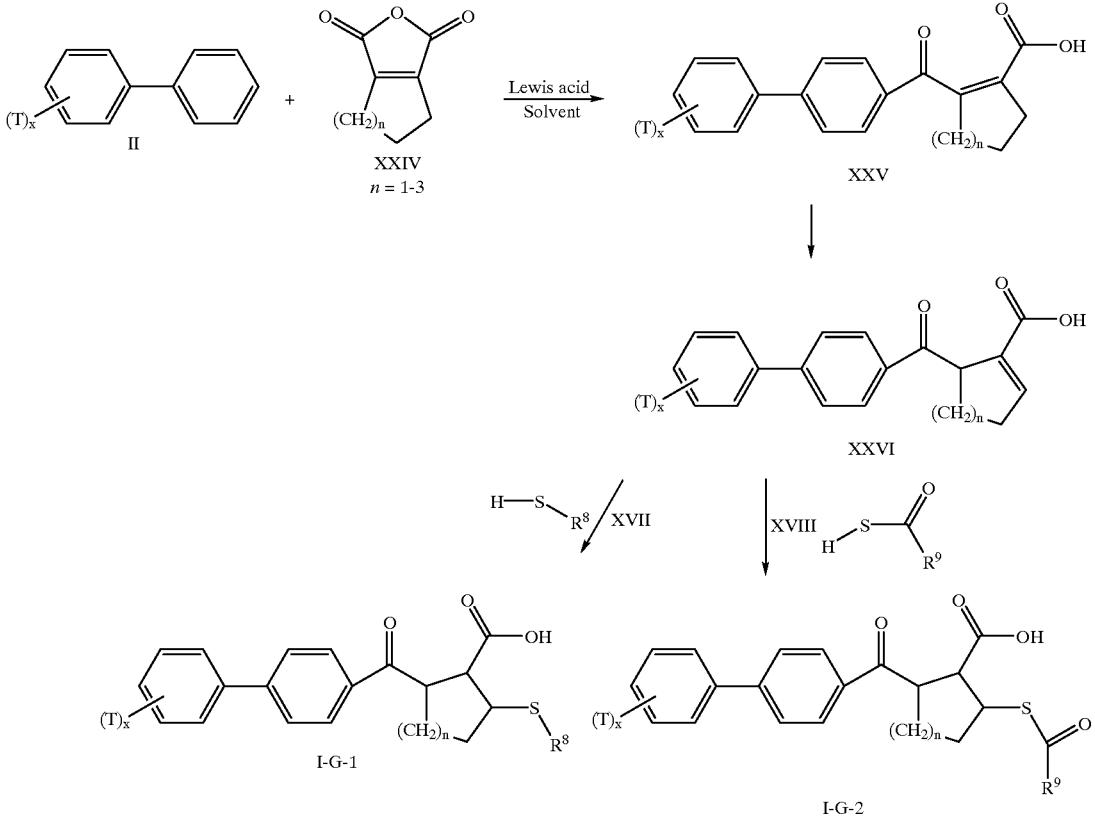

General Method H—Invention compounds in which two $R^6$ groups form a 4–7 member carbocyclic ring as in I-H below and $R^{14}$ is alkyl or arylalkyl are prepared according to method H. Starting material XXVII is reacted with two equivalents of a strong base such as lithium diisopropylamide (LDA) followed by an alkyl or arylalkyl halide ($R^{14}X$) to yield intermediate XXVIII. This material is then reduced to the alcohol with a reducing agent capable of selective reduction of the ketone such as sodium borohydride, folused instead of XXX. Substituted biphenyl halide XXXI is reacted with an alkyl lithium such as two equivalents of t-butyl lithium to yield lithiated biphenyl XXXII which is then reacted with activated acyl compound XXX. The resultant intermediate XXXIII is then treated with diethylaluminum cyanide to yield intermediate XXXIV which is then hydrolyzed with aqueous acid to yield invention compound I-H which is purified by chromatography on silical gel to afford pure isomers.

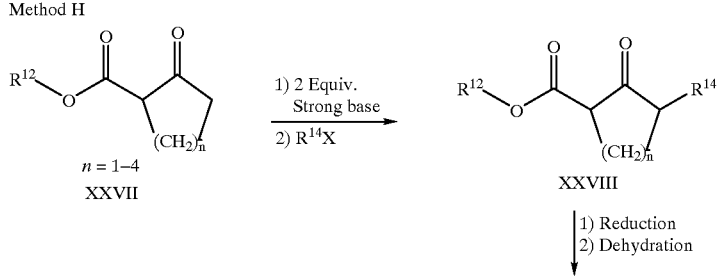

-continued

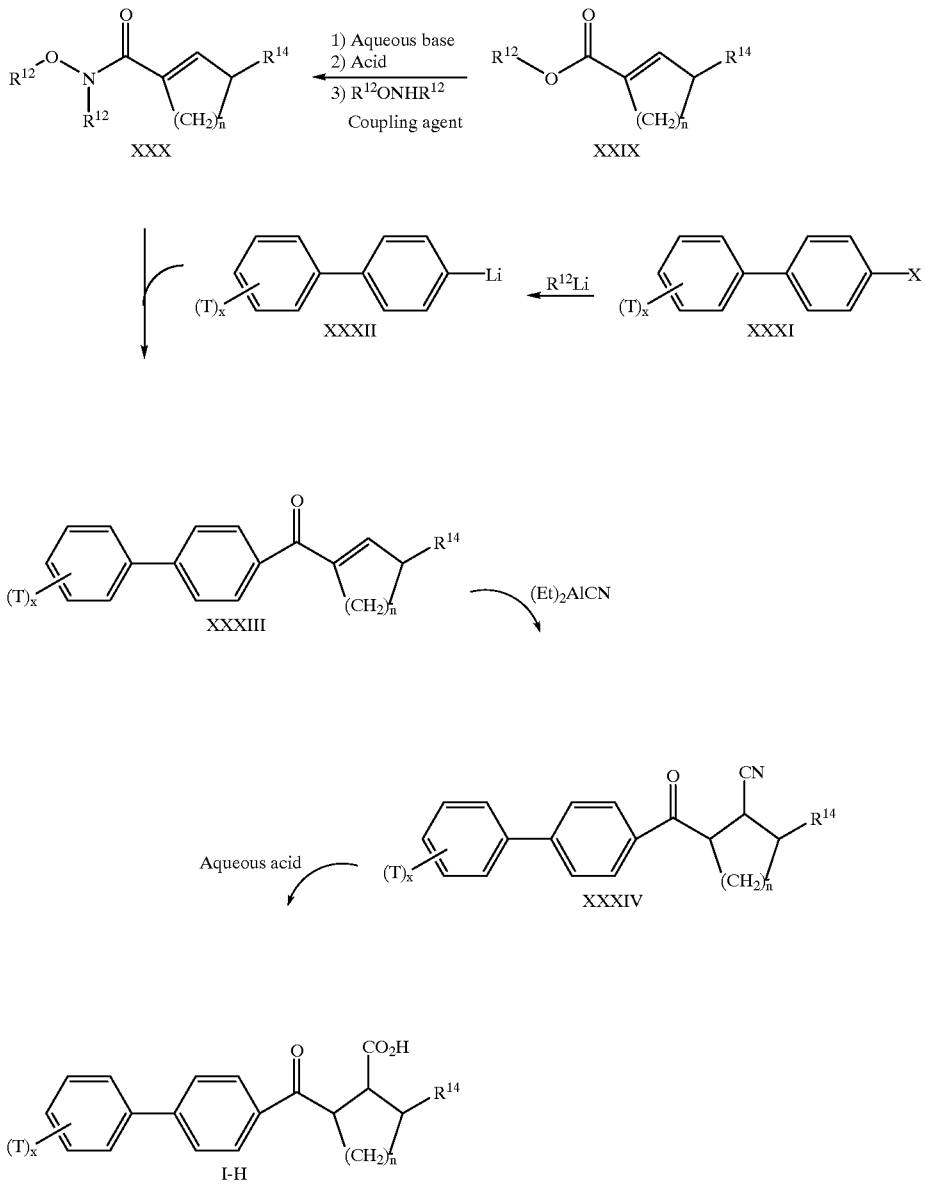

General Method I—Invention compounds in which two R6 groups together form a pyrrolidine ring are prepared according to method I. Starting material XXXV (L-pyroglutaminol) is reacted under acid catalysis with benzaldehyde XXXVI (may be substituted) to yield bicyclic derivative XXXVII. A double bond is then introduced using phenylselenenyl methodology well known to those skilled in the art to yield XXXVIII, which, in turn, is reacted with a vinylcopper (I) complex to yield conjugate addition product XXXIX. Such reactions in which Lig can be, for example, another equivalent of vinyl group or halide are well known to those skilled in the art. Hydride reduction (lithium aluminum hydride or the like) of XXXIX followed by standard blocking with, for example, t-butyldimethylsilylchloride yields XXXX which in turn is reacted with an optionally substituted benzylchloroformate XXXXI to yield XXXXII. Ozonolysis of this intermediate followed by reductive workup (dimethylsulfide, zinc/acetic acid or the like) leads to aldehyde XXXXIII. Reaction of this aldehyde with a biphenyl organometallic such as XXXII yields alcohol XXXXIV. Deblocking of the silyl group with, for example, tetrabutylammonium fluoride followed by oxidation with, for example, pyridiniumdichromate or the like yields claimed compound 1-I-1 in which $R^{14}$ is a carbobenzyloxy group.

Alternatively the carbobenzyloxy group is removed by reaction with hydrogen and a catalyst such as palladium on carbon to yield the unsubstituted invention compound 1-I-2 optionally followed by N-alkylation to yield compound 1-I-3. These final steps are well known to those skilled in the art. Alternatively the intermediate XXXX can be directly treated with ozone followed by the other steps of this method to yield 1-I-3 in which $R^{14}$ is optionally substituted benzyl rather than as in 1-I-1.

This method is especially useful to prepare single enantiomers because starting material XXXV is available as either the isomer as drawn or as D-pyroglutaminol to yield enantiomeric products.

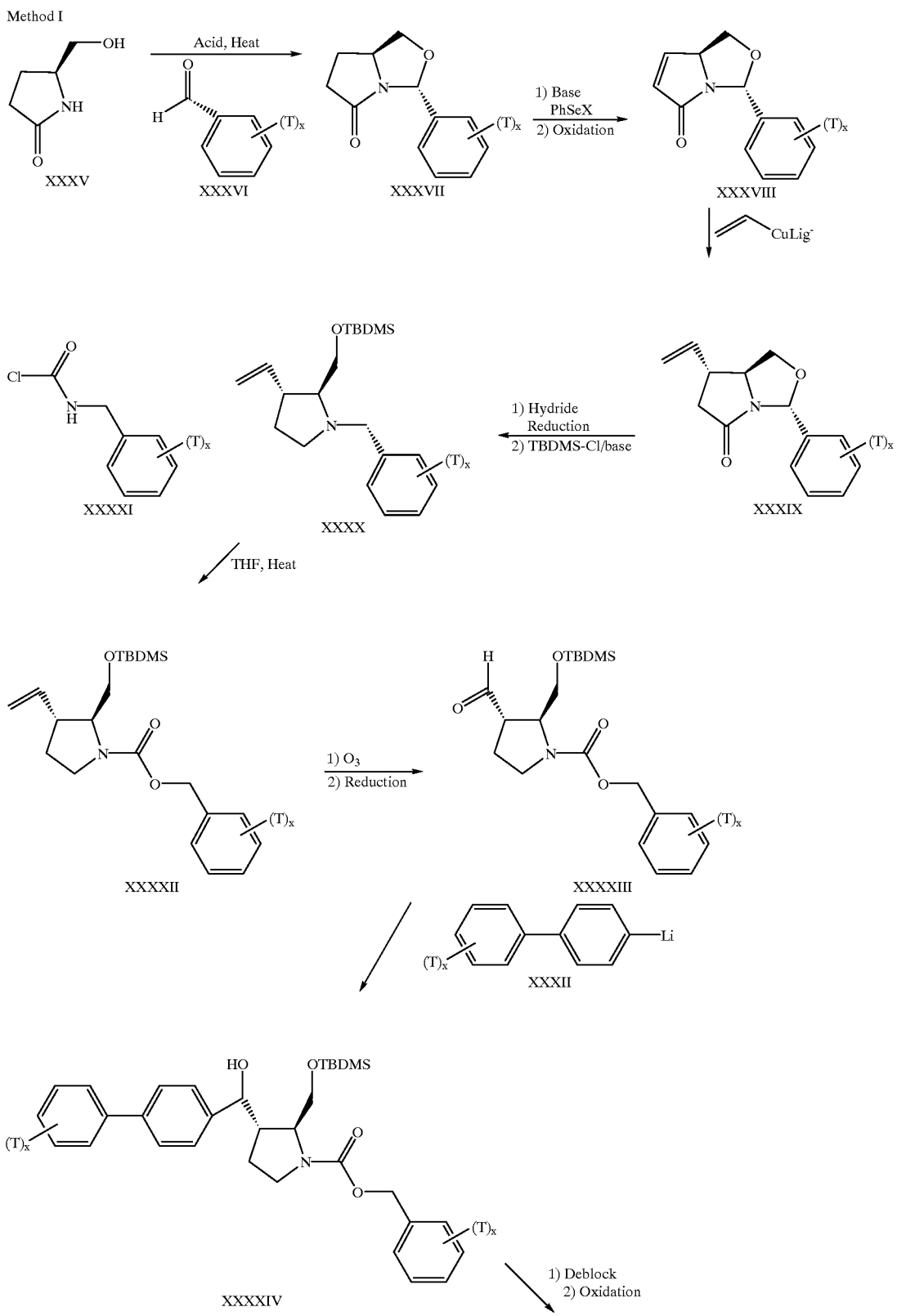

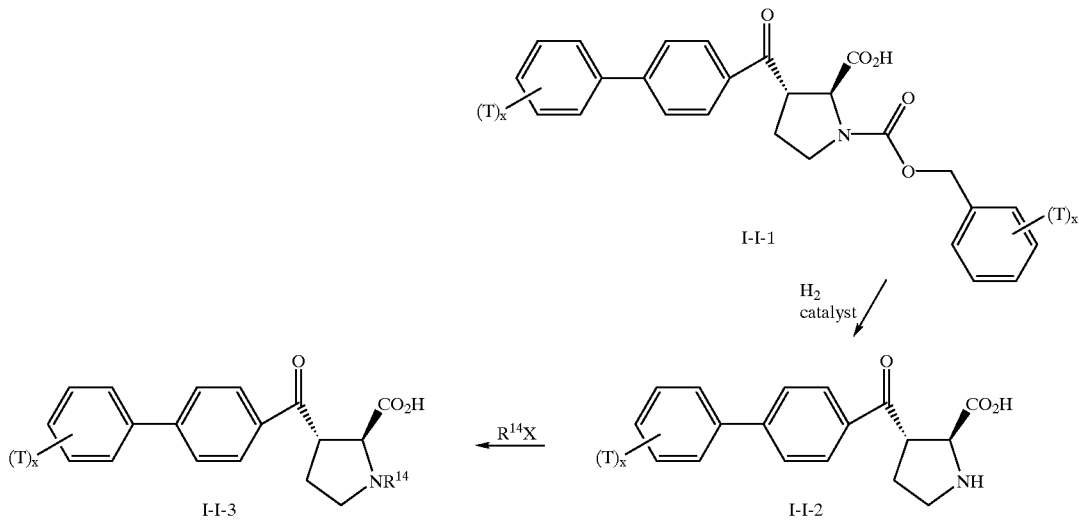

General Method J—The compounds of this invention in which E represents a substituted chain of 3 carbons are prepared by method J. Intermediates XXXXVII, if not available from commercial sources, are prepared by reaction of an activated biphenylcarboxylic acid derivative XXXXV with substituted acetic acid XXXXVI which has been converted to its bis anion with two equivalents of a strong base such as LDA followed by heating to decarboxylate the intermediate keto acid. Product XXXXVII is then treated with methylenemalonate derivative XXXXVIII in the presence of a strong base such as sodium hydride to yield substituted malonate XXXXIX. This malonate can be further alkylated under conditions familiar to those skilled in the art to yield L which in turn is treated with acid and then heated to yield invention compound 1-J-1. Alternatively the final alkylation can be omitted to yield products in which the R6 adjacent to the carboxyl is H. Alternatively XXXXVII can be alkylated with 3-halopropionate ester LI in the presence of base such as LDA to yield ester 1-J-2 which can then be hydrolyzed with aqueous base to yield invention compound 1-J-3 upon treatment with acid. This method is especially useful if any of the groups $R^6$ contain aromatic residues.

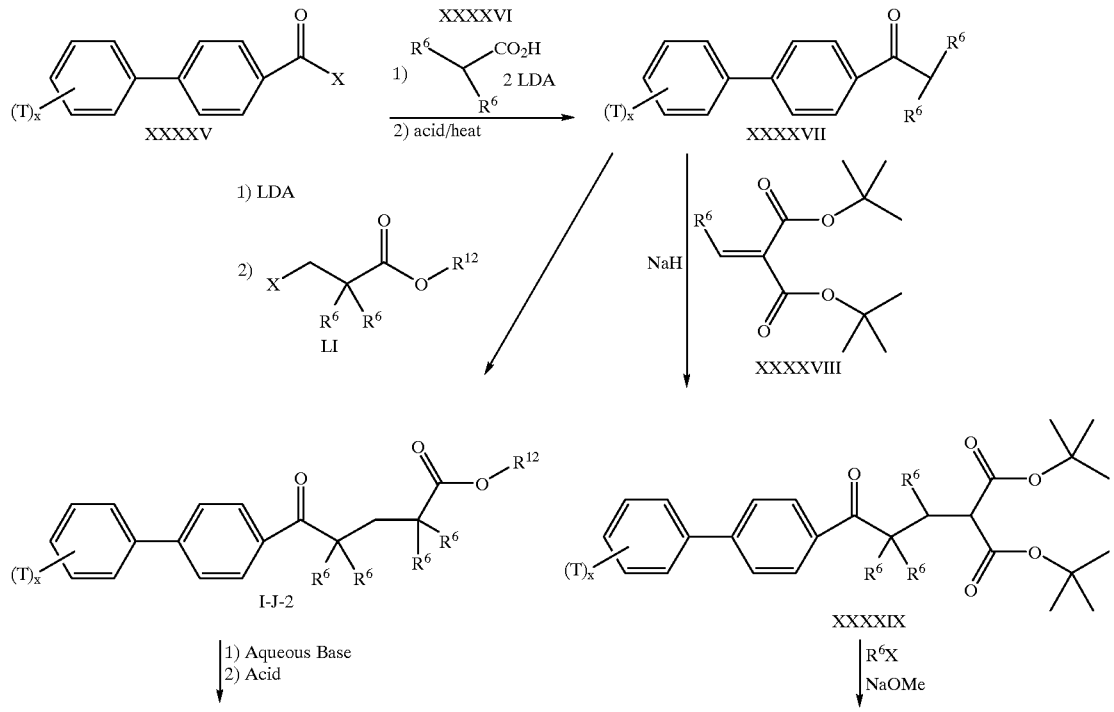

-continued

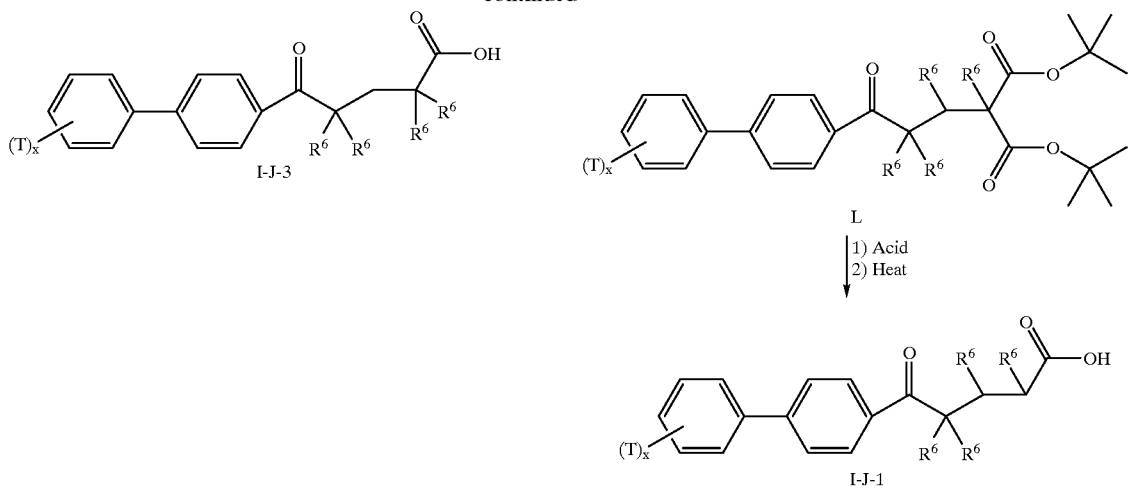

Method K—The compounds of this invention in which two R⁶ groups are joined to form a substituted 5-member ring are most conveniently prepared by method K. In this method acid LII (R=H) is prepared using the protocols described in *Tetrahedron*, Vol. 37, Suppl., 1981, 411. The acid is protected as an ester (R=benzyl or 2-(trimethylsilyl) ethyl) by use of coupling agents such as 1-(3-dimethylaminopropyl)-3-ethylcarbodiimide hydrochloride and procedures well known to those skilled in the art. Substituted bromobiphenyl LIII is converted to its Grignard reagent by treatment with magnesium which is then reacted with LII to yield alcohol LIV. Alcohol LIV is eliminated via base treatment of its mesylate by using conditions well known to those skilled in the art to yield olefin LV. Alternatively LIII is converted to a trimethyltin intermediate via initial metallation of the bromide with n-butyllithium at low temperature (−78°) followed by treatment with chlorotrimethyltin and LII is converted to an enoltriflate by reaction with 2-[N,N-bis(trifluoromethylsulfonyl)amino]-5-chloropyridine in the presence of a strong aprotic base. The tin and enoltriflate intermediates are then coupled in the presence of a Pd° catalyst, CuI and AsPh₃ to yield directly intermediate LV. Ozonolysis of LV (workup with methylsufide) yields aldehyde LVI. Alternatively treatment with OsO₄ followed by HIO₄ converts LV to LVI.

Conversion of key intermediate LVI to patent compound I-K is accomplished in several ways depending on the identity of side chain function X. Reaction of LVI with Wittig reagents followed by hydrogenation yields products in which X is alkyl, aryl or arylalkyl. Reduction of aldehyde LVI with LAH yields alcohol I-K (X=OH). The alcohol is converted to phenyl ethers or N-phthalimidoyl compounds by use of the appropriate starting materials and Mitsunobu conditions well known to those skilled in the art; see O Mitsunobu, Synthesis, 1 (1981). Alternatively the alcohol of I-K (X=OH) is converted to a leaving group such as tosylate (X=OTs) or bromide (X=Br) by conditions well known to those skilled in the art and then the leaving group is displaced by sulfur or azide nucleophiles to yield products with X=thioether or azide which in turn is reduced and acylated to yield amides (X=NHAcyl). Direct acylation of the alcohol I-K (X=OH) yields invention compounds in which X=O Acyl and reaction of the alcohol with various alkyl halides in the presence of base yields alkyl ethers (X=OR²). In each case a final step is removal of acid blocking group R to yield acids (R=H) by using conditions which depend on the stability of R and X, but in all cases well known to those skilled in the art such as removal of benzyl by base hydrolysis or of 2-(trimethylsilyl)ethyl by treatment with tetrabutylammonium fluoride.

Method K

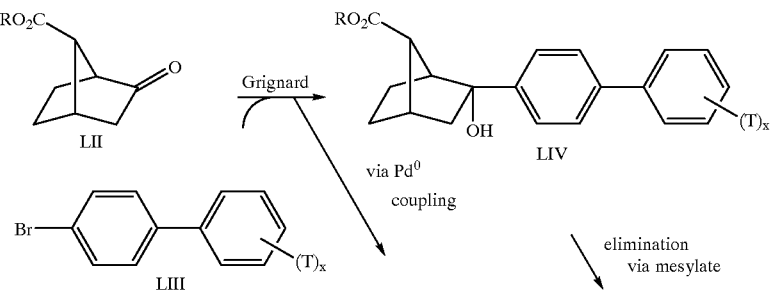

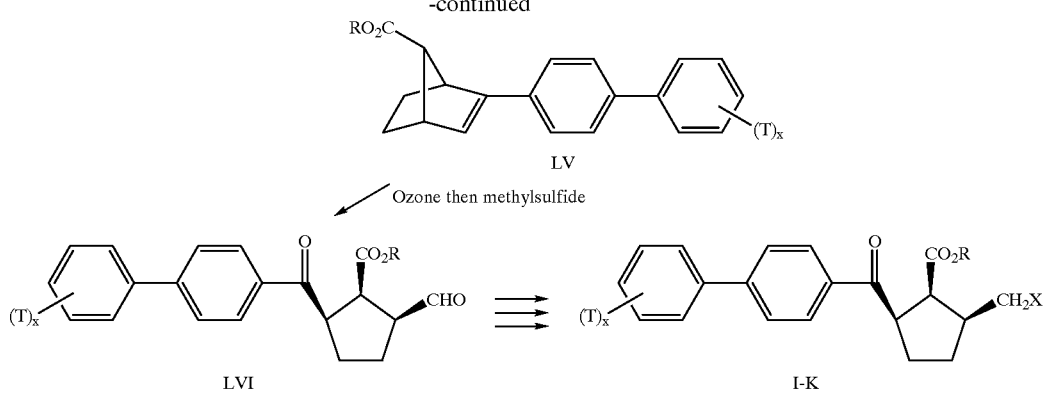

Method L—Amides of the acids of the invention compounds can be prepared from the acids by treatment in an appropriate solvent such as dichloromethane or dimethylforrnamide with a primary or secondary amine and a coupling agent such as dicyclohexylcarbodiimide. These reactions are well known to those skilled in the art. The amine component can be simple alkyl or arylalkyl substituted or can be amino acid derivatives in which the carboxyl is blocked and the amino group is free.

Suitable pharmaceutically acceptable salts of the compounds of the present invention include addition salts formed with organic or inorganic bases. The salt forming ion derived from such bases can be metal ions, e.g., aluminum, alkali metal ions, such as sodium of potassium, alkaline earth metal ions such as calcium or magnesium, or an amine salt ion, of which a number are known for this purpose. Examples include ammonium salts, arylalkylamines such as dibenzylamine and N,N-dibenzylethylenediamine, lower alkylamines such as methylamine, t-butylamine, procaine, lower alkylpiperidines such as N-ethylpiperidine, cycloalkylamines such as cyclohexylamine or dicyclohexylamine, 1-adamantylamine, benzathine, or salts derived from amino acids like arginine, lysine or the like. The physiologically acceptable salts such as the sodium or potassium salts and the amino acid salts can be used medicinally as described below and are preferred.

These and other salts which are not necessarily physiologically acceptable are useful in isolating or purifying a product acceptable for the purposes described below. For example, the use of commercially available enantiomerically pure amines such as (+)-cinchonine in suitable solvents can yield salt crystals of a single enantiomer of the invention compounds, leaving the opposite enantiomer in solution in a process often referred to as "classical resolution." As one enantiomer of a given invention compound is usually substantially greater in physiological effect than its antipode, this active isomer can thus be found purified in either the crystals or the liquid phase. The salts are produced by reacting the acid form of the invention compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compounds of the present invention have been found to inhibit the matrix metalloproteases MMP-3, MMP-9 and MMP-2, and to a lesser extent MMP-1, and are therefore useful for treating or preventing the conditions referred to in the background section. As other MMPs not listed above share a high degree of homology with those listed above, especially in the catalytic site, it is deemed that compounds of the invention should also inhibit such other MMPs to varying degrees. Varying the substituents on the biaryl portions of the molecules, as well as those of the propanoic or butanoic acid chains of the claimed compounds, has been demonstrated to affect the relative inhibition of the listed MMPs. Thus compounds of this general class can be "tuned" by selecting specific substituents such that inhibition of specific MMP(s) associated with specific pathological conditions can be enhanced while leaving non-involved MMPs less affected.

The method of treating matrix metalloprotease-mediated conditions may be practiced in mammals, including humans, which exhibit such conditions.

The inhibitors of the present invention are contemplated for use in veterinary and human applications. For such purposes, they will be employed in pharmaceutical compositions containing active ingredient(s) plus one or more pharmaceutically acceptable carriers, diluents, fillers, binders, and other excipients, depending on the administration mode and dosage form contemplated.

Administration of the inhibitors may be by any suitable mode known to those skilled in the art. Examples of suitable parenteral administration include intravenous, intraarticular, subcutaneous and intramuscular routes. Intravenous administration can be used to obtain acute regulation of peak plasma concentrations of the drug. Improved half-life and targeting of the drug to the joint cavities may be aided by entrapment of the drug in liposomes. It may be possible to improve the selectivity of liposomal targeting to the joint cavities by incorporation of ligands into the outside of the liposomes that bind to synovial-specific macromolecules. Alternatively intramuscular, intraarticular or subcutaneous depot injection with or without encapsulation of the drug into degradable microspheres e.g., comprising poly(DL-lactide-co-glycolide) may be used to obtain prolonged sustained drug release. For improved convenience of the dosage form it may be possible to use an i.p. implanted reservoir and septum such as the Percuseal system available from Pharmacia. Improved convenience and patient compliance may also be achieved by the use of either injector pens (e.g. the Novo Pin or Q-pen) or needle-free jet injectors (e.g. from Bioject, Mediject or Becton Dickinson). Prolonged zero-order or other precisely controlled release such as pulsatile release can also be achieved as needed using implantable pumps with delivery of the drug through a cannula into the synovial spaces. Examples include the subcutaneously implanted osmotic pumps available from ALZA, such as the ALZET osmotic pump.

Nasal delivery may be achieved by incorporation of the drug into bioadhesive particulate carriers (<200 μm) such as those comprising cellulose, polyacrylate or polycarbophil, in conjunction with suitable absorption enhancers such as phospholipids or acylcarnitines. Available systems include those developed by DanBiosys and Scios Nova.

A noteworthy attribute of the compounds of the present invention in contrast to those of various peptidic compounds referenced in the background section of this application is the demonstrated oral activity of the present compounds. Certain compounds have shown oral bioavailability in various animal models of up to 90–98%. Oral delivery may be achieved by incorporation of the drug into tablets, coated tablets, dragees, hard and soft gelatine capsules, solutions, emulsions or suspensions. Oral delivery may also be achieved by incorporation of the drug into enteric coated capsules designed to release the drug into the colon where digestive protease activity is low. Examples include the OROS-CT/Osmet™ and PULSINCAP™ systems from ALZA and Scherer Drug Delivery Systems respectively. Other systems use azo-crosslinked polymers that are degraded by colon specific bacterial azoreductases, or pH sensitive polyacrylate polymers that are activated by the rise in pH at the colon. The above systems may be used in conjunction with a wide range of available absorption enhancers.

Rectal delivery may be achieved by incorporation of the drug into suppositories.

The compounds of this invention can be manufactured into the above listed formulations by the addition of various therapeutically inert, inorganic or organic carriers well known to those skilled in the art. Examples of these include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like are also added, as required to assist in the stabilization of the formulation or to assist in increasing bioavailability of the active ingredient(s) or to yield a formulation of acceptable flavor or odor in the case of oral dosing.

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of target enzyme which must be inhibited in order to treat the condition.

The matrix metalloprotease inhibitors of the invention are useful not only for treatment of the physiological conditions discussed above, but are also useful in such activities as purification of metalloproteases and testing for matrix metalloprotease activity. Such activity testing can be both in vitro using natural or synthetic enzyme preparations or in vivo using, for example, animal models in which abnormal destructive enzyme levels are found spontaneously (use of genetically mutated or transgenic animals) or are induced by administration of exogenous agents or by surgery which disrupts joint stability.

EXPERIMENTAL

General Procedures:

All reactions were performed in flame-dried or oven-dried glassware under a positive pressure of argon and were stirred magnetically unless otherwise indicated. Sensitive liquids and solutions were transferred via syringe or cannula and were introduced into reaction vessels through rubber septa. Reaction product solutions were concentrated using a Buchi evaporator unless otherwise indicated.

Materials:

Commercial grade reagents and solvents were used without further purification except that diethyl ether and tetrahydrofuran were usually distilled under argon from benzophenone ketyl, and methylene chloride was distilled under argon from calcium hydride. Many of the specialty organic or organometallic starting materials and reagents were obtained from Aldrich, 1001 West Saint Paul Avenue, Milwaukee, Wis. 53233. Solvents are often obtained from EM Science as distributed by VWR Scientific.

Chromatography:

Analytical thin-layer chromatography (TLC) was performed on Whatman® pre-coated glass-backed silica gel 60 A F-254 250 μm plates. Visualization of spots was effected by one of the following techniques: (a) ultraviolet illumination, (b) exposure to iodine vapor, (c) immersion of the plate in a 10% solution of phosphomolybdic acid in ethanol followed by heating, and (d) immersion of the plate in a 3% solution of p-anisaldehyde in ethanol containing 0.5% concentrated sulfuric acid followed by heating.

Column chromatography was performed using 230–400 mesh EM Science® silica gel.

Analytical high performance liquid chromatography (HPLC) was performed at 1 mL min$^{-1}$ on a 4.6×250 mm Microsorb® column monitored at 288 nm, and semi-preparative HPLC was performed at 24 mL min$^{-1}$ on a 21.4×250 mm Microsorb® column monitored at 288 nm.

Instrumentation:

Melting points (mp) were determined with a Thomas-Hoover melting point apparatus and are uncorrected.

Proton ($^1$H) nuclear magnetic resonance (NMR) spectra were measured with a General Electric GN-OMEGA 300 (300 MHz) spectrometer, and carbon thirteen ($^{13}$C) NMR spectra were measured with a General Electric GN-OMEGA 300 (75 MHz) spectrometer. Most of the compounds systhesized in the experiments below were analyzed by nmr, and the spectra were consistent with the proposed structures in each case.

Mass spectral (MS) data were obtained on a Kratos Concept 1-H spectrometer by liquid-cesium secondary ion (LCIMS), an updated version of fast atom bombardment (FAB). Most of the compounds systhesized in the experiments below were analyzed by mass spectroscopy, and the spectra were consistent with the proposed structures in each case.

General Comments:

For multi-step procedures, sequential steps are noted by numbers. Variations within steps are noted by letters. Dashed lines in tabular data indicates point of attachment.

EXAMPLE 1, EXAMPLE 2, EXAMPLE 3, EXAMPLE 4, EXAMPLE 5, AND EXAMPLE 6

4-Chlorobiphenyl (2.859 g, 15.154 mmoles, supplied by TCI) was weighed into a 500 mL flask which had been purged with argon. Into this flask was transferred dihydro-3-(2-methylpropyl)-2,5-furandione (1.997 g, 15.110 mmoles, for preparation see below) with 1,1,2,2-tetrachloroethane (50 mL). The solution was cooled in an ice bath and then aluminum trichloride (4.09 g) was slowly added as a solid. The ice bath was removed and the reaction was allowed to warm to room temperature. The mixture was then heated in an oil bath for a total of 2.5 hours at which time the reaction was cooled in an ice bath and quenched with 10% HCL solution (200 mL). The aqueous mixture was extracted thrice with ethyl acetate and the combined organic extracts washed once with brine. The solution was dried over MgSO$_4$ and concentrated in vacuo. Purification by flash chromatography (hexane-ethyl acetate) provided an oil that was recrystallized twice (hexane-ethyl acetate) to provide 1.358 g of a light orange solid which was mostly one material. Chromatography (ethyl acetate-hexane) of a small amount of this material yielded 52.0 mg of Example 1 (MP 138.5–139.5° C.) as a white fluffy solid and 4.0 mg of Example 6 (MP 185.5–186.5° C.) as side product from succinic anhydride as a minor impurity of dihydro-3-(2-methylpropyl)-2,5-furandione [prepared by the procedure in Wolanin, et al., U.S. Pat. No. 4,771,038 (Sep. 13, 1988—Examples 6 and 5c)].

The mother liquors from a similarly prepared batch of Example 1 were evaporated in vacuo and the residue evaluated by NMR spectroscopy to show the presence of an isomer, 5-methyl-3-[oxo-(4'-chloro-4-biphenyl)methyl] hexanoic acid, as a significant component. This residue was prepurified by flash silica chromatography (methylene chloride-methanol) to remove extraneous contaminants and then separated on a Chiralpak AD ® HPLC column (65% n-heptane, 35% (1% water+0.2% TFA in ethanol)) to yield enantiomers of the regioisomer (Example 4/Example 5 mixed) along with those of Example 1. Separation of pure Example 1 on the same system yielded only the isomers of this compound as Example 2 (first off) and Example 3 (second off). Re-chromatography of the regioisomer mixture on a Chiralcel OJ® column gave pure samples of Example 5 (first off) and Example 4 (second off).

In a separate experiment run in a similar manner using pure succinic anhydride instead of the above anhydride, the only product was Example 6.

EXAMPLE 1

Later Preparations and General Procedure

4-Chlorobiphenyl (14.8 mmoles, 1 eq) was weighed into a 250 mL flask which had been purged with argon. Into this flask was transferred dihydro-3-(2-methylpropyl)-2,5-furandione (14.9 mmoles, 1 eq) with 1,1,2,2-tetrachloroethane (50 mL). The solution was cooled in an ice bath and then aluminum trichloride (30.8 mmoles, 2.07 eq) was slowly added as a solid. The ice bath was removed after approximately 30 minutes and the reaction was allowed to warm to room temperature and allowed to stir for at least 24 hours. It was then poured into cold 10% HCL solution and extracted three to five times with chloroform. The combined organic extracts were washed once with brine, dried over $MgSO_4$ and concentrated in vacuo. Purification by flash chromatography (methylene chloride-methanol) provided an oil that was recrystallized twice (hexanethyl acetate) to provide 1.066 g of white solid (Example 1). The mother liquors from recrystallization were a mixture of regioisomers and a small amount of Example 6.

The above methods for the preparation of Example 1 were used to prepare the following series of biphenyl products (TABLE I) using the appropriately substituted anhydride and the appropriately substituted biphenyl.

TABLE I

| example | $R^6a$ | $R^6b$ | $(T)_x$ | isomer | m.p.(° C.)/other characterization |
|---|---|---|---|---|---|
| 1 | i-Bu | H | 4-Cl | R, S | 138.5–139.5 |
| 2 | i-Bu | H | 4-Cl | | $[a]_D = -26.3$ (MeOH) |
| 3 | i-Bu | H | 4-Cl | | $[a]_D = +25.4$ (MeOH) |

TABLE I-continued

| example | $R^6a$ | $R^6b$ | $(T)_x$ | isomer | m.p.(° C.)/other characterization |
|---|---|---|---|---|---|
| 4 | H | i-Bu | 4-Cl | | $[a]_D -26.3$ (MeOH) |
| 5 | H | i-Bu | 4-Cl | | $[a]_D +26.1$ (MeOH) |
| 6[a] | H | H | 4-Cl | R, S | 185.5–186.5 |
| 7[a] | H | H | 4-Br | | 201.5–202.0 |
| 8[a] | H | H | 4-F | | 176.0–177.0 |
| 9[a] | H | H | 2-F | | 158.0–159.0 |
| 10[a] | H | H | 2-Cl | | 175.0–176.0 |
| 11[a] | H | H | 2,4-(F)$_2$ | | 133.0–134.0 |
| 12[a] | H | H | 3-Cl | | 147.0–148.0 |
| 13 | i-Bu | H | H | R, S | 134.5–135.0 |
| 14 | i-Bu | H | 4-Br | R, S | 149.0–150.0 |
| 15 | i-Bu | H | 4-F | R, S | 117.5–118.5 |
| 16 | i-Bu | H | 4-Et | R, S | 153.0 |
| 17 | i-Bu | H | 2-F | R, S | 119.0–120.0 |
| 18 | i-Bu | H | 2-Cl | R, S | 118.0–119.0 |
| 19 | i-Bu | H | 4-MeO | R, S | 141.0–142.0 |
| 20 | i-Bu | H | 2,4-(F)$_2$ | R, S | 133.0–134.0 |
| 21 | i-Bu | H | 4-Me | R, S | 131.5–132.5 |
| 22 | i-Bu | H | 4-n-Pent | R, S | 101.0–102.0 |
| 23[a] | =CH$_2$ | H | 4-Cl | | 169–170 |
| 24[a] | =CH$_2$ | H | 2-Cl | | 186.0–187.5 |
| 25[a] | Me | H | 4-Cl | R, S | 196–197 |
| 26[b] | n-pent | H | 4-Cl | R, S | 141–142 |

[a]Reference compound.
[b]This anhydride (2-n-pentylsuccinic anhydride) was prepared according to the procedures given for dihydro-3-(2-methylpropyl)-2,5-furandione, except that valeraldehyde was used instead of isobutyraldehyde.

The above methods for the preparation of Example 1 were used to prepare the following series of phenyl containing products (TABLE II) using the appropriately substituted anhydride and the appropriately substituted aryl starting material.

TABLE II

| example | $R^6a$ | $(T)_xA$ | isomer | m.p.(° C.)/other characterization |
|---|---|---|---|---|
| 27[a] | i-Bu | Cl | R, S | 123.5–124.5 |
| 28[a] | =CH$_2$ | Me | | 144.0–145.5 |

[a]Reference compound.

The above methods for the preparation of Example 1 were used to prepare the following series of olefin containing products (TABLE III) using the appropriately substituted anhydride along with the appropriately substituted aryl starting material.

TABLE III

| example | (T)$_x$A | m.p.(° C.)/other characterization |
|---------|----------|-----------------------------------|
| 29[a]   | Cl—⟨phenyl⟩—   | 123.5–124.5 |
| 30[a]   | Cl—⟨phenyl⟩—O— | 144.0–145.5 |

[a]Reference compound.

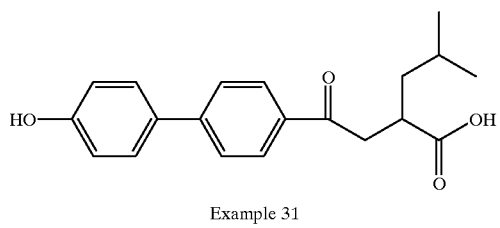

Example 31

EXAMPLE 31

Example 19 (52.2 mg, 0.153 mmol) was dissolved in 2.5 ml glacial acetic acid and 1.5 ml conc. HBr. This mixture was stirred overnight at ambient temperature and then refluxed for 13 hours. The reaction was allowed to cool before water was added to precipitate crude solid. This was dissolved in ethyl acetate and washed with brine. The solution was dried over MgSO$_4$ and concentrated in racuo to give a solid that recrystallized from hexane-ethyl acetate as 24.6 mg white crystals. MP 188.0–189.0° C.

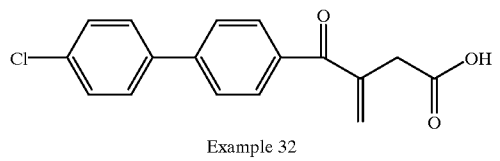

Example 32

EXAMPLE 32 (REFERENCE COMPOUND)

Example 6 (127.2 mg, 0.441 mmol) was dissolved in 2 ml of pyridine. To this solution was added 32 mg of paraformaldehyde and 0.5 ml of piperidine. The mixture was heated in an oil bath at 55–60° C. for 6 hours, then allowed to stir at ambient temperature overnight. The reaction was poured into 10% HCl and extracted with EtOAc, washed with saturated brine, dried over MgSO$_4$, filtered and solvent was removed in vacuo to give a crude solid. This solid was dissolved in EtOAc and filtered through a cotton plug to remove insoluble material. The residue was recrystallized with Hexane-EtOAc to give 54.4 mg (41%) white crystals. MP 127.0–128.0° C.

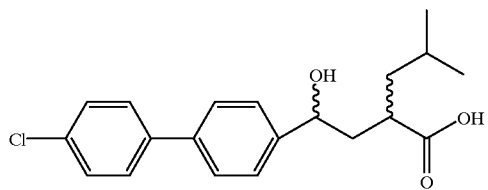

Example 33 Isomer A-First off chromatography column.
Example 34 Isomer B-Second off chromatography column.

EXAMPLE 33 AND EXAMPLE 34

Example 1 (103.5 mg, 0.300 mmol) was dissolved in 20 ml of water with the addition of 30.0 mg (0.687 mmol) of sodium hydroxide. The solution was cooled in an ice bath and then 13.0 mg (0.344 mmoles) of sodium borohydride was added as a solid. Stirring continued for 1 h. TLC (methylene chloride-2.5% methanol) indicated that starting material was still present, so the reaction was allowed to warm to room temperature overnight (16.5 h). Starting material was still present, so 13.0 mg more sodium borohydride was added at room temperature. The reaction was stirred for 2 h and then quenched with 10% HCl and extracted twice with ethyl acetate. The combined organic extracts were washed once with brine and dried over MgSO$_4$. The solution was concentrated in vacuo to give 57.0 mg of a crude solid. This was purified by silica gel chromatography (methylene chloride-methanol) to give two major products Example 33 (7.9 mg) and Example 34 (19.1 mg).

Example 33: $^1$H NMR (MeOD-d$_3$) d 7.56 (m, 4H), 7.38 (m, 4H), 4.66 (dd, J=9 Hz, J=3 Hz, 1H), 2.77 (m, 1H), 1.95 (m, 1H), 1.75, 1.57 (m, 3H), 1.26 (m, 1H), 0.8 (d, J=6 Hz, 3H), 0.79 (d, J=6 Hz, 3H).

Example 34: $^1$H NMR (MeOD-d$_3$) d 7.58 (m, 4H), 7.40 (m, 4H), 4.64 (t, J=6 Hz, 1H), 2.34 (m, 1H), 2.10 (m and solvent), 1.74 (m, 1H), 1.54 (m, 2H), 1.28 (m, 2H), 0.87 (d, J=6 Hz, 3H), 0.77 (d, J=6 Hz, 3H).

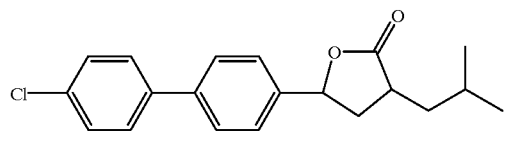

Example 35 and 36

EXAMPLE 35 and EXAMPLE 36 (REFERENCE COMPOUNDS)

The lactones Example 35 and Example 36 were prepared by dissolving a mixture of Example 33 and Example 34 (51 mg) in 25 ml benzene along with camphor sulfonic acid (11 mg). This mixture was refluxed for 12 hours using a Dean-Stark trap. The resultant solution was washed with aqueous sodium bicarbonate, dried over MgSO$_4$ and evaporated in vacuao. The residue was purified by silica gel chromatography with Hexane-EtOAc to give the separated lactones.

Example 28: $^1$H NMR (CDCl$_3$) d 7.3–7.7 (m, 8H), 5.6 (m, 1H), 2.75 (m, 1H), 2.45 (m, 2H), 2.20 (solvent), 1.75 (m, 2H), 1.45 (m, 1H), 1.01 (d, J=7 Hz, 3H), 0.87 (d, J=7 Hz, 3H); MS (FAB-LSIMS) 329 [M+H]$^+$(C$_{20}$H$_{21}$O$_2$Cl FW=328.87).

Example 29: $^1$H NMR (CDCl$_3$) d (m, 8H), (m, 1H), (m, 1H), 2 (m, 2H), 2.20 (solvent), 1.75 (m, 2H), 1.45 (m, 1H), 1.01

(d, J=7 Hz, 3H), 0.87 (d, J=7 Hz, 3H); MS (FAB-LSIMS) 328 [M]+(C20H21O2Cl FW=328.87).

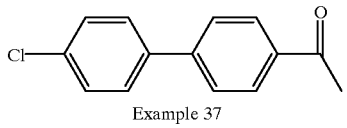

Example 37

EXAMPLE 37 (INTERMEDIATE)

The general method of Example 23 was used to prepare Example 37 by using acetyl chloride instead of itaconic anhydride. MP 100–101° C.

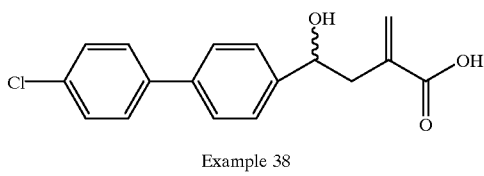

Example 38

EXAMPLE 38 (REFERENCE COMPOUND)

Example 23 (97.9 mg, 0.325 mmol) was dissolved in 1.0 ml of a 0.446 M solution of potassium hydroxide in water. Slowly, 76.8 mg (2.030 mmol) of sodium borohydride was added. The mixture was stirred at room temperature for 15 h. The reaction was quenched by addition of 6 N HCl and extracted twice with ethyl acetate and the combined organic extracts washed once with brine. The solution was dried over MgSO4 and concentrated in vacuo. The white solid was recrystallized (hexane-ethyl acetate) to provide 57.1 mg of white solid Example 38. MP 118–120° C.

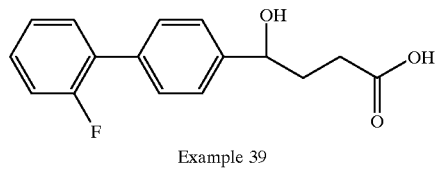

Example 39

EXAMPLE 39 (REFERENCE COMPOUND)

Example 39 was prepared from Example 9 in a way similar to the preparation of Example 38. Anal. C: calcd, 67.83; found, 67.80. H: calcd, 5.12; found, 5.50, with calcd 0.5 H2O.

EXAMPLE 40

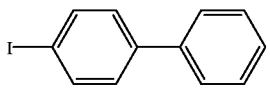

Step 1 A solution of trimethyltin chloride (5.5 g, 27.60 mmol) in 5 mL of DME was added to a stirred suspension of small cubes of metallic sodium (1.9 g, 82.64 mg atom) in 15 mL of DME under an argon stream in an ice bath. When the addition was complete the mixture was stirred and chilled in an ice bath for 2 h (the color changed to green). The mixture was transferred via cannula into another dry and under argon round bottom flask to remove excess sodium and cooled to 0° C. A solution of 4-bromobiphenyl (5.4 g, 22.70 mmoles) in 14 mL of DME was added dropwise to the chilled NaSnMe3 solution. The resulting solution was stirred at room temperature overnight at which time TLC analysis showed complete reaction. $R_f$ of the trimethyltin product=0.44 (silica, hexanes)l The reaction mixture was then cooled in an ice bath and treated with iodine (6.6 g, 26.00 mmol). After stirring at room temperature for 1.5 h, the mixture was diluted with EtOAc, washed with water, brine, dried over MgSO4, and the solvent removed at reduced pressure. The crude product was then purified by column chromatography with hexanes to afford 5.5 g (86% yield) of white solid. TLC (silica, hexanes) $R_f$=0.54.

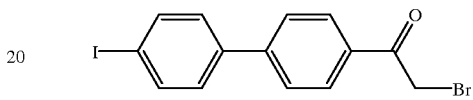

Step 2 A solution of 4-iodobiphenyl from step 1 (1.35 g, 4.82 mmol) in 25 mL of dry dichloroethane was treated with bromoacetyl bromide (0.47 mL, 5.21 mmol) and cooled to 0° C. under a stream of argon. The cooled mixture was then treated with AlCl3 (0.77 g, 5.77 mmol) and allowed to stir at room temperature overnight. The reaction mixture was poured into cold 10% HCl and extracted thrice with methylene chloride. The combined extracts were then washed with brine, dried over MgSO4; and concentrated at reduced pressure. Crystallization from EtOAc/hexanes afforded 1.1 g (58% yield) as light brown fine needles. $^1$H NMR (CD3OD) d 8.17 (d, J=8.4 Hz, 2H), 7.95 (d, J=8.4 Hz, 2H), 7.94 (d, J=8.7 Hz, 2H), 7.66 (d, J=8.1 Hz, 2H), 5.05 (s, 2H).

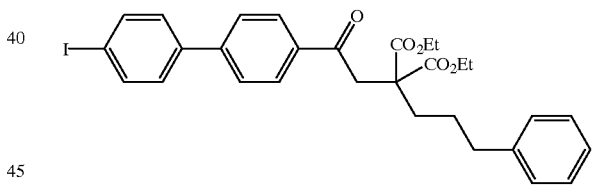

Step 3 A solution of diethyl-(3-phenyl)propyl malonate (product of step 1 from Example 114 preparation, 1.5 g, 5.28 mmoles) in 11 mL of dry THF was treated with NaH (0.12 g, 4.95 mmoles) under a stream of argon. The mixture was stirred at room temperature for 30 min at which time a homogenous mixture was obtained and the gas evolution ceased. A solution of 2-bromo-4-(4-iodophenyl)-acetophenone from step 2 (1.85g, 4.61 mmol) in 20 mL of dry THF was added and the reaction mixture was allowed to stir at room temperature for 4 h, at which time a TLC analysis showed complete reaction. The mixture was then quenched with 2N HCl, diluted with EtOAc, and the layers were separated. The aqueous layer was extracted twice with EtOAc and the combined extracts were washed with brine, dried over MgSO4, and the solvent removed at reduced pressure. The crude product was chromatographed with a gradient 3%–40% EtOAc in hexanes to afford 2.28 g (83% yield) of pure product. TLC (silica, EtOAc:hexanes, 1:4) $R_f$=0.37.

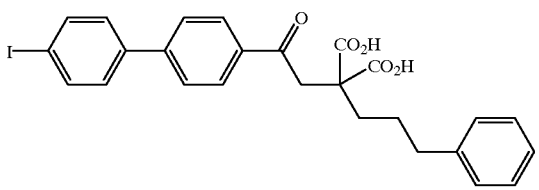

Step 4 A solution of the diethylester from step 3 (2.28 g, 3.81 mmol) in THF (5 mL)/EtOH (15 mL) was treated with 5 eq of NaOH in 5 mL of water and allowed to stir at room temperature overnight. At this time, the reaction mixture was acidified with 2N HCl and the solvent removed at reduced pressure. The solid formed was then filtered, washed with water, and dried to afford 1.6 g (77%) TLC (silica, $CH_2Cl_2$:MeOH, 9:1) $R_f$=0.14.

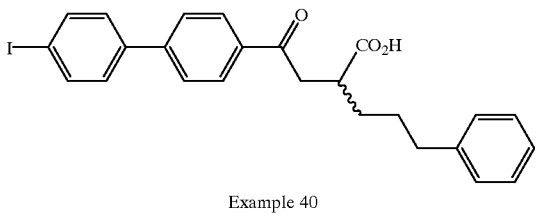

Example 40

Step 5—Preparation of Example 40. The diacid from step 4 (1.6 g, 2.95 mmoles) was dissolved in 30 mL of 1,4-dioxane and refluxed for 36 h. The reaction mixture was then cooled to room temperature and the solvent removed at reduced pressure. The residue obtained was crystallized from EtOAc/hexanes to afford 0.6 g (41% yield). MP 165–165.5° C.

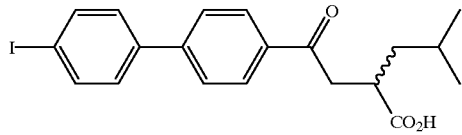

Example 41

EXAMPLE 41

This compound was prepared in a similar manner to Example 40, except that the diethyl isobutyl malonate was used instead of diethyl-(3-phenyl)propyl malonate. Elemental Analysis calcd. C; 55.06, H; 4.85; found C; 54.90, H; 4.79.

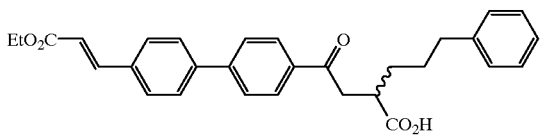

Example 42

EXAMPLE 42

Example 40 (300 mg, 0.60 mmol) was dissolved in DMF (3 mL) and treated with ethyl acrylate (0.15 mL, 1.38 mmol), Pd(OAc)2 (15 mg, 0.07 mmol), sodium bicarbonate (126 mg, 1.50 mmol), and tetrabutylammonium chloride (69 mg, 0.24 mmol). The mixture was refluxed for 3 days at which time it was diluted with ethyl acetate and transferred to a separatory funnel. The organic layer was washed with water, brine, dried over MgSO4, and the solvent removed at reduced pressure. The crude product was chromatographed with 0–4% methanol in methylene chloride to afford 120 mg of product. MP 155–157° C.

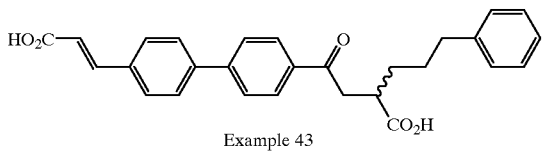

Example 43

EXAMPLE 43

A suspension of Example 42 (28 mg, 0.06 mmol) in ethanol (1.5 mL) was treated with a solution of NaOH (14 mg, 0.35 mmol) in water (0.3 mL) and the mixture was stirred at room temperature overnight. At this time, it was quenched with 2N HCl and extracted with methylene chloride (2×10 mL). The combined extracts were washed with brine, dried over MgSO4, and the solvent removed at reduced pressure to afford 23 mg (87%) of product. MP 230–232° C.

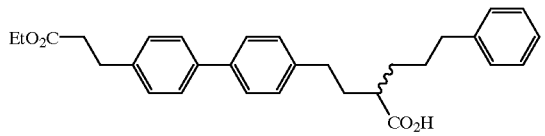

Example 44

EXAMPLE 44

A solution of Example 42 (60 mg, 0.13 mmol) in ethanol (2 mL) was treated with 10% Pd on C (10 mg) and the mixture was stirred at room temperature overnight under a hydrogen gas balloon. At this time, the reaction mixture was filtered through celite and the solvent was removed at reduced pressure to afford 43 mg of product as oil. MS (FAB-LSIMS) 458 [M]+.

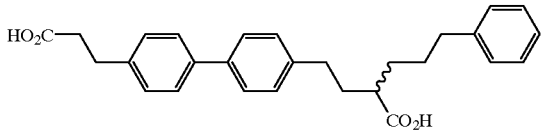

Example 45

EXAMPLE 45

A suspension of Example 44 (15 mg, 0.03 mmol) in ethanol (1 mL) was treated with a solution of sodium hydroxide (9 mg, 0.23 mmol) in water (0.2 mL) and allowed to stir at room temperature for 1.5 days. The reaction mixture was then quenched with 2N HCl, diluted with ethyl acetate and the layers were separated. The organic layer was washed with brine, dried over MgSO4, and the solvent was removed at reduced pressure to afford 12 mg of product. MP 131–132° C.

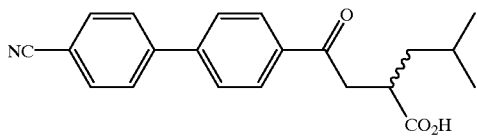

Example 46

EXAMPLE 46

Example 41 (50 mg, 0.12 mmol), Cu(I)CN (36 mg, 0.40 mmol), and 0.7 mL of 1-methyl-2-pyrrolidinone were mixed and heated at 125° C. for 24 h. The reaction mixture was diluted with methylene chloride and evaporated at reduced pressure. The crude product was then chromatographed with 0–8% methanol in methylene chloride on the MPLC to afford 26.5 mg (66% yield) of product. HRMS (FAB) calcd. for $C_{21}H_{22}NO_3S$ [M+H]$^+$ 336.15997, Found 336.16129.

EXAMPLE 47

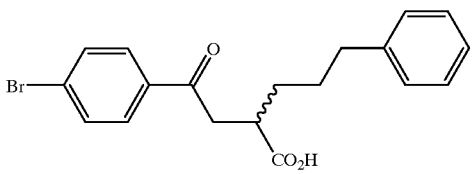

Step 1 This intermediate was prepared in a similar manner to Example 40 except 2,4'-dibromoacetophenone was used instead of 2-bromo-4-(4-iodophenyl)acetophenone. TLC (methylene chloride-10% methanol) $R_f$ 0.52.

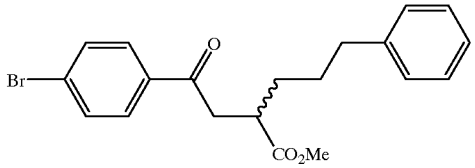

Step 2 Methylation of the product from step 1 with diazomethane in ethanol afforded quantitative yield of the methyl ester. TLC (hexanes, 10% ethyl acetate) $R_f$ 0.21.

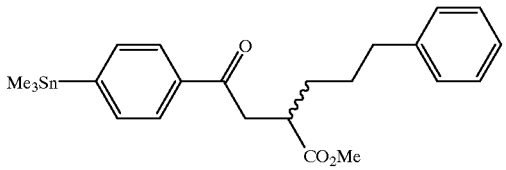

Step 3 The product from step 2 (1.85 g, 4.75 mmol), hexamethylditin (2.00 g, 5.80 mmol), and palladium tetrakistriphenylphosphine (44 mg, 0.038 mmol) in 7 mL of toluene were refluxed for 3 h under argon. TLC showed complete reaction. The reaction mixture was then cooled to room temperature, the solvent was removed at reduced pressure, and the residue was chromatographed on the MPLC with 3–30% ethyl acetate in hexanes to afford 2.25 g (100% yield) of the trimethyltin product. TLC (hexanes-10% ethyl acetate) $R_f$ 0.26.

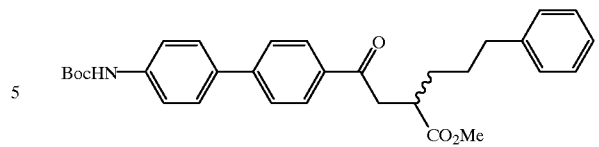

Step 4 4-Bromo-N-Boc-anionoe (0.61 g, 2.24 mmol), the product from step 3 (0.51 g, 1.08 mmol), and palladium tetrakistriphenyl-phosphine (94 mg, 0.08 mmol) in 9 mL of toluene were refluxed for 3 h under argon. After TLC showed complete reaction, the reaction mixture was filtered, concentrated at reduced pressure, and chromatographed with 3–60% ethyl acetate in hexanes to afford 180 mg of product (33% yield) as the methyl ester. TLC (hexanes-20% ethyl acetate) $R_f$ 0.26.

Step 5—Preparation of Example 47. The methyl ester (93 mg) was dissolved in 3 mL of ethanol and treated with 5 eq of sodium hydroxide in 0.5 mL of $H_2O$. The mixture was stirred at room temperature for 10 h at which time TLC showed complete hydrolysis of the methyl ester. The reaction mixture was acidified with 2N HCl, diluted with ethyl acetate, and the layers were separated. The organic layer was washed with brine, dried over $MgSO_4$, and the solvent removed at reduced pressure to afford 82 mg of product. MP 169–171° C.

The above methods for the preparation of Example 47 were used to prepare the following series of biphenyl products (TABLE IV) using the appropriate brormides instead of 4-bromo-Boc-aniline in step 4.

TABLE IV

| example | $(T)_x$ | isomer | m.p.(° C.)/other characterization |
|---------|---------|--------|-----------------------------------|
| 47 | NHBoc | R, S | 169–171 |
| 48 | t-Bu | R, S | 124–125 |
| 49 | $CH_2NHBoc$ | R, S | 156 |
| 50 | $CH_2CN$ | R, S | 139–140 |
| 51 | SMe | R, S | 174.5–175 |
| 52 | $O(CH_2)_2Cl$ | R, S | 155–156 |
| 53 | $CH_2OH$ | R, S | 165–166 |
| 54 | $O(CH_2)_2OH$ | R, S | 167–168 |
| 55 | $CH_2\!=\!CH_2$ | R, S | 156–157 |
| 56 | CN | R, S | 199–200 |

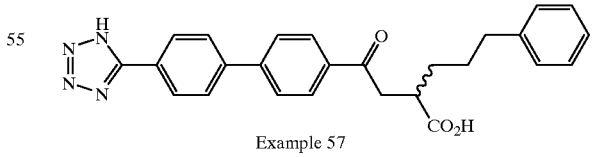

Example 57

EXAMPLE 57

The methyl ester of Example 56 (81 mg, 0.2 mmol, from treatment of an ethanol solution of Example 56 with diazomethane followed by solvent evaporation in vacuao) was dissolved in 1 mL of toluene and treated with trimethyltin azide (62 mg, 0.3 mmol). The reaction mixture was refluxed for 5 days. At this time, the reaction mixture was cooled to room temperature, diluted with ethyl acetate, washed with brine and dried over MgSO$_4$. The crude product was chromatographed with 0–20% methanol in methylene chloride to afford 56 mg of the methyl ester tetrazole product. The methyl ester product was suspended in ethanol and treated with 2N NaOH solution (0.5 mL) and stirred at room temperature for 3 h. The reaction mixture was then quenched with 2N HCl, diluted with ethyl acetate, and the layers were separated. The organic layer was washed with brine and dried over MgSO$_4$ to afford 34 mg of Example 57 crystallized from ethyl acetate/hexanes. MP 176–177° C.

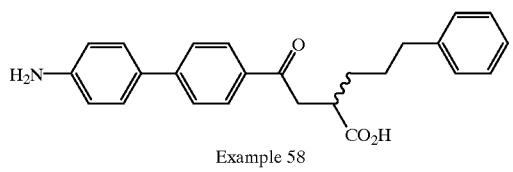

Example 58

EXAMPLE 58

Example 47 (46 mg, 0.094 mmol) was dissolved in 1.5 mL of methylene chloride and treated with trifluoroacetic acid (0.16 mL, 2.06 mmol). The mixture was stirred at room temperature for 32 h, when TLC showed complete reaction. The solvent was removed at reduced pressure and the solid obtained was washed with ethyl acetate/hexanes to afford 40 mg of product as TFA salt. MP 170–174° C. (dec.).

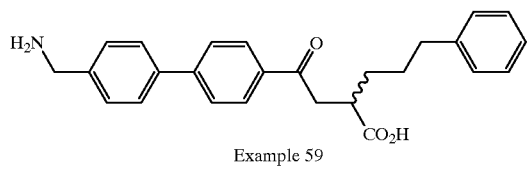

Example 59

EXAMPLE 59

This compound was prepared in a similar manner to that of Example 58, except Example 49 was used instead of Example 47. MP 146–148° C.

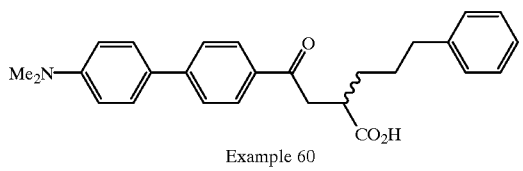

Example 60

EXAMPLE 60

The methyl ester of Example 58 (50 mg, 0.13 mmol) in methanol/tetrahydrofuran (0.7 mL/0.4 mL) was treated with 37% aqueous formaldehyde (0.11 mL, 1.46 mmol), glacial acetic acid (0.032 mL), and sodium cyanoborohydride (0.32 mL, 1.0 M in THF, 0.32 mmol). The reaction mixture was stirred at room temperature for 2 h at which time the solvent was removed at reduced pressure and saturated potassium carbonate was added to the residue. Ethyl acetate was added to the mixture and the layers were separated. The aqueous layers was extracted with ethyl acetate and the combined extracts were washed with brine, dried over MgSO$_4$, and the solvent removed at reduced pressure to afford 47 mg (88% yield) of the methyl ester product. TLC (hexanes-20% ethyl acetate) R$_f$0.35.

The methyl ester product (47 mg, 0.11 mmol) was suspended in ethanol (2 mL) and treated with 10 eq of sodium hydroxide in H$_2$O (1 ml). The mixture was stirred at room temperature for 16 h at which time TLC showed complete reaction. The ethanol was then removed at reduced pressure, the residue was diluted with ethyl acetate, and the mixture was acidified with 2N HCl. At this time, the layers were separated and the organic portion was washed with brine, dried over MgSO$_4$, and the solvent removed at reduced pressure to afford 48 mg (96% yield) of product as the hydrochloride salt. MP 166–168° C.

EXAMPLE 61

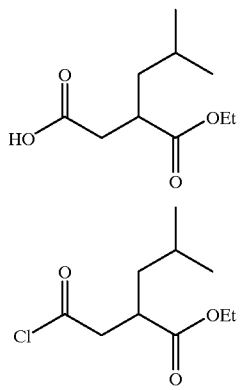

Steps 1, 2 and 3 A three neck 2 L flask equipped with a mechanical stirrer was charged, under argon atmosphere, with a potassium tert-butoxide/tert-butanol solution (800 mL, 1.0 M) and brought to reflux. Isobutyraldehyde (66.2 mL, 729 mmol) and diethyl succinate (151 mL, 907 mmol) were combined and added dropwise over 0.5 h. The reaction solution was refluxed an additional 1.5 h and cooled to ambient temperature. The solution was diluted with ethyl acetate (800 mL) and washed with 2N hydrochloric acid solution (500 mL). The ethyl acetate solution was separated and washed with 10% sodium carbonate solution (6×200 mL). The basic washings were combined and acidified with concentrated hydrochloric acid. Extraction of product was accomplished with ethyl acetate (5×250 mL). The washings were combined, dried over magnesium sulfate, and concentrated. A portion of this material was immediately hydrogenated with palladium on carbon using Parr apparatus. This afforded 90.18 grams of the desired acid ester compound shown above. This was then converted to the corresponding ester acid chloride by refluxing with oxalyl chloride (1 eq).

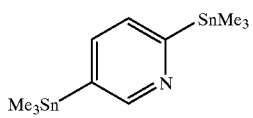

Step 4 A solution of trimethylsilyl tin chloride (21.8 g, 109.5 mmol) in freshly distilled dimethoxyethane (50 mL) was added to a suspension of sodium (7.6 g, 330 mL), naphthalene (200 mg, 1.56 mmol), and dimethoxyethane under argon atmosphere cooled to −20° C. After 2.5 h, the suspension had turned to a dark green color. The solution was then decanted from excess sodium. A solution of 1,4 dibromopyridine (10 g, 42.2 mmol) and dimethoxyethane was added over 0.3 hours at 0° C. under argon. The solution was slowly warmed to ambient temperature, the poured into 500 mL water. The solution was washed with dichloromethane (4×250 mL) and the extracts were combined and dried over MgSO$_4$. Concentration afforded a brownish solid that was recrystallized from acetonitrile to afford 13.8 g of 1,4 bis-trimethylsilyl tin pyridine.

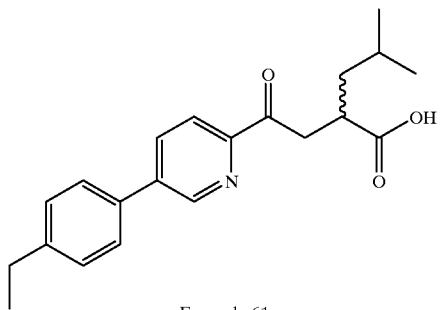

Example 61

Steps 5, 6 and 7—Preparation of Example 61. Potassium carbonate (100 mg) was suspended in a solution of the acid chloride from step 3 (1.91 g, 9.6 mmol), the product of step 4 (3.9 g, 9.6 mmol) and toluene (50 mL). This was then refluxed 48 h before being cooled to ambient temperature and diluted with ethyl acetate. Solids were filtered off and solvent removed. The remaining oil was chromatographed on silica with an ethyl acetate/hexane eluent. The resulting material was coupled to p-iodo ethyl benzene (1 eq) by refluxing in a solution of tetrahydrofuran in the presence of bis-(triphenylphosphine) palladium (II) chloride (20 mole %). The coupled product was chromatographed on silica with ethyl acetate/hexanes and saponified by addition of sodium hydroxide to an aqueous ethanol solution. Acidification to pH 5 afforded a yellow solid which was filtered off and recrystallized from ethyl acetate/hexanes. This afforded 53 mg of Example 61. MP 111–112° C.

EXAMPLE 62, EXAMPLE 63, AND EXAMPLE 64

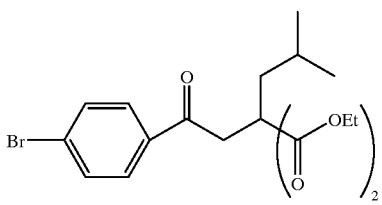

Step 1 (A) A one-necked, 50-mL, round-bottomed flask equipped with a rubber septum and an argon needle inlet was charged with 7 mL THF, sodium hydride (0.058 g, 2.42 mmol) and cooled to 0° C. while diethyl isobutylmalonate (0.476 g, 0.491 mL, 2.20 mmol) was added dropwise via syringe over ca. 2 min. The resulting mixture was stirred for 30 min at 0° C. and 1 h at room temperature. The reaction mixture was then cooled to 0° C. while a solution of 2,4'-dibromoacetophenone (0.556 g, 2.00 mmol in 3 mL THF) was added dropwise via cannula over ca. 1 min. The resulting mixture was stirred for 30 min at 0° C. and 13 h at room temperature. A mixture of water (30 mL) and hexanes (50 mL) was added and the resulting aqueous phase was extracted with a second 20-mL portion of hexanes. The combined organic phases were dried over MgSO$_4$, filtered, and concentrated to provide a yellow oil. Column chromatography on 30 g of silica gel (gradient elution with 1–5% ethyl acetate-hexanes) afforded 0.53 g (64%) of product as a colorless oil. TLC (5% ethyl acetate-hexanes) R$_f$=0.24.

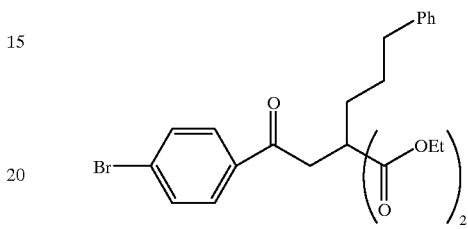

Step 1 (B) Treatment of diethyl phenylpropymaonate (1.00 g, 3.59 mmol) according to the general alkylation procedure of step 1 (A) afforded 1.11 g (71%) of product as a colorless oil. TLC (10% ethyl acetate-hexanes) R$_f$=0.19.

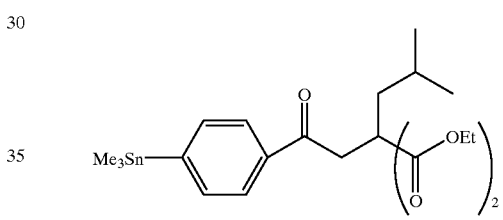

Step 2 (A) A one-necked, 10-mL, round-bottomed flask equipped with a reflux condenser fitted with an argon inlet adapter was charged with 4 mL toluene, the product of step 1 (A) (0.100 g, 0.242 mmol), hexamethyl ditin (0.159 g, 0.484 mmol), tetrakis(triphenyl-phosphine)palladium (0.014 g, 0.0121 mmol), and heated at reflux for 24 h. The resulting mixture was concentrated to provide a black oil. Column chromatography on 15 g of silica gel (elution with 5% ethyl acetate-hexanes) afforded 0.107 g (89%) of product as a colorless oil. TLC (5% ethyl acetate-hexanes) R$_f$=0.33.

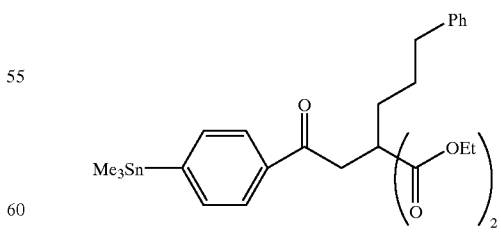

Step 2 (B) Treatment of product from step 1 (B) (0.150 g, 0.316 mmol) according to the general procedure of step 2 (A) afforded 0.155 g (88%) of product as a colorless oil. TLC (10% ethyl acetate-hexanes) R$_f$=0.19.

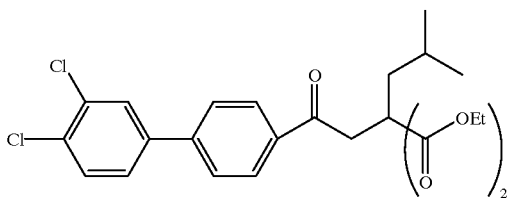

Step 3 (A) A one-necked, 10-mL, round-bottomed flask equipped with a reflux condenser fitted with an argon inlet adapter was charged with 1 mL dimethoxyethane or toluene, the product of step 2 (A) (0.107 g, 0.215 mmol), 1-bromo-3,4-dichlorobenzene (0.097 g, 0.429 mmol), tetrakis(triphenylphosphine)palladium (0.025 g, 0.0216 mmol), and heated at reflux for 24 h. The resulting mixture was concentrated to provide a black oil. Column chromatography on 15 g of silica gel (elution with 5% ethyl acetate-hexanes) afforded 0.058 g (57%) of product as a white solid. TLC (10% ethyl acetate-hexanes) $R_f$=0.26.

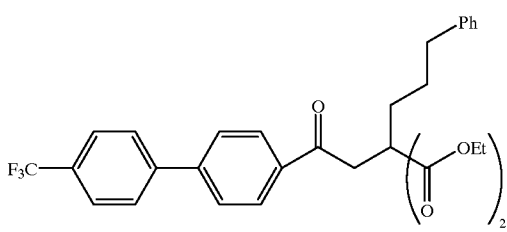

Step 3 (B) Reaction of the product of step 2 (B) (0.079 g, 0.141 mmol) with 4-bromobenzotrifluoride in toluene according to the general coupling procedure of step 3 (A) afforded 0.069 g (91%) of product as a white solid. TLC (10% ethyl acetate-hexanes) $R_f$=0.18.

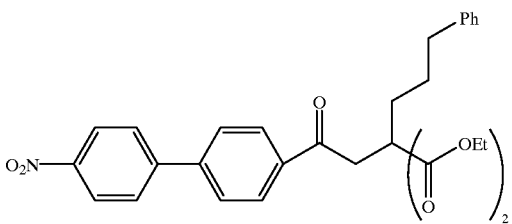

Step 3 (C) Reaction of the product of step 2 (B) (0.058 g, 0.104 mmol) with 1-bromo-4-nitrobenzene in toluene according to the general coupling procedure of step 3 (A) afforded 0.042 g (78%) of product as a white solid. TLC (10% ethyl acetate-hexanes) $R_f$=0.06.

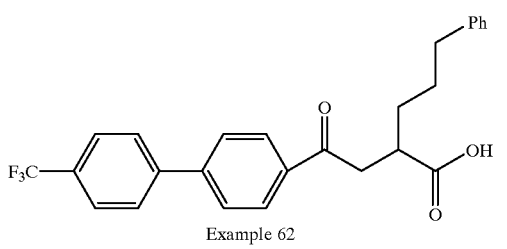

Example 62

Step 4 (B)—Preparation of Example 62. A one-necked, 10-mL, round-bottomed flask equipped with an argon inlet adapter was charged with 3 mL ethanol, product of step 3 (B) (0.069 g, 0.128 mmol), and 1 mL of an aqueous 25% sodium hydroxide solution. The resulting mixture was stirred for 10 h at room temperature. The reaction mixture was acidified with a 10% HCl solution, and extracted three times with 20 mL portions of ether. The organic phase was dried over MgSO$_4$, filtered, and concentrated to provide a yellow solid, which was dissolved in 2 mL of 1,4-dioxane and heated to reflux for 24 h in a one-necked, 10-mL, round-bottomed flask equipped with a reflux condenser fitted with an argon inlet adapter. The resulting mixture was concentrated to provide a yellow solid. Column chromatography on 10 g of silica gel (elution with 40% ethyl acetate-hexanes containing 1% acetic acid) afforded 0.033 g (59%) of Example 62 which was recrystallized once from ethyl acetate-hexanes to provide a white solid. MP 165° C.

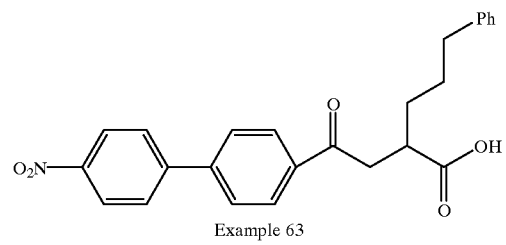

Example 63

Step 4 (C)—Preparation of Example 63. Treatment of the product of step 3 (C) (0.042 g, 0.081 mmol) according to the general procedure of Example 62 afforded 0.023 g (68%) of Example 63 which was recrystallized once from ethyl acetate-hexanes to provide a white solid. MP 183° C.

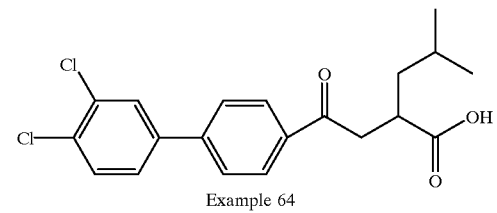

Example 64

Step 4 (A)—Preparation of Example 64. Treatment of the product of step 3 (A) (0.050 g, 0.104 mmol) according to the general procedure of Example 62 afforded 0.010 g (25%) of Example 64 which was recrystallized once from ethyl acetate-hexanes to provide a white solid. MP 132° C.

EXAMPLE 65

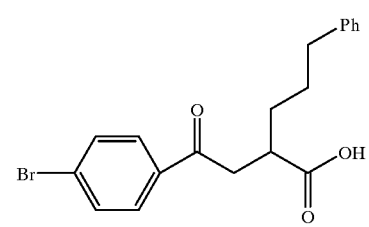

Step 1 Treatment of the product of step 1 (B) of the Example 62 preparation (13.34 g, 28.06 mmol) according to the general procedure of Example 62, step 4 (B) afforded 4.36 g (41%) of the above 4-bromophenyl intermediate which was recrystallized once from 1-chlorobutane to provide a white solid. MP 147° C.

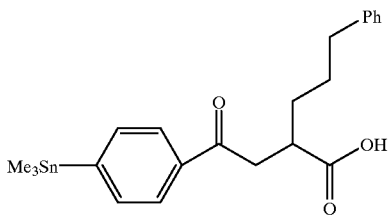

Step 2 Treatment of the 4-bromophenyl intermediate from step 1 (1.00 g, 2.66 mmol) in the presence of anhydrous $K_2CO_3$, according to the general procedure of step 2 (A) of the example 64 preparation afforded 0.706 g (58%) of the 4-trimethylstannylphenyl compound as a white solid. TLC (30% ethyl acetate-hexanes containing 1% acetic acid) $R_f$=0.47.

Step 3—Preparation of Example 65. A one-necked, 10-mL, round-bottomed flask equipped with a reflux condenser fitted with an argon inlet adapter was charged with 3 mL toluene, the product of step 2 (0.050 g, 0.108 mmol), 1-bromo-3,4-dichlorobenzene (0.049 g, 0.217 mmol), and tetrakis(triphenylphosphine)palladium (0.013 g, 0.0112 mmol). The resulting mixture was heated at reflux for 24 h, and then concentrated to provide a black oil. Column chromatography on 15 g of silica gel (elution with 20% ethyl acetate-hexanes containing 0.5% acetic acid) afforded 0.033 g (69%) of Example 65 which was recrystallized once from ethyl acetate-hexanes to provide a white solid. MP 137° C.

The above methods for the preparation of Example 65 were used to prepare the following series of biphenyl products (TABLE V) using the appropriate bromides in step 3.

TABLE V

| example | $(T)_xA$ | isomer | m.p.(° C.)/other characterization |
|---|---|---|---|
| 65 | 3,4-dichlorophenyl | R, S | 137 |
| 66 | 3,5-dichlorophenyl | R, S | 123 |
| 67[a] | 4-AcO-phenyl | R,S | 131 |
| 68 | 5-Cl-thiophen-2-yl | R, S | 120 |
| 69 | 5-HO2C-furan-2-yl | R, S | 154 |
| 70 | 3-pyridyl | R, S | MS (FAB-LSIMS) 374 [M+H]+ |
| 71 | 5-(n-pentO)-pyridin-2-yl | R, S | MS (FAB-LSIMS) 460 [M+H]+ |
| 72 | 4-(n-pentylS)phenyl | R, S | 113 |

[a]Preparation of 1-Acetoxy-4-bromobenzene: A one-necked, 25-mL, round-bottomed flask equipped with an argon inlet adapter was charged with 5 mL pyridine, 4-bromophenol (1.00 g, 5.78 mmol), and acetic anhydride (2.80 g, 27.4 mmol). The resulting mixture was stirred for 12 h at room temperature. A mixture of water (20 mL) and ether (50 mL) was added and the resulting organic phase was washed with a second 20-mL portion of water. The organic phase was dried over MgSO4, filtered, and concentrated to provide a colorless oil. TLC (10% ethyl acetate-hexanes) $R_f$ = 0.54.

EXAMPLE 73

A one-necked, 100-mL, round-bottomed flask equipped with a reflux condenser fitted with an argon inlet adapter was charged with 30 mL toluene, the product of step 1 of the example 65 preparation (1.00 g, 2.66 mmol), 4-methoxybenzeneboronic acid (1.60 g, 10.5 mmol), sodium carbonate or potassium carbonate (1.60 g, 11.6 mmol) and tetrakis(triphenylphoshine)palladium (0.300 g, 0.260 mmol). The resulting mixture was heated at reflux for 12 h. After cooling to room temperature, 5 mL of 30% hydrogen peroxide solution was added and the resulting mixture stirred for 1 h. A mixture of ether (300 mL) and a 10% HCl solution (300 mL) was added and the resulting organic phase was washed with 300 mL of saturated sodium chloride solution. The organic phase was dried over MgSO4, filtered, and concentrated to afford 0.879 g (82%) of Example 73 which was recrystallized once from 1-chlorobutane to provide a white solid. MP 169° C.

The above method for the preparation of Example 73 was used to prepare the following series of biphenyl products (TABLE VI) using the appropriate boronic acid.

TABLE VI (T)ₓA—[phenyl]—C(=O)—CH₂—CH(COOH)—CH₂CH₂CH₂—Ph

| ex. | (T)ₓA | isomer | m.p.(° C.)/other characterization |
|---|---|---|---|
| 73 | 4-MeO-phenyl | R, S | 169 |
| 74 | 3-Cl-4-F-phenyl | R, S | 141 |
| 75ᵃ | 4-EtO-phenyl | R, S | 144 |
| 76 | 3-thienyl | R, S | 145 |
| 77 | 2,4-dichlorophenyl | R, S | 138 |
| 78 | 4-OHC-phenyl | R, S | 174 |
| 79 | 3,5-bis(CF₃)-phenyl | R, S | 145 |
| 80 | 2-thienyl | R, S | $^1$H NMR (CDCl$_3$, 300 MHz) d 7.94(d, J=8.8 Hz, 2H), 7.67(d, J=8.8Hz, 2H), 7.41(br d, J=3.7 Hz, 1H), 7.36(br, d, J=5.2 Hz, 1H), 7.09–7.28(m, 6H), 3.43(dd, J=8.1, 16.5 Hz, 1H), 3.03–3.02(m, 2H), 2.64(brt, J=7.0 Hz, 2H), and 1.69–1.78(m, 4H) |
| 81 | 3-CF₃-phenyl | R,S | 118 |

TABLE VI-continued

| ex. | (T)ₓA | isomer | m.p.(° C.)/other characterization |
|---|---|---|---|
| 82 | ![CHO structure] | R, S | ¹H NMR (CDCl₃, 300 MHz) d 9.94(s, 1H), 8.04(d, J=8.5 Hz, 2H), 7.49–7.66(m, 3H), 7.47 (d, J=8.5 Hz, 2H), 7.42(d, J=8.1 Hz, 1H), 7.14–7.30(m, 5H), 3.49(dd, J=8.1, 16.5 Hz, 1H), 3.05–3.13(m, 2H), 2.66(brt, J=7.0 Hz, 2H), and 1.71–1.80(m, 4H) |

ªPreparation of 4-Ethoxybenzeneboronic Acid: A one-necked, 25-mL, round-bottomed flask equipped with a reflux condenser fitted with an argon inlet adapter was charged with magnesium powder (0.255 g, 10.5 mmol, −50 mesh), 7 mL THF, and 4-bromophenetol (1.41 g, 1.00 mL, 7.00 mmol). The resulting mixture was heated to reflux for 3 h. A second one-necked, 25-mL, round-bottomed flask equipped with a rubber septum and an argon inlet needle was charged with triIsopropyl borate (3.95 g, 4.85 mL, 21.00 mmol) and cooled to −78° C. while the Grignard reagent prepared above was added dropwise via cannula over ca. 5 min. The cooling bath was removed and the reaction mixture was stirred for 3 h at room temperature. A mixture of ether (50 mL) and a 10% HCl solution (50 mL) was added and the resulting organic phase was washed with a 100-mL portion of water. The organic phase was dried over MgSO₄, filtered, and concentrated to provide a yellow solid which was recrystallized from ether-hexanes to provide 0.783 g (67%) of a white solid. ¹H NMR (CDCl₃, 300 MHz)d 8.14(d, J=8.5 Hz, 2H), 6.98(d, J=8.5 Hz, 2H), 4.11(q, J=7.0 Hz, 2H), and 1.45(t, J=7.0 Hz, 3H).

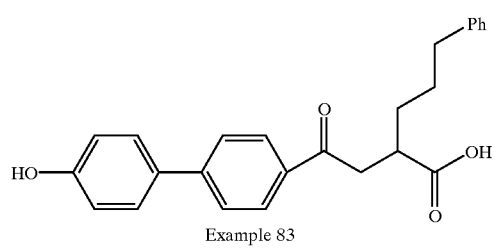

Example 83

EXAMPLE 83

A one-necked, 100-mL, round-bottomed flask equipped with a reflux condenser was charged with 35 mL acetic acid, Example 73 (0.751 g, 1.86 mmol), and 20 mL 48% hydrobromic acid. The resulting mixture was heated at 90° C. for 12 h. After cooling to room temperature, 100 mL of ethyl acetate was added and the resulting mixture was washed twice with 100 mL of water, and once with 100 mL saturated sodium chloride solution. The organic phase was dried over MgSO₄, filtered, and concentrated to afford a brown solid. Column chromatography on 50 g of silica gel (5% methanol-methylene chloride) afforded 0.530 g (73%) of Example 83 as a white solid. MP 189° C.

EXAMPLE 84

A one-necked, 10-mL, round-bottomed flask equipped with a rubber septum and an argon needle inlet was charged with 1 mL DMF and Example 83 (0.100 g, 0.257 mmol). Sodium hydride (0.014 g, 0.583 mmol) was added and the reaction mixture stirred 10 min at room temperature. 1-Iodopropane (0.130 g, 0.075 mL, 0.765 mmol) was added and the resulting mixture heated to 60° C. for 12 h. After cooling to room temperature, the reaction mixture was diluted with 50 mL of ethyl acetate, washed twice with 20 mL of water, and washed once with 20 mL saturated sodium chloride solution. The organic phase was dried over MgSO₄, filtered, and concentrated to afford an oil. A second one-necked, 10-mL, round-bottomed flask equipped with a rubber septum and an argon needle inlet was charged with the above oil, 1 mL THF, 1 mL methanol, and 2 mL of a 1 M sodium hydroxide solution. The resulting mixture was stirred 10 min at room temperature, dissolved in 20 mL ethyl acetate and washed twice with 20 mL of a 10% HCL solution. The organic phase was dried over MgSO₄, filtered, and concentrated to afford, after HPLC purification, 0.014 g (13%) of Example 84 as a white solid. MP 126° C.

The above method for the preparation of Example 84 was used to prepare the following series of biphenyl products (TABLE VII) using the appropriate alkylating agent.

TABLE VII

[Structure: $R^4$—O—(phenyl)—(phenyl)—C(=O)—CH$_2$—CH(COOH)—CH$_2$CH$_2$CH$_2$—Ph]

| example | R⁴ | isomer | m.p.(° C.)/other characterization |
|---|---|---|---|
| 84 | n-propyl | R, S | 126 |
| 85 | n-pentyl | R, S | 110 |
| 86 | n-pentyl | (−) | [a]D = −27.3(CHCl₃) |
| 87 | n-pentyl | (+) | |
| 88 | n-hexyl | R, S | 110 |
| 89 | n-butyl | R, S | 159 |
| 90 | Ph(CH₂)₃ | R, S | 138 |
| 91 | i-Pr | R, S | 122 |
| 92 | n-hept | R, S | 114 |
| 93 | cyclohexyl-CH₂ | R, S | 141 |
| 94 | i-Bu | R, S | 119 |
| 95 | allyl | R, S | 143 |
| 96 | isoamyl | R, S | 110 |
| 97 | cyclopropyl-CH₂ | R, S | 127 |
| 98 | 2-pentyl | R, S | 120 |
| 99 | PhCH₂ | R, S | 144 |
| 100 | PhCH₂ | (+) | [a]D = +26.7 (CHCl₃) |
| 101 | PhCH₂ | (−) | |
| 102 | Ph(CH₂)₂ | R, S | 152 |
| 103 | 4-methylbenzyl | R, S | 136 |
| 104 | 4-(CF₃)benzyl | R, S | 166 |
| 105 | 4-MeO-benzyl | R, S | 153 |
| 106 | 3-Cl-benzyl | R, S | 128 |
| 107 | 4-F-benzyl | R, S | 150 |
| 108 | n-decyl | R, S | 108 |
| 109 | 3-pyridyl-CH₂ | R, S | 178 |

TABLE VII-continued

| example | R⁴ | isomer | m.p.(° C.)/other characterization |
|---|---|---|---|
| 110 | 2-pyridyl-CH₂ | R, S | 166 |
| 111 | 4-pyridyl-CH₂ | R, S | 187 |
| 112 | H₂HOC-C₆H₄-CH₂ | R, S | 208 |
| 113 | HO₂C-C₆H₄-CH₂ | R, S | 236 |

EXAMPLE 114

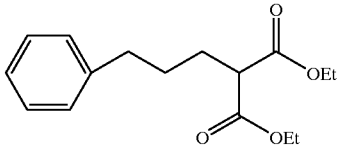

Step 1 A dry 2-L, three-necked, round-bottomed flask was equipped with a stir bar, a pressure equalizing addition funnel, an argon inlet and a thermometer. The flask was charged with a suspension of sodium hydride (8.4 g of 95% NaH; ~0.33 mol) in dry THF (700 mL) and was cooled with an ice water bath. Diethyl malonate (48.54 g, 0.30 mol) was added dropwise from the addition funnel over 25 min. Stirring was continued for 1.5 h before adding 1-bromo3-phenylpropane (47 mL, ~61 g, ~0.30 mol) over 10 min via the addition funnel. Rinses of the addition funnel (THF, 2×10 mL) were added to the reaction mixture and stirring was continued for 30 min. The addition funnel and thermometer were replaced with a reflux condenser and stopper, and the reaction was heated at reflux for 19 h. The mixture was cooled to room temperature and then with an ice water bath. Distilled water (400 mL) was slowly added with stirring. The layers were separated and the aqueous phase was extracted with chloroform (100 mL). The combined organics were washed with 10% HCl (250 mL) and the separated aqueous phase was back-extracted with chloroform (100 mL). The combined organics were washed with saturated NaHCO₃ (250 mL) and the separated aqueous phase was back-extracted with chloroform (100 mL). The organics were dried (Na₂SO₄) and concentrated to yield a yellow oil which was purified by distillation through a Vigreux column at reduced pressure (0.4 torr). The fraction boiling at 124–138° C. was clean desired product (57.21 g, 0.206 mol; 68% yield). TLC (hexanes-dichloromethane, 1:1): R_f=0.32.

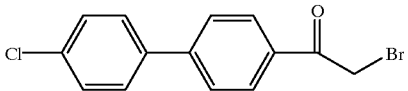

Step 2 A 2-L, three-necked, round-bottomed flask was equipped with a mechanical stirrer, a thermometer and an argon inlet. The flask was charged with a solution of 4-chlorobiphenyl (48.30 g, 0.256 mol) in dichloromethane (500 mL, freshly opened bottle). Bromoacetyl bromide (23 mL, ~53.3 g, ~0.26 mol) was added via syringe and the solution was cooled with an ice water bath to an internal temperature of 3° C. The thermometer was temporarily removed and AlCl₃ was added portionwise over 5 min. The internal temperature rose to 10° C. and white gas evolved from the opaque olive green reaction mixture. After 24 h of stirring, the reaction was quenched by cautiously pouring into cold 10% HCl (1 L). The organic layer became cloudy yellow green. Chloroform was added to help dissolve solids, but the organic layer never became transparent. The organics were concentrated on a rotary evaporator and were dried further under high vacuum. The crude product was a pale green solid (~82 g) which recrystallized from hot ethyl acetate to give 1-(2-bromoethanone)-4-(4-chlorophenyl)-benzene as brown needles (58.16 g). Concentration of the mother liquor followed by addition of hexanes delivered a second crop of crystals (11.06 g) which gave an NMR spectrum identical to that of the first crop. The total yield of the title product was 87%. TLC (hexanes-dichloromethane, 2:1): R_f=0.30.

The general method of the preparation of 1-(2-bromoethanone)-4-(4-chlorophenyl)-benzene was used to prepare 1-(2-bromoethanone)-4-(4-bromophenyl)-benzene, 1-(2-bromoethanone)-4-(4-nitrophenyl)-benzene and 1-(2-bromoethanone)-4-(4-cyanophenyl)-benzene.

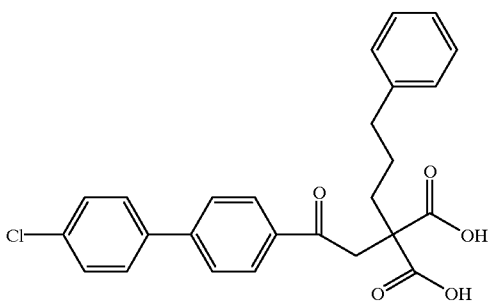

Step 3 A dry 1-L, three-necked, round-bottomed flask was equipped with a magnetic stir bar, a thermometer, an argon inlet and a pressure equalizing addition funnel. The flask was charged with a suspension of sodium hydride (4.7 g of 95% NaH; ~0.185 mol) in dry THF (400 mL), and the addition funnel was charged with the malonate product from step 1 (46.76 g, 0.168 mol). The reaction vessel was cooled with an ice water bath while the malonate was added dropwise over 18 min. After the reaction stirred for 45 min, a solution of the bromomethyl ketone product from step 2 (52.00 g, 0.168 mol) in dry THF (200 mL) was added via the addition funnel over 20 min. The deep orange reaction mixture was stirred under argon overnight while slowly warming to room temperature. The reaction vessel was cooled in an ice water bath while distilled water (300 mL) was added cautiously. The layers were separated and the aqueous phase was extracted with dichloromethane (100 mL). The combined organics were washed sequentially with 10% HCl and saturated sodium bicarbonate (200 mL). The combined aqueous washes were back-extracted with dichloromethane (50 mL). The combined organics were dried ($Na_2SO_4$) and concentrated to afford a dark orange oil (84.07 g). This crude material was used in the next step without purification.

A portion of the crude oil (24.09 g, ~47.5 mmol) was taken up in ethanol (400 mL; the sample did not completely dissolve). To this mixture was added NaOH solution (19.0 g of 50 wt. % aqueous NaOH, ~238 mmol) and the reaction was stirred under argon overnight at room temperature. After 20 h of stirring, the reaction showed no diester remaining by TLC. The mixture was brought to pH~1 by adding concentrated HCl (~20 mL) and was then concentrated to dryness. An attempt to partition this material between chloroform (200 mL) and water (100 mL) failed to dissolve all solids. Collection of the undissolved solid followed by drying under high vacuum gave clean desired (12.38 g, 27.46 mmol). Examination of the aqueous and organic phases by TLC showed a negligible amount of desired. The saponification procedure was repeated on the remaining crude diester (59.47 g, ~117 mol) to deliver additional diacid (28.34 g, 62.85 mmol). The total yield for the alkylation-saponification process to yield the diacid product was 54%. TLC (chloroform-methanol, 9:1 with trace amount of acetic acid): $R_f$=0.45.

Step 4—Preparation of Example 114. The diacid product from step 3 (28.34 g, 62.85 mmol) was dissolved in 1,4-dioxane (1.2 L) and was held at reflux under argon overnight. Concentration gave the crude product as a yellow-white solid (27.60 g) which was recrystallized from toluene to deliver the title compound Example 114 as a tan solid (21.81 g, 53.60 mmol) after overnight drying in a vacuum oven at 100° C. The decarboxylation was repeated on the remaining diacid (12.38 g) from step 3 to give additional recrystallized product (7.60 g, 18.68 mmol). The total yield for the decarboxylation step was 80%. The final product contains 5 mol % toluene even after extensive vacuum oven drying at 100° C. Anal. (for $C_{25}H_{23}O_3Cl.0.05C_7H_8$) C: calcd, 73.99; found, 73.75 H: calcd, 5.73; found, 5.74.

EXAMPLE 115

Step 1—Purification of Dehydroabietylamine. A solution of dehydroabietylamine (60%, 100 g, 0.21 mol) in toluene (170 mL) was treated with a second solution of glacial acetic acid (24 mL) in toluene (55 mL) at room temperature. The mixture was stored at room temperature overnight. The crystalline salt was collected by filtration, washed with cold toluene and recrystallized from boiling toluene (152 mL). The crystals were collected by filtration, washed with n-pentane and air-dried to give dehydroabietylamine acetate (47 g, 78%) as a white crystalline solid.

A solution of dehydroabietylarnine acetate (47 g, 0.16 mol) in water (175 mL) was gently warmed until the solution became homogeneous. An aqueous solution of NaOH (10% W/V, 61 mL) was carefully added and after cooling to room temperature. The aqueous solution was extracted with diethyl ether, dried over $MgSO_4$, filtered and concentrated to give dehydroabietylamine (35 g, 58%) as a viscous oil which solidified on standing. MP 44–45° C.

Step 2—Preparation of Example 115. A solution of Example 114 (45 g, 0.11 mol) and dehydroabietylamine (32 g, 0.11 mol) in an acetone/ethanol/water mixture (50:20:1; 1260 mL) was carefully warmed until the solution became clear (1 h). After cooling to room temperature and standing for 42 h, the solid was removed by filtration.

The solid product from the initial crystallization was diluted with a 10% dichloromethane/ethyl acetate mixture (700 mL) and treated with 10% phosphoric acid (300 mL). After stirring at room temperature for 1 h, the mixture was added to a separatory funnel and diluted with sat. aq. NaCl (200 mL). After the aqueous phase was drained off, the precipitate that remained in the organic layer was removed by filtration and dried to give 9.2 g of near racemic solid with an isomer ratio of 48:52 (Example 116:Example 115). The remaining solution was filtered through a short pad of silica gel and concentrated to give Example 115 (13.3 g, 60% theoretical; isomer ratio 0.8:99.2 (Example 116:Example 115)). MP 125–126° C.; $[a]_D$ +25.7° (c 1.4, acetone).

EXAMPLE 116

The filtrate from the initial crystallization in step 2 of the procedure for the preparation of Example 115 was concentrated under reduced pressure. The resulting solid material was processed using the same procedure as described for Example 115. The analogous sequence provided racemate (8.0 g, isomer ratio 57:43) and Example 116 (13.5 g, 60% theoretical; isomer ratio 99.1:0.9). MP 125–126° C., $[a]_D$ −25.6° (c 1.4, acetone).

The above methods for the preparation of Example 114, Example 115, and Example 116 were used to prepare the following series of biphenyl containing products (TABLE VIII) using the appropriate alkylating agent in step 1 and the appropriately substituted biaryl starting material in step 3.

TABLE VIII

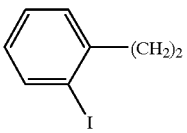

| ex. | R[6]a | (T)$_x$ | isomer | m.p.(° C)/other characterization |
|---|---|---|---|---|
| 114 | Ph(CH$_2$)$_3$ | Cl | R, S | Anal. C: calcd, 73.99; found, 73.75. H: calcd; 5.73; found, 5.74 |
| 115 | Ph(CH$_2$)$_3$ | Cl | | [a]$_D$ +25.7° (c 1.4, acetone) |
| 116 | Ph(CH$_2$)$_3$ | Cl | | [a]$_D$ −25.6° (c 1.4, acetone) |
| 117 | Et | Cl | R, S | 151–152 |
| 118 | n-propyl | Cl | R, S | 127–128 |
| 119 | allyl | Cl | R, S | 133–134 |
| 120 | n-butyl | Cl | R, S | 152–153 |
| 121 | propargyl | Cl | R, S | 130–132 |
| 122 | n-heptyl | Cl | R, S | 118–120 |
| 123 | n-decyl | Cl | R, S | 108–110 |
| 124 | Ph(CH$_2$)$_2$ | NO$_2$ | R, S | Anal. C: calcd, 71.45; found, 71.41. H: calcd, 5.25; found, 5.23. N: calcd, 3.47; found, 3.46 |
| 125 | Ph(CH$_2$)$_2$ | CN | R, S | HRMS calcd. 383.1521, found 383.1531 |
| 126[a] | 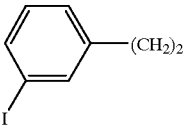 | Cl | R, S | 189–190 |
| 127[a] | 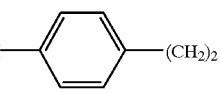 | Cl | R, S | 171–173 |
| 128[a] | 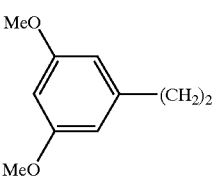 | Cl | R, S | 163.5–165 |
| 129[a] | MeO-C$_6$H$_3$(OMe)-(CH$_2$)$_2$ | Cl | R, S | 160–161 |
| 130[b] | Ph | Cl | R, S | $^1$H NMR (MeOD) d 8.03(d, J=8.8 Hz, 2H), 7.69(d, J=8.5 Hz, 2H), 7.62(d, J=8.8 Hz, 2H), 7.43(d, J=6.6 Hz, 2H), 7.28(m, 5H), 4.19(dd, J=10.3, 4.1 Hz, 1H), 3.91 (dd, J=14.0, 10.3 Hz, 1H), 3.27(dd, J=14.0, 4.1 Hz, 2H). |
| 131 | PhCH$_2$ | Cl | R, S | 167–171 |
| 132 | Ph(CH$_2$)$_2$ | Cl | R, S | 179 |
| 133 | Me$_3$SiCH$_2$ | Cl | R, S | 134–136 |
| 134 | Ph(CH$_2$)$_3$ | Br | R, S | 174 |

TABLE VIII-continued

[Structure: (T)x—phenyl—phenyl—C(=O)—CH2—CH(R6a)—C(=O)OH]

| ex. | R6a | (T)x | isomer | m.p.(° C)/other characterization |
|---|---|---|---|---|
| 135 | Ph(CH2)3 | H | R, S | HRMS calcd, 372.1725; found, 372.1735. |
| 430 | NHAc | Cl | R, S | 141–142 |

[a]Preparation of 2-(2-Iodophenyl)ethyl bromide: A solution of o-iodophenylacetic acid (19.87 g, 75.53 mmol) in dry tetrahydrofuran (110 mL) was added dropwise over 41 min to a solution of borane in tetrahydrofuran (151 mL of 1 M solution, ca. 151.0 mmol) which was cooled with an ice-water bath. The reaction was stirred at 0 to 10° C. for 2 h 15 min. After the reaction mixture was cooled to 0° C., it was quenched by cautious addition (frothing!) of 10 (vol.) % acetic acid in methanol over 20 min. Stirring was continued for 25 min before the reaction was concentrated on a rotary evaporator. The residue was dissolved in ethyl acetate and washed with saturated ammonium chloride followed by saturated sodium bicarbonate. The organics were dried (Na2SO4) and concentrated to a yellow oil (18.07 g) which was used in the next step without purification. Neat 2-(2-iodophenyl)ethanol (17.75 g, 71.55 mmol) was treated dropwise with phosphorous tribromide (3.5 mL, 36.85 mmol) over 6 min while the reaction vessel was placed in a water bath to modulate the exothermic reaction. Stirring was continued for 15 min at room temperature and then for 2 h while the mixture was heated in an oil bath at 100° C. The reaction was cooled to room temperature, diluted with ether and quenched carefully with water (frothing/exotherm!). The layers were separated, the organics were washed with saturated sodium bicarbonate and dried (Na2SO4). Concentration gave a yellow oil which was purified by Kugelrohr distillation (140° C./700 millitorr) to give a colorless oil (19.50 g, 62.71 mmol; 83% yield for above two steps). MS (EI) 310, 312 [M]+.
[b]Reference compound.

The general method of the preparation of 2-(2-iodophenyl)ethyl bromide was used to prepare 2-(3-iodophenyl)ethyl bromide, 2-(4-iodophenyl)ethyl bromide, and 2-(3,5-dimethoxyphenyl)ethyl bromide.

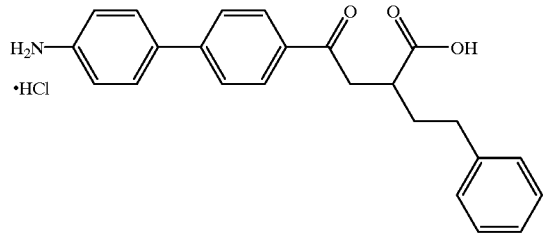

Example 136

EXAMPLE 136

A 125-mL Parr reaction vessel containing Example 124 (1.15 g, 2.85 mmol), 10% Pd/C (0.06 g), and glacial acetic acid (50 mL) was charged with hydrogen gas at 55 psi and shaken on a Parr apparatus until hydrogen uptake ceased. The Parr reaction vessel was then purged with argon and the reaction mixture was filtered through a pad of Celite, rinsing with acetone. The solution was concentrated to dryness via rotary evaporation using hexane to azeotrope the acetic acid. The solid was dissolved in hot 10% HCl, filtered and concentrated to dryness via rotary evaporation. The crude hydrochloride was then recrystallized from ethanol to afford off-white crystals which when dried in a vacuum oven (80° C., 3 days) became purple (0.18 g, 17%). MP 222.0–224.0° C.

EXAMPLE 137

Example 136 (0.30 g) was suspended in ethyl acetate (7 mL) and treated with aqueous K2CO3 (1.93 g in 7 mL) followed by benzyl chloroformate (0.165 mL). The mixture was stirred over the weekend. The reaction was partitioned between 10% HCl and ethyl acetate/methylene chloride. The organics were washed with water and brine, dried (Na2SO4) and concentrated to a yellow solid. Flash column chromatography (gradient elution, methylene chloride to 98:2 methylene chloride-methanol) gave the desired as a white solid. MP 148°–149° C.

Using the appropriate commercially available acylating agents, the general method of Example 137 was used to prepare the examples in Table IX from Example 136. Examples 140–141 were prepared by hydrolysis of the product from acylation of the ethyl ester of Example 136.

TABLE IX

[Structure: (T)x—phenyl—phenyl—C(=O)—CH2—CH(CH2Ph)—C(=O)CH3]

| ex. | (T)x | isomer | m.p.(° C.)/other characterization |
|---|---|---|---|
| 136 | NH2.HCl | R, S | 222.0–224.0 |
| 137 | PhOCONH | R, S | 148–149 |
| 138 | t-BuOCONH | R, S | 167–168 |
| 139 | CH3CONH | R, S | 209.5–211 |
| 140 | n-BuCONH | R, S | 168–169.5 |
| 141 | t-BuCH2CONH | R, S | 180.5–182.5 |

EXAMPLE 142

Acid Example 126 was dissolved in dimethylsulfoxide (1.5 mL) and methanol (1 mL). Triethylamine (0.21 mL, 1.51 mmol) was added followed by palladium(II) acetate (12.8 mg, 0.057 mmol) and 1,3-bis(diphenylphosphino) propane (23.0 mg, 0.056 mmol). Carbon monoxide was bubbled through the solution for three minutes. The orange solution was placed under a carbon monoxide atmosphere and was heated in an oil bath at 70–75° C. The reaction was worked up after 20 h 45 min of heating. The mixture was cooled to room temperature, diluted with ethyl acetate and washed with 10% HCl followed by water. The organics were dried ($Na_2SO_4$) and concentrated to a yellow solid. This material was purified by crystallization from hot hexane/ethyl acetate or from hot toluene/hexane to give the title compound as a tan solid (109.6 mg, 0.243 mmol, 50%). MP 129°–130° C.

EXAMPLE 143

Half acid ester Example 142 was dissolved in ethanol (3 mL), tetrahydrofuran (3 mL) and aqueous NaOH (0.20 g in 1 mL). The mixture still contained starting material after stirring for 4.5 h. 50% aqueous NaOH (1 mL) was added and the mixture was stirred overnight. The mixture was acidified with 10% HCl and extracted with ethyl acetate/chloroform. The extracts were dried ($Na_2SO_4$) and concentrated to a black solid which did not completely dissolve in fresh ethyl acetate. The suspension was filtered through celite and was concentrated to a yellow solid (354 mg). Purification by flash column chromatography (gradient elution, 100:1 chloroform-methanol with 1% acetic acid to 20:1 chloroform-methanol with 1% acetic acid) gave the desired product as an off-white solid (218.6 mg). MP 178°–186° C. (with darkening).

The examples in Table X were prepared by the palladium-mediated carbonylation method of Example 142 with water or the appropriate amine in place of the methanol. Example 153 was prepared from the ethyl ester of Example 144 by using water in the carbonylation method of Example 142 followed by hydrolysis according to the procedure of Example 143. Examples 145 and 146 are the separate stereoisomers of the racemate from Example 144. Separation was accomplished on a Chiralpak AS column (65:35 hexanes-absolute ethanol with 1% acetic acid) and the stereochemistry of the individual isomers was assigned by analogy to the relative activity of other definitive isomer pairs.

TABLE X

| ex. | $R^{6a}$ | isomer | m.p.(° C.)/other characterization |
|---|---|---|---|
| 142 | 2-($CH_2)_2$-C$_6$H$_4$-$CO_2Me$ | R, S | 129–130 |
| 143 | 2-($CH_2)_2$-C$_6$H$_4$-$CO_2H$ | R, S | 178–186 |
| 144 | 3-($CH_2)_2$-C$_6$H$_4$-$CONEt_2$ | R, S | 84–86 |
| 145 | 3-($CH_2)_2$-C$_6$H$_4$-$CONEt_2$ | R | 123.5–124.5 |
| 146 | 3-($CH_2)_2$-C$_6$H$_4$-$CONEt_2$ | S | 124–124.5 |

TABLE X-continued
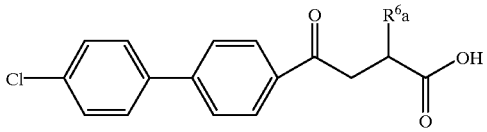
| ex. | R⁶a | isomer | m.p.(° C.)/other characterization |
|---|---|---|---|
| 147 | 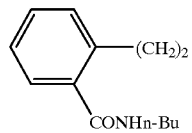 | R, S | 164–165 |
| 148 | 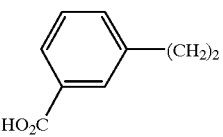 | R, S | 239–240 |
| 149 | 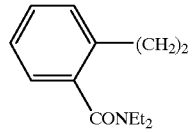 | R, S | 85.5–88.5 |
| 150 | 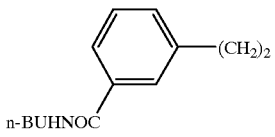 | R, S | 67–69.5 |
| 151 | 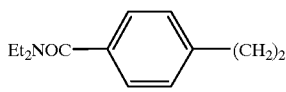 | R, S | 123–124 |
| 152 | 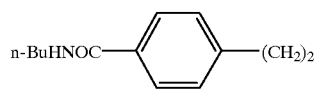 | R, S | 195.5–196.5 |
| 153 |  | R, S | 246–248 |
| 438 | 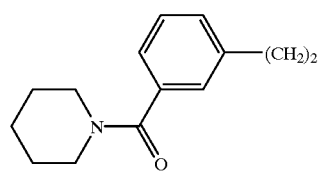 | R, S | 209–210 |

EXAMPLE 154

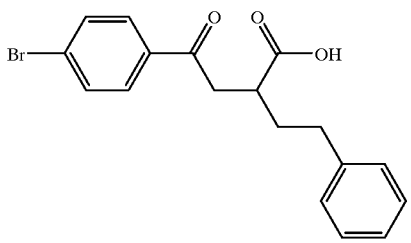

Step 1 The general methods which gave the product in Example 65, step 1 were utilized with diethyl phenethylmalonate as starting material to give the desired product as a white solid which recrystallized from ether. MP 148.5°–149.5° C.

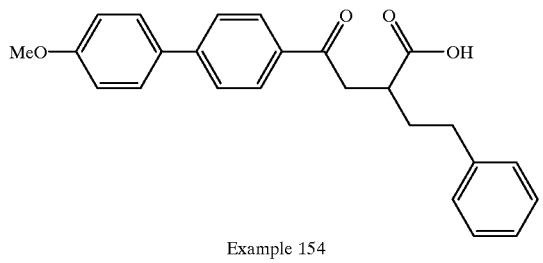

Example 154

Step 2—Preparation of Example 154

The product from step 1 was reacted according to the general procedure of Example 73 to afford Example 154 as yellow crystals. MP 177.5°–178° C.

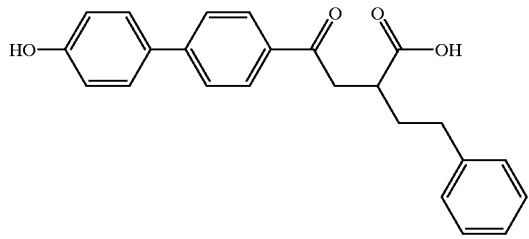

Example 155

EXAMPLE 155

The methyl ether of Example 154 was cleaved according to the general procedure of Example 83 to give Example 155 as a white solid. MP 165.5°–166° C.

Reaction of Example 155 with the appropriate alkylating agent according to the general procedure of Example 84 gave Examples 156–159 (TABLE XI). Reaction of the ethyl ester of Example 155 with the appropriate alkylating agent according to the general procedure of Example 84 delivered Examples 160 and 161.

TABLE XI

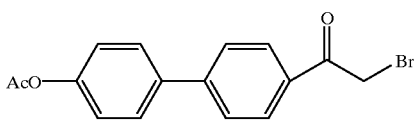

| example | $R^4$ | isomer | m.p.(° C.)/other characterization |
|---|---|---|---|
| 156 | Et | R, S | 160.5–161 |
| 157 | n-propyl | R, S | 147.5–148.5 |
| 158 | n-pentyl | R, S | 140.5–141 |
| 159 | n-hexyl | R, S | 135.5–137.5 |
| 160 | n-butyl | R, S | 149.5–151.5 |
| 161 | $PhCH_2$ | R, S | 156–157 |

EXAMPLE 162

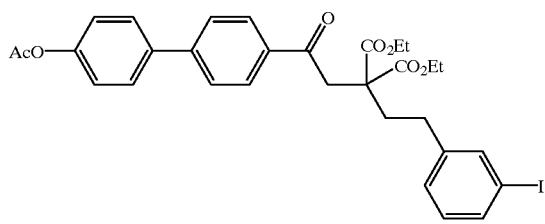

Step 1 A one-necked, 1000-mL, round-bottomed flask equipped with an argon inlet adapter was charged with 500 mL $CH_2Cl_2$, 4-phenylphenol acetate (50.0 g, 235 mmol), bromoacetyl bromide (73.2 g, 31.6 mL, 363 mmol) and cooled to 0° C. while aluminum trichloride (94.2 g, 707 mmol) was added in small portions ca. over 5 min. The resulting mixture was stirred for 30 min at 0° C. and 12 h at room temperature. The reaction mixture was added to a cold 10% HCl solution (500 mL), and extracted three times with 200-mL portions of ethyl acetate. The organic phase was dried over $MgSO_4$, filtered, and concentrated to provide a black solid. Recrystallization from ethyl acetate-hexanes afforded 44.3 g (56%) of the desired compound as a brown solid. TLC (10% ethyl acetate-hexanes) $R_f=0.14$.

Step 2 The desired compound was synthesized from the product of step 1 above by a method analogous to procedures contained in Example 114 except that 2-(3-iodophenyl)ethyl bromide was used in lieu of 1-bromo-3-phenylpropane. TLC (hexanes-ethyl acetate, 3:1) $R_f=0.49$.

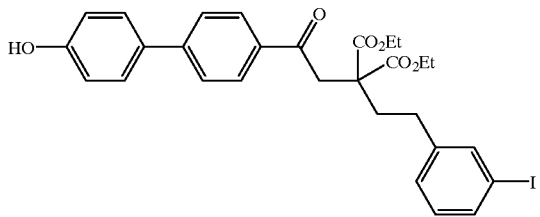

Step 3 A tetrahydrofuran (400 mL) and ethanol (50 mL) solution of the product from step 2 (18.4 g) was treated with $K_2CO_3$ and stirred under argon at room temperature overnight. Because a significant amount of starting material remained, the volume of the reaction was reduced by one half and additional $K_2CO_3$ (12 g) was added. The reaction was complete after 3 h. The reaction was concentrated and acidified with 10% HCl. The product was extracted with ethyl acetate, dried ($Na_2SO_4$) and concentrated to a brown oily residue. Purification by flash chromatography (hexanes-ethyl acetate, 3:1) gave the product as a yellow oil (14.8 g; 86%). TLC (hexanes-ethyl acetate, 3:1) $R_f$=0.20.

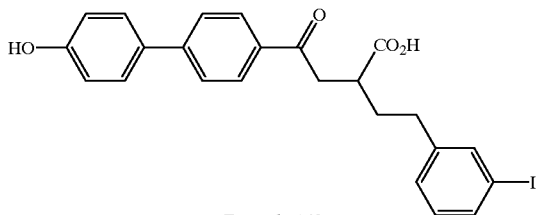

Example 162

Step 4—Preparation of Example 162. Reaction of the product from step 3 with pentyl iodide according to the general procedure of Example 84 gave Example 162. MP 156°–157° C.

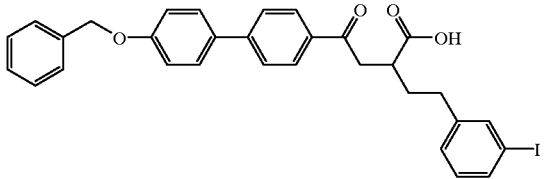

Example 163

EXAMPLE 163

Alkylation of the product from Example 162, step 3 with benzyl bromide according to the general procedure of Example 84 gave Example 163. MP 173°–174° C.

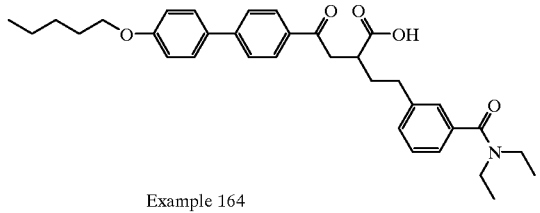

Example 164

EXAMPLE 164

Example 164 was prepared from Example 162 by the palladium-mediated carbonylation method of Example 142 with diethylamine as the nucleophile. Anal. (for $C_{34}H_{41}NO_5 \cdot 0.75\ H_2O$) C: calcd, 73.29; found, 73.35. H: calcd, 7.69; found, 7.43. N: calcd, 2.51; found, 2.33.

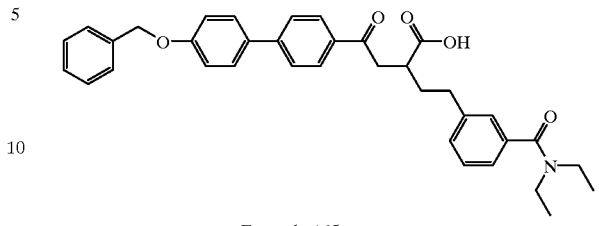

Example 165

EXAMPLE 165

Example 165 was prepared from Example 163 by the palladium-mediated carbonylation method of Example 142 with diethylamine as the nucleophile. MP 92°–95° C.

EXAMPLE 166

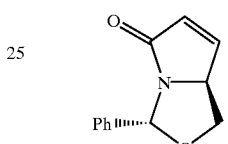

Step 1 The above a,b-unsaturated lactam was prepared from commercially available L-pyroglutaminol in a two step procedure analogous to literature precedent (see: *J. Am. Chem. Soc.* 1989, 111, 1525–1527). TLC (hexanes-ethyl acetate, 3:2): $R_f$ 0.29.

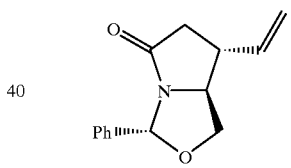

Step 2 A dry, 500 mL, three-necked, round-bottomed flask was fitted with a magnetic stirring bar, a threeway stopcock, a low temperature thermometer and a teflon stopper. The flask was flushed with argon and charged with tetravinyl tin (5.9 mL, 32.3 mmol) and 50 mL of freshly distilled ether. The cooled (0° C.) solution was treated with methyl lithium (86.9 mL of a 1.43 M solution in diethyl ether; 124.3 mmol) over 20 min. The mixture was stirred at 0° C. for 30 min, cooled to −78° C. and treated with CuCN (4.45 g, 49.7 mmol) in one portion. The reaction was allowed to warm to −30° C. over 1 h and 35 min and was stirred at −30° C. for an additional 40 min. The stopper was replaced with a dry addition funnel charged with a solution of the enone from step 1 (5.0 g, 24.85 mmol) in ether (150 mL). The enone was added to the reaction mixture over 30 min while maintaining an internal temperature of −30° C. The reaction was complete after 40 min as judged by tlc. Saturated ammonium chloride (350 mL) was added and the stirred mixture was warmed to ~10° C. The gray solid which formed was removed by filtration through celite on a medium fritted funnel. The filter cake was washed with fresh ether. The filtrate layers were separated and the aqueous phase was extracted with fresh ether (2×100 mL). The combined extracts were dried (MgSO$_4$) and concentrated to a yellow oil which was purified by flash column chromatography (hexanes-ethyl acetate, 3:1) to give the product as a yellow oil (4.6 g, 81%). TLC (hexanes-ethyl acetate, 3:1): R$_f$ 0.34.

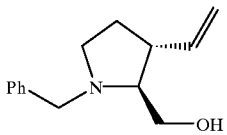

Step 3 A solution of the product of step 2 (8.20 g, 35.8 mmol) in dry tetrahydrofuran (100 mL) was added to a solution of lithium aluminum hydride (2.04 g, 53.6 mmol) in dry tetrahydrofuran (100 mL) at reflux. Reflux was continued for 1 h 15 min. The reaction mixture was cooled and treated dropwise with a solution of saturated Na$_2$SO$_4$ until a thick precipitate formed. Ethyl acetate (100 mL) was added and the mixture was stirred briefly before filtering through celite; the filter cake was washed with ethyl acetate. The combined filtrates were dried (Na$_2$SO$_4$) and concentrated. The dark yellow oil (6.67 g, 86%) used in the next step without further purification. TLC (hexanes-ethyl acetate, 3:1): R$_f$ 0.21.

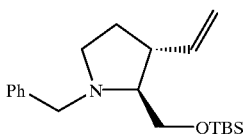

Step 4 A dry, 250-mL, round-bottomed flask was charged with dry dichloromethane (60 mL), tert-butyldimethylsilylchloride (4.9 g, 32.03 mmol) and imidazole (4.54 g, 66.73 mmol). This mixture was stirred for 10 min before it was treated with a solution of the product from step 3 (5.8 g, 26.69 mmol) in dry dichloromethane (50 mL). The reaction was stirred under argon for 1 h. The mixture was concentrated and the residue was purified by flash column chromatography (hexanes-ethyl acetate, 9:1) to give the desired as a yellow oil (9.19 g, 100%). TLC (hexans-ethyl acetate, 9:1).

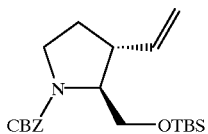

Step 5 A tetrahydrofuran (190 mL) solution of benzyl chloroformate (13.34 mL, 93.42 mmol) and the product from step 4 (8.85 g, 26.69 mmol) was held at reflux for several hours. The mixture was cooled to room temperature, diluted with diethyl ether (250 mL) and washed successively with 10% HCl (2×150 mL) and saturated NaHCO$_3$ (150 mL). The aqueous layers were back-extracted with ether and the combined organics were dried (Na$_2$SO$_4$) and concentrated. Purification by flash column chromatography (gradient elution, 99:1 to 95:5 hexanes-ethyl acetate) gave dean desired (7.62 g, 76%). TLC (hexanes-ethyl acetate, 9:1): R$_f$ 0.40.

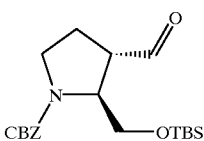

Step 6 A solution of the product of step 5 (1.225 g, 3.26 mmol) in 5% methanol-CH$_2$Cl$_2$ (20 mL) was cooled to −78° C. and purged with argon. Ozone was bubbled through the mixture until a blue color persisted. The mixture was purged with argon and treated with dimethyl sulfide (1.2 mL, 16.3 mmol). The mixture was stirred with warming to room temperature over 2 h, concentrated to dryness and left under high vacuum overnight. The crude product was purified by flash column chromatography (gradient elution, 9:1 to 7:3 hexanes-ethyl acetate) to give the desired as a colorless oil (890 mg, 73%). TLC (hexanes-ethyl acetate, 9:1): R$_f$ 0.11.

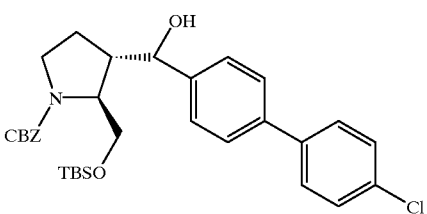

Step 7 A dry, 250 mL, round-bottomed flask was charged with 4-bromo-4'-chlorobiphenyl (4.17 g, 15.58 mmol) in dry tetrahydrofuran (50 mL) under argon. The solution was cooled to −78° C. and treated dropwise with n-butyl lithium (5.65 mL of a 2.64 M solution in hexanes, 14.92 mmol). The mixture was stirred at −78° C. for 1 h 45 min. A solution of the product of step 6 (4.9 g, 12.98 mmol) in dry tetrahydrofuran (20 mL) was added via cannula. The reaction was warmed to −20° C. with stirring over 2 h 10 min, and stirring was continued at −20° C. for an additional 50 min. The reaction was quenched with saturated ammonium chloride (150 mL) and transferred to a separatory funnel. The mixture was extracted with dichloromethane (3×80 mL) and the combined extracts were dried (MgSO$_4$) and concentrated to a yellow oil. Flash column chromatography (gradient elution, 9:1 to 3:2 hexanes-ethyl acetate) gave the desired as a mixture of diastereomers (5.21 g, 71%). TLC (hexanes-ethyl acetate, 3:1).

Step 8 A solution of the Product from step 7 (3.25 g, 5.74 mmol) in dry tetrahydrofuran (60 mL) and acetic acid (0.85 mL) was treated with tetrabutylammonium fluoride (14.35 mL of a 1.0 M solution in tetrahydrofuran) and stirred overnight. The mixture was diluted with dichloromethane (120 mL) and washed with water (75 mL). The organics were dried (Na$_2$SO$_4$) and concentrated to a yellow oil. Flash column chromatography (gradient elution, 3:2 hexanes-ethyl acetate to 100% ethyl acetate) gave clean diol (2.00 g, 77%). TLC (hexanes-ethyl acetate, 1:3).

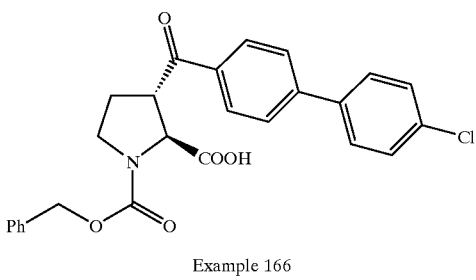

Example 166

Step 9—Preparation of Example 166. A solution of the diol from step 8 (1.50 g, 3.32 mmol) in acetone (40 mL) was cooled to −40° C. and was treated dropwise with $CrO_3$/AcOH (24 mL of a 0.083 g $CrO_3$/mL AcOH solution) over 40 min. The dark brown mixture was stirred for 4 h before it was diluted with water (300 mL) and extracted with chloroform (3×100 mL). The combined organics were dried ($Na_2SO_4$) and concentrated to a green residue which was concentrated from hexanes to remove residual acetic acid. Flash column chromatography (chloroform-methanol, 95:5) gave the keto acid as a gray solid (1.1 g, 73%). Anal. (for $C_{26}H_{22Cl}NO_5$) C: calcd, 67.32; found, 67.10. H: calcd, 4.78; found, 4.97. N: calcd, 3.02; found, 3.11.

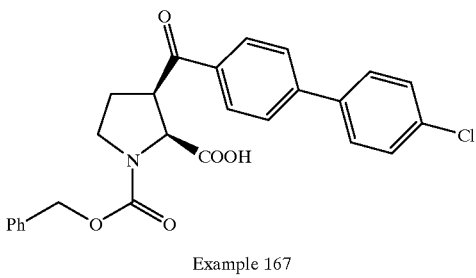

Example 167

EXAMPLE 167

This material was prepared by a procedure analogous to that for Example 166 from commercially available D-pyroglutaminol. Example 167 was spectroscopically identical to Example 166.

EXAMPLE 168

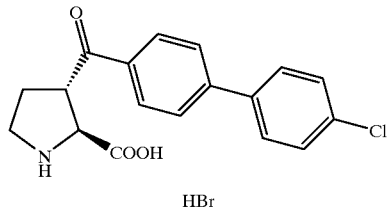

HBr

Step 1 Example 166 (1.2 g, 259 mmol) was dissolved in glacial acetic acid (30 mL) and 30% HBr in glacial acetic acid (3.5 mL). The solution was stirred overnight. The reaction mixture was diluted with ether (250 mL) and the resultant suspension was stirred for 30 min to break up large chunks of solid. The mixture was filtered and the collected solid was suspended in fresh ether and stirred for 1 h. The solid was collected by filtration and dried under vacuum overnight. The crude product (790 mg, 75%) was used in the next step without further purification. TLC (ethyl acetate-formic acid-water, 8:1:1): $R_f$ 0.63.

Step 2—Preparation of Example 168. The product of step 1 (100.0 mg, 0.25 mmol) was dissolved in dry tetrahydrofuran (3.2 mL). Triethylamine (73 mL) was added and the resultant suspension was cooled with an ice bath at 0° C. Benzyl isocyanate (34 mL) was added, the ice bath was removed and the mixture was warmed to room temperature with stirring over 3 h. The mixture was diluted with tetrahydrofuran, filtered and concentrated. Flash column chromatography (chloroform with 2% acetic acid) gave the desired as a colorless solid (43.8 mg, 38%). MP 132.0–134.0° C.

Using the appropriate acylating agent in the general method of Example 168 produced the examples in TABLE XII.

TABLE XII

| example | $R^4$ | m.p.(° C.)/other characterization |
|---------|-------|-----------------------------------|
| 168 | $PhCH_2OCO$ | 132.0–134.0 |
| 169 | $PhCH_2CH_2CO$ | 75–78 |
| 170 | $PhCH_2CO$ | 77–79 |
| 171 | $t\text{-}BuCH_2CO$ | 182–185 |
| 172 | $i\text{-}BuOCO$ | 160–163 |
| 173 | $PhNHCO$ | 231–232 |

EXAMPLE 174

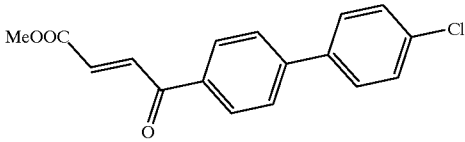

Step 1 Example 29 (10 gm, 34.9 mmol) was suspended in dry tetrahydrofuran (100 mL) under argon and cooled to 0° C. First 1,8-diazabicyclo[5.4.0]undec-7-ene (5.2 mL, 34.9 mmol) was added by syringe followed by methyl iodide (6.5 mL, 104.6 mmol). The reaction mixture was warmed to room temperature with overnight stirring. The reaction mixture was filtered and the filter cake was washed with ether. The filtrate was concentrated, the residue was dissolved in dichloromethane and washed with 10% HCl (2×125 mL). The organics were dried ($Na_2SO_4$) and concentrated to a yellow solid (9.08 g, 87%). TLC (chloroform-methanol, 97.5:2.5): $R_f$ 0.90.

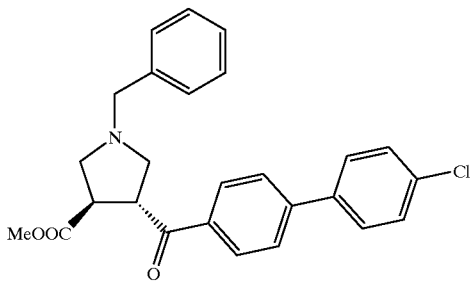

Step 2 N-Benzy-N-(cyanomethyl)-N-[(trimethylsilyl) methyl]amine (4.06 gm, 17.5 mmol) and the product from step 1 (5.0 g, 16.6 mmol) were suspended in acetonitrile (40 mL) under argon and enough dichloromethane was added to dissolve all the solids. The flask was wrapped in aluminum foil and AgF (2.32 g, 18.3 mmol) was added. The mixture was stirred in the dark overnight. The black mixture was filtered through celite and the filtrates were concentrated to a brown, oily residue. Flash chromatography (gradient elution, hexanes-ethyl acetate, 9:1 to 75:25) gave the desired as a yellow oil (3.87 g, 54%). TLC (chloroform-methanol, 97.5:2.5): $R_f$ 0.48.

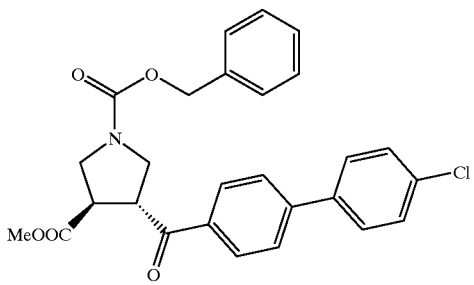

Step 3 Benzyl chloroformate (1.77 g, 10.4 mmol) was added to a tetrahydrofuran (20 mL) solution of the product from step 2 (1.5 g, 3.46 mmol). The solution was heated at reflux overnight. Methanol was added (3 mL), the mixture was stirred for 10 min and then concentrated to a yellow oil. Flash chromatography (hexanes-ethyl acetate 3:1) gave a pale yellow foam (1.07 g, 65%). TLC (hexanes-ethyl acetate, 3:1): $R_f$ 0.27.

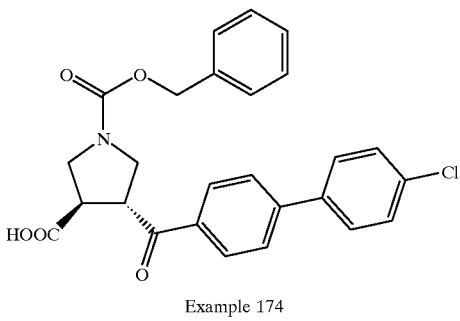

Example 174

Step 4—Preparation of Example 174. A solution of the methyl ester from step 3 (201 mg, 0.42 mmol) in 1:1 tetrahydrofuran-ethanol (10 mL) was treated with 1N NaOH (2.1 mL) and the mixture was stirred at room temperature overnight. The reaction was concentrated to dryness and the residue was partitioned between 10% HCl and ethyl acetate. The organics were separated, dried (Na$_2$SO$_4$) and concentrated to a semi-crystalline residue. Flash chromatography (hexanes-ethyl acetate, 1:1 with 1% acetic acid) gave the desired as an off-white solid (62.2 mg). MP 157–158° C.

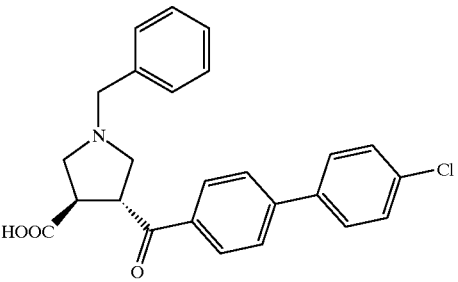

Example 175

EXAMPLE 175

Material from step 2 of Example 174 (202 mg, 0.47 mmol) was hydrolyzed according to the general method of step 4 of Example 174 to give the title compound as a colorless solid. Anal. (for C$_{25}$H$_{22}$NClO$_3$) C: calcd, 71.51; found, 71.42. H: calcd, 5.28; found, 5.30. N: calcd, 3.34; found, 3.33.

EXAMPLE 176 AND EXAMPLE 177

Step 1—Mixture of Examples 176 and 177. Dicydopentadiene was cracked by distillation (oil bath at 190° C.) through a Vigreux column to give cyclopentadiene collected at 40° C. Cyclopentadiene (1.25 mL, 15.13 mmol) was added to a suspension of dienophile Example 29 (3.30 g) in a mixture of dichloromethane (15 mL) and tetrahydrofuran (15 mL). The mixture was stirred under argon at room temperature for 2.5 h and was then concentrated to a white solid. TLC (chloroform-methanol, 100:1 with acetic acid): $R_f$ 0.47.

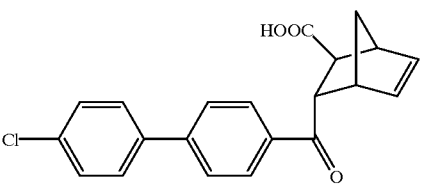

Example 177

Step 2—Preparation of Example 177. The product mixture of step 1 (2.29 g, 6.49 mmol) was dissolved in tetrahydrofuran (50 mL) and treated with aqueous. NaHCO$_3$ (50 mL). A mixture of iodine (3.11 g, 12.25 mmol) and KI (2.17 g, 13.07 mmol) in water-tetrahydrofuran (2:1, 50 mL) was added rapidly over 3 min and the brown mixture was stirred under argon overnight. The reaction was quenched with saturated aqueous NaHSO$_3$ and extracted with ethyl acetate. The combined organics were dried and concentrated to a yellow foam. Purification by flash column (gradient elution, ethyl acetate-hexanes, 6:1 with 0.5% AcOH to 3:1 with 0.5% AcOH) gave a semi-pure sample of exo-acid (0.49 g) and the iodolactone (0.88 g). The exo acid was rechromatographed (gradient elution, 100:1 chloroform-ethanol to 100:1 chloroform-ethanol with 0.5% acetic acid to 100:1:1 chloroform-ethanol-methanol with 0.5% acetic acid) to give pure Example 177 (426.4 mg). Anal. (for $C_{21}H_{17}ClO_3$) C: calcd, 71.49; found, 71.20. H: calcd, 4.86; found, 4.72.

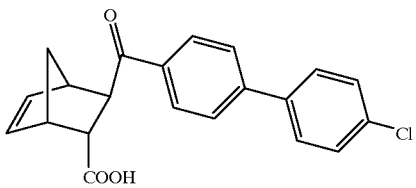

Example 176

Step 3—Preparation of Example 176. The iodolactone from step 2 (0.93 g, 1.94 mmol) was dissolved in tetrahydrofuran (20 mL) and glacial acetic acid (15 mL). The solution was treated with zinc dust (1.27 g, 19.43 mmol) in one portion and stirred under argon for 2.5 h. The mixture was diluted with ethyl acetate and filtered through a celite plug. The filtrate was washed with 10% HCl, the organics were dried ($Na_2SO_4$) and concentrated to a yellow solid. Trituration with a mixture of ether and ethyl acetate gave a tan powder (425 mg, 62%). Anal. (for $C_{21}H_{17}ClO_3 \cdot 0.25H_2O$) C: calcd, 70.59; found, 70.68. H: calcd, 4.94; found, 4.94.

EXAMPLE 178

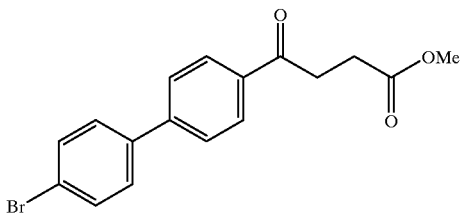

Step 1 4-Bromobiphenyl (11.6 g, 50 mmol) was dissolved in 1,2-dichloroethane (25 mL) and added to a suspension of succinic anhydride (5.0 g, 50 mmol) in 1,2-dichloroethane (70 mL) and the mixture was cooled to 0° C. Solid aluminum chloride (14.0 g, 105 mmol) was added in six portions resulting in a dark green solution. After 10 min, the reaction was allowed to warm to rt and stirred a further 72 h under Ar. The reaction mixture was poured into a beaker containing 200 mL crushed ice/water. Hexane (200 mL) was added and the mixture stirred for 1 h. The pale orange solid was filtered off to give 16.8 g (100%) of crude acid. A portion of the acid (7.0 g) was then 15 suspended in methanol (25 mL)/toluene (25 mL) and conc. $H_2SO_4$ (2.5 mL) was added dropwise. The mixture stirred 14 h at rt then was heated to 75° C. for 3 h. The solvent was removed in vacuo and the residue dissolved in $CH_2Cl_2$ and slowly poured into a mixture of saturated aqueous sodium bicarbonate/ice. The ester was extracted with methylene chloride and dried over $MgSO_4$. Filtration and removal of the solvent in vacuo gave 6.44 g (88%) of pale yellow powder. $^1H$ NMR (300 MHz, $CDCl_3$) d 2.81 (t, J=6.6 Hz, 2 H), 3.36 (t, J=6.6 Hz, 2 H), 3.73 (s, 3 H), 7.49 (m, 2 H), 7.59 (m, 4 H), 8.07 (dd, J=1.8, 6.6 Hz, 2 H).

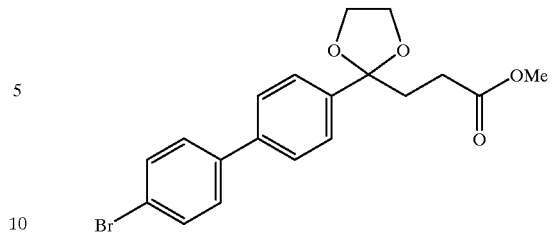

Step 2 A solution of 1,2-bis(trimethylsiloxy)ethane (4.8 mL, 20 mmol) in $CH_2Cl_2$ (1 mL) was cooled to −70° C. Catalytic trimethylsilyl trifluoromethanesulfonate (10 μL, 0.05 mmol) and then methyl ester product from step 1 (1.70 g, 5 mmol) dissolved in $CH_2Cl_2$ (4 mL) were added resulting in a thick slurry. The ice bath was allowed to warm to rt (over 3 h) and the reaction stirred a further 24 h before water was added. The product was extracted with $CH_2Cl_2$ and the organic layers were dried over sodium sulfate. After filtration, the solvent was removed in vacuao and the residue purified by MPLC (15% ethyl acetate/85% hexanes) to give 1.71 g (85%) ester as a colorless powder. $^1H$ NMR (300 MHz, $CDCl_3$) d 2.28 (m, 2 H), 2.46 (m, 2 H), 3.65 (s, 3 H), 3.81 (m, 2 H), 4.04 (m, 2 H), 7.45 (dd, J=2.2, 6.6 Hz, 2 H), 7.51 (m, 4 H), 7.57 (dd, J=2.2, 6.6 Hz, 2 H).

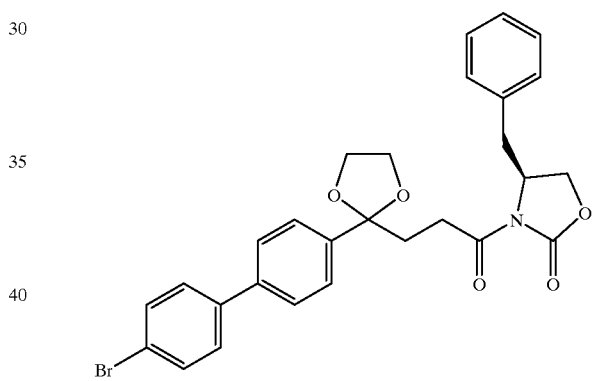

Step 3 The ketal from step 2 (4.61 g, 12 mmol) was dissolved in THF (45 mL) and $H_2O$ (15 mL) at rt. NaOH (480 mg, 12 mmol) was added and the reaction stirred at rt for 19 h. Ester was still present by TLC so another portion of NaOH (210 mg) was added. After a further 2 h the reaction was acidified to pH 3 with 4 M HCl at 0° C. and the product was extracted with ethyl acetate. Removal of solvent in vacuo gave 4.63 g of a colorless solid that was taken on to the next step crude. A portion of the acid (2.50 g, 6.6 mmol) was dissolved in $CH_2Cl_2$ (37 mL). (S)-(−)-4-Benzyl-2-oxazolidinone (1.44 g, 11.1 mmol), 1-(3-dimethylaminopropyl)-3-ethylcarbodiimide hydrochloride (1.56 g, 8.1 mmol), and dimethylarninopyridine (181 mg, 1.5 mmol) respectively were added at rt. A few minutes after the addition of the DMAP, all solid goes into solution. The reaction stirred for 3 d at rt and was then poured into saturated aqueous $NH_4Cl$. The product was extracted with $CH_2Cl_2$ and dried over sodium sulfate. After removal of the solvent in vacuo, the residue was purified by MPLC (2% $CH_3OH/98\%$ $CH_2Cl_2$) to give 2.64 g (74%) of the above shown benzyloxazolidinone as a colorless solid. $^1H$ NMR (300 MHz, $CDCl_3$) d 2.38 (m, 2 H), 2.72 (dd, J=9.6, 13.2 Hz, 1 H), 3.13 (m, 2 H), 3.29 (dd, J=3.3, 13.6 Hz, 1 H), 3.82 (m, 2 H), 4.08 (m, 2 H), 4.17 (m, 2 H), 4.52 (m, 1 H), 7.19–7.33 (comp m, 5 H), 7.45 (m, 2 H), 7.56 (m, 6 H).

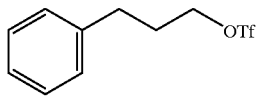

Step 4 A solution of pyridine (0.90 mL, 11 mmol) in CH$_2$Cl$_2$ (33 mL) was cooled to −70° C. Triflic anhydride (1.68 mL, 10 mmol) was added over 6 min resulting in a yellowish, slushy solution. After 5 min, 3-phenyl-1-propanol (1.40 mL, 10 mmol) was added over 4 min. The reaction stirred for 30 min at −70° C. and was then warmed to −20° C. for 75 min. The cold solution was poured through a fritted funnel containing silica gel. The silica was washed with CH$_2$Cl$_2$ and the solvent was removed in vacuao to give the above triflate as a pale orange liquid which was kept under vacuum until it was used in the next reaction (approximately 1 h).

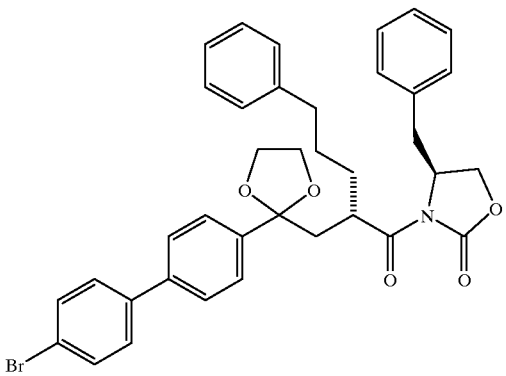

Step 5 Benzyloxazolidinone from step 3 (1.0 g, 1.9 mmol) was dissolved in THF (5 mL) and cooled to −70° C. Sodium bis(trimethylsilyl)amide (1 M in THF, 2.0 mL, 2 mmol) was added to the oxazolidinone over 5 min and the reaction stirred a further 30 min. A solution of phenylpropyl triflate from step 4 (2.7 g, 10 mmol) in THF (5 mL) and diisopropylethylamine (1.8 mL, 10 mmol) was added to the sodium anion and the reaction stirred for 2 h at −70° C. The reaction was quenched at −70° C. with saturated aqueous NH$_4$Cl (100 mL) and then the flask was warmed to rt. The solvent was removed in vacuo and the residue was dissolved in ethyl acetate and washed with saturated aqueous NH$_4$Cl. The aqueous layer was extracted with ethyl acetate and dried over sodium sulfate. After filtration, the solvent was removed in vacuao and the residue purified by MPLC (20% ethyl acetate/80% hexane to 30% ethyl acetate/70% hexane) to afford 66 mg of recovered starting oxazolidinone, 34 mg of the (R)-diastereomer product and 630 mg of the (S)-diastereomer product as shown above. $^{13}$C NMR (75 MHz, CDCl$_3$) d 28.6, 33.6, 35.8, 38.3, 42.3, 55.6, 64.3, 64.8, 65.9, 109.6, 119.7, 121.8, 125.8, 126.5, 126.7, 127.3, 128.3, 128.5, 128.7, 129.0, 129.5, 132.0, 135.4, 139.7, 141.6, 142.1, 153.3, 177.1.

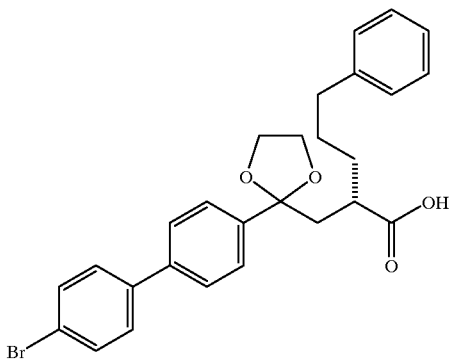

Step 6 The product step 5 (350 mg, 0.53 mmol) was dissolved in THF (3.75 mL) and H$_2$O (1.25 mL) and cooled to 0° C. Hydrogen peroxide (30%, 485 mL, 4.2 mmol) then lithium hydroxide monohydrate (90 mg, 2.1 mmol) were added. After 30 min the ice bath was removed and the reaction stirred 6 h at rt. Aqueous sodium bisulfite (10%) was added and the mixture stirred overnight. The aqueous layer was extracted with CH$_2$Cl$_2$ and the organic solution was dried over sodium sulfate. After filtration the residue was purified by MPLC (20% ethyl acetate/80% hexanes) to give 31 mg of pure acid as shown above and 103 mg of a mixture of starting benzyl oxazolidinone and the product. The mixed fractions were dissolved in 30% ethyl acetate/70% hexanes; crystals formed that were 70% oxazolidinone by HPLC while the mother liquor was pure acid product. $^{13}$C NMR (75 MHz, CDCl$_3$) d 28.9, 32.7, 35.6, 40.3, 42.8, 64.7, 64.8, 109.4, 125.8, 126.2, 126.8, 128.3, 128.3, 128.4, 128.4, 128.8, 132.0, 139.8, 142.0, 142.1, 181.4.

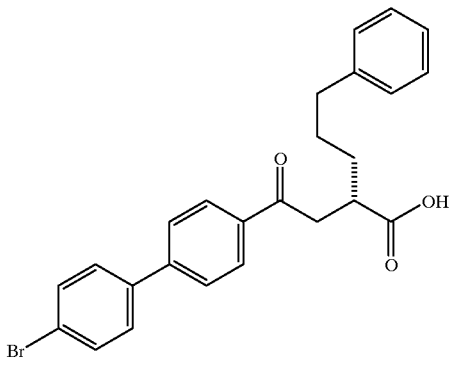

Example 178

Step 7—Preparation of Example 178. The above ketal from step 6 (38 mg, 0.08 mmol) was dissolved in CH$_2$Cl$_2$ (475 mL) and cooled to 0° C. A drop of conc. HClO$_4$ (9.4 mL) was added and the reaction stirred for 3.5 h at 0° C. Saturated sodium bicarbonate was added and the product was extracted with methylene chloride. The combined organic portions were dried over sodium sulfate. Removal of solvent in vacuo gave material (29 mg, 84%) that was pure by analytical HPLC analysis. [a]$_D$ −22.1° (c 1.2, CHCl$_3$).

EXAMPLE 179

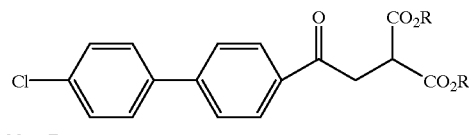

R = Me or Et

Step 1: R=Me Diethylmalonate (2.46 mL, 16.2 mmol) was added dropwise over 20 min to a suspension of sodium hydride (0.43 g, 17.8 mmol) in THF (24 mL) at 0° C. The solution was allowed to stir for 20 min then 4(4'-chlorophenyl)-a-bromoacetophenone (5.0 g, 16.2 mmol) in THF (24 mL) was added over 20 min. The reaction was warmed to rt and stirred a further 12 h then poured into EtOAc (250 mL) and water (250 mL). The phases were separated and the aqueous phase was extracted with EtOAc (2×100 mL). The combined organic phases were washed with 1 M phosphoric acid (2×200 mL), saturated sodium bicarbonate (2×200 mL), and brine (100 mL) then dried (MgSO$_4$), filtered, and concentrated in vacuo. The resulting oil was purified by flash chromatography on silica gel using a gradient of ethyl acetate/hexane (10% to 50% ethyl acetate) as the eluent to afford a crystalline solid which was recrystallized using hexane and ethyl acetate to afford ethyl 2-carboethoxy-4[4'-(4"-chlorophenyl)phenyl]-4-oxobutanoate (1.24 g, 20%). $^1$H NMR (CDCl$_3$) d 8.06 (d, J=8.1 Hz, 2H), 7.66 (d, J=8.5 Hz, 2H), 7.56 (d, J=8.5 Hz, 2H), 7.45 (d, J=8.1 Hz, 2H), 4.26 (q, J=7.4 Hz, 4H)), 4.09 (t, J=7.0 Hz, 1H), 3.66 (d, J=7.0 Hz, 2H), 1.31 (t, J=7.0 Hz, 6H, CH$_3$).

Step 1(A): R=Me Dimethyl malonate (5.7 mL, 50.0 mmol) was added in one portion to a solution of sodium methoxide (6.6 g, 50.0 mmol) in DME (45 mL) at rt and stirred for 15 min. In a separate reaction vessel, 4(4'-chlorophenyl)-a-bromoacetophenone (14.0 g, 45.0 mmol) was dissolved in DME (136 mL) along with sodium iodide (6.7 g, 45.0 mmol). The NaI solution was allowed to stir for 15 min at rt. The sodium dimethylmalonate solution was transferred via cannula dropwise into the 4(4'-chlorophenyl)-a-bromoacetophenone solution; stirring continued 1 hr at rt. The solvent was removed in vacuo and the resulting oil dissolved in 1:1 methylene chloride:diethyl ether (700 mL). The organic phase was washed with water (250 mL), and saturated sodium chloride solution (250 mL). The organic layer was dried (MgSO$_4$), filtered, and concentrated in vacuo. The resulting oil was recrystallized using 4:1 chloroform:methanol with hexane to precipitate the methyl 2-carbomethoxy-4[4'-(4"-chloro phenyl)phenyl]-4-oxobutanoate (10.43 g, 64%). $^1$H NMR (DMSO) d 8.06 (d, J=8.1 Hz, 2H), 7.66 (d, J=8.5 Hz, 2H), 7.56 (d, J=8.5 Hz, 2H), 7.45 (d, J=8.1 Hz, 2H), 3.95 (t, J=7.0 Hz, 1H), 3.70 (s, J=7.0 Hz, 6H), 3.66 (s, 2H).

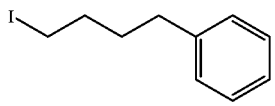

Step 2 (A)—Preparation of 4-phenyl-1-iodobutane. Sodium iodide (8.9 g, 59.2 mol) and 4-phenyl-1-chlorobutane (5.0 g, 29.6 mol) were added to acetone (29.6 mL) at rt. The mixture was heated to 70° C. for 12 h. The resulting solution was gravity filtered to remove salts. The solvent was removed under reduced pressure and excess salts were dissolved in water (100 mL). Hexane (100 mL) was added to the aqueous mixture. The phases were separated and the organic phase was washed with saturated sodium bisulfite solution (3×50 mL), treated with decolorizing carbon, and gravity filtered. The organic layer was then dried (MgSO$_4$), filtered, and concentrated in vacuo to afford 4-phenyl-1-iodobutane (6.94 g, 90%).

The general method of the preparation of 4-phenyl-1-iodobutane was used to prepare 5-phenyl-1-iodopentane, 6-phenyl-1-iodohexane, and 4-(iodomethyl)biphenyl using commercially available 5-phenyl-1-chloropentane, 6-phenyl-1-chlorohexane, and 4-(chloromethyl)biphenyl.

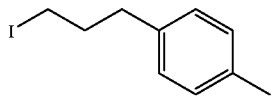

Step 2 (B)—Preparation of 3-(p-methylphenyl)-1-iodopropane. Potassium iodide (0.90 g, 5.4 mmol) and 3-(p-methylphenyl)propan-1-ol (0.4 g, 2.7 mmol) was added to 85% phosphonic acid (5.4 mL) at rt. The solution was heated to 120° C. for 3 h, during which time an oil separated from the acid layer. The mixture was cooled to rt and poured into 150 mL of water and 150 mL of diethyl ether. The organic layer was separated, decolorized with saturated sodium bisulfite solution (100 mL), and washed with saturated sodium chloride solution (100 mL). The organic layer was then dried (MgSO$_4$), filtered, and concentrated in vacuo to afford 3-(4-methylphenyl)-1-iodopropane (0.48 g, 68%).

The general method of the preparation of 3-(4-methylphenyl)-1-iodopropane was used to prepare 3-(4-chlorophenyl)-1-iodopropane using 3-(4-chlorophenyl) propan-1-ol, 3-(4-hydroxyphenyl)-1-iodopropane, 4-hydroxyphenethyl iodide, and 3-hydroxyphenethyl iodide using commercially available 3-(4-hydroxyphenyl)-1-propanol, 4-hydroxyphenethyl alcohol, and 3-hydroxyphenethyl alcohol respectively.

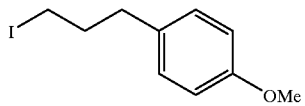

Step 2 (C)—Preparation of 3-(p-methoxyphenyl)-1-iodopropane. Anhydrous potassium carbonate (4.14 g, 30.0 mmol), iodomethane (3.74 mL, 60.0 mmol), and 3-(4-hydroxyphenyl)-1-iodopropane (1.58 g, 6.0 mmol) were added to acetone (25 mL) at rt. The mixture was heated to 70° C. for 8 h. The resulting solution was gravity filtered to remove salts and the filtrate was concentrated in vacuo to afford 3-(4-methoxyphenyl)-1-iodopropane (1.22 g, 73%).

The general method of the preparation of 3-(4-methoxyphenyl)-1-iodopropane was used to prepare 4-methoxyphenethyl iodide, and 3-methoxyphenethyl iodide from 4-hydroxyphenethyl iodide and 3-hydroxyphenethyl iodide.

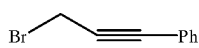

Step 2 (D)—Preparation of 1-phenyl-3-bromo-1-propyne. Phosphorous tribromide (2.62 mL, 27.6 mmol) was added to a solution of 3-phenyl-2-propyn-1-ol (10.0 g, 76 mmol) and pyridine (0.14 mL, 1.77 mmol) in diethyl ether (22 mL) at a rate to maintain reflux. After addition, the mixture was heated at 40° C. for 2 h. The mixture was cooled and poured onto ice. The organic layer was separated and diluted with diethyl ether (100 mL), washed with saturated sodium bicarbonate (2×50 mL) and saturated sodium chloride (50 mL). The organic layer was dried (MgSO$_4$), filtered and concentrated in vacuo to afford 1-phenyl-3-bromo-1-propyne (13.4 g, 90%).

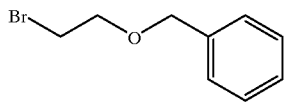

Step 2 (E)—Preparation of 2-(benzyloxy)bromoethane. A solution of triphenyl phosphine (2.1 g, 7.9 mmol) in dry methylene chloride (16 mL) was added dropwise over 10 min to a stirred mixture of N-bromosucccinimnide (1.4 g, 7.9 mmol) in dry methylene chloride (23 mL) at −78° C. The reaction was kept in the dark and stirring was continued until all the N-bromosucccinimide had dissolved (10 min). A solution of 2-(benzyloxy)ethanol in dry methylene chloride (10 mL) was added dropwise. The cooling bath was removed and stirring was continued for 12 h at rt. The organic layer was then concentrated in vacuo and passed through a silica plug with 1:1 hexane:methylene chloride to afford 2-benzyloxy)bromoethane (1.20 g, 85%).

Step 3 Ethyl 2-carboethoxy-4[4'-(4"-chlorophenyl)phenyl]-4-oxobutanoate (0.40 g, 1.02 mmol) was added in one portion at rt to a solution of sodium ethoxide (0.08 g, 1.12 mmol) in DME (1 mL). After 15 min, 4-phenyl-1-iodobutane (0.24 g, 0.93 mmol) in DME (3 mL) was added. The resulting solution was stirred for 18 h. The solvent was concentrated in vacuo and the resulting oil dissolved in CH$_2$Cl$_2$ (100 mL) and washed with water (100 mL). The phases were separated and the aqueous phase was extracted with CH$_2$Cl$_2$ (2×50 mL). The combined organic phases were dried (MgSO$_4$), filtered, and concentrated in vacuo. The resulting oil was purified by flash chromatography on silica gel using a gradient of ethyl acetate/hexane (10% to 25% ethyl acetate) as the eluent to afford a crystalline solid which was recrystallized with hexane and ethyl acetate to afford 1-[4'-(4"-chlorophenyl)phenyl]-3,3-dicarboethoxy-1-oxo-7-phenylheptane (0.272 g, 28%). MP 67–69° C.

Steps 4 and 5—Preparation of Example 179. The diester from step 3 was converted to the monoacid following the general method for Example 40 steps 4 and 5. MP 127–130° C.

The above methods for the preparation of Example 179 were used to prepare the following series of biphenyl containing products (TABLE XIII) using the appropriate alkylating reagent and the appropriately substituted biaryl starting material.

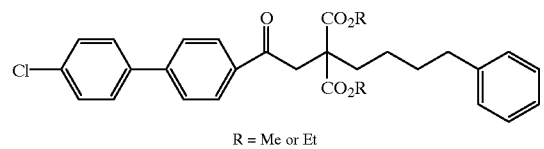

R = Me or Et

TABLE XIII

| example | R$^6$a | isomer | m.p.(° C.)/other characterization |
|---|---|---|---|
| 179 | Ph(CH$_2$)$_4$ | R, S | 127–130 |
| 180 | Ph(CH$_2$)$_5$ | R, S | 131–132 |
| 181 | Ph(CH$_2$)$_6$ | R, S | 104–105 |
| 182 | 4-Ph-PhCH$_2$ | R, S | 228–230 |
| 183 | | R, S | 171–172 |
| 184 | | R, S | 158–159 |
| 185 | | R, S | 148–149 |
| 186 | | R, S | 125–126 |

TABLE XIII-continued

[Structure: Cl-C6H4-C6H4-C(=O)-CH2-C*H(R6a)-C(=O)-OH]

| example | R⁶a | isomer | m.p.(° C.)/other characterization |
|---|---|---|---|
| 187 | 4-Me-C6H4-CH2 | R, S | 127–129 |
| 188 | 3-MeO-C6H4-CH2 | R, S | 155–156 |
| 189 | PhC/CCH2 | R, S | 141–142 |
| 190 | PhCH2O(CH2)2 | R, S | 99–100 |
| 191 | CH3O(CH2)2OCH2 | R, S | 95–97 |
| 192 | PhCH2OCH2 | R, S | Anal. C: calcd, 70.50; found, 70.73. H: calcd, 5.18; found, 5.14 |

EXAMPLE 193

Methods similar to those of Chem. Pharm. Bull. 36(6), 2050–2060, (1988) were used to prepare Example 193 as follows:

In a 250 mL round bottom flask, 9.84 g (32.77 mmol) of Example 23 was dissolved in 48 mL of DMF. The flask was placed under Ar. Thiopivalic acid (8.4 mL, 66.09 mmol, 2 eq) was added to the flask via syringe followed by addition of 3.2 mL of a 1.93M solution of $K_2CO_3$ in $H_2O$. The mixture was then stirred at 25° C. for 23 h.

The reaction was diluted with 200 mL $H_2O$ and acidified with 10% HCl to pH=1. The mixture was extracted with ethyl acetate (100 mL, x3). The combined organic extracts were washed with water (100 mL, x4), dried over magnesium sulfate and concentrated in vacuo to yield crude product (13.16 g, 96% crude).

The crude material was dissolved in ethanol, treated with activated carbon, filtered and concentrated in vacuo. The residue was recrystallized from ethyl acetate and hexane to yield 11.2g (81%) of white crystals. MP 119–120° C.

EXAMPLE 194 AND EXAMPLE 195

Example 193 (1.38 g injected in several portions) was separated by chromatography on a Chiralcel® OJ HPLC column (2 cmx25 cm) using 9 ml/min. 85% hexane/15% (0.2% trifluoroacetic acid in ethanol) and peak detection by UV at 320 nM. The best fractions of each isomer were combined and each material was then recrystallized from ethyl acetate/hexane to yield 520 mg of pure Example 194 (first to elute) and 504 mg of pure Example 195 (second to elute).
Example 194: $[a]_D$ +26.4 ($CHCl_3$).
Example 195: $[a]_D$ −27.0 ($CHCl_3$).

EXAMPLE 196

The above method for the preparation of Example 193 was used to prepare Example 196 using thiophenol and Example 23. MP 125–126° C.

EXAMPLE 197

A solution of Example 196 (24 g, 0.058 mol) and (+)-cinchonine (10 g, 0.034 mol) in acetone (150 mL) was allowed to stand at room temperature for 46 h. The white precipitate was removed by filtration, suspended in ethyl acetate and washed successively with 2N HCl (150 mL) and sat. aq. NaCl (100 mL). The organic layer was dried over $MgSO_4$, filtered and concentrated under reduced pressure to give a white solid (8.4 g, isomer ratio 95.3:4.7 (Example 197:Example 198)). A second iteration (Cinchonine, 6.75 g; acetone, 140 mL) followed by simple crystallization with an ethyl acetate/hexanes mixture (1:2) provided Example 197 (6.67 g, 56% theoretical; isomer ratio 99.3:0.7) as a white crystalline solid. $[a]_D$ +84.8° (c 1.5, acetone).

EXAMPLE 198

Purified samples of this isomer could be obtained by HPLC on a Chiralpak® AD column (cmx25 cm) using ethanol/hexane (1:9.+0.15% trifluoroacetic acid added to the ethanol). With these conditions Example 198 eluted second and could be obtained pure only from very small injections. Use of a proprietary chiral stationary phase according to the general procedures of: D. Arlt, B. Boemer, R. Grosser and W. Lange, Angew. Chem. Int. Ed. Engl. 30 (1991) No. 12, pages 1662–1664 yielded larger quantities of pure material with isomer ratio <1:>99. The best chromatograpy fractions were freed of solvent by evaporation in vacuo and then the residue (830 mg) was recrystallized from ethyl acetate/hexane mixture to yield pure material (479 mg). $[a]_D$ −79.8° (c 1.0, acetone).

The above methods for the preparation of Examples 193–198 were used to prepare the following series of biphenyl containing products (TABLE XIV) using the appropriate thiol-containing reagent and Example 23.

TABLE XIV

Structure: 4'-chloro-biphenyl-4-yl-CO-CH2-CH(CH2-S-R8)-COOH

| ex. | R8 | isomer | m.p.(° C.)/other characterization |
|---|---|---|---|
| 193 | (CH3)3CCO | R, S | 119–120 |
| 194 | (CH3)3CCO | | [a]$_D$ +26.4 (CHCl3) |
| 195 | (CH3)3CCO | | [a]$_D$ −27.0 (CHCl3) |
| 196 | Ph | R, S | 125–126 |
| 197 | Ph | | [a]$_D$ +84.8° (c 1.5, acetone) |
| 198 | Ph | | |
| 199 | 2-thiophene | R, S | 136–137 |
| 200 | Ac | R, S | 140–141 |
| 201 | 4-methoxybenzyl | R, S | 126–127 |
| 202 | PhCO | R, S | 162–164 |
| 203 | PhCH2 | R, S | 155–157 |
| 204 | 4-hydroxyphenyl | R, S | 162–163 |
| 205 | 2-phenylethyl | R, S | 105–106 |
| 206 | 4-methoxyphenyl | R, S | 138–139 |
| 207 | 3-phenylpropyl | R, S | 82–83 |
| 208 | 4-fluorophenyl | R, S | 112–113 |
| 209 | 4-chlorophenyl | R, S | 152–153 |
| 210 | 4-bromophenyl | R, S | 153–154 |
| 211 | 4-methylphenyl | R, S | 125–127 |
| 212 | 4-ethylphenyl | R, S | 122–123 |
| 213 | 4-t-butylphenyl | R, S | 122–123 |
| 214 | cyclohexyl | R, S | MS (FAB-LSIMS) 417[M+H]+ |
| 215 | 3,4-dimethoxypheny | R, S | 144–145 |
| 216 | 3,4-dichlorophenyl | R, S | 156–157 |
| 217 | 2-hydroxymethylphenyl | R, S | 111–112 |
| 218 | 2-fluorophenyl | R, S | 131–132 |
| 219 | 2-bromophenyl | R, S | 159–160 |
| 220 | 2-ethylphenyl | R, S | 134–135 |
| 221 | 2-isopropylphenyl | R, S | 149–150 |
| 222 | 4-pyridyl | R, S | 190–191 |
| 223 | 4-acetaminophenyl | R, S | 165–166 |
| 224 | 4-nitrophenyl | R, S | 211–212 |
| 225 | HO-CO-CH2-CH2-C6H4---- | R, S | 172–173 |
| 226 | 2-naphthyl | R, S | 155–156 |
| 227 | 1-naphthyl | R, S | 168–169 |
| 228 | 3-bromophenyl | R, S | 167–168 |
| 229 | 2-methoxyphenyl | R, S | 115–116 |
| 230 | 2-chlorophenyl | R, S | 153–154 |
| 231 | 3-methylphenyl | R, S | 137–138 |
| 232 | 2-methylphenyl | R, S | 130–131 |
| 233 | 2-(CO2H)-C6H4---- | R,S | 221–222 |
| 234 | 3-methoxyphenyl | R, S | 143–144 |
| 235 | 3,5-dimethoxyphenyl | R, S | 175–176 |
| 236 | 3-trifluoromethylphenyl | R,S | 114–115 |
| 237 | 4-carbomethoxyphenyl | R, S | 152–153 |

TABLE XIV-continued

[Structure: 4'-chloro-biphenyl-4-yl ketone with CH2-S-R8 and CO2H substituents]

| ex. | R⁸ | isomer | m.p.(° C.)/other characterization |
|---|---|---|---|
| 238 | 4-(HO₂CCH₂)phenyl | R, S | 162–163 |
| 239 | i-Pr | R, S | 110–111 |
| 240 | 2-hydroxyphenyl | R, S | 148–149 |
| 241 | quinolin-8-yl | R, S | 172–173 |
| 242 | 3-chlorophenyl | R, S | 164–165 |
| 243 | 3-fluorophenyl | R, S | 135–136 |
| 244 | 2-(CO₂Me)phenyl | R, S | 167–168 |
| 432 | 3-(CO₂Me)phenyl | R, S | 132–133 |
| 433 | 2,6-dimethylphenyl | R, S | 190–191 |
| 434 | 5-fluoro-2-(CO₂Me)phenyl | R, S | 160–161 |
| 435 | 3-(Et₂NOC)phenyl | R, S | 165–166 |
| 436 | 2-(CONMe₂)phenyl | R, S | |
| 437 | 3-(Me₂NOC)phenyl | R, S | 156–157 |

EXAMPLE 444

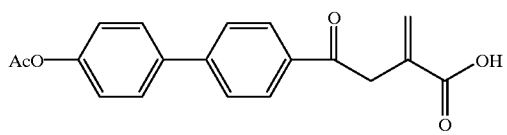

Step 1 The desired product was obtained from acetoxybiphenyl and itaconic anhydride according to the procedure of Example 23. MP 200–201° C.

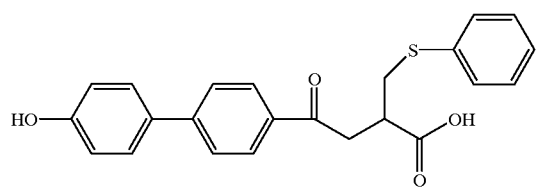

Step 2—Preparation of Example 444. Example 444 was prepared from the product of step 1 and thiophenol according to the procedure for the preparation of Example 193. Reaction conditions led to cleavage of the acetyl group as well as addition of thiophenol to the acrylate. MP 137–138° C.

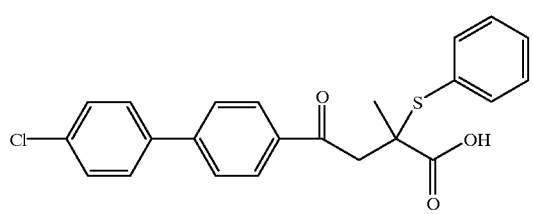

Example 245

EXAMPLE 245

Mother liquors from crystallization of crude Example 196 were chromatographed on silica gel to yield a purified sample of the isomeric product Example 245. Anal. C: calcd, 67.23; found, 66.92. H: calcd, 4.66; found, 4.66. Cl: calcd, 8.63; found, 8.72. S: calcd, 7.80; found 7.69.

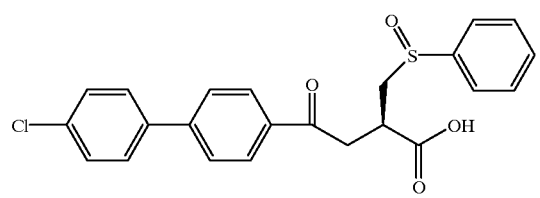

Example 246 and Example 247

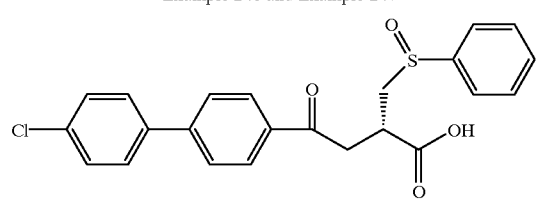

Example 248 and Example 249

EXAMPLE 246, EXAMPLE 247, EXAMPLE 248 AND EXAMPLE 249

A sample of Example 196 was stored for several days as a solution in a mixed solvent containing tetrahydrofuran which also contained significant quantities of peroxides. This resulted in the formation of significant quantities of the isomeric sulfoxides Example 246, Example 247, Example 248 and Example 249 which were separated into pure fractions by chromatography on chiral HPLC stationary phases. These same compounds can also be isolated from aged samples of Example 196 or its isomers Example 197 or Example 198 or samples of the same materials in solution with added hydrogen peroxide. The two sulfoxides Example 248 and Example 249 are often found as contaminants in aged air oxidized samples of Example 197 and therefore must share the C-2 stereochemistry of Example 197, but differ in the stereochemistry at the sulfoxide oxygen. Likewise Example 246 $[a]_D$ –99.7 (c 0.6, acetone) and Example 247 are found in aged samples of Example 198 and therefore share the C-2 stereochemistry of Example 198, but differ in stereochemistry at sulfoxide.

Example 246: $[a]_D$ –99.7 (c 0.6, acetone).
Example 247: $[a]_D$ +100.6 (c 0.6, acetone).
Example 248: $[a]_D$ –97.4 (c 0.6, acetone).
Example 249: $[a]_D$ +95.6 (c 0.6, acetone).

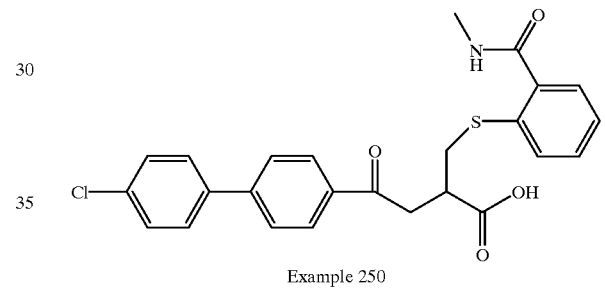

Example 250

EXAMPLE 250

A solution of Example 244 (20.9 mg, 0.0445 mmol) in THF (1.5 mL) was cooled in a dry ice/acetone bath. The reaction vessel was sealed with a rubber septum and methylamine gas was bubbled through for approximately 1 min. The reaction was allowed to warm to room temperature and stirred for several h. Concentration under reduced pressure and recrystallization from ethyl acetate and hexane provided Example 250 as white crystals. MP 185–186° C.

EXAMPLE 251

In a 25 mL round bottom flask, 209.8 mg (0.732 mmol) of Example 29 was dissolved in 5 mL of 1,4-Dioxane. The flask was placed under Ar. Thiophenol, 0.1 mL (0.934 mmol, 1.33 eq) was added to the flask via syringe. The mixture was then stirred at 25° C. At 102 h an additional 0.1 mL of thiophenol was added via syringe. The mixture stirred for a total of 125 h. The reaction was then concentrated in vacuo and the residue was recrystallized from ethyl acetate and hexane to yield 93.0 mg (32%) of white crystals. MP 168–169° C.

The above method for the preparation of Example 251 was used to prepare the following biphenyl containing products (TABLE XV) using Example 29 and the appropriately substituted thiol starting material.

TABLE XV

| example | R⁶a | isomer | m.p.(° C.)/other characterization |
|---|---|---|---|
| 251 | PhS | R, S | 168–169 |
| 252 | PhCH₂S | R, S | 162–164 |

EXAMPLE 253 (REFERENCE COMPOUND)

This compound was prepared using a method similar to that used for Example 193 except that thiolacetic acid was used instead of thiopivalic acid and Example 28 was used instead of Example 23. MP 94.0–95.0° C.

The above method for the preparation of Example 253 was used to prepare the following phenyl containing products (TABLE XVI) using thiol acetic acid and the appropnately substituted olefinic starting material.

TABLE XVI

| example | (T)ₓA | isomer | m.p.(° C.)/other characterization |
|---|---|---|---|
| 253ᵃ | Me | R, S | 94–95 |
| 254ᵃ | Cl-C₆H₄-O- | R, S | 91–92 |

ᵃReference compound.

EXAMPLE 255

195.3 mg (0.650 mmol) of Example 32 and 120.9 mg 2-mercaptothiophene were dissolved in 3 ml of distilled THF. The reaction was purged with argon and stirred at ambient temperature overnight. The volatile components were removed in vacuo to give a crude solid that was recrystallized (EtOAc-hexane) to give 140.0 mg (52%) of Example 255. MP 160.0–161.0° C.

The above method for the preparation of Example 255 was used to prepare the following series of biphenyl containing products (TABLE XVII) using the appropriate thiol-containing reagent and Example 32.

TABLE XVII

| example | R⁸ | isomer | m.p.(° C.)/other characterization |
|---|---|---|---|
| 255 | 2-thiophene | R, S | 160–161 |
| 256 | (CH₃)₃CCO | R, S | 106–107.5 |
| 257 | Ph | R, S | 135–136 |
| 258ᵃ | Ac | R, S | 118–119 |

ᵃReference compound.

EXAMPLE 259

Example 29 (0.36 mmol) was dissolved in 10 ml of 1,4-dioxane under argon at ambient temperature 1.06 eq of thiomorpholine was added to the solution and within 5 minutes a precipitate began to form. Some additional 1,4-dioxane was added to make the mixture easier to stir. Stirring continued overnight. The solid was removed by filtration and dried in vacuo to yield 129 mg of the free base form of Example 259 as a solid product.

The hydrochloride salt of the product was formed by suspending the initial solid in EtOH and bubbling HCl gas into the suspension until clear. Et₂O was used to precipitate the salt which was collected by filtration to give final product Example 259. MS (FAB-LSIMS) 390 [M+H]⁺.

The above method for the preparation of Example 259 was used to prepare the following biphenyl containing products (TABLE XVIII) using Example 29 and the appropriate amine starting material. In each case the initial products were converted to hydrochlorides as above before assay as inhibitors of MMPs.

TABLE XVIII

| example | R⁶a | isomer | m.p.(° C.)/other characterization |
|---|---|---|---|
| 259 | thiomorpholine·HCl | R, S | MS (FAB-LSIMS) 390 [M+H]⁺ |

TABLE XVIII-continued

![structure showing Cl-biphenyl-C(O)-CH2-CH(R6a)-C(O)OH]

| example | R⁶a | isomer | m.p.(° C.)/other characterization |
|---|---|---|---|
| 260 | [diphenylmethylamine·HCl structure] | R, S | MS (FAB-LSIMS) 470 [M+H]⁺ |
| 261 | [2,6-dimethylmorpholine·HCl structure] | R, S | MS (FAB-LSIMS) 402 [M+H]⁺ |

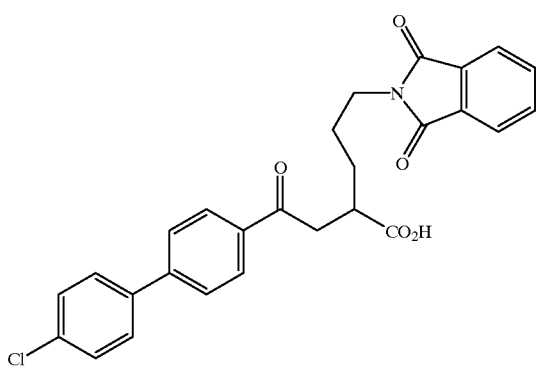

Example 262

EXAMPLE 262

This compound was prepared using the general procedure of Example 114 except that commercial dimethyl 2-(3-N-phthalimidopropyl)malonate was used instead of ethyl 2-carboethoxy-5-phenylpentanoate. Also the following procedures were used instead of the treatment of the crude oil with NaOH in ethanol/water and successive steps. The substituted diester (product from steps 1,2, and the first half of 3) was dissolved in a 1:4 solution of concentrated hydrochloric acid:glacial acetic acid in a sealed vessel and heated to 110° C. for 18h. After cooling, solvent was removed under reduce pressure. The resultant was concentrated from hexanes (2×25 mL) and toluene (2×25 mL) affording a solid which was chromatographed on silica gel with 3% acetic acid/ethyl acetate. MP 191–192° C.

EXAMPLE 263

Step 1 The bromomethylketone product from step 2 of the Example 114 preparation was recrystallized from ethyl acetate. In a 50 mL round bottom flask, 1.22 g (3.94 mmol) of this purified material was dissolved in 12 mL of dimethoxyethane (DME). Sodium iodide, 618.9 mg (4.13 mmol, 1.05 eq) was added to the flask to yield solution 1.

In a separate flask, 1.00 g (4.34 mmol, 1.1 eq) of commercial diethyl (2-dimethylaminoethyl)malonate was dissolved in 4 mL of DME. Sodium ethoxide, 336 mg (4.69 mmol) was added to the flask to yield solution 2.

Solution 1 was added to solution 2 and the mixture stirred at 25° C. for 1.5 h. The reaction was concentrated in vacuo and the residue dissolved in chloroform. The chloroform was washed twice with a 10% solution of potassium carbonate and once with a solution of sodium bisulfite. The organic layer was dried over magnesium sulfate, filtered and concentrated in vacuo.

Step 2 The residue from step 1 was dissolved in 20 mL of a 1:1:1 mixture of ethanol/water/tetrahydrofuran and 6 mL of 1.0 N NaOH was added. The mixture was refluxed for several days, diluted with water, acidified with 10% HCl to pH=3 and condensed.

Step 3—Preparation of Example 263. The resultant solid was mixed with 100 mL of 1 N HCl and refluxed for 8 h. The mixture was filtered and the solid was washed with hot ethanol. The ethanol washes were concentrated and crystals were collected. The filtrate was concentrated to dryness and recrystallized from ethyl acetate to produce 15.6 mg (3.7%) of white crystals of Example 263. MP 207–208° C.

The above method for the preparation of Example 263 was used to prepare the following biphenyl containing products (TABLE XIX). In each case the initial products were converted to hydrochlorides as above before assay as inhibitors of MMPs.

TABLE XIX

![structure: Cl-biphenyl-C(O)-CH2-CH(R6a)-C(O)OH]

| example | R⁶a | isomer | m.p.(° C.)/other characterization |
|---|---|---|---|
| 263 | HCl.Me₂N(CH₂)₂ | R, S | 207–208 |
| 264 | HCl.Et₂N(CH₂)₂ | R, S | 185–186 |
| 265 | CF₃CO₂H.Et₂N(CH₂) | R, S | MS (FAB-LSIMS) 402[M+H]⁺ |

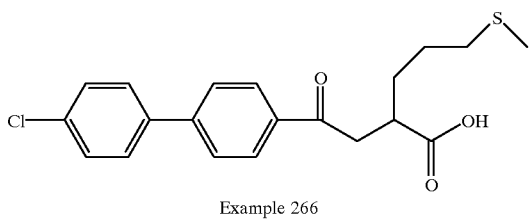

Example 266

EXAMPLE 266

Example 266 was prepared in a manner similar to Example 263 except that diethyl 2-(3-methylthiopropyl)malonate was used instead of diethyl (2-dimethylaminoethyl)malonate. The crude diester intermediate was not washed with base. It was chromatographed over silica gel using hexanes and ethyl acetate. After the final acidification the product was extracted into ethyl acetate and concentrated. The residue was dissolved in 1,4-dioxane and refluxed to decarboxylate. The crude product was then chromatographed over silica gel using ethyl acetate and acetic acid. The product was recrystallized from ethyl acetate and hexane. MP 134–135° C.

EXAMPLE 267

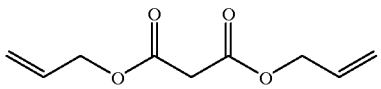

Step 1 A solution of malonic acid (100 g, 0.9 mol) in allyl alcohol (250 mL) was treated with sulfuric acid (0.25 mL) and heated to 70° C. for 12 h. After cooling to room temperature the solution was concentrated to about ⅓ of its original volume and diluted with hexanes (500 mL). The mixture was washed successively with satd. aq. $K_2CO_3$ and NaCl. The organic layer was dried over $Na_2SO_4$, filtered and concentrated under reduced pressure. Purification by distillation (85° C.@0.01 mmHg) provided diallyl malonate (156 g, 88%) as a colorless oil. $^1H$ NMR (300 MHz, $CDCl_3$) d 5.85 (m, 2H), 5.30 (m, 2H), 5.20 (m, 2H), 4.60 (m, 4H), 3.40 (s, 2H).

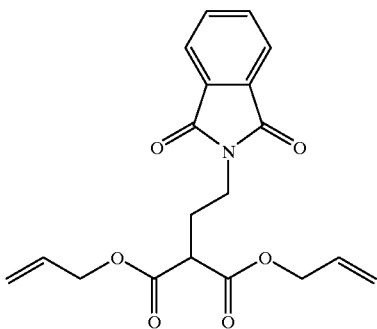

Step 2 A solution of sodium hydride (4.35 g, 0.18 mol) in freshly distilled THF (100 mL) was cooled to 0° C. and treated with diallyl malonate (35 g, 0.19 mol) over 40 min via a dropping funnel. After stirring at room temperature for 30 min, N-(2-bromoethyl)phthalimide (43.9 g, 0.17 mol) was added to the solution in one portion and the mixture was heated to reflux. After 48 h the solution was cooled to 0° C., quenched with 2N HCl and concentrated to about 20% of its original volume. The concentrate was diluted with ethyl acetate (300 mL) and washed successively with satd. aq. $K_2CO_3$ and NaCl. The organic layer was dried over $MgSO_4$, filtered and concentrated under reduced pressure. Purification by flash column chromatography (5–25% ethyl acetate:hexanes) provided diallyl 2-phthalimidoethylmalonate (41.2 g, 67%) as a colorless oil. $^1H$ NMR (300 MHz, $CDCl_3$) d 7.82 (m, 2H), 7.72 (m, 2H), 5.85 (m, 2H), 5.30 (m, 2H), 5.22 (m, 2H), 4.60 (m, 4H), 3.80 (t, J=6.6 Hz, 2H), 3.46 (t, J=7.2 Hz, 1H), 2.30 (dd, J=13.8, 6.9 Hz, 2H).

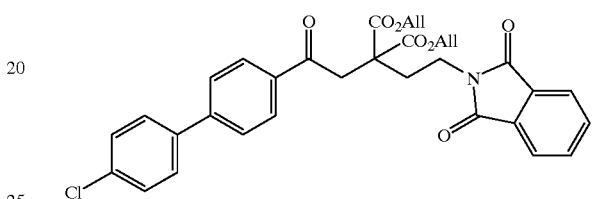

Step 3 A solution of diallyl 2-phthalimidoethylmalonate (38.0 g, 0.106 mol) in freshly distilled THF (200 mL) was cooled to 0° C. and added via cannula to a second solution of NaH (2.5 g, 0.106 mol) in THF (50 mL) at 0° C. After warming to room temperature and stirring for 40 min, the product of Example 114, step 2 (36.1 g, 0.117 mol) was added in three portions over 5 min and the mixture was heated to reflux. After 12 h the solution was cooled to 0° C., quenched with 2N HCl and concentrated under reduced pressure. The concentrate was diluted with dichloromethane (250 mL) and washed successively with satd. aq. $K_2CO_3$ and NaCl. The organic layer was dried over $MgSO_4$, filtered and concentrated. Crystallization from ethyl acetate provided diallyl (2-phthalimidoethyl) 4'-(4'-chlorophenyl) acetophenone malonate (49.1 g, 83%) as an off white crystalline solid (additional material was recovered with successive recrystallizations): $R_F$ 0.4 (30% ethyl acetate:hexanes).

Step 4—Preparation of Example 267. A solution of the diallyl disubstituted malonate (45.6 g, 77.5 mmol) in a 1,4-dioxane/water soln (300 mL, 5% water) was treated with tetrakis(triphenylphosphine)palladium (0.5 g, 0.4 mmol) in one portion followed by pyrrolidine (14.2 mL, 171 mmol) dropwise over 1 h. After stirring for an additional 30 min, the solution was diluted with ethyl acetate (600 mL) and washed with 2N HCl. The organic layer was concentrated under reduced pressure to give the corresponding diacid as a white crystalline solid. The diacid could be easily recrystallized from chloroform or ethyl acetate, but was generally taken on to the next step without further purification. The diacid was dissolved in 1,4-dioxane (300 mL) and heated to reflux for 36 h. After cooling to room temperature, the solution was concentrated and recrystallized from 1,4-dioxane: toluene to give the desired acid (31 g, 86%) as a white crystalline solid. MP 209–210° C.

EXAMPLE 268

Example 267 (racemate) was separated into its most active (Example 268 first off column) and less active (Example 269 second off column) enantiomers on a Pirkle type L-Leucine HPLC column using a 2%-acetic acid in ethanol/dichloromethane/hexanes mixture (2/25/73) as an eluent.

Example 268: $[a]_D$ –9.7° (c 1.3, DMF).

The above methods for the preparation of Examples 267–269 were used to prepare the following biphenyl containing products (TABLE XX) using the appropriate a-haloketone in step 3.

TABLE XX

| example | $(T)_x$ | isomer | m.p.(° C./other characterization |
|---|---|---|---|
| 267 | Cl | R, S | 209–210 |
| 268 | Cl | | $[a]_D$ –9.7° (c 1.3, DMF). |
| 269 | Cl | | Second off Pirkle type L-Leucine HPLC column |
| 270 | Br | R, S | 223 |
| 271[a] | PhCH$_2$O | R, S | 210 |
| 272[a] | n-pentO | R, S | 163–164 |
| 273[a] | EtO | R, S | 106–107 |

[a]Preparation of 1-(2-bromoethanone)-4-(4-benzyloxyphenyl)-benzene:

Step 1 A one-necked, 250-mL, round-bottomed flask equipped with an argon inlet adapter was charged with 50 mL acetone, 50 mL H$_2$O, 4'-hydroxy-4-biphenylcarbonitrile (10.0 g, 51.2 mmol), benzyl bromide (35.0 g, 24.3 mL, 20.5 mmol) and potassium carbonate (28.0 g, 203 mmol). The resulting mixture was heated at reflux for 12 h. Upon cooling to room temperature, the product precipitated as white hexagonal crystals in the acetone layer. The aqueous layer was removed, and 4'-benzyloxy-4-biphenylcarbonitrile isolated in quantitative yield via filtration. MP 151° C.

Step 2

A one-necked, 250-mL, round-bottomed flask equipped with a rubber septum and an argon needle inlet was charged with 70 mL THF, 4'-benzyloxy-4-biphenylcarbonitrile (10.0 g, 35.0 mmol) and cooled to o° C. while a solution of methyllithium (1.4 M in diethyl ether, 37.5 mL, 52.5 mmol) was added dropwise via syringe over ca. 2 min. The resulting mixture was stirred for 12 h at room temperature. The reaction mixture was added to an ice cold solution of 1:1 water:concentrated sulfuric acid (600 mL) and extracted with ethyl acetate. The resulting organic phase was dried over Na$_2$SO$_4$, filtered, and concentrated to afford a yellow solid which was recrystallized from ethyl acetate to provide a quantitative yield of the desired methyl ketone. TLC (50% ethyl acetate-hexanes) R$_f$ = 0.64.

Step 3

A one-necked, 100-mL, round-bottomed flask equipped with a rubber septum and an argon needle inlet was charged with 35 mL THF, 4'-benzyloxy-4-biphenyl methyl ketone (1.00 g, 3.31 mmol) and cooled to –78° C. while a solution of LiHMDS (1.0 M in THF, 3.31 mL, 3.31 mmol) was added dropwise via syringe over ca. 1 min. The cooling bath was removed and the resulting mixture was stirred at room temperature until the solution was clear. The reaction mixutre was cooled to –78° C. while trimethylsilyl chloride (0.395 g, 0.461 mL, 3.64 mmol) was added dropwise via syringe over ca. 1 min. The resulting mixture was stirred for 30 min at –78° C. The reaction mixture was added to an ice cold mixture of hexanes (100 mL) and a saturated NaHCO$_3$ solution (100 mL). The resulting organic phase was dried over Na$_2$SO$_4$, filtered, and concentrated to afford a yellow solid which was immediately subjected to the next transformation. TLC (C-18 silica, MeCN) R$_f$ = 0.59.

TABLE XX-continued

| example | $(T)_x$ | isomer | m.p.(° C./other characterization |
|---|---|---|---|

Step 4 A one-necked, 100-mL, round-bottomed flask equipped with a rubber septum and an argon needle inlet containing crude silyl enol ether was charged with 25 mL and cooled to 0° C. while N-bromosuccinimide (0.587 g, 3.30 mmol) was added in one portion. After 15 min, the cooling bath was removed and the reaction mixture was added to a mixture of ehtyl acetate (50 mL) and water (100 mL). The resulting organic phase was dried over Na$_2$SO$_4$, filtered, and concentrated to afford 1-(2-bromoethanone)-4-(4-benzyloxyphenyl)-benzene which was suitable for immediate use as an alkylating agent. TLC (C-18 silica, MeCN) R$_f$ = 0.71. This procedure was also used to prepare 1-(2-bromoethanone)-4-(4-ethoxyphenyl)-benzene and 1-(2-bromoethanone)-4-(4-pentyloxyphenyl)-benzene.

Example 276

EXAMPLE 276

The methods for the preparation of Example 267 were used to prepare Example 276 using commercially available N-(bromomethyl)phthalimide in step 2. MP 190–193° C.

Example 431

EXAMPLE 431

The methods for the preparation of Example 267 were used to prepare Example 431 using commercially available N-(4-bromobutyl)phthalimide in step 2. MP 168–169° C.

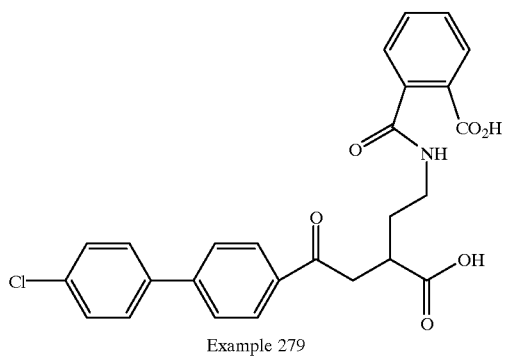

Example 279

EXAMPLE 279

Example 267 (50 mg, 0.11 mmol) was suspended in 5 ml water. A solution of NaOH (9.1 mg, 0.23 mmol) in 5 mL water was added and stirred for 18 h. Concentrated HCl was added dropwise until the solution was acidified. Precipitate was filtered off and dried in vacuo to afford 33 mg (64%) of the desired product. MP 93–100° C.

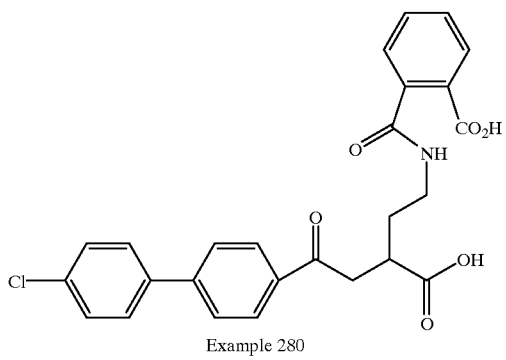

Example 280

EXAMPLE 280

The method for the preparation of Example 279 was used to prepare enantiomerically pure Example 280 from enantiomerically pure Example 268. MP 79–89° C.

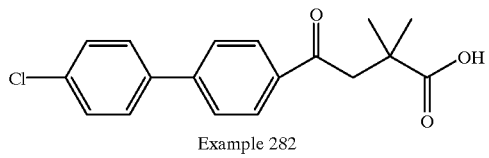

Example 282

EXAMPLE 282

This compound was prepared by a similar method to that used for Example 23, except that 2,2-dimethylsuccinic anhydride was used instead of itaconic anhydride. MP 179–180° C.

The above method for the preparation of Example 282 was used to prepare the following biphenyl containing products (TABLE XXI).

TABLE XXI

| ex. | $R^6a$ | $R^6b$ | $R^6c$ | $R^6d$ | isomer | m.p.(° C.)/other characterization |
|---|---|---|---|---|---|---|
| 282 | Me | Me | H | H | | 179–180 |
| 283a | Me | H | Me | H | racemic | 157–159 |
| 284a | H | Me | Me | H | racemic | 165–167 |

[a]Preparation of 2,3-Dimethyl succinic anhydride: To the 2,3-dimethyl succinic acid (5.13 g, 35.1 mmol), was added acetyl chloride (8.27 g, 7.49 mL, 105 mmol) at room temperature. The reaction mixture was refluxed at about 65° C. for 2 h. Workup consisted of concentration in vacuo, and drying in high vacuo.
The desired product (4.95 g. with a little impurity of acetic acid) was obtained as a white solid. H-NMR ($CDCl_3$) d isomer #1: 1.25(d, 6H), 3.18–3.23(m, 2H); isomer #2: 1.36(d, 6H). 2.71–2.77(m, 2H).

EXAMPLE 285, EXAMPLE 286, AND EXAMPLE 287

These compounds were prepared in a similar manner to Example 1, except that the indicated anhydrides were used instead of dihydro-3-(2-methylpropyl)-2,5-furandione:

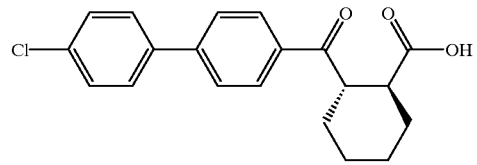

Example 285 (racemate)

Example 285: From trans-cyclohexane-1,2-dicarboxylic acid anhydride: MP 187–188° C.

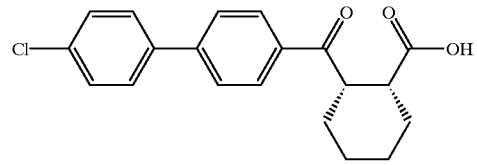

Example 286 (racemate)

Example 286: From cis-cyclohexane-1,2-dicarboxylic acid anhydride: MP 180–181° C.

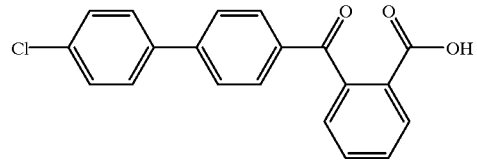

Example 287

Example 287: From phthalic anhydride: MP >230° C.

EXAMPLE 288

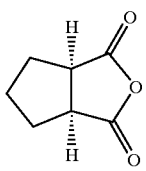

Step 1 To trans-cyclopentane-1,2-dicarboxylic acid (1.16 g, 7.33 mmol) at room temperature, was added acetic anhydride (10 mL). The reaction mixture was refluxed at about 165° C. for 14 h. Workup consisted of concentration in vacuo and co-evaporation with toluene three times. The crude product (1.0 g, ~100%, with a little impunty of acetic anhydride) was given as a brown oily solid. $^1$H-NMR (CDCl$_3$) d 3.55–3.35 (m, 2H), 2.4–2.2 (m, 2H), 2.15–1.75 (m, 5H), 1.55–1.35 (m, 1H).

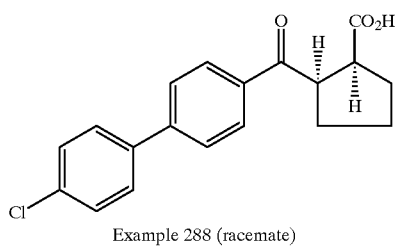

Example 288 (racemate)

Step 2—Preparation of Example 288.

Produced using the general method of Example 1 except that 1,2-dichloroethane was used as solvent and the anhydride made in step 1 was used instead of dihydro-3-(2-methylpropyl)-2,5-furandione. The product (1.0 g, 43%) purified by chromatography on silica gel to yield a residue containing both cis and trans isomers. The cis isomer Example 288 (160 mg) was isolated by several recrystallizations. MP 176–178° C.

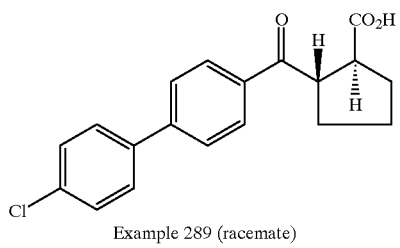

Example 289 (racemate)

EXAMPLE 289

To the trans isomer containing mother liquor of Example 288 (110 mg, 0.334 mmol) in THF (5 mL), was added 1,8-Diazabicyclo [5.4.0] undec-7-ene (75 mL, 0.502 mmol) at room temperature. The reaction mixture was stirred under argon for 48 h. Workup consisted of dilution with CH$_2$Cl$_2$ (15 mL), addition of 1N HCl (15 mL), separation, extraction of the aqueous with CH$_2$Cl$_2$ (15 mL×3), drying the combined organic layers over MgSO$_4$, filtration and concentration in vacuo. The crude product (98 mg, 89%) was purified by HPLC, to provide pure trans compound Example 289 as a white solid. MP 169–172° C.

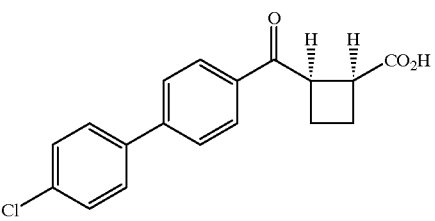

Example 290 (racemate)

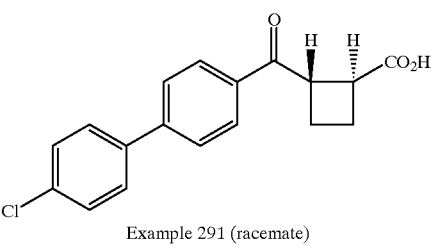

Example 291 (racemate)

EXAMPLE 290 AND EXAMPLE 291

These compounds were produced using the general method of Example 1 except that 1,2-dichloroethane was used as solvent and cyclobutanedicarboxylic anhydride was used instead of dihydro-3-(2-methylpropyl)-2,5-furandione. The crude product (0.72 g, 30%) contained a mixture of cis and trans isomers (cis: trans=2/1). MS (FAB-LSIMS) 315 [M+H]$^+$.

Example 290: The crude product was purified by chromatography on silica gel to provide 40 mg of the cis isomer as a white solid. MP 154–156° C.

Example 291: To the suspension of the crude two component product (14.5 g, 46.06 mmol) in MeOH (250 mL) at room temperature, was added excess K$_2$CO$_3$. The reaction mixture was stirred at room temperature for 48 h. Workup consisted of addition of 2N HCl (500 mL), extraction of the aqueous layer with CH$_2$Cl$_2$ (7×400 mL), washing the combined organic layers with sat. NaCl (1200 mL), drying over MgSO$_4$, filtration and concentration in vacuo. The crude product (13.2 g, 91%) was given as off-white solid with 84% de in favor of the trans isomer. The recrystallization was carried out to provide 9.1 g of pure trans material as white crystals. MP 184–186° C.

EXAMPLE 292

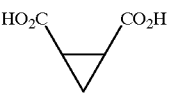

Step 1 To a solution of 1,2-cis-dimethylcyclopropane dicarboxylate ester (4.71 g, 29.8 mmol) in THF (100 mL) at room temperature, was added 1N NaOH (150 mL). The reaction mixture was stirred under argon for 14 h. Workup consisted of separation of THF layer from the aqueous, washing the aqueous with diethyl ether, acidification the aqueous with 2N HCl, concentration to dryness, dilution with EtOAc, filtration and concentration in vacuo. The desired product (3.5 g, 90%) was given as a white solid. $^1$H-NMR (DMSO-d6) d 4.21 (bs, 2H), 1.29–1.24 (m, 1H), 0.71–0.65 (m, 1H).

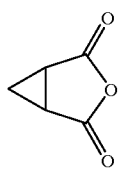

Step 2 To the cyclopropane-1,2-dicarboxylec acid (3.24 g, 24.9 mmol) at room temperature, was added acetic anhydride (30 mL). The reaction mixture was refluxed for 4 h. Workup consisted of concentration in vacuo to provide the desired product. $^1$H-NMR (DMSO-d6) d 2.00 (dd, J=4.04, J'=8.08, 2H), 0.90–0.83 (m, 2H).

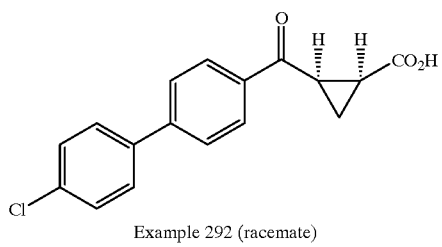

Example 292 (racemate)

Step 3—Preparation of Example 292 (Reference compound). Produced using the general method of Example 1 except that 1,2-dichloroethane was used as solvent and the anhydride of step 2 above was used instead of dihydro-3-(2-methylpropyl)-2,5-furandione. MP 175–176° C.

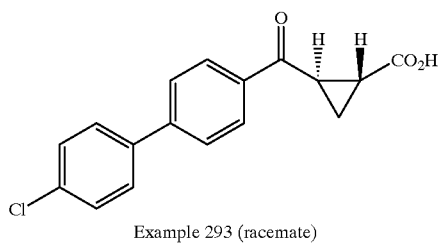

Example 293 (racemate)

EXAMPLE 293 (REFERENCE COMPOUND)

To a solution of Example 292 (50 mg, 0.166 mmol) in MeOH (20 mL) at room temperature, was added excess $K_2CO_3$. The reaction mixture was stirred at room temperature for 48 h. Workup consisted of addition of 1N HCl (25 mL), extraction of the aqueous layer with $CH_2Cl_2$ (4×25 mL), washing the combined organic layers with sat. NaCl (50 mL), drying over $MgSO_4$, filtration and concentration in vacuo. The product (50 mg, 100%) was given as a white solid with >99% de in favor of the trans isomer. MP 181–183° C.

EXAMPLE 294 AND EXAMPLE 295

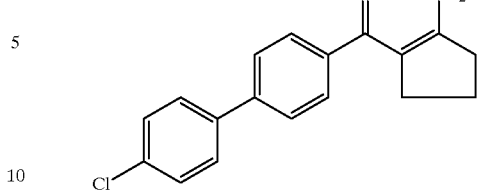

Step 1 Using the general method of Example 1 except that the solvent was 1,2-dichloroethane and 1-Cyclopentene-1,2-dicarboxylic anhydride was used instead of dihydro-3-(2-methylpropyl)-2,5-furandione, the above compound (27.7 g) was obtained as white crystals in 91% yield. MP 226–227° C.

EXAMPLE 439

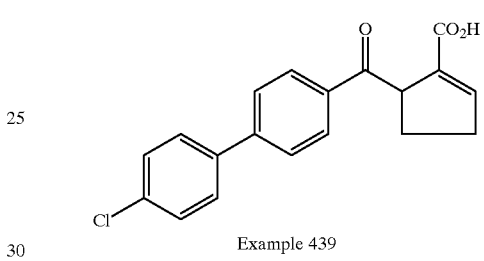

Example 439

Step 2—Preparation of Example 439. To a solution of diisopropylamine (19 mL, 130 mmol) in THF (60 mL) at −78° C., was added n-butyllithium (78 mL, 125 mmol). The LDA was stirred for 30 min at −78° C. and then treated with a solution of the product from step 1 (10.2 g, 31.2 mmol) in THF (100 mL). The reaction mixture was stirred under argon at −78° C. for 1.5 h, and quenched with AcOH (21 mL, 375 mmol). The resulting mixture was allowed to warm to room temperature during a period of 2 h. Workup consisted of addition of 1N HCl (100 mL), extraction of the aqueous with $CH_2Cl_2$ (3×150 mL), and concentration in vacuo. The crude product was recrystallized from EtOAc to provide 6.22 g of the above compound as off-white crystals. MP 202–204° C.
Step 3—Preparation of Example 294 and Example 295. To a solution of the product from step 2 (919 mg, 2.81 mmol) in DMF (6 mL) at room temperature under argon, was added thiophenol (433 mL, 4.22 mmol) and $K_2CO_3$ in $H_2O$ (2 M, 141 mL, 0.281 mmol). The reaction mixture was stirred under argon at room temperature for 18 h. Workup consisted of dilution with $CH_2Cl_2$ (15 mL), acidification with 2N HCl, addition of $H_2O$ (20 mL), washing the organic layer with $H_2O$ (3×40 mL), sat. NaCl (30 mL), drying over $MgSO_4$, filtration and concentration in vacuo. The crude product was purified by chromatography on silica gel to provide two separated diastereomers, trans-trans Example 294 and trans-cis Example 295 in a total yield of 46%.
Example 294: MP 177–178° C.
Example 295: MP 184–185° C.

EXAMPLE 296 AND EXAMPLE 297

Enantiomeric separation of Example 294 was carried out by using a Diacel® AD semi-prep column (2 cm×25 cm) with 15% IPA (with 1% $H_2O$ and 0.1% TFA) in hexane to provide enantiomer Example 296 with >98% ee, and enantiomer Example 297 with >97% ee.

Example 296: (+)-enantiomer; MP 165–167° C.
Example 297: (−)-enantiomer; MP 168–169° C.

EXAMPLE 298

The above methods for the preparation of Example 294 were used to prepare Example 298 using the appropriate commercially available thiol. MP 227–228° C.

EXAMPLE 299 AND EXAMPLE 300

Isomers of Example 298 were separated by chromatography on a chiralpak AD® HPLC column to yield the enantiomers Example 1299 and Example 300.
Example 299. MP 124–125° C.; $[a]_D$ +18.69 (c 0.73, acetone)
Example 300: MP 132–133° C.; $[a]_D$ −17.92 (c 1.16, acetone)

EXAMPLE 301

A 0.6 ml portion of 1 N sodium hydroxide was added to a suspension of 100 mg of Example 298 in 3 ml of methanol. After stirring at ambient temperature, tlc assay still showed starting material, so another 0.3 ml of NaOH solution was added and stirring was continued for a total of 40 h, after which tlc showed no starting material remained. Solvent was removed by evaporation in vacuo and the residue was mixed with water and 10% HCl and then extracted several times with ethyl acetate. The combined extracts were dried ($MgSO_4$) and evaporated in vacuo. The residue was recrystallized from ethyl acetate/hexane to yield 72.6 mg of Example 301 as a white powder. MP 216–217° C. (dec.).

The above methods for the preparation of Examples 294–301 were used to prepare the following biphenyl containing products (TABLE XXII).

TABLE XXII

|       |                | stereochemistry |      |         | m.p.(° C.)/other           |
|-------|----------------|------|------|---------|---------------------------|
| ex.   | $R^8$          | 1,2  | 2,3  | isomer  | characterization          |
| 294   | Ph             | trans | trans | racemic | 179–180 |
| 295   | Ph             | trans | cis   | racemic | 184–185 |
| 296   | Ph             | trans | trans | (+)     | 165–167 |
| 297   | Ph             | trans | trans | (−)     | 168–169 |
| 298   | $CO_2Me$ (phenyl) | trans | cis | racemic | 227–228 |
| 299   | $CO_2Me$ (phenyl) | trans | cis | (+)     | $[a]_D$ +18.69 (c 0.73, acetone) |
| 300   | $CO_2Me$ (phenyl) | trans | cis | (−)     | $[a]_D$ −17.92 (c 1.16, acetone) |
| 301   | $CO_2M$ (phenyl) | trans | cis | racemic | 216–217 (dec) |
| 302   | 4-fluorophenyl | cis   | cis   | racemic | MS (FAB-LSIMS) 455 $[M+H]^+$ |
| 303   | 4-fluorophenyl | trans | cis   | racemic | 211–212 |
| 304   | 2-methylphenyl | trans | trans | racemic | 173–176 |
| 305   | 2-methylphenyl | cis   | cis   | racemic | MS (FAB-LSIMS) 451 $[M+H]^+$ |
| 306   | 2-methylphenyl | trans | cis   | racemic | 196–197 |

TABLE XXII-continued

| | | stereochemistry | | | m.p.(° C.)/other |
|---|---|---|---|---|---|
| ex. | R[8] | 1,2 | 2,3 | isomer | characterization |
| 307 | 2-CO2Me-phenyl | trans | trans | racemic | MS (FAB-LSIMS) 495 [M+H]+ |
| 308 | 2-CO2Me-phenyl | cis | cis | racemic | MS (FAB-LSIMS) 495 [M+H]+ |
| 399 | 4-fluorophenyl | trans | trans | racemic | 164–166 |
| 310 | 4-chlorophenyl | trans | trans | racemic | 213–214 |
| 311 | 4-chlorophenyl | trans | cis | racemic | 210–211 |
| 440 | PhCH2 | trans | cis | racemic | 155–156 |
| 441 | PhCH2 | trans | trans | racemic | |

Example 312

Example 313

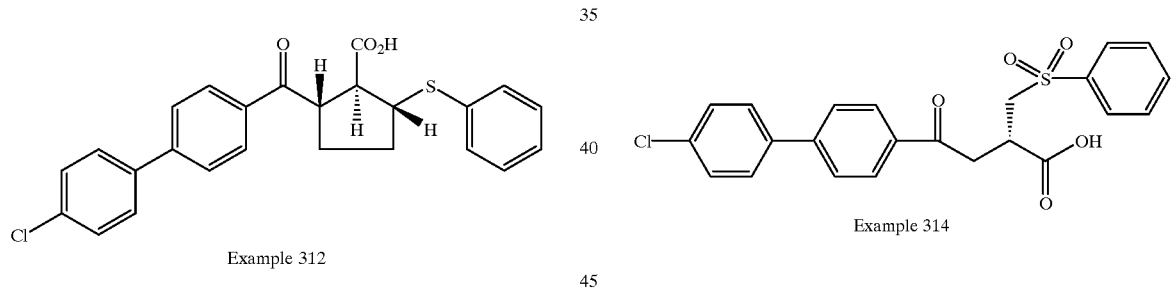

Example 314

EXAMPLE 312 AND EXAMPLE 313

The racemate from Example 295 was separated into enantiomers by chromatography on a Chiralpak AD® HPLC column. Example 312 eluted first. $^1$H-NMR spectra identical to that of Example 295.

EXAMPLE 314

A 5 ml portion of 30% aqueous hydrogen peroxide was added to a suspension of 2.00 g of Example 197 in 25 ml of acetic acid/water (1:1). After stirring this mixture overnight, another 2 ml of hydrogen peroxide solution was added followed by another 24 h stirring. The mixture was heated to 40–60° C. for 2.5 h and then stirred at room temperature overnight. The resultant solution was diluted with water and extracted three times with ethyl acetate and then three times with methylene chloride. The combined extracts were dried (MgSO$_4$) and evaporated in vacuo. The residue was recrystallized from ethyl acetate/hexane to yield a total of 1.64 g of Example 314 in three crops of white powder, MP 159.5–161.0° C.; [a]$_D$ +19.59 (c=0.485, acetone).

EXAMPLE 315 AND EXAMPLE 316

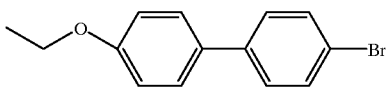

Step 1 To a solution of 4-(4-bromophenyl)-phenol (4.06 g, 16.3 mmol) in acetone (30 mL) at room temperature, was added 4.5 eq $K_2CO_3$ (4.0 M, 18 mL, 73.3 mmol) in water and 4.0 eq iodoethane (5.26 mL, 65.2 mmol). The reaction mixture was stirred overnight, and heated to reflux for 6 hr. The product was crystallized out of the solution, and filtered. The crude product was recrystallized from hexane to provide ethyl 4-(4-bromophenyl) phenyl ether (4.1 g, 91%) as white crystals. $^1$H NMR (CDCl$_3$) d 7.53 (d, J=8.83 Hz, 2H), 7.47 (d, J=6.62 Hz, 2H), 7.41 (d, J=8.46 Hz, 2H), 6.96 (d, J=8.82 Hz, 2H), 4.07 (q, J=6.99 Hz, 2H), 1.44 (t, J=6.99 Hz, 3H).

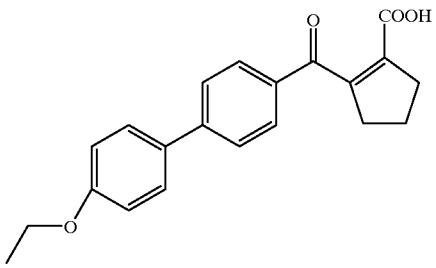

Step 2 To the solution of ethyl 4-(4-bromophenyl) phenyl ether (12.87 g, 46.43 mmol) in THF (90 mL), was added t-BuLi (1.7 M, 54.6 mL, 92.87 mmol) at −78° C. The reaction mixture was stirred under argon at −78° C. for 3 h, and treated with 1-cyclopentene-1,2-dicarboxylic anhydride (6.73 g, 48.75 mmol). The resulting mixture was stirred at −78° C. for 2 h, and then warmed to room temperature. Workup consisted of addition of 1N HCl (150 mL), extraction with EtOAc (4×200 mL), and concentration in vacuo. The crude product (18 g) was recrystallized from EtOAc to provide the intermediate acylacrylic acid (6.8 g, 43%) as an off-white solid. $^1$H NMR (CDCl$_3$) d 7.88 (d, J=8.09 Hz, 2H), 7.63 (d, J=8.45 Hz, 2H), 7.56 (d, J=8.82 Hz, 2H), 6.98 (d, J=9.19 Hz, 2H), 4.09 (q, J=6.99 Hz, 2H), 2.84 (m, 4H), 2.10 (m, 2H), 1.45 (t, J=6.99 Hz, 3H).

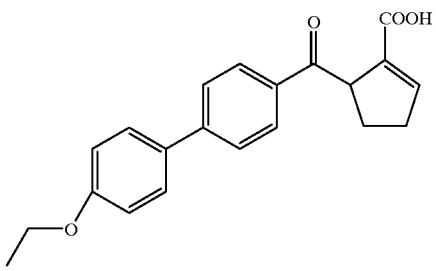

Step 3 To the solution of intermediate from step 2 (3.45 g, 10.25 mmol) in THF (100 mL) at −78° C., was added 4.0 eq LiN(TMS)$_2$ (1 M, 41.03 mL, 41.03 mmol). The resulting yellow mixture was stirred under argon at −78° C. for 18 h, quenched with AcOH (~10 mL), and then allowed to warm to room temperature. Workup consisted of addition of 1N HCl (120 mL), extraction with EtOAc (4×130 mL), washing the combined organic layers with sat. NaCl (250 mL), drying over MgSO$_4$, filtration and concentration in vacuo. The crude product was purified by recrystallization from EtOAc to provide a rearranged acrylic acid intermediate (2.40 g, 70%) as an off-white solid. $^1$H NMR (CDCl$_3$) d 7.89 (d, J=8.64 Hz, 2H), 7.50 (d, J=8.09 Hz, 2H), 7.42 (d, J=8.83 Hz, 2H), 6.85 (s, 1H), 6.83 (d, J=8.83 Hz, 2H), 4.64 (m, 1H), 3.94 (q, J=6.99 Hz, 2H), 2.47 (m, 2H), 2.35 (m, 1H), 1.85 (m, 1H), 1.29 (t, J=6.99 Hz, 3H).

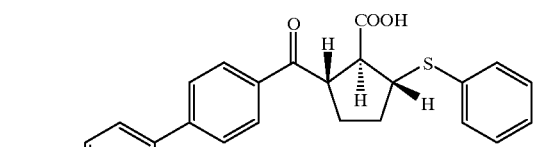

Example 315 (racemate)

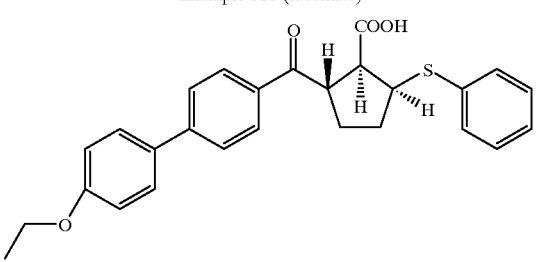

Example 316 (racemate)

Step 4—Preparation of Example 315 and Example 316. To the solution of intermediate from step 3 (510 mg, 1.52 mmol) in DMF (2 mL) at room temperature under argon, was added thiophenol (311 mL, 3.03 mmol) and freshly made K$_2$CO$_3$ in H$_2$O (2 M, 75 mL, 0.15 mmol). The homogeneous solution was stirred at room temperature overnight. Workup consisted of acidification with 2N HCl (1 mL), addition of H$_2$O (10 mL), extraction with CH$_2$Cl$_2$ (2×15 mL), filtration through silica, and concentration in vacuo. The crude product was purified by HPLC (0–8% EtOAc/CH$_2$Cl$_2$) to provide two separated diastereomers, trans-trans isomer Example 315 and trans-cis isomer Example 316.

Example 315: Anal. C: calcd, 72.62; found, 72.74; H: calcd, 5.87; found, 5.84.

Example 316: Anal. C: calcd, 72.62; found, 72.39; H: calcd, 5.87; found, 5.87.

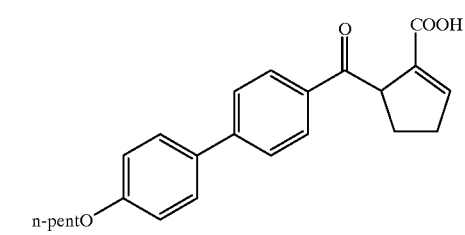

Example 442

EXAMPLE 442

Example 442 was prepared according to steps 1–3 of the procedure for the preparation of Example 315 and Example 316. MP 172–173° C.

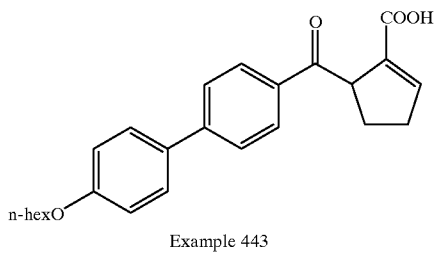

Example 443

EXAMPLE 443

Example 443 was prepared according to steps 1–3 of the procedure for the preparation of Example 315 and Example 316. MP 174–177° C.

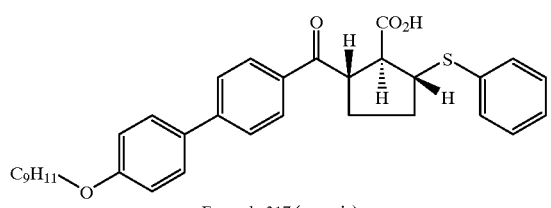

Example 317 (racemic)

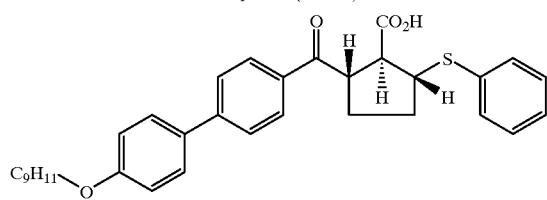

Example 318 (racemic)

EXAMPLE 317 AND EXAMPLE 318

These materials were made in a similar method to that used for Examples 315 and 316 except that 1-iodopentane was used instead of iodoethane in step 1. All intermediates and the final products were characterized by $^1$H-NMR.

Example 317: MP 148–150° C.

EXAMPLE 319, EXAMPLE 320, EXAMPLE 321 AND EXAMPLE 322

A mixture (1.8 g) of the compounds Example 317 and Example 318 was separated by chromatography on a Chiralcel OJ® HPLC column to yield the enantiomers of each compound. The enantiomers of each compound were identified by having identical $^1$H-NMR spectra to their respective racemates.

Example 319: 105 mg; (−) isomer of Example 318

Example 320: 75 mg; (+) isomer of Example 318

Example 321: 160 mg; (−) isomer of Example 317

Example 322: 115 mg; (+) isomer of Example 317

EXAMPLE 323

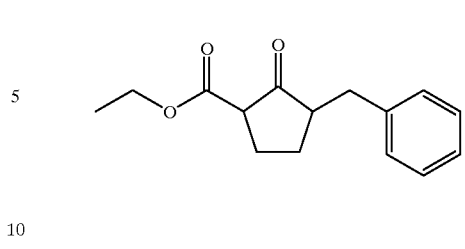

Step 1 To a solution of diisopropylamine (30.8 mL, 220 mmol) in THF (100 mL) at −78° C., was added n-BuLi (2 M, 100 mL, 200 mmol). The LDA solution was stirred at −78° C. for 30 min., and followed by addition of ethyl-2-oxocyclopentanecarboxylate (15.6 g, 14.8 mL, 100 mmol). The reaction mixture was allowed to warm to 0° C. for 30 min. After cooling down to −78° C., the reaction mixture was treated with benzyl chloride (12.66 g, 11.51 mL, 100 mmol). The resulting mixture was warmed to 0° C. for 3 h. Workup consisted of acidification with 2N HCl (100 mL), extraction with EtOAc (4×100 mL), drying over MgSO$_4$, filtration and concentration in vacuao. The crude product was purified by MPLC (5–15% EtOAc/hexane) to provide the indicated intermediate (7.1 g, 29%) as a clear oil.

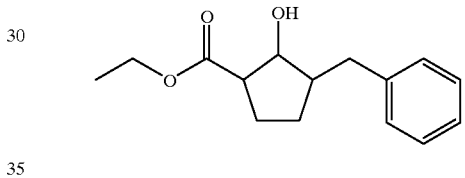

Step 2 To a solution of intermediate from step 1 (7.28 g, 29.56 mmol) in EtOH (50 mL) at 0° C., was added NaBH$_4$ (1.12 g, 29.56 mmol). The reaction mixture was stirred at room temperature for 3 h under argon, and then quenched by sat. NH$_4$Cl (100 mL). Workup consisted of extraction with EtOAc (4×100 mL), drying over MgSO$_4$, filtration and concentration in vacuo. The crude product was given as a yellow oil.

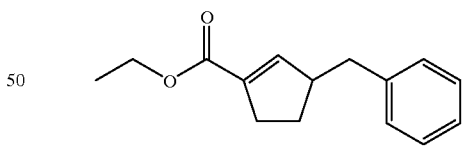

Step 3 To a solution of triphenylphosphine (14.64 g, 55.8 mmol) and DEAD (7.99 mL, 50.74 mmol) in THF (100 mL) at room temperature, was added the solution of intermediate from step 2 (6.30 g, 25.37 mmol) in THF (~50 mL). The reaction mixture was refluxed overnight under argon. Workup consisted of concentration in vacuo. The crude product was purified by MPLC twice (2% EtOAc/hexane) to provide the above intermediate (2.85 g, 49%). $^1$H NMR (CDCl$_3$) d 7.35–7.15 (m, 5H), 6.68 (bs, 1H), 4.20 (q, 2H), 3.15 (m, 1H), 2.80–2.45 (m, 4H), 2.10 (m, 1H), 1.65 (m, 1H), 1.29 (t, 3H).

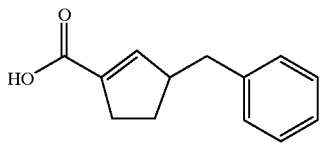

Step 4 To a solution of intermediate from step 3 (2.8 g, 12.16 mmol) in DME (35 mL) at room temperature, was added LiOH.H$_2$O (5.1 g, 121.6 mmol) in H$_2$O (~35 mL). The resulting mixture was heated to reflux for 3 h. Workup consisted of acidification with 2N HCl (~100 mL), extraction with EtOAc (4×100 mL), washing the combined organic layers with sat. NaCl, drying over MgSO$_4$, filtration, concentration and co-evaporation with toluene (3×50 mL). The desired intermediate as shown above (2.35 g, 96%) was given as a white solid. $^1$H NMR (CDCl$_3$) d 7.35–7.15 (m, 5H), 3.15 (m, 1H), 2.80–2.65 (m, 2H), 2.65–2.45 (m, 2H), 2.15 (m, 1H), 1.70 (m, 1H).

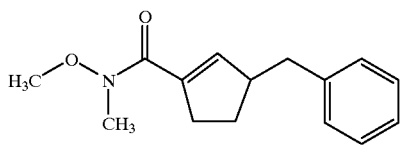

Step 5 To a solution of intermediate from step 4 (2.3 g, 11.34 mmol) in THF (80 mL) at 0° C., was added DCC (2.82 g, 13.65 mmol), and HOBT (1.84 g, 13.65 mmol). The resulting mixture was stirred for about 1 h, and followed by addition of N,O-dimethyl-hydroxylamine hydrochloride (2.22 g, 22.74 mmol) and Et$_3$N (3.96 mL, 28.43 mmol). The reaction mixture was allowed to warm to room temperature and stirred overnight. Workup consisted of filtration, washing the filter cake with EtOAc, concentration in vacuo. The crude product was purified by HPLC (elution: 7–15% EtOAc/CH$_2$Cl$_2$) to provide intermediate as shown above (2.56 g, 92%) as light yellow oil. $^1$H NMR (CDCl$_3$) d 7.25 (m, 2H), 7.15 (m, 3H), 6.38 (m, 1H), 3.55 (s, 3H), 3.20 (s, 3H), 3.10 (m, 1H), 2.65 (m, 4H), 2.05 (m, 1H), 1.60 (m, 1H).

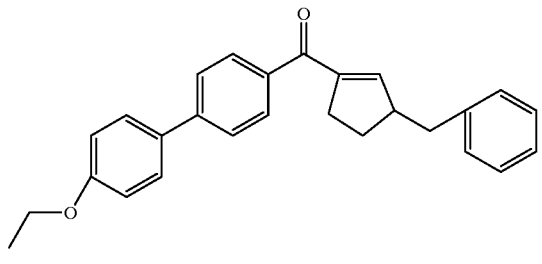

Step 6 To a solution of ethyl 4-(4-bromophenyl) phenyl ether (830 mg, 2.99 mmol) in THF (6 mL), was added t-BuLi (1.7 M, 3.52 mL, 5.99 mmol) at −78° C. The reaction mixture was stirred under argon at −78° C. for 1 h, and treated with intermediate from step 5 (770 mg, 3.14 mmol). The resulting mixture was stirred at −78° C. for 30 min, 0° C. for 30 min, and room temperature for 30 min. Workup consisted of addition of 1N HCl (25 mL), extraction with EtOAc (4×20 mL), filtration through silica, and concentration in vacuo. The crude product was purified by HPLC (elution: 5–20% EtOAc/hexane) to provide the intermediate as shown above (400 mg, 35%) as an off-white solid. $^1$H NMR (CDCl$_3$) d 7.80 (d, J=8.46 Hz, 2H), 7.62 (d, J=8.46 Hz, 2H), 7.57 (d, J=8.83 Hz, 2H), 7.29 (m, 2H), 7.21 (m, 3H), 7.00 (d, J=8.82, 2H), 6.46 (bs, 1H), 4.10 (q, J=6.99 Hz, 2H), 3.30 (m, 1H), 2.84 (m, 4H), 2.20 (m, 1H), 1.75 (m, 1H), 1.46 (t, J=6.99 Hz, 3H).

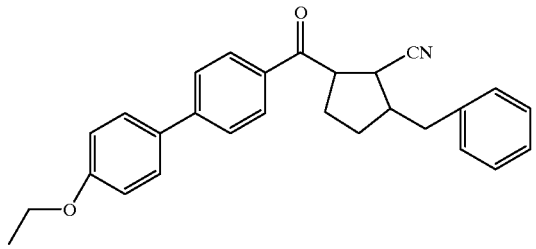

Step 7 To a solution of intermediate from step 6 (205 mg, 0.53 mmol) in toluene (5 mL) at 0° C., was added diethylaluminum cyanide (1N, 2.1 mL, 2.1 mmol) in toluene. The reaction mixture was stirred at room temperature for 2 h under argon. Workup consisted of addition of 1N HCl (20 mL), extraction with EtOAc (4×20 mL), washing the combined organic layers with sat. NaCl, drying over MgSO$_4$, filtration and concentration in vacuo. The crude product was carried to the next step.

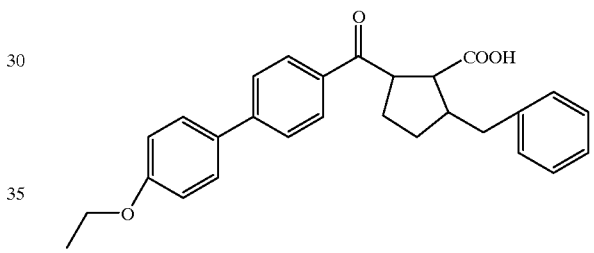

Step 8 To a solution of the crude intermediate from step 7 in dioxane (5 mL) at room temperature, was added 50% H$_2$SO$_4$ (5 mL). The reaction mixture was refluxed for 18 h. Workup consisted of addition of EtOAc (25 mL), washing the organic layer with H$_2$O (3×15 mL), drying over MgSO$_4$, filtration and concentration in vacuo. The crude product was carried to the next step.

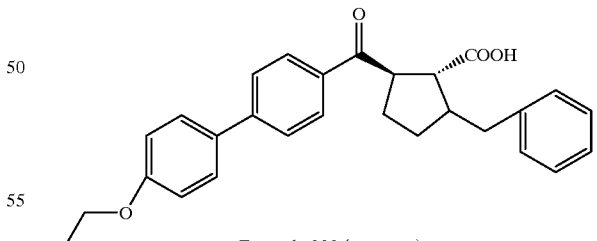

Example 323 (racemate)

Step 9—Preparation of Example 323. To a solution of crude intermediate from step 8 in THF (5 mL) at room temperature, was added excess DBU. The reaction mixture was stirred overnight. Workup consisted of dilution with EtOAc (30 mL), washing with 2N HCl (2×10 mL), filtration through silica and concentration in vacuo. The crude product was purified by HPLC and recrystallization from EtOAc to provide Example 323 as off-white solid. MP 138–139° C.

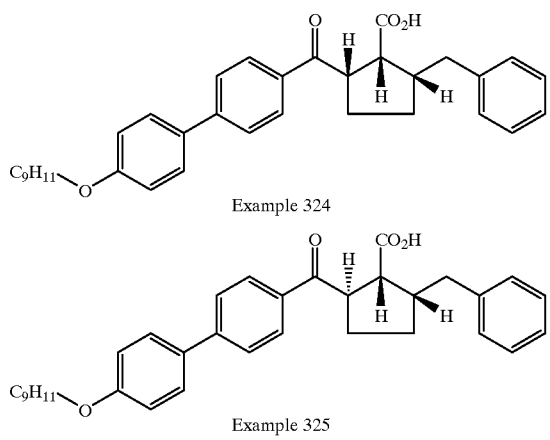

Example 324

Example 325

EXAMPLE 324 AND EXAMPLE 325

The racemate was made in a similar method to that used for Example 323 except that pentyl 4-(4-bromophenyl)phenyl ether (as prepared in the Example 317 synthesis) was used instead of ethyl 4-(4-bromophenyl)phenyl ether in step 6. The racemate was then separated into enantiomers using a Chiralpak AD column with Example 324 eluting first. Intermediates and final products were identified by $^1$H-NMR.

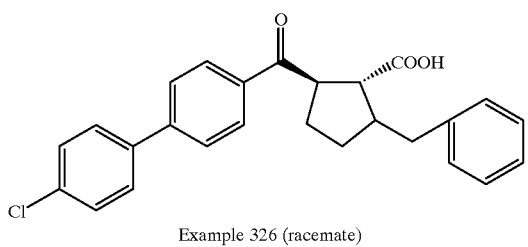

Example 326 (racemate)

EXAMPLE 326

Example 326 was obtained through the same synthetic sequence preparing Example 323, by using 4-bromo-4'-chloro biphenyl in the place of ethyl 4-(4-bromophenyl)phenyl ether at step 6. MP 170–171° C.

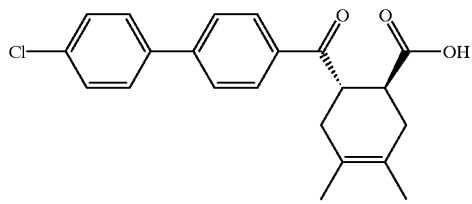

Example 327 (racemate)

EXAMPLE 327

To a suspension of 4-Oxo-4-(4'-chloro-4-biphenyl)but-2-enoic acid, Example 29 (0.941 g, 3.28 mmol) in MeOH (5 mL) at room temperature, was added 2,3-dimethyl-1,3-butadiene (2.69 g, 3.71 mL, 32.8 mmol). The reaction mixture was refluxed under argon for a total of 2.5 h. Workup consisted of concentration in vacuo. The crude product was purified by recrystallization from MeOH to yield 950 mg of Example 327 as a white solid. MP 217.0–220.0° C.

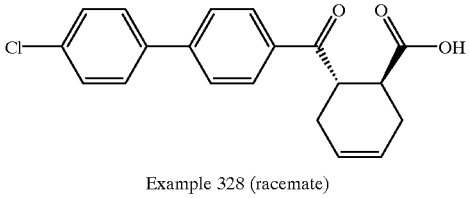

Example 328 (racemate)

EXAMPLE 328

To a suspension of 4-Oxo-4-(4'-chloro-4-biphenyl)but-2-enoic acid, Example 29 (1.01 g, 3.53 mmol) in MeOH (5 mL) at −78° C., was added excess butadiene for 30 min, and followed by addition of DMF (5 mL). The reaction mixture was refluxed under argon for a total of 72 h. Workup consisted of dilution with EtOAc (15 mL), addition of water (15 mL), and extraction of the aqueous layer with EtOAc (3×15 mL). The combined organic layers were washed with sat. NaCl, dried over MgSO$_4$, and concentrated in vacuo. The crude product was purified by chromatography (EtOAc/hexane) to yield 140 mg of Example 328 as a white solid. MP 185.0–186.0° C.

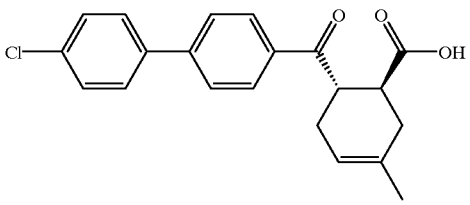

Example 329 (racemate)

EXAMPLE 329

To a suspension of 4-Oxo-4-(4'-chloro-4-biphenyl)but-2-enoic acid, Example 29 (1.208 g, 4.21 mmol) in MeOH (5 mL) at room temperature, was added isoprene (2.87 g, 4.21 mL, 42.1 mmol). The reaction mixture was refluxed under argon overnight. Workup consisted of concentration in vacuo. The crude product was purified by chromatography (EtOAc/hexane) and recrystallization (three times) to yield 20 mg of Example 329 as a white solid. MP 174.0–177.0° C.

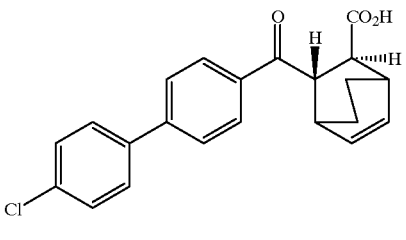

Example 330 (racemate)

EXAMPLE 330

To a solution of 4-Oxo-4-(4'-chloro-4-biphenyl)but-2-enoic acid, Example 29 (1.123 g, 3.915 mmol) in THF (7 mL) at room temperature, was added 5 eq 1,3-cyclohexadiene (1.87 mL, 19.577 mmol). The reaction mixture was stirred under refluxed for 18 h. Workup consisted of concentration in vacuo. The crude product was purified by HPLC to provide the desired product Example 330 (570 mg, 40%) as a white solid containing two isomers. MP 174–176° C.

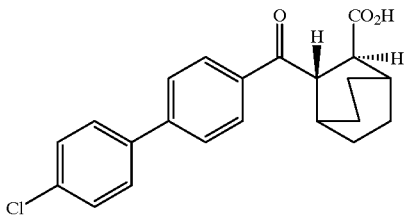

Example 331 (racemate)

EXAMPLE 331

The mixture of Example 330 (299 mg, 0.815 mmol) and p-Toluenesulfono hydrazide (1.5 g, 8.15 mmol) was dissolved in dimethoxyethane (20 mL), and allowed to warm to reflux. A solution of sodium acetate (1.0 g, 12.2 mmol) in water (16 mL) was added over a period of 4 h. The reaction mixture was cooled to room temperature, poured into water (120 mL), and extracted with $CH_2Cl_2$ (4×70 mL). The combined organic layers were washed with 150 mL water, dried over $MgSO_4$ and concentrated in vacuo. The crude product was purified by HPLC to provide the desired product Example 331 (85 mg, 28%). MP 191–193° C.

EXAMPLE 332

A dry dichloromethane (10 mL) solution of 4-chlorobiphenyl (0.76 g, 4 mmol) and 3-methylglutaric anhydride (0.52 g, 4 mmol) in a 50-mL flask was chilled using an ice bath. Solid aluminum chloride (1.1 g, 8 mmol) was cautiously added over several minutes. The reaction mixture was stirred for 20 h while warming to room temperature. After 20 h, the reaction mixture was re-cooled with an ice bath and quenched with 10% HCl (10 mL). The layers were separated and the aqueous phase was back-extracted with dichloromethane (2×10 mL) The combined organic portions were washed with brine (25 mL), dried ($Na_2SO_4$), and concentrated in vacuo. The resulting yellow-white solid was recrystallized (ethyl acetate-hexane) to afford white microcrystals of Example 332. MP 140.5–142.5° C.

The above method for the preparation of Example 332 was used to prepare the following biphenyl containing products (TABLE XXIII).

TABLE XXIII

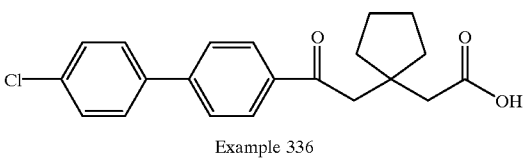

| ex. | $R^6a$ | $R^6b$ | isomer | m.p.(°C.)/other characterization |
|---|---|---|---|---|
| 332[a] | H | Me | R, S | 140.5–142.5 |
| 333[a] | H | H |  | 174–176 |
| 334 | Me | Me |  | 152–154.5 |
| 335 | Et | Me | R, S | 130.0–131.0 |

[a]Reference compound.

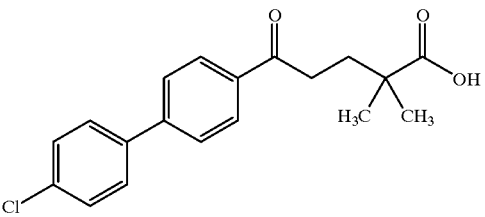

Example 336

EXAMPLE 336

This compound was prepared in a similar manner to Example 1, except that 3,3-tetramethyleneglutaric anhydride was used instead of dihydro-3-(2-methylpropyl)-2,5-furandione. MP 139–140° C.

Example 337

EXAMPLE 337

This compound was prepared in a similar manner to Example 1, except that 2,2-dimethylglutaric anhydride was used instead of dihydro-3-(2-methylpropyl)-2,5-furandione. The crude product was purified via flash column chromatography (gradient elution, dichloromethane to dichloromethane-methanol (99.5:0.5)) followed by recrystallization (ethyl acetate-hexane) to provide white microcrystals of Example 337. MP 163.5–164.0° C.

EXAMPLE 338

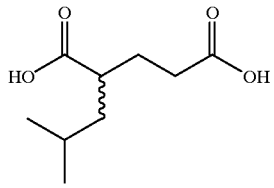

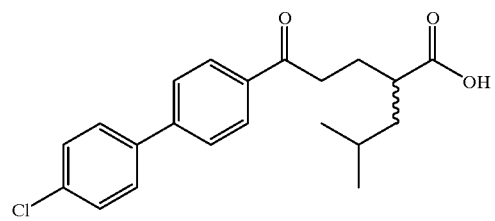

Example 338

Step 1 To a 25-mL round-bottomed flask was added diethyl isobutyl malonate (2.82 g, 13 mmol), t-butanol (8.6 mL), and 30% methanolic KOH solution (0.25 mL, 1.3 mmol). Acrylonitrile (0.86 mL, 13 mmol) was added via syringe and the reaction mixture was heated to 33° C. using an oil bath. After stirring for 3 h under inert atmosphere the reaction mixture was quenched with 2M HCl (1 mL) and diluted with distilled water (15 mL) and ether (20 mL). The separated aqueous phase was back-extracted with ether (2×20 mL). The combined organic portions were dried ($Na_2SO_4$) and concentrated in vacuo to afford an oil with solid precipitate (3.42 g). This crude material was used in the next step without purification. A portion of the crude oil and solid (1.5 g) was dissolved in 48% HBr (6 mL). The solution was held at reflux under inert atmosphere for 24.5 h after which the solution was concentrated almost to dryness. The residue was partitioned between distilled water (20 mL) and ether (20 mL). The separated aqueous layer was back-extracted with ether (2×20 mL). The combined organic portions were then dried and concentrated in vacuo to yield an oily residue (1.5 g). $^1$H-NMR indicated reaction completion, so the remaining crude nitrile diester (1.9 g) was subjected to the above hydrolytic conditions to provide an additional amount of the crude substituted glutaric acid (1.5 g). The crude lots were combined (3.0 g total) and purified via flash column chromatography [gradient elution, dichloromethane to dichloromethane-methanol (98.2)] to afford the desired compound as a white solid (1.64 g, 69%). $^1$H NMR (DMSO-$d_6$) d 0.83 (dd, J=6.6 Hz, 2.9 Hz, 6H), 1.16 (m, 1H), 1.36–1.56 (m, 2H), 1.61 (q, J=7.4 Hz, 2H), 2.17 (m, 2H), 2.28 (m, 1H), 12.11 (s, 2H).

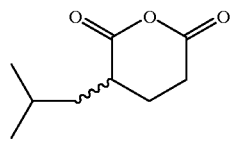

Step 2 To a 100-mL round-bottomed flask was added the product of step 1 (1.62 g, 8.6 mmol) and acetic anhydride (10 mL). The reaction mixture was held at reflux for 2 h, and then cooled to room temperature. Volatiles were removed via vacuum distillation (0.1 Torr, 20–60° C.). The crude product was dried under vacuum (0.1 Torr) at 80° C. for 14 h to yield the desired compound as a brown oil which was used without further purification (1.15 g, 79%). IR (neat) 1805, 1762 cm$^{-1}$.

Step 3—Preparation of Example 338. From 2-isobutylglutaric anhydride rather than 3-methylglutaric anhydride and using the general procedure of Example 334. The crude product was purified via flash column chromatography [gradient elution, dichloromethane to dichloromethane-methanol (98.5:1.5)] followed by recrystallization (ethyl acetate-hexane) to provide white microcrystals of Example 338. MP 129.0–130.5° C.

EXAMPLE 339

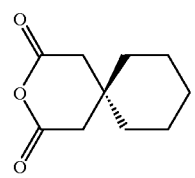

Step 1 To a 100-mL round-bottomed flask was added 1,1-cyclohexanediacetic acid (2.03 g, 9.99 mmol) and acetic anhydride (11.6 mL). The reaction mixture was held at reflux for 2 h, and then cooled to room temperature. Volatiles were removed via vacuum distillation (0.1 Torr, 20–60° C.). The resulting crude product was dried under vacuum (0.1 Torr) at 80° C. for 14 h to yield the desired compound as a white solid which was used without further purification (1.75 g, 96%). IR (neat) 1813, 1770 cm$^{-1}$.

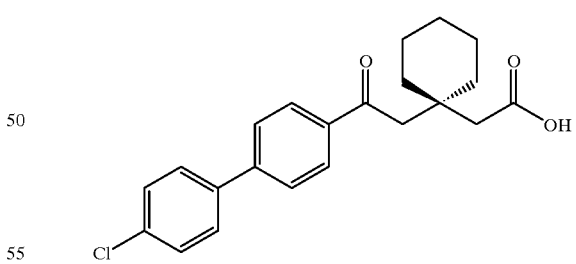

Example 339

Step 2—Preparation of Example 339. From 3,3-pentamethyleneglutaric anhydride rather than 3-methylglutaric anhydride and using the general procedure of Example 332. The crude product was purified via flash column chromatography (gradient elution, dichloromethane to dichloromethanemethanol (97:3)) followed by recrystallization (ethyl acetate-hexane) to provide white microcrystals of Example 339. MP 129.0–131.5° C.

EXAMPLE 340

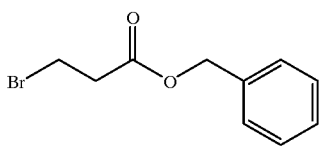

Step 1 A spatula tip full of p-toluenesulfonic acid monohydrate was added to a solution of 3-bromopropionic acid (20.49 g, 0.134 mol) and benzyl alcohol (15 mL, ~15.7 g, 0.145 mol) in benzene (150 mL). A Dean-Stark trap was fitted to the reaction vessel and the solution was held at reflux with overnight stirring. After 16 h at reflux, the reaction was cooled, washed with saturated sodium bicarbonate, dried ($Na_2SO_4$), and concentrated to an oil (28.78 g). Fractional distillation at reduced pressure (0.18 torr) gave the desired product as a colorless liquid 118.49 g, 56%) boiling in the range 99–109° C.

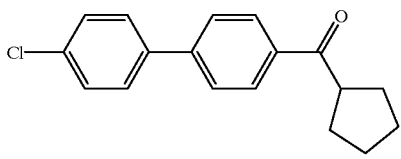

Step 2 A dry dichloromethane (50 mL) solution of 4-chlorobiphenyl (3.57 g, 18.9 mmol) and cyclopentanecarbonyl chloride (2.6 g, 18.9 mmol) in a 100-mL flask was chilled using an ice bath. Solid aluminum chloride (5 g, 37.7 mmol) was cautiously added over several minutes. The reaction mixture was stirred for 6 h while warming to room temperature. After 6 h, the reaction mixture was re-cooled with an ice bath and quenched with 10% HCl (50 mL). The layers were separated and the aqueous phase was back-extracted with dichloromethane (2×50 mL). The combined organic portions were washed with brine (100 mL), dried ($Na_2SO_4$), and concentrated in vacuo. The resulting yellow solid was used without further purification (5.5 g, 100%). TLC (hexane-ethyl acetate, 3:1): $R_f$ 0.22.

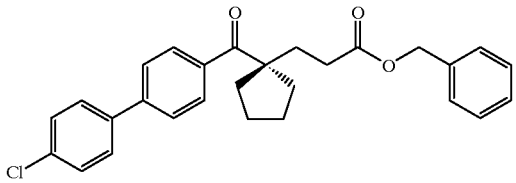

Step 3 n-Butyl lithium (2.64 M in hexanes, 0.8 mL, 2.16 mmol) was added dropwise to freshly distilled diisopropylamine (0.3 mL, 0.22 g, 2.16 mmol) in anhydrous tetrahydrofuran (4 mL) at 0° C. and under an argon atmosphere. The solution was stirred for 30 minutes and then cooled to −70° C. A solution of the product from step 2 (0.59 g, 2.06 mmol) in tetrahydrofuran (1 mL, with 0.5 mL rinse) was added via syringe over 20 minutes. Stirring was continued for 75 minutes at −70° C. A solution of benzyl-3-bromopropionate from step 1 (0.50 g, 2.06 mmol) in tetrahydrofuran (1 mL, with 0.5 mL rinse) was added via syringe over 20 minutes. The reaction stirred at −70° C. for 1 h and was then warmed slowly to room temperature overnight. After 14.25 h of stirring under inert atmosphere, the reaction mixture was quenched with 10% HCl (10 mL) after dilution with ether (25 mL) and dichloromethane (15 mL). The separated organics were then washed sequentially with 10% HCl (10 mL), saturated sodium bicarbonate (2×10 mL), and brine (2×10 mL). The combined aqueous washes were then back-extracted with dichloromethane (10 mL). The combined organic phases were dried ($Na_2SO_4$) and concentrated in vacuo to yield an orange-yellow residue which was purified via flash column chromatography [gradient elution, hexane-dichloromethane (1:1) to hexane-dichloromethane (2:3)] to afford the desired product as an off-white solid (0.18 g, 20%). TLC (hexane-dichloromethane, 1:1): $R_f$ 0.45.

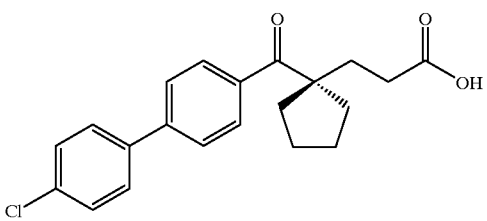

Example 340

Step 4—Preparation of Example 340. To a solution of the benzyl ester from step 3 (0.14 g, 0.31 mmol) in absolute ethanol (0.62 mL) was added a solution of aqueous sodium hydroxide (1M, 0.46 mL, 0.46 mmol). After stirring for three hours, the reaction mixture was diluted with ethyl acetate (10 mL) and distilled water (10 mL). The separated aqueous layer was acidified to pH ~1 with concentrated HCl and was extracted with ethyl acetate (2×10 mL). Extractions were combined, dried ($Na_2SO_4$), and concentrated in vacuo to provide the product (0.08 g, 73%). MP 161.0–164.0° C.

EXAMPLE 341

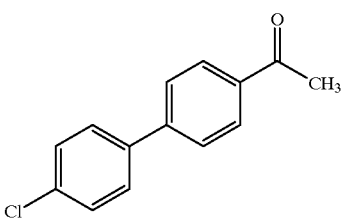

Step 1 A dry 1,2-dichloroethane (300 mL) solution of 4-chlorobiphenyl (22.64 g, 120 mmol) and acetyl chloride (9.6 g, 120 mmol) in a 500-mL flask was chilled using an ice bath. Solid aluminum chloride (17.8 g, 132 mmol) was cautiously added over ten minutes. The reaction mixture was stirred for 20 h while warming to room temperature. After 20 h, the reaction mixture was quenched by slowly adding it to a stirred chilled solution of 10% HCl (300 mL). Ethyl acetate (200 mL) was added to help dissolve solids. The layers were separated and the aqueous phase was back-extracted with ethyl acetate (200 mL). The combined organic portions were washed with brine (300 mL), dried ($Na_2SO_4$), and concentrated in vacuo. The resulting yellow-white solid was recrystallized (ethyl acetate-hexane) to provide multiple, crystalline crops of the desired ketone (25.66 g, 93%). TLC (hexane-dichloromethane, 2:1): $R_f$ 0.61.

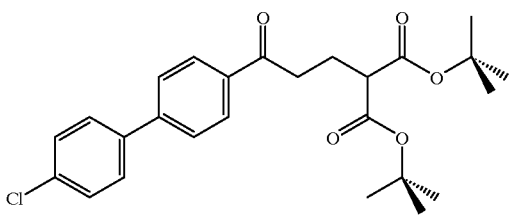

Step 2 A dry 100-mL round-bottomed flask was charged with a suspension of sodium hydride (0.24 g of 95% NaH, ~9.1 mmol) in dry N,N-dimethylformamide (43 mL) and was cooled to 0° C. A solution of 4-(4'-chlorobiphenyl) methylketone from step 1 (2.0 g, 8.67 mmol) in N,N-dimethylformamide (7 mL) was then added via syringe over 15 minutes and stirring was continued for one hour at 0° C. under inert atmosphere. A solution of di-tert-butyl methylenemalonate (1.98 g, 8.67 mmol) (This compound was prepared and purified according to literature precedent: Roberts, et. al., *J. Org. Chem*, 1983, 48, 3603) in N,N-dimethylformamide (5 mL) was added via syringe over 15 minutes. After stirring for 15.5 h with gradual warming to room temperature, the reaction mixture was diluted with ether (350 mL) and quenched with 10% HCl (550 mL). The separated aqueous layer was then back-extracted with ether (100 mL). The combined organics were washed with brine (2×500 mL). Again, the combined aqueous phases were back-extracted with ether (100 mL). The combined organic phases were dried ($Na_2SO_4$) and concentrated in vacuo to yield an orange solid which was purified initially via recrystallization (hexane) to give white fluffy crystals of the desired product (1.64 g). A significant amount of the desired compound remained in the mother liquors and was purified via flash column chromatography [gradient elution, hexane-dichloromethane (1:1) to dichloromethane-methanol (98:2)] to provide additional desired material as an off-white solid (0.47 g, total 2.11 g, 53%). TLC (hexane-ethyl acetate, 9:1): $R_f$ 0.43.

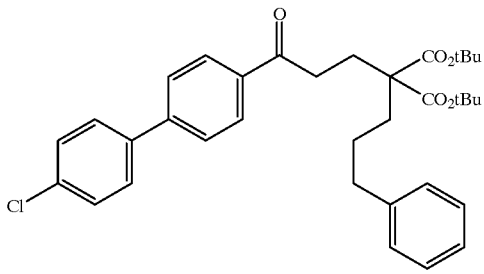

Step 3 A dry 25-mL round-bottomed flask was charged with a suspension of sodium methoxide (0.26 g of 95% NaOMe, ~4.75 mmol) and the pure product from step 2 (2.0 g, 4.36 mmol) in dry dimethoxyethane (4.7 mL). Simultaneously, a dry dimethoxyethane (13.5 mL) suspension of 1-bromo-3-phenylpropane (0.67 mL, 0.87 g, 4.36 mmol) and sodium iodide (0.66 g, 4.36 mmol) was formed in a 50-mL round-bottomed flask. After stirring 40 minutes under inert atmosphere, the orange enolate suspension was added via syringe over 10 minutes to the yellow bromide-iodide suspension. After 40 h of stirring, the reaction was not complete as judged by TLC. Additional sodium methoxide (0.13 g, 2.38 mmol) and 1-bromo-3-phenylpropane (0.33 mL, 0.44 g, 2.18 mmol) were added. After 24 h of stirring, the reaction mixture was concentrated to dryness. The residue was dissolved in ethyl acetate (50 mL) and quenched with 10% HCl (50 mL). The separated organics were washed with 10% HCl (50 mL). Combined aqueous phases were back-extracted with dichloromethane (50 mL). Combined organic phases were dried ($Na_2SO_4$) and concentrated in vacuo to yield an orange oil which was purified via flash column chromatography [gradient elution, hexane to hexane-ethyl acetate (19:1)] to afford the desired product as an off-white solid (1.66 g, 66%). MS (FAB-LSIMS) 577 $[M+H]^+$.

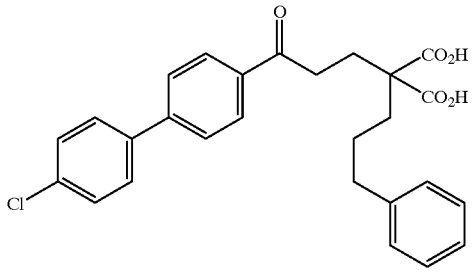

Step 4 A dichloromethane (10 mL) solution of the product from step 3 (1.66 g, 2.88 mmol), anisole (7.81 mL, 7.77 g, 71.90 mmol), and trifluoroacetic acid (2.22 mL, 3.28 g, 28.76 mmol) was stirred for 55 h in a 50-mL round-bottomed flask. The reaction mixture was partitioned between ether (50 mL) and brine (50 mL). Some distilled water was added to solubilize precipitating salts. The organic phase was separated, dried ($Na_2SO_4$), and concentrated in vacuo to yield a white-pink solid which was purified via flash column chromatography [gradient elution, ethyl acetate-hexane-acetic acid (25:74:1) to ethyl acetate-hexaneacetic acid (49:50:1)] to afford the desired product as an off-white solid (0.53 g, 39%) MP 168.5–170.0° C.

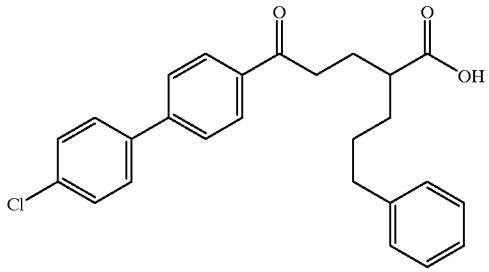

Example 341

Step 5—Preparation of Example 341. A 1,4-dioxane (7.5 mL) solution of the diacid from step 4 (0.4 g, 0.86 mmol) was held at reflux for 44 h with stirring under inert atmosphere. The reaction mixture was then concentrated to dryness and purified via flash column chromatography [ethyl acetate-hexane-acetic acid (24:75:1)] to afford the title compound as a white solid (0.25 g, 69%). MP 97.0–98.5° C.

EXAMPLE 342

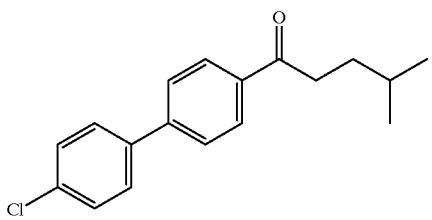

Step 1 A dry dichlromethane (93.5 mL) solution of 4-chlorobiphenyl (7.06 g, 37.4 mmol) and g-methylvaleroyl chloride (5.0 g, 37.4 mmol) in a 250-mL flask was chilled using an ice bath. Solid aluminum chloride (9.97 g, 74.8 mmol) was cautiously added over ten minutes. Stirring was continued for 23 h while warming slowly to room temperature. The reaction mixture was quenched by slowly adding it to a stirred chilled solution of 10% HCl (100 mL). The layers were separated and the aqueous phase was back-extracted with dichloromethane (2×50 mL). The combined organic portions (cloudy) were washed with brine (50 mL), dried ($Na_2SO_4$), and filtered. Dilution with dichloromethane (100 mL) and finally ethyl acetate (100 mL) clarified the solution which was re-dried ($Na_2SO_4$) and concentrated in vacuo to produce a yellow solid (10.33 g). A portion of this crude product (2.97 g) was purified via flash column chromatography [dichloromethane-hexane (2:3)] to yield the desired product as a pale-yellow solid (2.54 g, 82%). TLC (hexane-ethyl acetate, 9:1): $R_f$ 0.54.

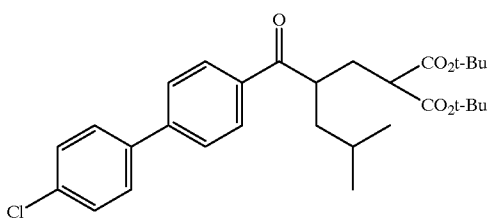

Step 2 A dry 25-mL round-bottomed flask was charged with a suspension of sodium hydride (0.044 g of 95% NaH, ~1.74 mmol) in dry N,N-dimethylformamide (7.9 mL) and was cooled to 0° C. Solid ketone from step 1 (0.5 g, 1.74 mmol) was cautiously added to the suspension and stirring was continued for one hour at 0° C. under inert atmosphere. A solution of di-tert-butyl methylenemalonate from Example 341 step 2 (0.4 g, 1.74 mmol) in N,N-dimethylformamide (3 mL) was added via syringe over 15 minutes. After stirring for 19 h with gradual warming to room temperature, the reaction mixture was diluted with ether (70 mL) and quenched with 10% HCl (120 mL). The separated organic phase was washed with brine (2×100 mL), dried ($Na_2SO_4$), and concentrated in vacuo to yield a yellow oil. The crude product was purified via flash column chromatography (gradient elution, hexane-dichloromethane (3:1) to hexane-dichloromethane (1:2)) to afford the desired compound in two fractions, the first slightly contaminated with high $R_f$ spots (0.36 g, 40%), and the second pure by TLC (0.22 g, 24% (total 64%)). TLC (hexane-dichloromethane, 1:2): $R_f$ 0.20.

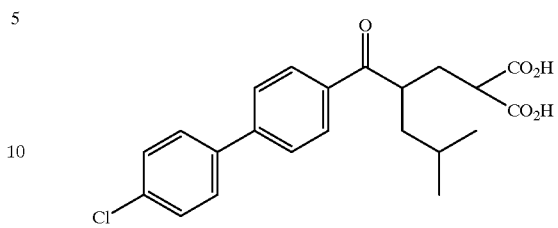

Step 3 The two fractions of product from step 2 were reacted separately in this step. The order of parenthetical notations of stoichiometry refer to the first fraction and the second fraction respectively. Dichloromethane (4.6 mL and 2.9 mL) solutions of each fraction of the product from step 2 (0.36 g, 0.7 mmol and 0.22 g, 0.43 mmol ), anisole (1.9 mL, 1.9 g, 17.5 mmol and 1.17 mL, 1.16 g, 10.75 mmol), and trifluoroacetic acid (0.54 mL, 0.8 g, 7.0 mmol and 0.33 mL, 0.49 g, 4.3 mmol) were formed in separate 25-mL round-bottomed flasks. After stirring under inert atmosphere for 22 h, both reaction mixtures were separately partitioned between ethyl acetate (20 mL) and brine (20 mL). Some distilled water was added to solubilize precipitated salts. Each organic phase was separated, then the two fractions were combined, washed with distilled water (2×15 mL), dried ($Na_2SO_4$), and concentrated in vacuo to yield a faint pink oil which was purified via flash column chromatography [gradient elution, ethyl acetate-hexane-acetic acid (25:74:1) to ethyl acetate-hexane-acetic acid (49:50:1)] to yield fractions whose $^1$H-NMRs indicated that the reaction had not gone to completion. The fractions were recombined and resubjected to the reaction conditions for 16 h. When the reaction was complete as indicated by TLC, the reaction mixture was worked-up and chromatographed using the same conditions described above to afford the desired diacid as an off-white solid (0.2 g, 44%). TLC (chloroform-methanol, 9:1 with trace amount of acetic acid): $R_f$ 0.17.

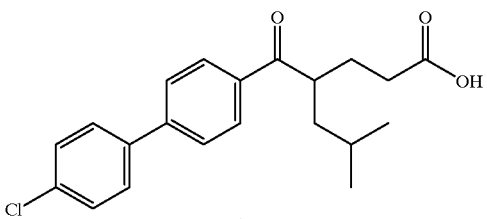

Example 342

Step 4—Preparation of Example 342. A 1,4-dioxane (9.1 mL) solution of diacid from step 3 (0.2 g, 0.5 mmol) was held at reflux for 15 h with stirring under inert atmosphere. The reaction mixture was then concentrated to dryness and purified via flash column chromatography (dichloromethane-methanol (99:1)) to afford the title compound as a white solid (0.11 g, 61%). MP 102.0–103.0° C.

EXAMPLE 343

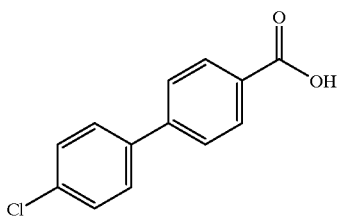

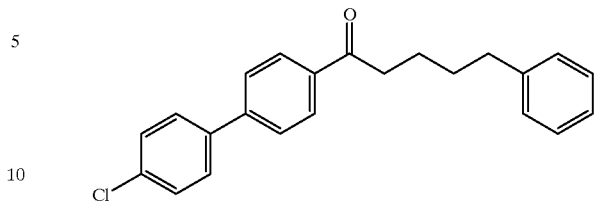

Step 1 Bromine (5.6 mL, 17.3 g, 108.35 mmol) was added to a solution of sodium hydroxide (15.2 g, 379 mmol) in distilled water (75.8 mL) at 0° C. and was stirred for 15 minutes. To this reagent mixture was added a solution of 4-(4'-chlorobiphenyl)methylketone from the Example 341 preparation step 1 (5.0 g, 21.67 mmol) in 1,4-dioxane (54.2 mL). The reaction mixture was heated for 18 h at 40° C. using an oil bath and was cooled to room temperature. A solution of sodium thiosulfate pentahydrate (21.5 g, 86.68 mmol) in distilled water (60 mL) was added to the reaction mixture to quench the remaining bromoform. The mixture was acidified to pH ~1 with concentrated HCl (~25 mL) causing foaming. The solids which precipitated were isolated via filtration and recrystallized (ethyl acetate) to provide multiple, crystalline crops of the title compound (4.44 g, 88%). MP 286.0–288.0° C.

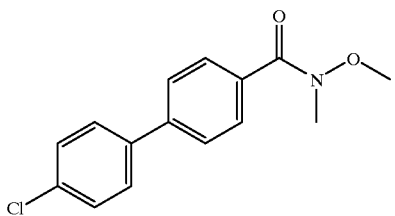

Step 2 A dry dichloromethane (66 mL) solution of 4-(4'-chlorobiphenyl)carboxylic acid from step 1 (3.7 g, 15.9 mmol), N,O-dimethylhydroxylamine hydrochloride (2.34 g, 23.85 mmol), and 1-hydroxybenzotriazole (2.36 g, 17.49 mmol) in a 100-mL round-bottomed flask was chilled using an ice bath and stirred for a few minutes. N-methylmorpholine (2.62 mL, 2.41 g, 23.85 mmol) was added quickly via syringe followed by solid 1-ethyl-3-(3-dimethylaminopropyl)carbodiimide (3.36 g, 17.49 mmol). The reaction mixture was stirred for several hours at 0° C. under inert atmosphere. Stirring was continued while warming to room temperature overnight. After a total of 23 h of stirring, the reaction was incomplete as judged by TLC. Dry N,N-dimethylformaride (2 mL) was added at 0° C. to clarify the reaction mixture. TLC after 1 h showed no further conversion, so additional reagents were added [N,O-dimethylhydroxylamine hydrochloride (0.46 g), 1-hydroxybenzotriazole (0.47 g), N-methylmorpholine (0.52 mL), and 1-ethyl-3-(3-dimethylaninopropyl) carbodiimide (0.66 g)] at 0° C. TLC after 3 h indicated complete conversion so the reaction mixture was diluted with dichloromethane (200 mL) and washed sequentially with saturated sodium bicarbonate (2×100 mL), 10% HCl (100 mL), and saturated sodium bicarbonate (100 mL). The combined aqueous portions were back-extracted with ether (50 mL). The combined organic phases were dried (Na$_2$SO$_4$) and concentrated in vacuo to yield an orange solid which was purified via flash column chromatography (gradient elution, dichloromethane to dichloromethane-methanol (99.5:0.5)) to afford the desired product as a white solid (3.89 g, 89%). MS (FAB-LSIMS) 276 [M+H]$^+$.

Step 3 n-Butyl lithium (2.64 M in hexanes, 10.2 mL, 26.98 mmol) was added dropwise to freshly distilled diisopropylamine (3.78 mL, 2.73 g, 26.98 mmol) in anhydrous tetrahydrofuran (50 mL) at –40° C. and under an argon atmosphere. The solution was stirred for 25 minutes with warming to –20° C. and then cooled to –40° C. A solution of 5-phenylvaleric acid (2.40 g, 13.49 mmol) in tetrahydrofuran (4 mL, with 1 mL rinse) was added via syringe over 7 minutes causing precipitation of a solid. The stirred solution was heated at 50° C. for 2 h and was then recooled to –40° C. A solution of the product from step 2 (3.1 g, 11.24 mmol) in tetrahydrofuran (4 mL, with 1 mL rinse) was added via syringe over 8 minutes. The reaction stirred at –40° C. for 3 h and was then quenched by cautious decanting into 10% HCl (50 mL). The mixture was extracted with ether (150 mL). The separated aqueous phase was back-extracted with ethyl acetate (2×50 mL). The combined organic phases were washed with brine (75 mL), dried (Na$_2$SO$_4$), and concentrated in vacuo to provide an orange solid which was then purified via flash column chromatography (gradient elution, hexane-dichloromethane (3:1) to hexane-dichloromethane (3:2)) to afford the desired product as a yellow-white solid (1.80 g, 46%). MS (FAB-LSIMS) 349 [M+H]$^+$.

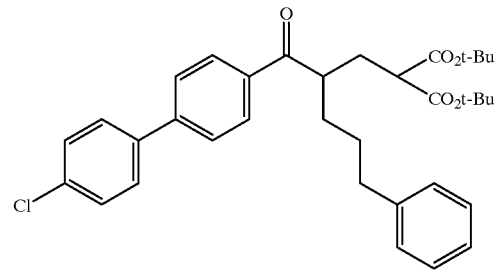

Step 4 A dry 50-mL round-bottomed flask was charged with a suspension of sodium hydride (0.15 g of 95% NaH, ~5.8 mmol) in dry N,N-dimethylforrnamde (20 mL) and was cooled to 0° C. A solution of the ketone product from step 3 (1.93 g, 5.53 mmol) in N,N-dimethylformamide (10 mL) was added via syringe over 10 minutes. Stirring was continued for one hour at 0° C. under inert atmosphere. A solution of the di-tert-butyl methylenemalonate from the Example 341 preparation step 2 (1.26 g, 5.53 mmol) in N,N-dimethyl-formamide (3 mL) was added via syringe over 4 minutes to the dark orange reaction mixture. After stirring for 15 h with gradual warming to room temperature, the reaction mixture was diluted with ether (300 mL) and quenched with 10% HCl (500 mL). The separated organic phase was washed with brine (2×500 mL), dried (Na$_2$SO$_4$), and concentrated in vacuo to yield a yellow oil which was purified via flash column chromatography [gradient elution, hexane-dichloromethane (4:1) to hexane-dichloromethane (1:1)] to yield the desired material as an off-white solid (2.13 g, 67%). MS (FAB-LSIMS) 577 [M+H]+.

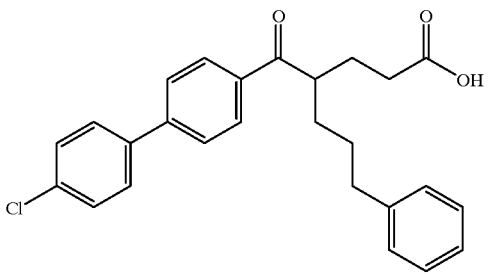

Example 343

Step 5—Preparation of Example 343. A dichloromethane (15 mL) solution of the product from step 4 (2.1 g, 3.64 mmol), anisole (9.9 mL, 91 mmol), and trifluoroacetic acid (2.8 mL, 36.4 mmol) was stirred in a 50-mL round-bottomed flask. After 72 h, the reaction had not gone to completion. Additional trifluoroacetic acid (5 mL, 65 mmol) was added. After stirring for an additional 4.5 h the reaction mixture was partitioned between ethyl acetate (75 mL) and brine (75 mL). Some distilled water was added to solubilize precipitated salts. The organic phase was separated, dried ($Na_2SO_4$), and concentrated in vacuo to yield an orange-brown oil which was purified via flash column chromatography [gradient elution, ethyl acetate-hexane-acetic acid (25:74:1) to ethyl acetate-hexane-acetic add (49:50:1)] to afford the desired diacid plus decarboxylated compound (after vacuum oven drying) as a white solid (1.35 g, ~80%, MP 45.0–51.0° C. (dec.)): TLC (chloroform-methanol, 9:1 with trace amount of acetic acid): $R_f$ 0.34. A 1,4-dioxane (18 mL) solution of a portion of the partially converted diacid (1.0 g, ~2.15 mmol) was held at reflux for 20 h with stirring under inert atmosphere. The reaction mixture was then concentrated to dryness and purified via flash column chromatography (ethyl acetate-hexane-acetic acid (19:80:1)) to afford the title compound as a clear gum (0.75 g, 83%). Anal. C: calcd, 74.19; found, 73.95. H: calcd, 5.99; found, 5.82.

EXAMPLE 344

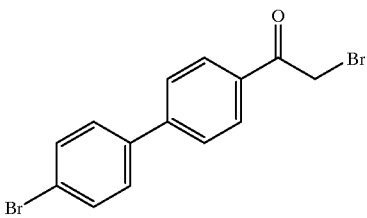

Step 1 A solution of p-bromobiphenyl (200 g, 0.0858 mol) and a-bromoacetyl bromide (7.5 mL, 0.0858 mol, 1.0 eq) in $CH_2Cl_2$ (400 mL) under argon was cooled to 0° C. and $AlCl_3$ (24.0 g, 0.180 mol, 2.1 eq) was added in four parts. The resulting dark green solution was allowed to slowly warm to room temperature, then stirred for 14 h. The reaction was then cooled to 0° C. and quenched with a 10% HCl solution (200 mL). The resulting aqueous layer was separated and extracted with $CH_2Cl_2$ (3×100 mL). The combined organic layers were washed with a saturated NaCl solution (150 mL), dried (anh. $MgSO_4$) and concentrated under reduced pressure to afford a brown solid (29.3 g, 96%) which was used in the next step without further purification

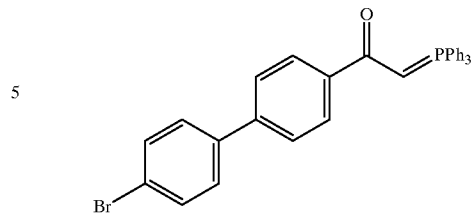

Step 2 A slurry of the intermediate from step 1 (29.3 g, 0.0827 mol) and $PPh_3$ (23.9 g, 0.0910 mol, 1.1 eq) in dry THF (400 mL) was heated at the reflux temperature for 14 h. The resulting solids were removed by filtration and washed with diethyl ether to give the phosphonium bromide (467 g, 92%). A mixture of the bromide (7.60 g, 1.23 mmol), $CH_2Cl_2$ (50 mL) and a 10% NaOH solution (20 mL) was vigorously stirred for 30 min. The aqueous layer was extracted with $CH_2Cl_2$ (30 mL) and the combined organic were washed with $H_2O$ (30 mL) and dried (anh. $MgSO_4$). The resulting solids were triturated with EtOAc to give the desired ylid as a light brown powder (5.17 g, 78%) which was used in the next step: TLC $R_f$ (EtOAc) 0.55.

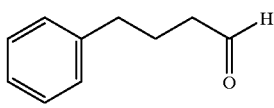

Step 3 To a solution of N-methylmorpholine oxide (11.4 g, 0.0973 mol, 1.40 eq) in $CH_2Cl_2$ (200 mL) was added 4-phenylbutanol (10.2 mL, 0.0696 mol) and powdered 4 Å sieves (2.0 g). After stirring for 10 min, tetrapropylammonium perruthenate (0.218 g, 6.20 mmol. 9 mol %), and the resulting mixture was allowed to stir for 48 h. The reaction mixture was filtered through Florisil® with the aid of $CH_2Cl_2$ (200 mL) and the resulting solution was washed with a saturated $Na_2SO_3$ solution (200 mL), a saturated NaCl solution (200 mL), a 1M $CuSO_4$ solution (200 mL) and dried (anh. $MgSO_4$). Concentration under reduced pressure followed by bulb-to-bulb distillation afforded the desired aldehyde as a colorless oil (9.3 g, 90%), which slowly oxidized on exposure to air. TLC $R_f$ (25% EtOAc/hexane) 0.60.

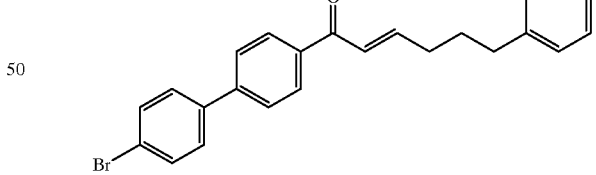

Step 4 A mixture of compound from step 2 (12.5 g, 0.0233 mol) and compound from step 3 (4.13 g, 0.0280 mol, 1.5 eq) in dry THF (230 mL) were heated at the reflux temperature for 80 h. The resulting mixture was concentrated under reduced pressure, dissolved in acetone (250 mL), cooled to 0° C. and treated dropwise with Jones reagent until all starting aldehyde was consumed as shown by TLC analysis. The acetone mixture was concentrated under reduced pressure, dissolved in EtOAc (250 mL), washed with a saturated $NaHCO_3$ solution (150 mL), and dried (anh. $MgSO_4$). The resulting solution was concentrated under reduced pressure, dissolved in $CH_2Cl_2$, and filtered through a small pad of SiO$_2$ with the aid of 25% EtOAc/hexane to remove remaining 4-phenylbutyric acid and Ph$_3$PO to afford the desired enone as a single diastereomer (3.85 g, 41%). Anal. Calcd for C$_{24}$H$_{21}$BrO: C, 71.05; H, 5.22; O, Br; 19.71. Found: C, 70.77; H, 5.23; O, 19.56.

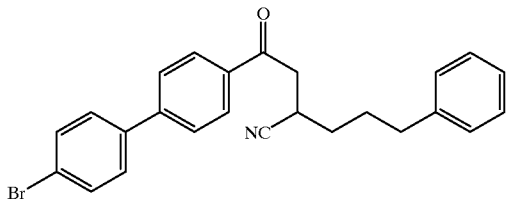

Step 5 To a solution of the product from step 4 (0.405 g, 1.00 mmol) and acetic acid (0.060 mL, 1.0 mmol, 1.0 eq) in abs. EtOH (15 mL) at 35° C. was slowly added a solution of KCN (0.130 g, 2.00 mmol, 2.0 eq) in H$_2$O (1.2 mL). The mixture was stirred at 35° C. for 14 h and the resulting slurry was separated between CHCl$_3$ (50 mL) and H$_2$O (50 mL). The aqueous layer was extracted with CHCl$_3$ (2×20 mL), and the combined organics were washed with H$_2$O (3×40 mL), dried (anh. MgSO$_4$) and concentrated under reduced pressure. The resulting solids were recrystallized using EtOAc/hexane to afford the cyano product as a white powder (0.252 g, 58%). MP 139–141° C.

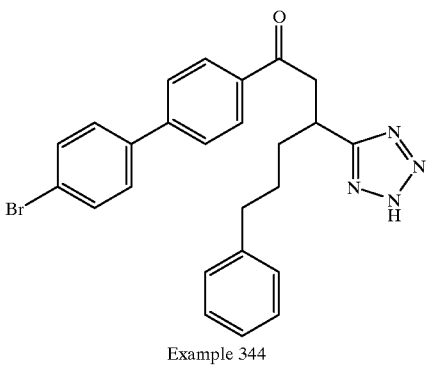

Example 344

Step 6—Preparation of Example 344. A mixture of the product of step 5 and trimethyltin azide (0.180 g, 0.874 mmol, 2.00 equiv.) in toluene (25 mL) was heated at 105° C. for 60 h, after which volatiles were removed at 105° C. to afford the trinmethylstannyl tetrazole as a single compound. The foamy brown solids were redissolved in toluene (10 mL) and treated with HCl (4.0 M in dioxane, 0.33 mL, 1.32 mmol, 3.02 eq). The resulting mixture was stirred at room temperature for 14 h, then separated between EtOAc (50 mL) and H$_2$O (50 mL). The organic phase was washed with H$_2$O (2×50 mL) and a saturated NaCl solution (2×50 mL) and concentrated to give the desired tetrazole as a yellow solid (0.211 g, 100%). MP 17–180° C. (dec).

EXAMPLE 345

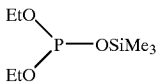

Step 1 To a mixture of diethyl phosphite (2.8 mL, 0.0217 mol) and triethylamine (9 mL, 0.065 mol, 3.0 eq) in dry diethyl ether (250 mL) at 0° C. was slowly added freshly distilled trimethylsilyl chloride (3.3 mL, 0.0260 mol, 1.2 eq) via syringe. The resulting slurry was allowed to slowly warm to room temperature, and was then warmed to 45° C. for 14 h. Volatiles were removed by distillation using a 55° C. oil bath. The resulting mixture was diluted with pentane (150 mL), filtered to remove triethylammonium salts, and concentrated at atmospheric pressure using a 55° C. oil bath. Distillation of the resulting oil gave diethyl trimethylsilyl phosphite as a colorless oil (3.64 g, 80%). BP 60° C. (5 mmHg).

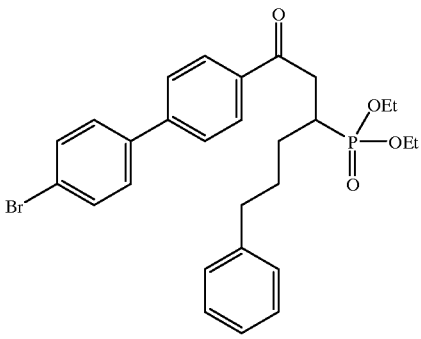

Step 2 A slurry of product from step 4 of the Example 344 preparation (0.200 g, 0.490 mmol) and diethyl trimethylsilyl phosphite (0.105 g, 0.490 mmol, 1.0 eq) in a dry NMR tube under argon was dissolved using a 50° C. sonicator bath, then heated at 50° C. for 14 h. This was concentrated under reduced pressure and treated with an additional portion of diethyl trimethylsilyl phosphite (0.5 mL) and heated at 50° C. for 24 h. The reaction mixture was concentrated under reduced pressure, dissolved in CDCl$_3$ (which apparently cleaved the silyl enol ether), concentrated under 1 mmHg at 50° C. for 3 h to afford the above diethyl ester as a viscous, slightly yellow oil (0.23 g, 95%). Anal. Calcd for C$_{28}$H$_{32}$BrO$_4$P: C, 61.83; H, 5.94. Found: C, 62.05; H, 6.11.

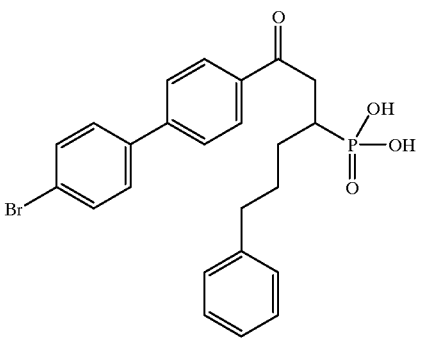

Example 345

Step 3—Preparation of Example 345. To a solution of the product from step 2 (0.243 g, 0.490 mmol) in dry CH$_2$Cl$_2$ (15 mL) was added trimethylsilyl bromide (0.48 mL, 3.64 mmol, 7.4 eq) via syringe. This was allowed to stir at room temperature for 14 h. The resulting solution was then concentrated to approximately 8 mL under reduced pressure then treated with MeOH (10 mL). This concentration/dilution regimen was repeated five more times, after which the reaction mixture was concentrated under reduced pressure. The resulting solids were triturated with hexanes to afford the desired phosphonic acid (0.150 g, 63%). MP 150–152° C.

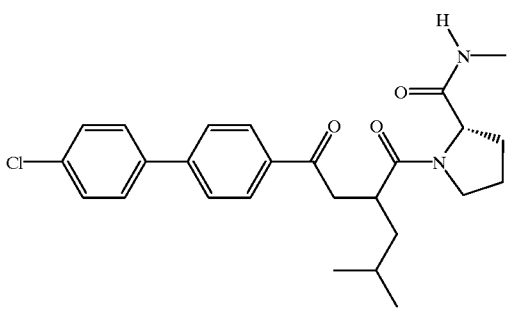

Example 346

EXAMPLE 346

A dry dichloromethane (3 mL) solution of Example 1 (0.25 g, 0.725 mmol), proline N-methyl amide hydrochloride (0.48 g, 2.90 mmol), and 1-hydroxybenzotriazole (0.10 g, 0.725 mmol) in a 10-mL round-bottomed flask was chilled using an ice bath and stirred for a few minutes. N-methylmorpholine (0.32 mL, 0.29 g, 2.90 mmol) was added quickly via syringe followed by solid 1-ethyl-3-(3-dimethylaminopropyl)carbodiimide (0.146 g, 0.76 mmol). The reaction mixture was stirred under argon for several hours at 0° C. and was then warmed to room temperature overnight. The reaction mixture was then diluted with chloroform (30 mL) and washed with 10% HCl (10 mL). The separated aqueous layer was back-extracted with chloroform (5 mL). The combined organic portions were washed with saturated NaHCO$_3$ (10 mL), dried (Na$_2$SO$_4$), and concentrated in vacuo. The crude oil was purified via flash column chromatography [dichloromethane-methanol (98:2)] to provide the title compound as a white solid (0.26 g, 79%). MP 75.5–78.0° C.

EXAMPLE 347

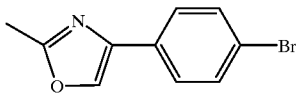

Step 1 A solution of 2,4'-dibromoacetophenone (0.62 g, 2.19 mmoles) and acetamide (0.20 g, 3.32 mmoles) in 6 mL of toluene was refluxed for 3 d. The solvent was removed at reduced pressure and the residue was chromatographed with 0–30% ethyl acetate in hexanes to afford 0.20 mg (38%) of product as a white solid. TLC (methylene chloride) R$_f$ 0.42.

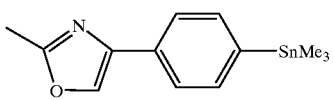

Step 2 A solution of trimethyltin chloride (0.81 g, 4.06 mmoles) in DME (1.5 mL) was added to a stirred suspension of small cubes of metallic sodium (0.3 g, 13.05 mmol) in DME (2.5 mL) under a stream of argon in an ice cold round bottom flask. The mixture was stirred in the ice bath for 3.5 h when the mixture turned green. The mixture was transferred via syringe into a cooled round bottom flask and treated with a solution of the product of step 1 (0.8 g, 3.36 mmol) in DME (4 mL). The reaction mixture was then allowed to warm and stir at room temperature overnight. At this time, it was diluted with ethyl acetate, washed with water, brine, and dried over MgSO$_4$. The crude product was chromatographed with 3–20% ethyl acetate in hexanes to afford 0.76 g (70%) of product as an oil. TLC (hexanes-20% ethyl acetate) R$_f$ 0.37.

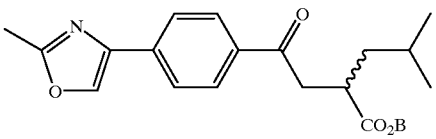

Step 3 A solution of the product of step 2 (0.21 g, 0.65 mmol), the acid chloride from step 3 of the Example 61 preparation (0.16 g, 0.74 mmol), and PdCl$_2$(PPh$_3$)$_2$ (0.078 g, 0.14 mmol) in 1,2-dichloroethane (1.5 mL) was refluxed overnight. The reaction mixture was diluted with ethyl acetate and filtered. The filtrate was concentrated at reduced pressure and chromatographed with 3–50% ethyl acetate in hexanes to afford 66 mg of product as a solid. HRMS (FAB) calcd. for C$_{20}$H$_{26}$NO$_4$ [M+H]$^+$ 344.18618, Found 344.18600.

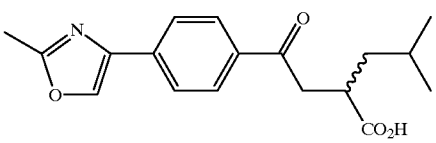

Example 347

Step 4—Preparation of Example 347. The product of step 3 (56 mg, 0.16 mmol) was suspended in ethanol (1.3 mL) and treated with 4N NaOH (0.4 mL). The mixture was stirred at room temperature overnight. The reaction mixture was then quenched with 2N HCl, diluted with ethyl acetate, and the layers were separated. The organic layer was washed with brine and dried over MgSO$_4$. The product was chromatographed with 0–12% methanol in methylene chloride to afford 40 mg (78%) of Example 248 as a solid. MP 120° C.

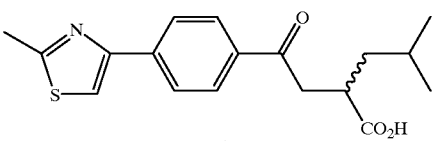

Example 348

EXAMPLE 348

The procedure was analogous to that of Example 347 except thioacetamide was used instead of acetamide. HRMS (FAB) calcd. for C$_{18}$H$_{22}$NO$_3$S [M+H]$^+$ 332.13204, Found 332.13287.

EXAMPLE 349

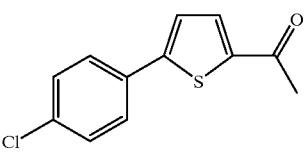

Step 1 A solution of 2-acetyl-5-bromothiophene (0.55 g, 2.64 mmoles) in toluene (5 mL) was treated with Pd(PPh$_3$)$_4$ and allowed to stir at room temperature for 30 min at which time 4-chlorobenzeneboronic acid (0.46 g, 2.91 mmol) and NaOMe in MeOH (1.21 mL, 25% wt, 5.29 mmol) were added. The reaction mixture was then refluxed for 4 h. The mixture was cooled to room temperature and 2N NaOH (3 mL) was added and stirring was continued for another 2 h. The mixture was then diluted with methylene chloride, washed with brine and dried over $MgSO_4$. The crude product was chromatographed with 0–30% ethyl acetate in hexanes to afford 0.51 g (82%) of product. TLC (hexanes-10% ethyl acetate) $R_f$ 0.24.

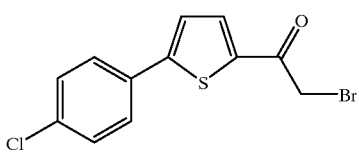

Step 2 The product of step 1 (0.51 g, 2.17 mmol) was dissolved in THF (10 mL), cooled to 0° C., and treated with phenyltrimethyl-ammonium tribromide (0.84 g, 2.17 mmol). The reaction mixture was then stirred at room temperature for 5 h. The mixture was quenched with $H_2O$ and extracted with ethyl acetate (2×15 mL). The extracts were washed with brine and dried over $MgSO_4$ to afford 0.62 g (91%) crystallized from ether/hexanes. TLC (hexanes-10% ethyl acetate) $R_f$ 0.27.

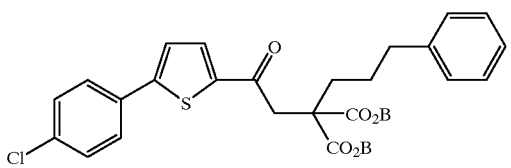

Step 3 A solution of 3-phenyl-propyl diethyl malonate (0.85 g, 3.05 mmol) in THF (10 mL) was treated with NaH (0.068 g, 2.81 mmol) under a stream of argon. The solution was stirred at room temperature for 30 min. At this time, a solution of the product of step 2 (0.62 g, 1.98 mmol) in THF (14 mL) was added dropwise. After the addition, the reaction mixture was stirred at room temperature for 15 min when it was quenched with $H_2O$, diluted with ethyl acetate, and the layers were separated. The organic layer was washed with brine, dried over $MgSO_4$. The residue was then chromatographed with 0–40% ethyl acetate in hexanes to afford 0.63 g of product. TLC (hexanes-20% ethyl acetate) $R_f$ 0.39.

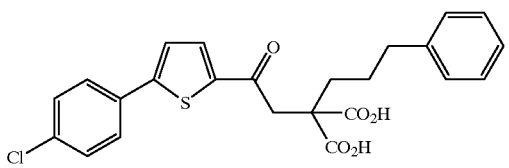

Step 4 A solution of the product of step 3 (0.63 g, 1.23 mmol) in ethanol (5 mL) was treated with sodium hydroxide (0.24 g, 6.16 mmol) in $H_2O$ (0.5 mL) and the mixture was stirred at room temperature for 2 h. At this time, the reaction mixture was acidified with 2N HCl, diluted with ethyl acetate, and the layers were separated. The organic layer was washed with brine and dried over $MgSO_4$ to afford 0.54 g of the diacid product after decolorizing with activated carbon. TLC (methylene chloride-10% methanol) $R_f$ 0.13.

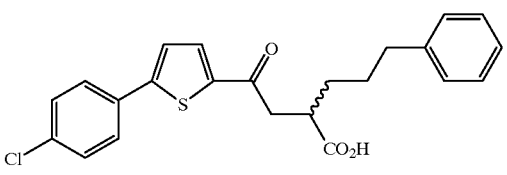

Example 349

Step 5—Preparation of Example 349. The product of step 4 (50 mg, 0.11 mmol) was dissolved in dry acetonitrile (1.5 mL) and treated with copper oxide (2 mg, 0.014 mmol). The mixture was refluxed for 36 h under a stream of argon. At this time, it was diluted with ethyl acetate and quenched with 2N HCl. The layers were separated, and the organic was washed with brine and dried over $MgSO_4$ to afford 34 mg of Example 349 crystallized from ether/hexanes. MP 149° C.

EXAMPLE 350

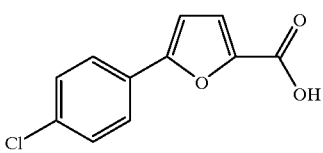

Step 1 The methyl ester of 5-bromofuroic acid (204 mg, 0.99 mmol) was dissolved in DME (3.5 mL) followed by the addition of $Pd(OAc)_2$ (24 mg, 0.11 mmol), $P(o-tolyl)_2$ (60 mg, 0.20 mmol), 4-chlorobenzeneboronic acid (168 mg, 1.07 mmol), and sodium carbonate (1.0 mL, 2N in $H_2O$, 2 mmol). The reaction mixture was refluxed for 1 h when thin layer chromatography showed complete reaction. The mixture was cooled to room temperature, diluted with water, and extracted with methylene chloride (2×15 mL). The combined extracts were washed with brine, dried over $MgSO_4$, and the solvent removed at reduced pressure to afford 170 mg (72%) of product as the methyl ester. The methyl ester was then suspended in 2 mL of ethanol, treated with 5 eq of aqueous NaOH and the mixture was stirred at room temperature for 1 h. At this time, the reaction mixture was quenched with 2N HCl, diluted with ethyl acetate, and the layers were separated. The aqueous layer was extracted with ethyl acetate, and the combined extracts were washed with brine, dried over $MgSO_4$, and the solvent removed at reduced pressure to afford 140 mg of product. TLC (methylene chloride-10% methanol) $R_f$ 0.17.

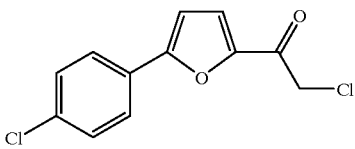

Step 2 A suspension of the product of step 1 (1.42 g, 6.38 mmol) in methylene chloride was treated with oxalyl chloride (3.5 mL, 2M in $CH_2Cl_2$, 7.00 mmol) and one drop of DMF. The mixture was refluxed for 1 h under argon. At this time, the mixture was cooled to 0° C. and transferred via cannula into an ice cold solution of diazomethane (50 mL, 0.6M in $Et_2O$, 30 mmol). The reaction mixture was allowed to stir at 0° C. for 1 h before it was quenched with HCl (30 mL, 1N in $Et_2O$, 30 mmol). The mixture was then stirred at room temperature for 1.5 h, transferred to a separatory funnel with ethyl acetate, washed with saturated sodium bicarbonate solution, brine, and dried over MgSO$_4$. The crude product was chromatographed with 0–30% ethyl acetate in hexanes to afford 1.28 g (79%) of product. TLC (hexanes-10% ethyl acetate) R$_f$ 0.13.

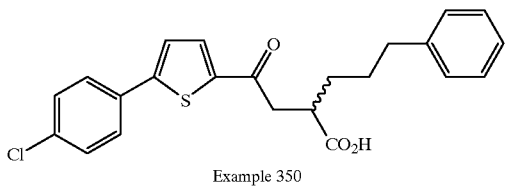

Example 350

Step 3—Preparation of Example 350. The procedure was analogous to that of Example 349 except the product of step 2 was used instead of the corresponding product from the Example 349 preparation. MP 129–130° C.

EXAMPLE 351

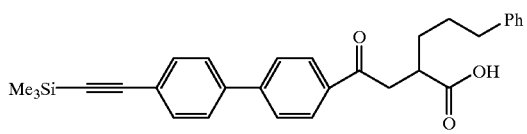

Step 1 A one-necked, 10-mL, round-bottomed flask equipped with a rubber septum and an argon needle inlet containing 4 mL of triethylamine was charged with Example 40 (0.200 g, 0.401 mmol), trimethylsilylacetylene (0.063 mL, 0.050 g, 0.401 mmol), copper (I) iodide (0.764 g, 0.401 mmol), and trans-dichlorobis(triphenylphosphine)palladate (0.011 g, 0.016 mmol). The resulting mixture was stirred for 12 h at room temperature. The reaction mixture was concentrated and the product isolated via column chromatography on 100 g of silica gel (20% ethyl acetate-hexanes with 0.5% acetic acid) afforded 0.163 g (87%) of coupling product as a white solid. MP 149° C.

Step 2—Preparation of Example 351. A screw-top, 2-mL, vial was charged with silyl acetylene (0.150 g, 0.320 mmol) and a methanolic solution of KOH (2 mL, 0.320 mmol). The resulting mixture was stirred for 12 h at room temperature. The reaction mixture was acidified to pH 1 and extracted with ethyl acetate (10 mL). The resulting organic phase was dried over Na$_2$SO$_4$, filtered, and concentrated to afford crude Example 15–9799. Column chromatography on 20 g of silica gel (20% ethyl acetate-hexanes with 0.5% acetic acid) afforded 0.104 g (88%) of Example 15–9799 as an off-white solid. MP 151° C.

Step 1 from the above method for the preparation of Example 351 was used to prepare the following series of biphenyl products (TABLE XXIV) from Example 40 or Example 134 and the appropriate 1-alkyne.

TABLE XXIV

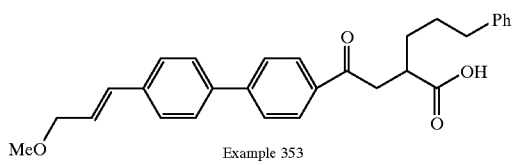

| example | (T)$_x$ | isomer | m.p.(° C.)/other characterization |
|---|---|---|---|
| 351 | HC/C | R, S | 151 |
| 352 | CH$_3$(CH$_2$)$_3$C/C | R, S | 132 |

EXAMPLE 353, EXAMPLE 354, EXAMPLE 355

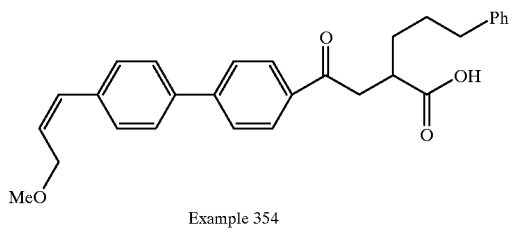

Step 1 Step 1 from the above method for the preparation of Example 351 was used to prepare the propargyl methoxy acetylene starting material for the preparation of Example 353, Example 354, and Example 355. MP 151° C.

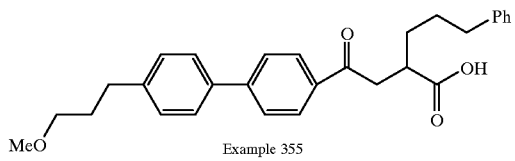

Example 353

Example 354

Example 355

Step 2—Preparation of Example 353, Example 354, Example 355. A one-necked, 10-mL, round-bottomed flask equipped with a rubber septum and a hydrogen balloon connected via a needle inlet was charged with 2 mL of MeOH, acetylenic substrate from Step 1 (0.030 g, 0.068 mmol), and 0.002 g of 5% palladium in carbon. The resulting mixture was stirred for 12 h at room temperature, at which time a second 0.002 g portion of catalyst was added. The reaction mixture was stirred 24 h at room temperature, after which half of the material was filtered through celite, and concentrated. Example 253 (0.001 g), Example 354 (0.003 g), and Example 355 (0.001 g) were isolated via HPLC (SiO$_2$ column, 1% ethyl acetate-methylene chloride with 0.01% TFA).

Example 353: HPLC (elution 1% ethyl acetate-methylene chloride containing 0.01% TFA)t$_R$=17.6 min; MS (FAB-LSIMS) 443 [M+H]$^+$.

Example 354: HPLC (elution 1% ethyl acetate-methylene chloride containing 0.01% TFA)$t_R$=15.5 min; MS (FAB-LSIMS) 443 [M+H]$^+$.

Example 355: HPLC (elution 1% ethyl acetate-methylene chloride containing 0.01% TFA)$t_R$=20.6 min; MS (FAB-LSIMS) 445 [M+H]$^+$.

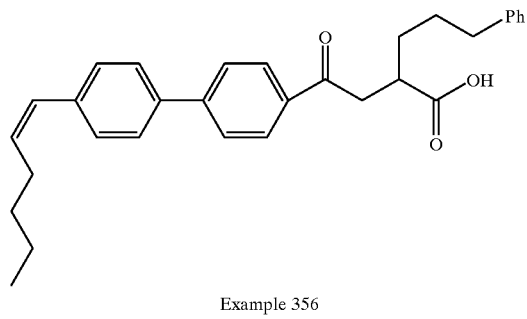

Example 356

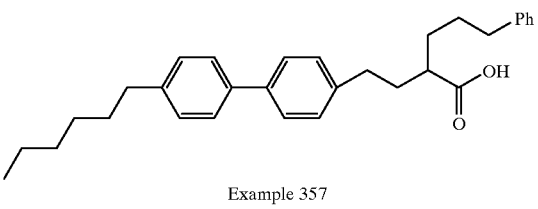

Example 357

EXAMPLE 356 AND EXAMPLE 357

Step 2 from the above method for the preparation of Example 353, Example 354, Example 355 was used to prepare Example 356 and Example 357.

Example 356: HPLC (elution 1% ethyl acetate-methylene chloride containing 0.01% TFA)$t_R$=11.5 min; MS (FAB-LSIMS) 455 [M+H]$^+$.

Example 357: HPLC (elution 1% ethyl acetate-methylene chloride containing 0.01% TFA)$t_R$=3.2 min; MS (FAB-LSIMS) 442 [M+H]$^+$.

EXAMPLE 358, AND EXAMPLE 359

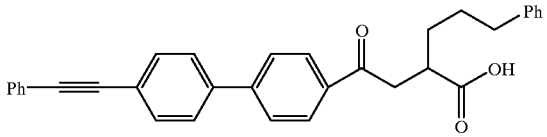

Step 1 Step 1 from the above method for the preparation of Example 351 was used to prepare the phenyl acetylene starting material for the preparation of Example 358, and Example 359. MP 154° C.

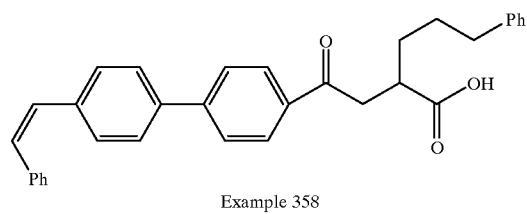

Example 358

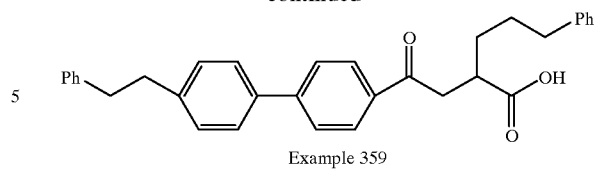

Example 359

Step 2—Preparation of Example 358 and Example 359. Step 2 from the above method for the preparation of Example 353, Example 354, Example 355 was used to prepare Example 358 and Example 359.

Example 358: HPLC (elution 1% ethyl acetate-methylene chloride containing 0.01% TFA)$t_R$=13.9 min; MS (FAB-LSIMS) 475 [M+H]$^+$.

Example 359: HPLC (elution 1% ethyl acetate-methylene chloride containing 0.01% TFA)$t_R$=25.2 min; MS (FAB-LSIMS) 477 [M+H]$^+$.

EXAMPLE 1360

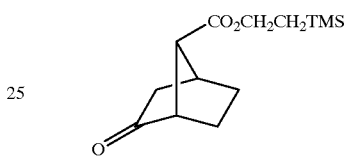

Step 1 A solution of exo-2-oxobicyclo [2.2.1] heptane-7-carboxylic acid [prepared using the protocols described in *Tetrahedron*, Vol. 37, Suppl., 1981, 4111] (3.04 g, 19.7 mmol) in $CH_2Cl_2$ (45 mL) was cooled to 0° C. and treated with 2-(trimethylsilyl) ethanol (2.7 mL, 18.6 mmol), EDC (3.94 g, 20.55 mmol) and DMAP (0.11 g, 0.9 mmol). After warming to room temperature and stirring for 2 h the reaction mixture was quenched with water and diluted with $CH_2Cl_2$. After separating the layers, the organic phase was washed with satd. aq. NaCl, dried over $MgSO_4$ and concentrated. Purification by MPLC (0–25% EtOAc/hexanes) provided the target compound (3.9 g, 78%) as a colorless oil. $^1$H NMR ($CDCl_3$) d 4.18 (m, 2 H), 2.88 (m, 2 H), 2.76 (m, 1 H), 2.05 (m, 4 H), 1.50 (m, 2 H), 0.99 (t, J=8.4 Hz, 2 H), 0.09 (s, 9).

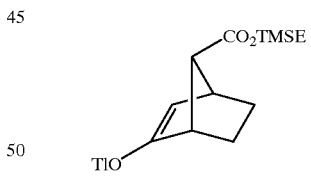

Step 2 A solution of the ketone from step 1 (3.18 g, 12.50 mmol) and 2-[N,N-bis(trifluoromethysulfonyl) amino]-5-chloropyridine (6.6 g, 16.30 mmol) in THF was cooled to −78° C. and carefully treated with a 0.5 M solution of KHMDS in toluene (24 mL, 12 mmol). After the addition was complete and the solution stirred for 2 h, the reaction mixture was quenched with water (30 mL), warmed to room temperature and diluted with EtOAc. The two phases were separated. The organic layer was washed with satd. aq. NaCl, dried over $MgSO_4$ and concentrated Purification by MPLC (0–15% EtOAc/hexanes) provided the target compound (4.2 g, 91%) as a colorless oil. $^1$H NMR ($CDCl_3$) d 5.75 (d, J=4.8 Hz, 1 H), 4.13 (t, J=9.0 Hz, 2 H), 3.18 (m, 2 H), 2.62 (m, 1 H), 1.89 (m, 2 H), 1.41 (t, J=9.3 Hz, 1 H), 1.23 (t, J=9.1 Hz, 1 H), 0.96 (t, J=8.4 Hz, 2 H), 0.04 (s, 9 H).

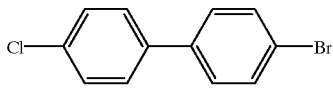

Step 3 A solution 4-chlorobiphenyl (3.0 g, 15.9 mmol) in acetic add (50 mL) was carefully treated with bromine (1.1 mL, 20.7 mmol) at room temperature. The reaction mixture was heated to reflux for 4 h, cooled to room temperature and treated with excess propene until the mixture became clear. The solution was concentrated to a thick slurry, diluted with $CH_2Cl_2$ (50 mL) and washed successively with water and 2N NaOH. The organic extract was dried over $MgSO_4$, filtered and concentrated. Purification by recrystallization from EtOAc gave the aryl bromide (3.57 g, 84%) as a white crystalline solid. $^1H$ NMR (CDCl$_3$) d 7.57 (m, 2 H), 7.48 (m, 2 H), 7.41 (m, 4 H).

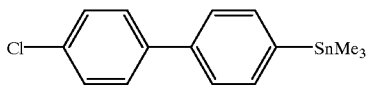

Step 4 A solution of 4-Bromo-4'-chlorobiphenyl (8.0 g, 30.0 mmol) in THF (120 mL) was cooled to −78° C. and carefully treated with n-BuLi (19.7 mL, 1.6 M soln. in hexanes, 31.5 mmol). After stirring for 1 h, the mixture was treated with chlorotrimethyltin (33 mL, 1.0 M soln., 33.0 mmol). After an additional 30 min, the solution was warmed to room temperature and concentrated. The off-white solid was diluted with $CH_2Cl_2$ (300 mL) and washed successively with water and sat. aq. NaCl. The organic layer was dried over $MgSO_4$, filtered and concentrated. Purification by MPLC (hexanes) gave the aryltin (9.38 g, 89%) as a white crystalline solid. $^1H$ NMR (CDCl$_3$) d 7.62 (m, 6 H), 7.54 (m, 2 H), 0.39 (s, 9 H).

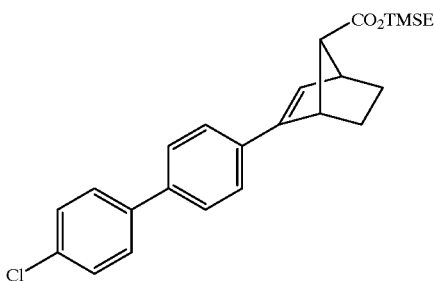

Step 5 A solution of the triflate from step 2 (4.2 g, 10.89 mmol), CuI (0.215 g, 1.1 mmol), AsPh$_3$ (0.339 g, 1.1 mmol), Cl$_2$Pd(MeCN)$_2$ (0.215 g, 0.56 mmol) and a few crystals of BHT in 1-methyl-2-pyrrolidinone (11.5 mL) was lowered into a oil bath preheated to 85° C. After stirring 4 min, the biphenyltin derivative from step 4 (7.3 g, 20.7 mmol) was added in one portion. The mixture was stirred for 30 min, cooled to room temperature and diluted with EtOAc. After separating the phases, the aq. layer was back extracted with EtOAc and the combined organic layers were dried over $MgSO_4$, filtered and concentrated. The resulting residue was adsorbed on silica gel and purified by MPLC (0–15% EtOAc/hexanes) to give the coupled product (4.0 g, 86%) as a white crystalline solid. $^1H$ NMR (CDCl$_3$) d 7.52 (m, 6 H), 7.42 (m, 2 H), 6.40 (d, J=3.3 Hz, 1 H), 4.19 (t, J=10.2 Hz, 2 H), 3.58 (m, 1 H), 3.23 (m, 1 H), 2.60 (m, 1 H), 1.95 (m, 2 H), 1.20 (m, 2 H), 1.02 (d, J=7.5 Hz, 2 H), 0.08 (s, 9H).

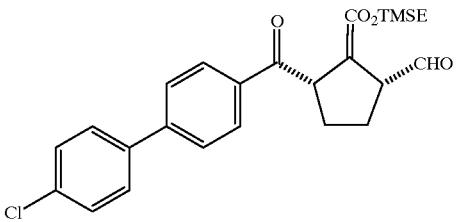

Step 6 A solution of the olefin from step 5 (3.60 g, 8.47 mmol) in 10% MeOH/CH$_2$Cl$_2$ (200 mL) was cooled to −78° C. and treated with ozone as a gas added directly into the reaction mixture (10 min, 1 l/min). After TLC indicated the absence of starting material the solution was purged with argon (15 min), treated with methylsulfide (13 mL) and warmed to room temperature. After stirring overnight, the solution was concentrated to a residue which was purified by MPLC (0–15% EtOAc/hexanes) to give a mixture of the desired aldehyde and the corresponding dimethyl acetal. The product mixture was dissolved in acetone (45 mL) and treated with CSA (0.192 g, 0.83 mmol) and water (0.3 mL, 16.5 mmol). After stirring overnight, the solution was concentrated and purified by MPLC (0–15% EtOAc/hexanes) to give the desired aldehyde (3.45 g, 89%) as a colorless oil: $^1H$ NMR (CDCl$_3$) d 9.78 (d, J=1.8 Hz, 1 H), 8.05 (d, J=6.6 Hz, 2 H), 7.65 (d, J=6.6 Hz, 2 H), 7.55 (d, J=9.0 Hz, 2 H), 7.44 (d, J=9.0 Hz, 2 H), 4.15 (m, 3 H), 3.87 (t, J=7.2 Hz, 1 H), 3.15 (m, 1 H), 2.20, (m, 1 H), 2.03 (m, 1 H), 1.86 (m, 1 H), 1.58 (s, 1 H), 1.25 (t, J=6.9 Hz, 1 H), 0.93 (m, 2 H), 0.00 (s, 9 H).

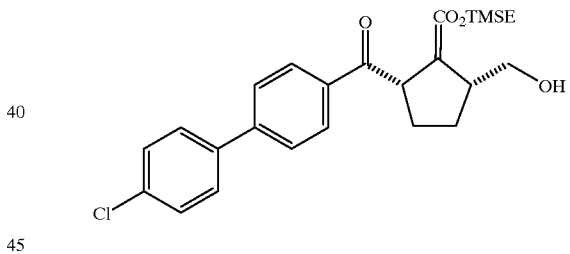

Step 7 A solution of lithium aluminum hydride (1.9 mL, 1.0 M THF) in THF (6 mL) was treated with 3-ethyl-3-pentanol (0.83 mL, 5.77 mmol) and heated to a gentle reflux for 1 h. The mixture was then cooled to room temperature.

A solution of the aldehyde intermediate from step 6 (0.85 g, 1.86 mmol) in THF (15 mL) was cooled to −78° C. and treated with the previously prepared solution of LTEPA in THE (above) via cannula in a dropwise manner. After the addition was complete, the solution was stirred at −78° C. for 4 h and subsequently quenched with 2 N HCl (4.6 mL). The reaction mixture was diluted with EtOAc and washed with water. The organic layer was dried over $MgSO_4$, filtered and concentrated. Purification by MPLC (5–40% ETOAc/hexanes) afforded the desired aldehyde (0.640 g, 75%) as a white crystalline solid. $^1H$ NMR (CDCl$_3$) d 8.05 (d, J=8.7 Hz, 2 H), 7.65 (d, J=8.5 Hz, 2 H), 7.55 (d, J=8.4 Hz, 2 H), 7.44 (d, J=8.4 Hz, 2 H), 4.15 (m, 2 H), 3.76 (t, J=6.3 Hz, 2 H), 3.28 (t, J=8.7 Hz, 1 H), 2.48 (m, 1 H), 2.35 (t, J=6 Hz, 1 H), 2.18 (m, 1 H), 1.91 (m, 2 H), 1.57 (m, 1 H), 1.35 (t, J=6.9 Hz, 1 H), 0.91 (m, 2 H), −0.01 (s, 9 H).

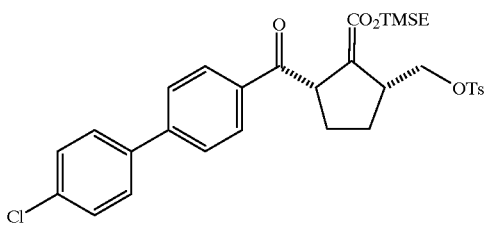

Step 8 A solution of the alcohol from step 7 (0.200 g, 0.436 mmol) and triethylamine (0.09 mL, 0.65 mmol) in CH$_2$Cl$_2$ (6 mL) was treated with p-toluenesulfonyl chloride (0.101 g, 0.524 mmol) and a crystal of DMAP. The mixture was stirred at room temperature for 16 h, concentrated under reduced pressure and purified by MPLC (0–20% EtOAc/hexanes) to give the tosylate (0.240 g, 89%) as a colorless oil: $^1$H NMR (CDCl$_3$) d 8.02 (d, J=8.4 Hz, 2 H), 7.82 (d, J=8.1 Hz, 2 H), 7.64 (d, J=8.4 Hz, 2 H), 7.56 (m, 2 H), 7.45 (m, 2 H), 7.36 (d, J=8.1 Hz, 2 H), 4.28 (m, 1 H), 4.10 (m, 4 H), 3.14 (m, 1 H), 2.61 (m, 1 H), 2.46 (s, 3 H), 2.13 (m, 1 H), 2.00 (m, 1 H), 1.82, (m, 1 H), 1.56 (m, 1 H), 0.87 (m, 2 H), 0.00 (s, 9 H).

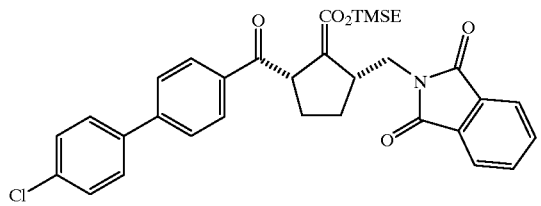

Step 9 A solution of the tosylate from step 8 (0.250 g, 0.408 mmol), potassium phthalimide (0.232 g, 1.23 mmol), 18-crown-6 (0.341 g, 1.29 mmol) in DMF (3 mL) was heated to 40° C. and stirred for 2 h. After cooling to room temperature, the reaction mixture was diluted with EtOAc and water. After separating the phases, the organic layer was washed with satd. aq. NaCl, dried over MgSO$_4$, filtered and concentrated. Purification by MPLC (3–20% EtOAc/hexanes) provided the desired phthalimide (0.187 g, 78%) as a white crystalline solid: $^1$H NMR (CDCl$_3$) d 8.04 (d, J=8.4 Hz, 2 H), 7.86 (dd, J$_1$=5.1 Hz, J$_2$=3.0 Hz, 2 H), 7.71 (dd, J$_1$=5.4 Hz, J$_2$=2.7 Hz, 2 H), 7.63 (d, J=6.6 Hz, 2 H), 7.55 (d, J=8.7 Hz, 2 H), 7.44 (d, J=8.4 Hz, 2 H), 4.20 (m, 1 H), 4.00 (m, 1 H), 3.91 (m, 2 H), 3.81 (m, 1 H), 3.33 (dd, J$_1$=13.5 Hz, J$_2$=6.9 Hz, 1 H), 3.32 (dd, J$_1$=11.1 Hz, J$_2$=3.9 Hz, 2 H), 2.80 (m, 1 H), 2.15, (m, 1 H), 1.94, (m, 2 H), 1.60 (m, 1 H), 0.66 (m, 2 H), −0.08 (s,9 H).

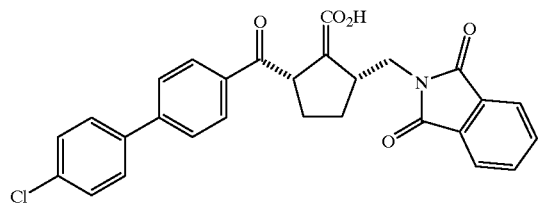

Step 10—Preparation of Example 360. A solution of the ester from step 9 (0.168 g, 0.286 mmol) in THF (5 mL) was treated TBAF (0.43 mL, 0.43 mmol) and subsequently stirred at room temperature for 2 h. The reaction mixture was quenched with 2 N HCl and diluted with EtOAc. After separating the phases, the organic layer was washed with satd. aq. NaCl. Purification by MPLC (0–5% MeOH/CH$_2$Cl$_2$) provided the desired acid (0.128 g, 92%) as a white crystalline solid. MP 203–205° C.

EXAMPLE 361 AND EXAMPLE 362

Example 360 (racemate) was separated into its most active (Example 361) and less active (Example 362) enantiomers on a Chiralcel" AS HPLC column using an ethanol/hexanes mixture as an eluent. Example 361: [a]$_D$ +44° (c 0.3, CHCl$_3$).

EXAMPLE 363

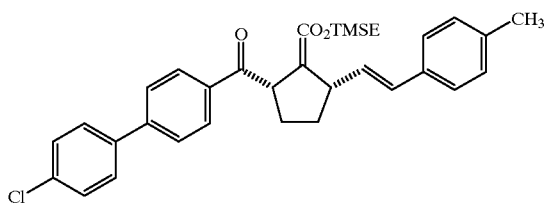

Step 1 A solution of 4-methylbenzyl triphenylphosphine bromide in THF (2.5 mL) was cooled to −78° C. and treated with n-BuLi (0.13 mL, 1.6 M soln. in hexanes). After stirring for 30 min, a solution of the aldehyde intermediate from Example 360, step 6 (0.112 g, 0.245 mmol) in THF (1.5 mL) was added, and the mixture was warmed to room temperature over 3 h. The reaction mixture was diluted with ethyl acetate and washed with water. The organic layer was washed with satd. aq. NaCl and dried over MgSO$_4$. Purification by flash column chromatography (0–10% EtOAc/hexanes) gave a the desired olefin (0.022 g, 16%) as a white crystalline solid. TLC R$_f$ 0.22 (silica, 10% EtOAc/hexanes).

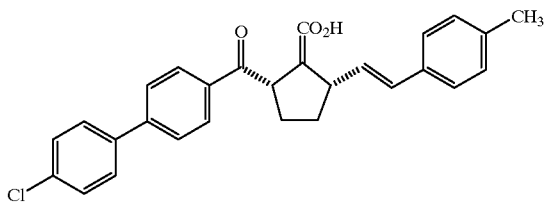

Step 2—Preparation of Example 363. Deprotection of the 2-(trimethylsilyl)ethyl ester from step 1 was carried out using the same protocol described for the deprotection of the intermediate in Example 360, step 10. MP 213° C.

EXAMPLE 364

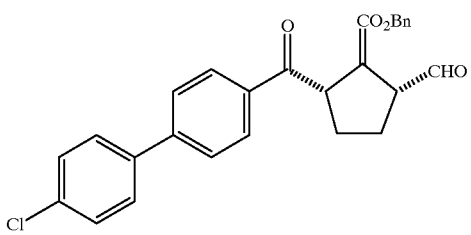

Step 1 The benzyl ester was prepared in a manner analogous to the one described for the corresponding 2-trimethylsilyl ester intermediate (Example 360, steps 1–6). In this case, benzyl alcohol was used instead of 2-trimethylsilylethanol in step 1.

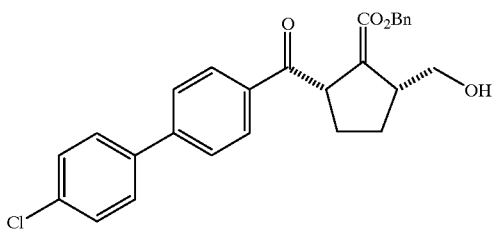

Step 2 The reduction of the intermediate from step 1 was carried out using the same protocol described for the corresponding 2-(trimethylsilyl)ethanol intermediate (Example 360, step 7).

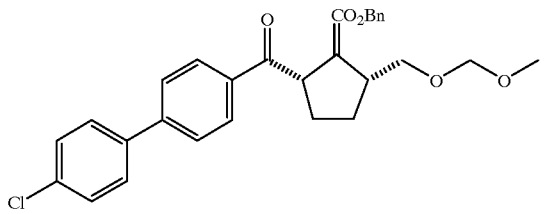

Step 3 A solution of the intermediate from step 2 (0.025 g, 0.0557 mmol) and diisopropylethylamine (0.03 mL, 0.167 mmol) in $CH_2Cl_2$ (2 mL) was treated with chloromethyl methylether (0.01 mL, 0.11 mmol) and stirred at room temperature overnight. Purification of the concentrated reaction mixture, by flash column chromatography (3–20% EtOAc/hexanes) provided the desired ether (0.025 g, 91%). $R_f$: 0.16 (silica, 25% EtOAc/hexanes).

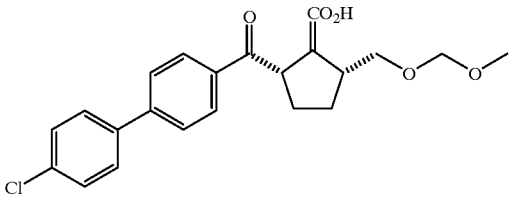

Step 4—Example 364. A solution of the intermediate benzyl ester from step 3 (0.023 g, 0.047 mmol) in THF (0.5 mL) and ethanol (0.4 mL) was treated with a NaOH solution (0.19 mL, 0.5 g/10 mL water). After stirring for 1.5 h at room temperature, the mixture was diluted with EtOAc and quenched with aq. 2N HCl (0.6 mL). The organic layer was washed with satd. aq. NaCl, dried over $MgSO_4$ and concentrated. The remaining residue was crystallized from diethyl ether and hexanes to give the desired acid (0.017 g, 90%). MP 89–90° C.

EXAMPLE 365

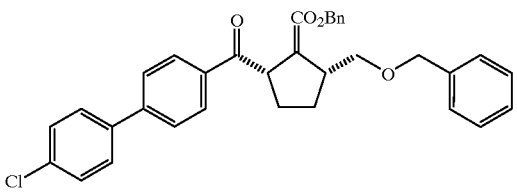

Step 1 A solution of the intermediate from Example 364, step 2 (0.150 g, 0.334 mmol) in $CH_2Cl_2$ (1 mL) and cyclohexane (2 mL) was treated with benzyl 2,2,2-trichloroacetimidate (0.068 mL, 0.37 mmol) and $BF_3 \cdot Et_2O$ (7 μL). After stirring for 30 min. solid $NaHCO_3$ was added and the solution was diluted with $CH_2Cl_2$. After filtering through a short pad of silica gel, the solution was concentrated and purified by flash column chromatography (0–15% EtOAc/hexanes) to give the desired compound in low yield. $R_f$: 0.39 (25% EtOAc/hexanes).

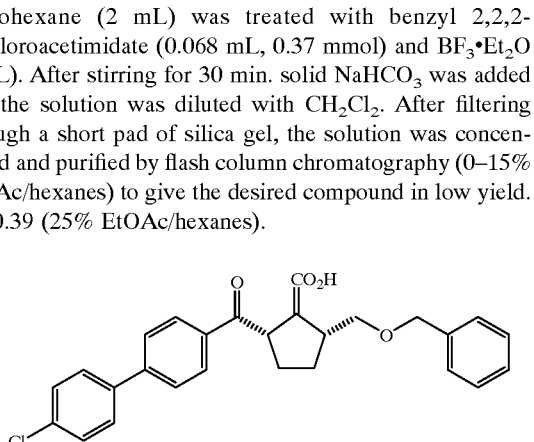

Step 2—Preparation of Example 365. The deprotection of the benzyl ester intermediate from step 1 was accomplished using the same protocol described for Example 364 in step 4. MP 157–158° C.

EXAMPLE 366

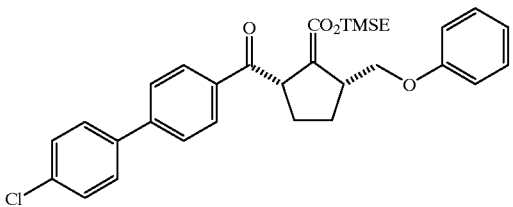

Step 1 A solution of the alcohol from Example 360, step 7 (0.054 g, 0.118 mmol), phenol (0.015 g, 0.159 mmol) and triphenylphosphine (0.069 g, 0.263 mmol) in THF was treated with diethylazodicarboxylate (0.04 mL, 0.254 mmol) and stirred at room temperature for 24 h. After concentrating the reaction mixture, the remaining residue was purified by flash column chromatography (0–10% EtOAc/hexanes) to give the desired phenol (0.031 g, 52%). $R_f$: 0.41 (silica, 15% EtOAc/hexanes).

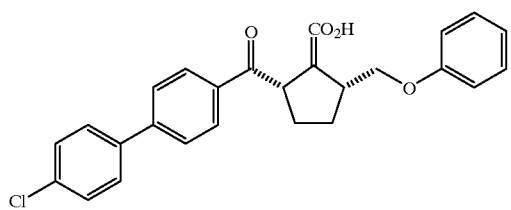

Step 2—Preparation of Example 366. The deprotection of the 2-(trimethylsilyl) ethanol ester intermediate from step 1 was accomplished using the same protocol described for Example 360 in step 10. MP 189–190° C.

EXAMPLE 367

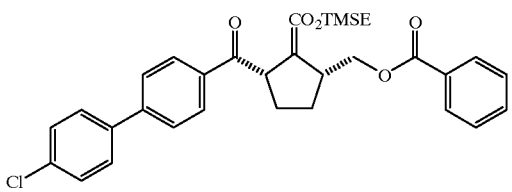

Step 1 A solution of the alcohol from Example 360, step 7 (0.040 g, 0.087 mmol) and triethylamine (0.02 mL, 0.144 mmol) in $CH_2Cl_2$ (2 mL) was treated with benzoyl chloride (0.015 mL, 0.129 mmol) and DMAP (1 mg). After stirring at room temperature for 5 h, the solution was concentrated and purified by flash column chromatography (0–15% EtOAc/hexanes) to give the desired ester (0.044 g, 92%). $R_f$: 0.4 (silica, 25% EtOAc/hexanes).

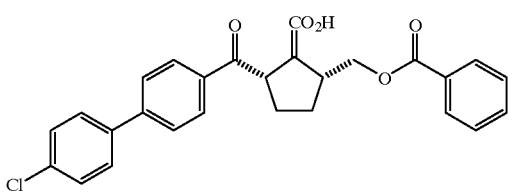

Step 2—Preparation of Example 367. The deprotection of the 2-(trimethylsilyl) ethanol ester intermediate from step 1 was accomplished using the same protocol described for Example 360 in step 10. MP 166–167° C.

EXAMPLE 368

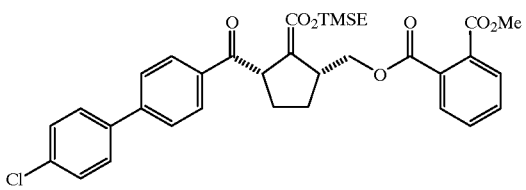

Step 1 A solution of the alcohol from Example 360, step 7 (0.039 g, 0.085 mmol), mono-methyl phthalate (0.032 g, 0.172 mmol), 1-(3-dimethylaminopropyl)-3-ethylcarbodiimide methiodide (0.033 g, 0.172 mmol) and N,N-dimethylaminopyridine (0.005 g, 0.04 mmol) in $CH_2Cl_2$ (2 mL) was stirred at room temperature for 32 h. The reaction was diluted $CH_2Cl_2$ and washed with water. The organic extracts were dried over $MgSO_4$, filtered and purified by flash column chromatography (0–20% EtOAc/hexanes) to give the desired ester (0.039 g, 74%). $R_f$: 0.35 (silica, 30% EtOAc/hexanes).

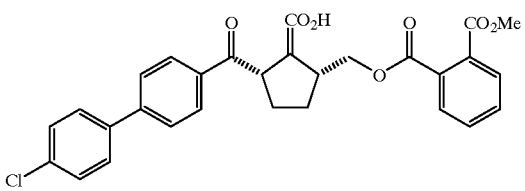

Step 2—Preparation of Example 368. The deprotection of the 2-(trimethylsilyl) ethanol ester intermediate from step 1 was accomplished using the same protocol as that described for Example 360 in step 10. MP 102–104° C.

EXAMPLE 369

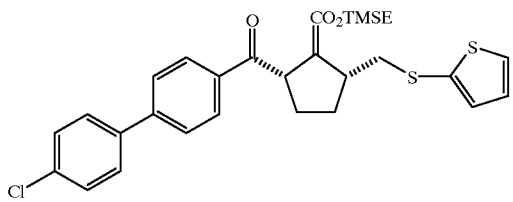

Step 1 A suspension of sodium hydride (0.0093 g, 0.368 mmol) in THF (1 mL) was treated with 2-mercaptothiophene (0.062 g, 0.534 mmol). After stirring for 30 min, a solution of the tosylate from Example 360, step 8 (0.05 g, 0.082 mmol) in DMF (0.03 mL) was added and the mixture was stirred at room temperature for 2 h. The reaction mixture was diluted with EtOAc and washed with satd. aq. NaCl. The organic extracts were dried over $MgSO_4$, filtered, concentrated and purified by flash column chromatography (0–5% EtOAc/hexanes) to give the desired product (0.037 g, 12%). $R_f$: 0.21 (silica, 10% EtOAc/hexanes).

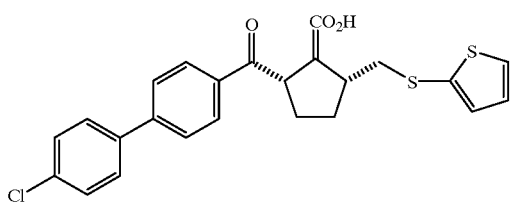

Step 2—Preparation of Example 369. The deprotection of the 2-(trimethylsilyl) ethanol ester intermediate from step 1 was accomplished using the same protocol as that described for 360 in step 10. MP 184° C.

EXAMPLE 370

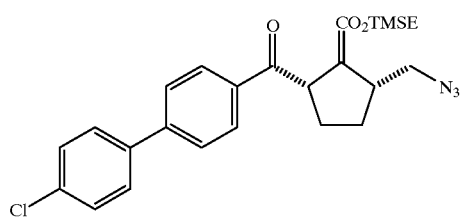

Step 1 A solution of the tosylate from 360, step 8 (0.5 g, 0.82 mmol) in DMF (3 mL) was treated with sodium azide (0.160 g, 2.5 mmol). After stirring for 24 h at room temperature, the mixture was diluted with diethylether and washed with water. The organic extracts were dried over $MgSO_4$, filtered, concentrated and purified by MPLC (0–10% EtOAc/hexanes) to give the desired azide (0.341 g, 86%). $R_f$: 0.22 (silica, 10% EtOAc/hexanes).

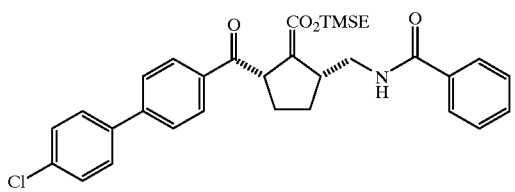

Step 2 A solution of the azide from step 1 (0.49 g, 0.101 mmol) in THF (1 mL) was treated with triphenylphosphine (0.030 g, 0.114 mmol) and water (0.015 mL). After being heated to 70° C. for 6 h, the mixture was diluted with EtOAc, washed with satd. aq. NaCl and dried over MgSO₄. The resulting solution was concentrated under reduced pressure and redissolved in CH₂Cl₂. The mixture was treated with benzoyl chloride (0.03 mL, 0.258 mmol) and stirred at room temperature for 24 h. After concentrating the solution, the resulting residue was purified by flash column chromatography (5–35% EtOAc/hexanes) to give the desired compound (0.025 g, 44%). $R_f$: 0.15 (silica, 30% EtOAc/hexanes).

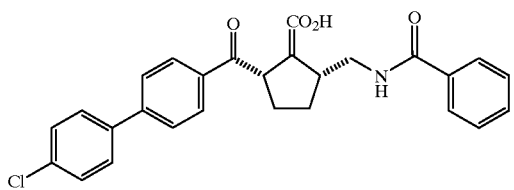

Step 3—Preparation of Example 370. The deprotection of the 2-(trimethylsilyl) ethanol ester intermediate from step 1 was accomplished using the same protocol as that described for Example 16–7387 in step 3. MP 204–206° C.

The above methods for the preparation of Example 360–370 were used to prepare the following series of biphenyl containing products (TABLE XXV).

TABLE XXV

| ex. | R¹⁴ | isomer | m.p.(° C.)/other characterization |
|---|---|---|---|
| 360 | (phthalimido-CH₂N) | racemic | 203–205 |
| 361 | (phthalimido-CH₂N) | (+) | $[a]_D$ +48(CHCl₃) |
| 362 | (phthalimido-CH₂N) | (−) | |
| 363 | (4-methylstyryl) | racemic | 213 |
| 364 | CH₂OCH₂OCH₃ | racemic | 89–90 |
| 365 | CH₂OCH₂Ph | racemic | 157–158 |
| 366 | CH₂OPh | racemic | 189–190 |
| 367 | CH₂O₂CPh | racemic | 166–167 |

TABLE XXV-continued
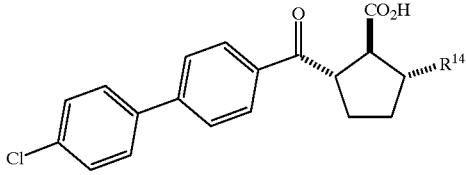
| ex. | R[14] | isomer | m.p.(° C.)/other characterization |
|---|---|---|---|
| 368 | 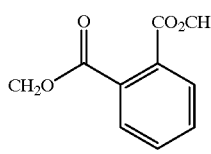 | racemic | 102–104 |
| 369 | 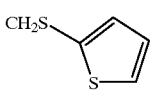 | racemic | 184 |
| 370 | CH$_2$NHCOPh | racemic | 204–206 |
| 371 | CH$_2$OCH$_2$O(CH$_2$)$_2$OMe | racemic | 107–108 |
| 372 | CH$_2$SCH$_2$Ph | racemic | 145–146 |
| 373 | CH$_2$SPh | racemic | 173–175 |
| 374 | CH$_2$SCH$_2$CH$_2$CH$_3$ | racemic | 163–165 |
| 375 | 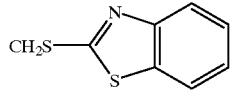 | racemic | 195–196 |
| 376 | 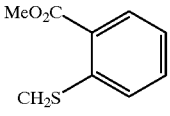 | racemic | 146–147 |
| 377 | 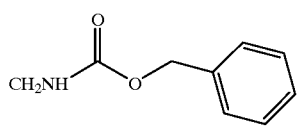 | racemic | 136–137 |
| 378 | 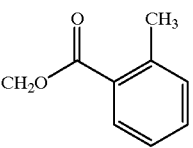 | racemic | 152–154 |
| 379 | 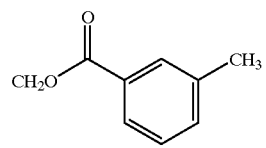 | racemic | 150–151 |
| 380 | 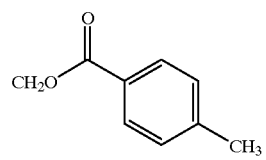 | racemic | 145 |

TABLE XXV-continued

| ex. | R$^{14}$ | isomer | m.p.(° C.)/other characterization |
|---|---|---|---|
| 381 | 2-methoxybenzoate-CH$_2$O- | racemic | 146–148 |
| 382 | 3-methoxybenzoate-CH$_2$O- | racemic | 162–164 |
| 383 | 4-methoxybenzoate-CH$_2$O- | racemic | |
| 384 | benzoxazol-2-yl-SCH$_2$- | racemic | 180–183 |
| 385 | (4-nitrophthalimido)-CH$_2$N- | racemic | 203–204 |
| 386 | (5-nitrophthalimido)-CH$_2$N- | racemic | 178–179 |
| 387 | (naphthalimido)-CH$_2$N- | racemic | 247–248 |
| 388 | 4-chlorophenoxy-CH$_2$- | racemic | 215–217 |

TABLE XXV-continued

[Structure: 4-chlorobiphenyl-CO-cyclopentane with CO2H and R14 substituents]

| ex. | R14 | isomer | m.p.(° C.)/other characterization |
|-----|-----|--------|-----------------------------------|
| 389 | [phthalimide-CH2O-] | racemic | 191–192 |
| 390 | [4-Cl-5-NO2-phthalimide-CH2-] | racemic | 201–203 |
| 391 | [4,5-dichlorophthalimide-CH2-] | racemic | 257–258 |
| 392 | [3-amino-phthalimide-CH2-] | racemic | 220–223 |

EXAMPLE 393 AND EXAMPLE 394

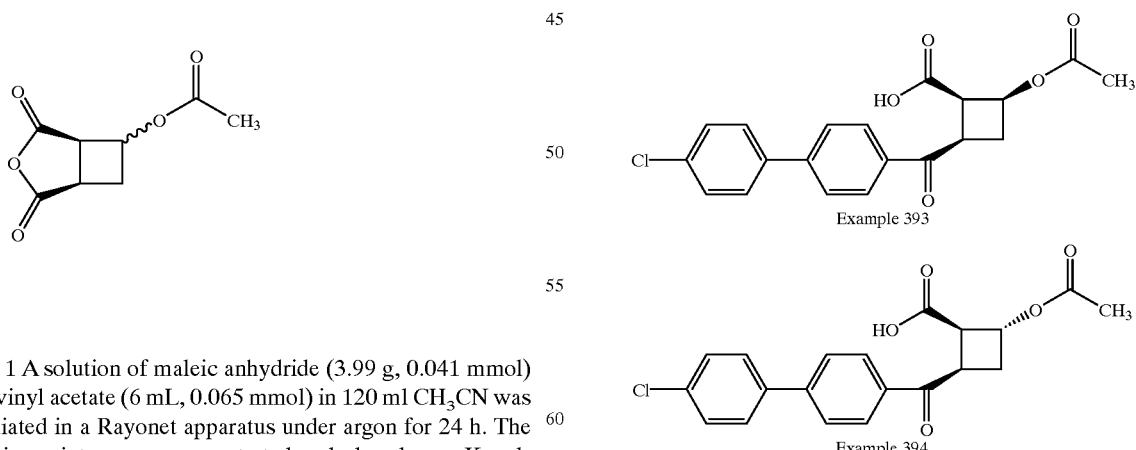

Example 393

Example 394

Step 1 A solution of maleic anhydride (3.99 g, 0.041 mmol) and vinyl acetate (6 mL, 0.065 mmol) in 120 ml CH$_3$CN was irradiated in a Rayonet apparatus under argon for 24 h. The reaction mixture was concentrated and placed on a Kugelrohr to remove remaining maleic anhydride. A crude brown oil (2.03 g) was used in next step without further purification. $^1$HNMR (CDCl$_3$) showed a mixture of cis and trans acetate groups (s, d 2.03 and 1.96 ppm).

Step 2—Preparation of Example 393 and Example 394. A solution of anhydride (2.00 g, 10.60 mmol) and 4-chlorobiphenyl (2.00 g, 10.69 mmol) was dissolved in 50 ml CH$_2$Cl$_2$ under argon. The solution was chilled in an ice bath. Aluminum trichloride (4.03 g, 32.25 mmol) was added in one portion and the reaction was allowed to warm to ambient temperature. After 21 h, the reaction was quenched with chilled 10% HCl and the CH$_2$Cl$_2$ layer was drained. The aqueous layer was extracted with EtOAc and the combined organics were washed with brine, dried with MgSO$_4$ and concentrated. A major product Example 393 (953 mg) was crystallized (MP 202–204° C. dec) using EtOAc-hexane from the crude product. Another isomer Example 394 (116 mg) was crystallized (MP 189–190° C.) with EtOAc-Hexane from the filtrate.

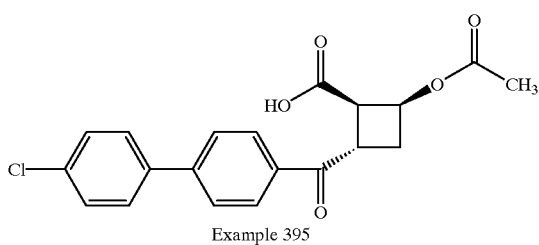

Example 395

EXAMPLE 395

Example 393 (252 mg, 0.680 mmol) in 5 ml THF under argon. DBU was added (0.15 ml, 1.003 mmol) and allowed to stir for 24 h. The reaction mixture was diluted with CH$_2$Cl$_2$, then washed with 10% HCl, brine and dried over MgSO$_4$. The concentrated crude material was crystallized with EtOAc-Hexane to give 117 mg Example 395. MP 197–199° C. (dec).

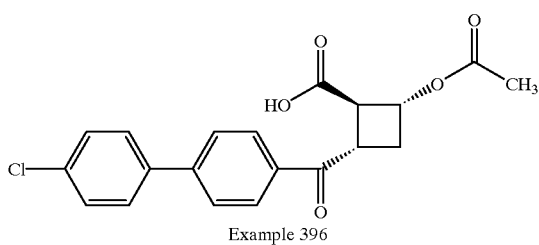

Example 396

EXAMPLE 396

Example 396 was prepared from Example 394 using the procedure for the preparation of Example 395. MP 151–1525° C.

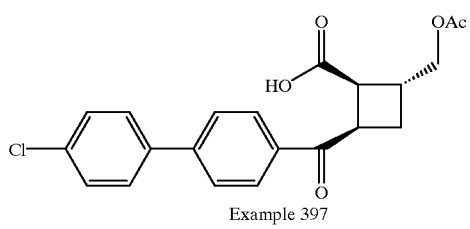

Example 397

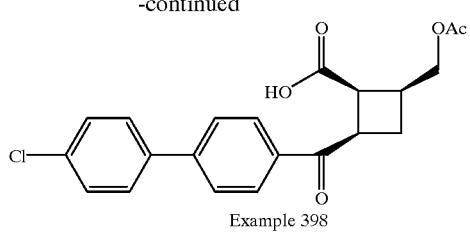

Example 398

EXAMPLE 397 AND EXAMPLE 398

These examples were prepared in a similar manner to Example 393 and Example 394 except that allyl acetate was used in step 1 instead of vinyl acetate. Example 397 was crystallized from the crude product by using EtOAc-Hexane as solvent. Isomer Example 398 could be isolated from the mother liquors by HPLC.

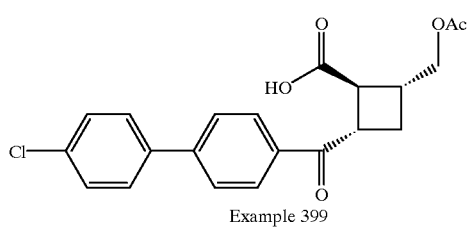

Example 399

EXAMPLE 399

Example 399 was prepared from Example 397 using the procedure for the preparation of Example 395 MS (FAB) M$^+$=387.

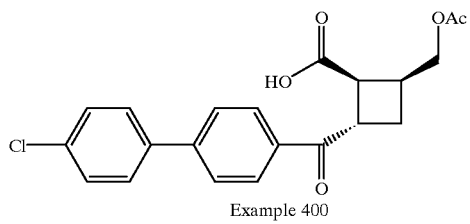

Example 400

EXAMPLE 400

Example 400 could be prepared from Example 398 using the procedure for the preparation of Example 395.

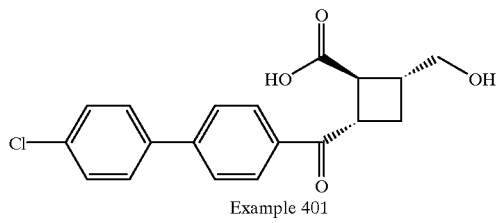

Example 401

EXAMPLE 401

This compound was prepared by removing the acetate group of Example 399 with K$_2$CO$_3$—MeOH and subsequent hydrolysis of the methyl ester (formed during deblocking) with LiOH in MeOH—H$_2$O.

EXAMPLE 402

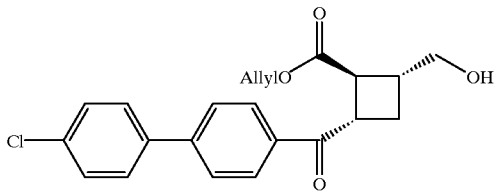

Step 1 This esters was prepared from Example 401 by treatment with the allyl alcohol and a catalytic amount of concentrated H₂SO₄.

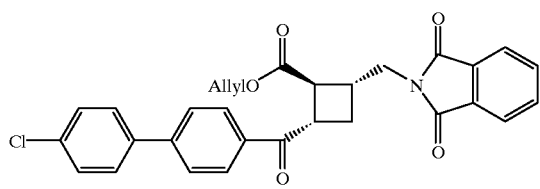

Step 2 This phthalimide derivative was prepared from the product of step 1 together with the reagents used in the general procedure of Example 360, step 9.

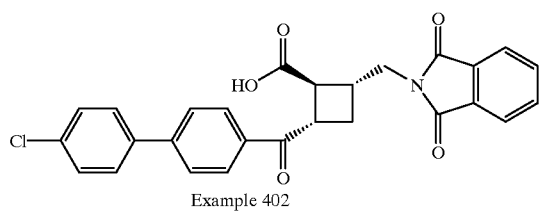

Example 402

Step 3—Preparation of Example 402. Example 402 was prepared from the product of step 2 using the procedure of Example 267, step 4.

EXAMPLE 403

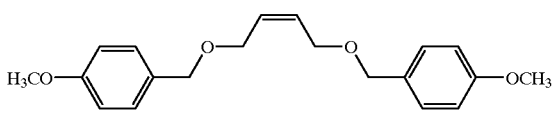

Step 1 To a slurry of 95% NaH (8.17 g, 0.34 mol) in 170 mL of anh. DMF was added 1,4-dihydroxy-2-butene (10.00 g, 0.11 mol) in 110 mL of anh. DMF over 30 min. The resulting mixture was stirred at room temperature for 2 h, then cooled to 0° C. and a solution of 4-methoxybenzyl chloride (37.33 g, 0.24 mol) in 170 mL of anhydrous DMF was added over 20 min, while vigorous gas evolution was observed. The reaction mixture was stirred at 0° C. for 15 min and at room temperature for 30 min, then was cooled to 0° C. and quenched by the dropwise addition of 100 mL of H₂O. The mixture was vigorously stirred at room temperature for 15 min, then diluted with 400 mL of EtOAc. The aqueous layer was extracted with 2×400 mL of EtOAc. The combined organic layers were washed with a saturated NaCl solution, dried (Na₂SO₄), and concentrated in vacuo. The crude product was purified by chromatography (11 cm×6.5 cm silica gel; hexane, then 20% EtOAc-hexane) affording 34.94 g (94%) of the alkene as a colorless oil. TLC Rf (30% EtOAc-hexane) 0.47.

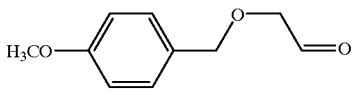

Step 2 The alkene (5.00 g, 15 mmol) was dissolved in a mixture of 225 mL of dioxane, 60 mL of H₂O and 15 mL of 2N H₂SO₄. Osmium tetraoxide was added and the solution was stirred for 10 min. NaIO₄ (13.00 g, 60 mmol) was added in small portions over 10 min. To this was added 15 mL of 2N H₂SO₄ and the mixture was stirred for 5 h, as a white solid formed. To this slurry was added 250 mL of H₂O to obtain a clear solution which was then extracted with Et₂O (6×250 mL). The organic layers were combined, washed with a saturated NaCl solution, dried (Na₂SO₄), and concentrated in vacuo. The crude product was purified by chromatography (150 g silica gel; 30% EtOAc-hexane) affording 4.69 g (85%) of the aldehyde as a colorless oil. TLC Rf (30% EtOAc-hexane) 0.25.

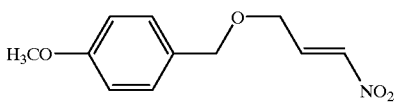

Step 3 To a 0° C. solution of the aldehyde (5.44 g, 30 mmol) in a mixture of freshly distilled THF (65 mL) and anh. tBuOH (65 mL) was added nitromethane (5.53 g, 91 mmol) and KOtBu (0.34 g, 3 mmol). The mixture was stirred for 4 h, then diluted with 200 mL of Et₂O, and washed with 2×50 mL of NH₄Cl. The combined aqueous layers were back extracted with 100 mL of Et₂O. The organic layers were combined, washed with brine, dried over Na₂SO₄ and concentrated in vacuo.

The resulting crude nitro alcohol was dissolved in 160 mL of freshly distilled CH₂Cl₂ and cooled to 0° C. Methanesulfonyl chloride (2.3 mL, 30 mmol) was added and stirred for 6 min. Freshly distilled triethylamine (8.4 mL, 61 mmol) was added and stirred for 15 min. The reaction was quenched at 0° C. by the addition of 25 mL of a saturated NH₄Cl solution. The mixture was extracted with 300 mL of CH₂Cl₂. The organic layer was washed with 50 mL of a saturated NH₄Cl solution. The combined aqueous layers were back extracted with 100 mL of CH₂Cl₂. The combined organic layers were washed with a saturated NaCl solution, dried (Na₂SO₄), and concentrated in vacuo. The crude product was purified by chromatography (150 g silica gel; 20% EtOAc-hexane) affording 5.56 g (82%) of the nitroalkene as a colorless oil. TLC Rf (20% EtOAc-hexane) 0.36.

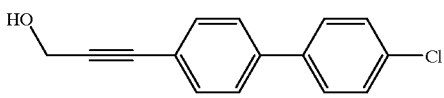

Step 4 A mixture of propargyl alcohol (3.14 g, 56 mmol), 1-bromo4-(4'-chlorophenyl)-benzene (10.00 g, 37.3 mmol), bis(triphenylphosphine)palladium(II) chloride (0.19 g, 0.3 mmol), triphenylphosphine (0.37 g, 1.4 mmol) and cuprous iodide (0.37 g, 1.9 mmol) in 1500 mL of freshly distilled triethylamine was heated at the reflux temperature for 16 h. Additional bis(triphenylphosphine)palladium(II) chloride (0.19 g, 0.3 mmol), triphenylphosphine (0.37 g, 1.4 mmol) and cuprous iodide (0.37 g, 1.9 mmol) were added and the mixture was heated at the reflux temperature for an additional 7 h. The mixture was allowed to cool to room temperature, filtered and the filtrate was concentrated in vacuo. The crude product was purified by chromatography (11 cm×11 cm silica gel; CH$_2$Cl$_2$), and by recrystallization (from EtOAc-hexane mixture) yielding 7.32 g (80%) of the biphenyl-alcohol as a yellowish solid. TLC Rf (CH$_2$Cl$_2$) 0.48.

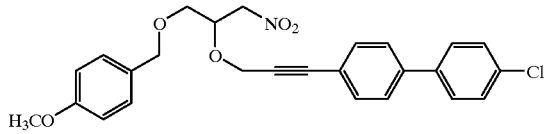

Step 5 To a slurry of 95% NaH (0.72 g, 30 mmol) in 50 mL of distilled THF was added the biphenyl alcohol (7.31 g, 30 mmol) in 200 mL of distilled THF. The mixture was stirred for 1 h, then cooled to −40° C. The nitroalkene (3.36 g, 15 mmol) in 50 mL of distilled THF was added dropwise over 10 min. The mixture was allowed to warm to 0° C., then quenched by the addition of 100 mL of 1N HCl. The resulting mixture was extracted with 3×250 mL of EtOAc. The organic layers were combined, washed with a 1:1 mixture of saturated NaHCO$_3$ solution and H$_2$O, a saturated NaCl solution, dried (Na$_2$SO$_4$), and concentrated in vacuo. The crude product was purified by chromatography (150 g silica gel, CH$_2$Cl$_2$; and 150 g silica gel, 60% CH$_2$Cl$_2$-hexane) yielding 4.05 g (58%) of the Michael-adduct as a yellow oil. TLC Rf (80% CH$_2$Cl$_2$-hexane) 0.36.

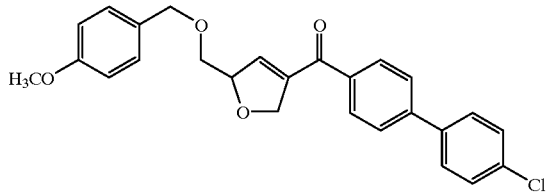

Step 6 To a solution of the Michael-adduct (2.81 g, 6.0 mmol) in 14 mL of anh. toluene was added a slurry of freshly distilled TMSCl (1.97 g, 18.0 mmol) and freshly distilled Et$_3$N (1.83 g, 18.0 mmol) in 10 mL of anh. toluene. The mixture was stirred for 1 h, then 15 mL of THF and 13 mL of 10% HCl were added. The mixture was vigorously stirred for 1.5 h, then extracted with EtOAc (3×100 mL). The organic layers were combined, washed with a saturated NaCl solution, dried (Na$_2$SO$_4$), and concentrated in vacuo. The crude product was purified by chromatography (100 g silica gel; 2% EtOAc-CH$_2$Cl$_2$) affording 1.42 g (54%) of the dihydrofuran as a yellow solid. TLC Rf (5% EtOAc-CH$_2$Cl$_2$) 0.46.

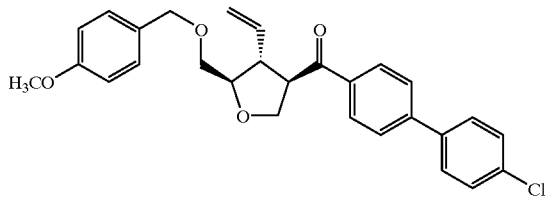

Step 7 To a 0° C. solution of tetravinyltin (289 mg, 1.3 mmol) in 15 mL of freshly distilled Et$_2$O was added 1.43 M methyllithium (2.6 mL, 3.7 mmol) dropwise over 15 min. The mixture was stirred at 0° C. for 15 min, then cooled to −78° C. Cuprous cyanide (228 mg, 2.5 mmol) was added in one portion. The mixture was allowed to warm to −30° C. over 75 min, and stirred at −30° C. for 45 min. A solution of the dihydrofuran (390 mg, 0.9 mmol) in 24 mL of freshly distilled Et$_2$O was added dropwise over 15 min and the resulting mixture was stirred at −30° C. for 45 min. A mixture of 10 mL of a saturated NH$_4$Cl solution and 10 mL of H$_2$O was slowly added, keeping the temperature under −25° C., as the reaction mixture turned brown. The mixture was allowed to warm to 15° C., then was filtered through a pad of Celite. The Celite was washed with 50 mL of H$_2$O and 100 mL of EtOAc. The two layers of the filtrate were separated, the blue aqueous layer was washed with 100 mL of EtOAc. The organic layers were combined, washed with a saturated NaCl solution, dried (Na$_2$SO$_4$), and concentrated in vacuo. The $^1$H NMR spectrum of the crude product showed the presence of two isomers(trans-trans and trans-cis)in a 7:3 ratio. The crude mixture was purified by chromatography (15 g silica gel; 3% EtOAc-CH$_2$Cl$_2$) affording 222 mg of the major vinyltetrahydrofuran isomer as a yellow oil and 120 mg of the mixture of the two vinyltetrahydrofuran isomers as a yellow oil (combined yield 82%). major isomer TLC Rf (5% EtOAc-CH$_2$Cl$_2$) 0.49; minor isomer TLC Rf (5% EtOAc-CH$_2$Cl$_2$) 0.38.

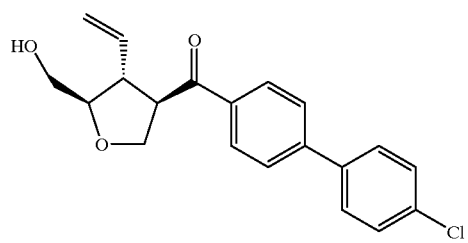

Step 8 To a solution of the trans-trans-vinyl isomer (874 mg, 1.9 mmol) in 16 mL of CH$_2$Cl$_2$ was added 0.8 mL H$_2$O and DDQ (643 mg, 2.8 mmol). The mixture was stirred for 40 min. The precipitated solid was filtered and washed with 150 mL of CH$_2$Cl$_2$. The filtrate was washed with 50 mL of saturated NaHCO$_3$ solution, a saturated NaCl solution, dried (Na$_2$SO$_4$), and concentrated in vacuo. The crude mixture was purified by chromatography (30 g silica gel; 10% EtOAc-CH$_2$Cl$_2$) yielding 534 mg (83%) of the hydroxymethyl-analog as a white solid. TLC Rf (10% EtOAc-CH$_2$Cl$_2$) 0.30.

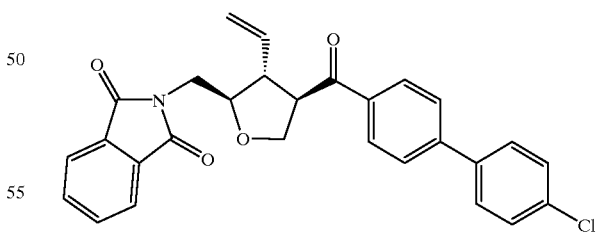

Step 9 To a 0° C. solution-of the hydroxymethyl-analog (303 mg, 0.88 mmol) in 18 mL of freshly distilled THF were added triphenylphospine (324 mg, 1.24 mmol), phthalimide (182 mg, 1.24 mmol) and DEAD (215 mg, 1.24 mmol). The mixture was allowed to warm to room temperature, stirred for 1 h, and concentrated in vacuo. The crude mixture was purified by chromatography (50 g silica gel; 2% EtOAc-CH$_2$Cl$_2$) yielding 266 mg (64%) of the phthalimido-analog as a white solid. TLC Rf (5% EtOAc-CH$_2$Cl$_2$) 0.71.

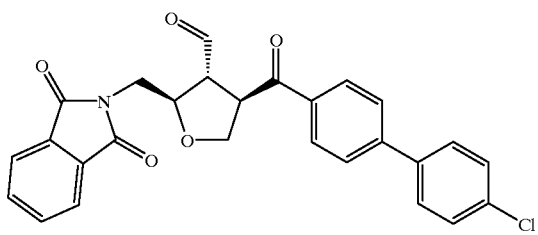

Step 10 Into a −78° C. solution of the phthalimido-analog (262 mg, 0.55 mmol) in 5 mL of CH2Cl2 was bubbled $O_2$ for 15 min. $O_3$ was bubbled into the mixture until it turned gray-blue (5 min). $O_2$ was again bubbled into the solution until blue color disappeared, then the mixture was purged with Ar. Triphenylphosphine (288 mg, 1.10 mmol) was added, and he mixture was allowed to warm to room temperature, and was stirred overnight. The crude mixture was purified by chromatography (40 g silica gel; 2% EtOAc-$CH_2Cl_2$ eluent) affording 265 mg (100%) of the aldehyde as a white solid. TLC Rf (5% EtOAc-$CH_2Cl_2$) 0.35.

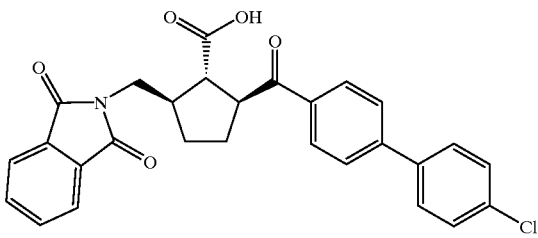

Step 11—Preparation of Example 403. To a 0° C. solution of the aldehyde (50 mg, 0.11 mmol) in 5 mL of acetone was added Jones' reagent until a deep yellow color persisted The mixture was stirred for 5 min, then was quenched by the addition of 2 mL of isopropanol. The resulting mixture was stirred at room temperature for 10 min, as it turned green, then was concentrated in vacuo. The crude mixture was purified by chromatography (10 g silica gel; 3% MeOH-0.5% AcOH-EtOAc eluent) affording 44 mg (85%) of Example 403 as a white solid. MP 113–114° C.

EXAMPLE 404

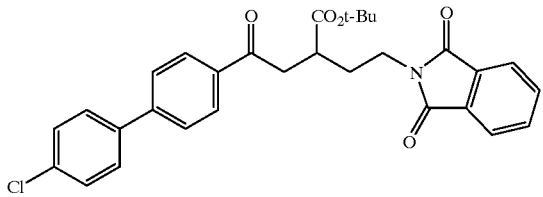

Step 1 To a solution of Example 267 in dry THF (397 mL) was added a solution of tert-butyl trichloroacetimidate (23.0 mL, 86.0 mmoL) in cyclohexane (93 mL) followed by $BF_3 \cdot Et_2O$ (1.76 mL, 14.3 mmol). The mixture was stirred at room temperature for 18 h after which $NaHCO_3$ (~5 g) was added to quench the reaction. The resulting slurry was filtered and the filtrate was concentrated under reduced pressure. The resulting crude solid was partitioned between $CH_2Cl_2$ (500 mL) and water (500 mL). The organic phase was washed with a saturated NaCl solution, dried ($MgSO_4$) and concentrated under reduced pressure. The resulting solids were recrystallized (EtOAc/hexane) to afford a white solid (11.4 g, 51%). TLC (25% EtOAc/hexane) $R_f$ 0.73.

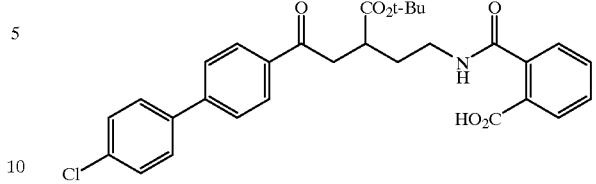

Step 2 To a mixture product of step 1 (0.20 g, 0.38 mmol) in abs. EtOH (3.8 mL) was added a 1 M NaOH solution (0.8 mL, 0.8 mmol). The resulting slurry was stirred at room temperature for 6 h and concentrated under reduced pressure. The resulting residue was partitioned between EtOAc (10 mL) and water (10 mL). The aqueous layer was acidified with 10% aq HCl (10 mL) and extracted with EtOAc (3×10 mL). The organic phase was washed with a saturated NaCl solution (10 mL), dried ($MgSO_4$) and concentrated under reduced pressure to afford a white solid (0.13 g, 62%). TLC (10% MeOH/$CH_2Cl_2$) $R_f$ 0.38.

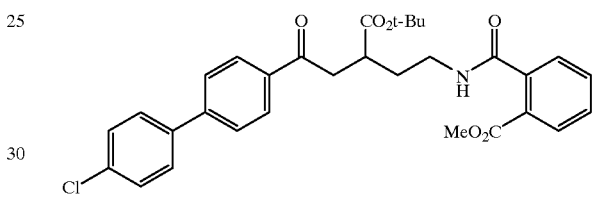

Step 3 To a solution of the product of step 2 (0.12 g, 0.23 mmol) in $Et_2O$ (50 mL) was added a solution of diazomethane in diethyl ether until a yellow color persisted, then excess diazomethane was quenched with glacial acetic acid (~5 mL). The resulting solution was diluted with EtOAc (50 mL), washed with water (50 mL) and a saturated NaCl solution (50 mL), dried ($MgSO_4$), and concentrated under reduced pressure to afford a yellow solid which was purified using rotary chromatography ($SiO_2$, 0–5% MeOH/$CH_2Cl_2$) to afford a colorless oil (0.10 g, 82%). TLC (50% EtOAc/hexane) $R_f$ 0.49.

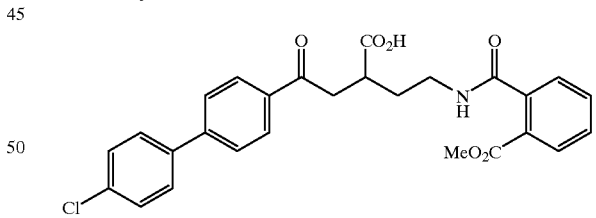

Example 404

Step 4—Preparation of Example 404. A mixture of the product of step 3 (0.11 g, 0.20 mmol) in a solution of HCl in dioxane (8.0 mL, 4 M, 32 mmol) was stirred at room temperature for 2 h, then concentrated under reduced pressure. The resulting residue was partitioned between EtOAc (100 mL) and water (100 mL). The organic phase was washed with a saturated NaCl solution (50 mL), dried ($MgSO_4$) and concentrated under reduced pressure to afford a semi-solid which was purified using rotary chromatography ($SiO_2$, 0–5% MeOH/$CH_2Cl_2$) to afford a light yellow solid (82 mg, 82%). HRMS Calcd for $C_{27}H_{25}ClNO_6$ ($M^+$+ H): 494.1370. Found: 494.1365.

EXAMPLE 405

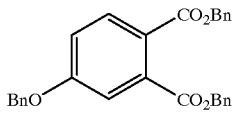

Step 1 4-Hydroxyphthalic acid (3.50 g, 19.2 mmol) and K₂CO₃ (23.9 g, 173 mmol) in acetone (100 mL) and water (50 mL) were stirred at rt for 15 min. Benzyl bromide (20.6 mL, 173 mmol) was added and the mixture was heated under reflux for 3 d. Vacuum distillation (45–50° C./1.1 mm) removed residual benzyl alcohol and the distillation residue was purified by gradient flash chromatography (10–30% ethyl acetate:hexane) to give dibenzyl 4-benzyloxyphthalate (7.20 g, 83%) as a pale yellow oil. TLC $R_f$ 0.65 (25% ethyl acetate:hexane).

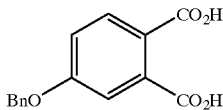

Step 2 The diester from step 1 (7.20 g, 15.5 mmol) in THF (60 mL) and LiOH•H₂O (2.00 g, 47.7 mmol) in water (60 mL) were mixed at rt for 4 d. The THF was removed in vacuo, and the basic layer was washed with diethyl ether (twice). The solution was acidified to pH 3 with conc. HCl and the colorless precipitate was filtered and dried in vacuo to give 4-benzyloxyphthalic acid (3.1 g, 73%) as a colorless solid. TLC $R_f$ 0.15 (50% ethyl acetate:hexane).

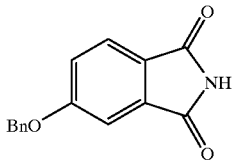

Step 3 Urea (1.32 g, 22 mmol) was added to the product of step 2 (3.00 g, 11.0 mmol) in glacial acetic acid (40 mL) and heated to 140° C. for 3.5 h. The solution was cooled to rt and slowly added to dilute sodium bicarbonate solution. The resulting precipitate was collected and dissolved in acetone, filtered and dried in vacuo to give 4-benzyloxyphthaliraide (1.98 g, 71%) as an off-white solid. TLC $R_f$ 0.90 (50% ethyl acetate:hexane).

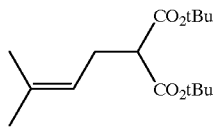

Step 4 A suspension of NaH (1.69 g, 67.0 mmol) in dry THF (90 ml) was cooled to 0° C. and placed under argon. Di-tert-butyl malonate (15.0 mL, 67.0 mmol) was added dropwise over 10 min, then stirred at rt for 20 min. 3,3-Dimethylallyl bromide (7.43 mL, 63.6 mmol) was added over 5 min and stirred at rt for 18 h. The reaction mixture was concentrated to a slurry, and partitioned between ethyl acetate and water. The water layer was washed with ethyl acetate, and the combined organic extracts were then washed with 10% HCl, brine, dried over MgSO₄, filtered, and concentrated to an orange oil (19.71 g, >100% crude). The crude product was washed through a 15 cm plug of silica with 30% ethyl acetate:hexane and dried in vacuo to give a yellow oil (19.37 g, >100%). TLC $R_f$ 0.60 (20% ethyl acetate:hexane).

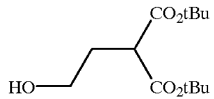

Step 5 A solution of crude olefin from step 4 (17.4 g, 61.2 mmol) in dichloromethane (240 mL) and methanol (60 mL) was cooled to −78° C. and purged with O₂(g) for 10 min. O₃(g) was bubbled through the solution for about 90 min until a blue color remained. The solution was then purged with O₂ for 10 min and argon for about 20 min until the solution was colorless again. NaBH₄ (2.31 g, 61.2 mmol) was added in one portion and the mixture was stirred overnight, allowing to warm to rt. The mixture was concentrated, rediluted in dichloromethane, washed with water, 10% HCl (twice), brine, dried over MgSO₄, filtered, and concentrated to a colorless oil (13.71 g, 86% crude). Purification of 4.00 g of crude material by gradient flash chromatography (15/15/70-25/25/50 ethyl acetate:dichloromethane:hexane) gave di-tert-butyl 2-hydroxyethylmalonate (2.42 g, 52%) as a colorless oil. TLC $R_f$ 0.25 (25% ethyl acetate:hexane).

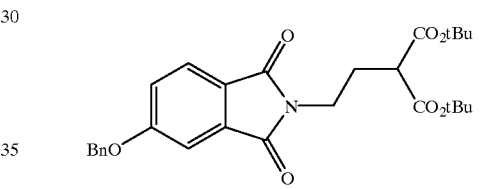

Step 6 Imide from step 3 (1.56 g, 6.15 mmol), di-t-butyl 2-hydroxyethylmalonate from step 5 (1.60 g, 6.15 mmol), and PPh₃ (1.61 g, 6.15 mmol) were dissolved in dry THF (100 mL) and treated dropwise with diethyl azodicarboxylate (970 mL, 6.15 mmol). The solution was stirred at rt under argon for 6 d, then adsorbed onto silica. Purification by flash chromatography (5/5/90-30/30/70 ethyl acetate:dichloromethane:hexane) gave recovered imide (1.03 g) and di-tert-butyl 2-(4-benzyloxyphthalimido) ethylmalonate (799 mg, 26%). TLC $R_f$ 0.75 (1:1:2 ethyl acetate:dichloromethane:hexane).

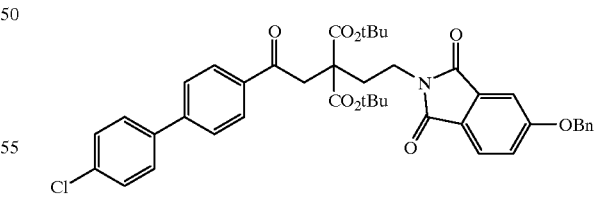

Step 7 A solution of malonate from step 6 (2.33 g, 4.70 mmol) in dry THF (30 ml) was added dropwise to a suspension of NaH (112 mg, 4.70 mmol) in THF (10 mL) under argon and stirred until a clear solution remained (20 min). a-Bromo ketone from step 2 of Example 114 (2.18 g, 7.05 mmol) was added in one portion and stirred at rt for 2 d. The mixture was then concentrated to a slurry and partitioned between dichloromethane and water. The organic layer was washed with saturated NH₄Cl, water, and brine, dried over MgSO$_4$, filtered, and adsorbed onto silica. Purification by flash chromatography (12–20% ethyl acetate:hexane) gave the disubstituted di-tert-butyl malonate (730 mg, 21%) as a colorless solid, plus unreacted malonate (1.70 g). TLC R$_f$ 0.40 (25% ethyl acetate:hexane).

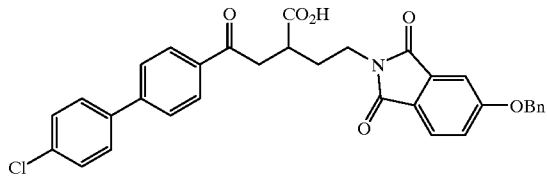

Step 8 Diester from step 7 (84 mg, 0.11 mmol) in dioxane (7 mL) was treated with 4M HCl in dioxane (1.0 mL) and heated under reflux for 10 h. The mixture was then concentrated to an oil. Purification by flash chromatography (0–5% methanol:dichloromethane) gave solid with trace impurities. Further purification by prep HPLC (8% ethyl acetate:dichloromethane/0.01% TFA) gave Example 405 (32 mg, 49%) as an off-white solid. MP 187–190° C.

The above methods for the preparation of Example 405 was used to prepare the following series of biphenyl products (TABLE XXVI). The imides were prepared from the commercially available hydroxyphthalic acids.

TABLE XXVI

| example | R$^6$a | isomer | m.p.(° C.)/other characterization |
|---|---|---|---|
| 405 | (CH$_2$)$_2$N-phthalimide-OBn | R, S | 187–190 |
| 406 | (CH$_2$)$_2$N-phthalimide-OEt | R, S | 79–81 |
| 407 | (CH$_2$)$_2$N-phthalimide-OBn (4-position) | R, S | 93–95 |

The following examples (TABLE XXVII) were prepared from commercially available imides using the procedure for Example 405, steps 6–8.

TABLE XXVII
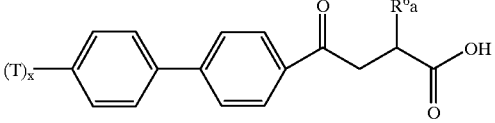
| ex. | (T)$_x$ | R$^{6a}$ | isomer | m.p.(° C.)/other characterization |
|---|---|---|---|---|
| 408 | Cl | 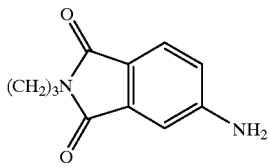 | R, S | |
| 409 | Cl | 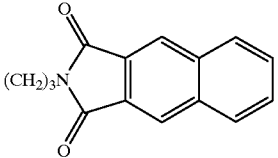 | R, S | 241–242 (dec) |
| 410 | Cl | 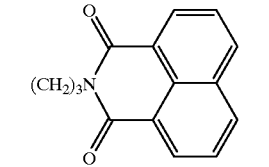 | R, S | 230 (dec) |
| 411 | Cl | 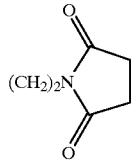 | R, S | 171–172 (dec) |
| 412 | EtO | 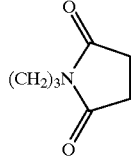 | R, S | 201–203 (dec) |
| 413 | Cl | 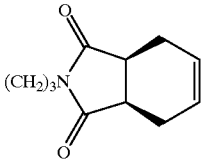 | R, S | 146–148 |
| 414$^a$ | Cl | 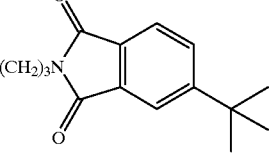 | R, S | 187–189 (dec) |

TABLE XXVII-continued

[Structure: (T)x-biphenyl-C(O)-CH(R6a)-C(O)-OH]

| ex. | (T)x | R6a | isomer | m.p.(° C.)/other characterization |
|---|---|---|---|---|
| 415[a] | Cl | (CH2)3N-phthalimide with 2 Cl substituents | R, S | 190 (dec) |
| 416[a] | Cl | (CH2)3N-phthalimide with methyl substituent | R, S | 175 (dec) |
| 417[a] | Cl | (CH2)3N-pyridine-fused imide | R, S | 153–157 |
| 418[b] | Cl | (CH2)3N-naphthalimide with Br | R, S | 214–215 (dec) |

[a]Imides for Examples 414–417 were prepared by the following method: t-Butyl phthalic anhydride (1.0 g, 4.9 mmol) and urea (0.60 g, 10.0 mmol) were heated to 150° C. to give a melt for 3 h. After cooling to rt, the crude solid was titurated from water twice and filtered. The solid was dissolved in ethyl acetate and dried over sodium sulfate. Solvent removed in vacuo to give a colorless solid (0.83 g, 83%). TLC $R_f$ 0.62 (25% EtOAc/75% Hexane).
6 [b]The imide for Example 418 was prepared by the following method: A solution of 4-bromo-1,8-naphthalic anhydride (2.50 g, 9.02 mmol) in NH4OH (100 mL) was heated to reflux at 70° C. for 3 h. The solution was cooled to rt, causing a tan solid to precipitate. The solid was filtered, washing with water. The crude product was recrystallized from HNO3 (conc.) at reflux to give 4-bromo-1,-naphthalimide (2.20 g, 89%) as near-colorless needles: TLC $R_f$ 0.25 (25% ethyl acetate:hexane).

EXAMPLE 419

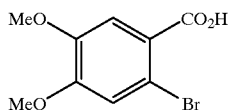

Step 1 A solution of KMnO4 (7.25 g, 39.2 mmol) in water (100 mL) was added over 30 min through a dropping funnel to solution of 6-bromoveratraldehyde (6.00 g, 24.5 mmol) in dioxane (150 mL) preheated to 70° C. After the addition was complete, the mixture was heated to 85° C. for 40 min, then treated with 15 mL of 1M NaOH. The resulting suspension was filtered hot through a Celite pad, washing with 3 portions of hot water. Upon cooling to rt, unreacted starting material precipitated in the filtrate as a colorless solid. The suspension was refrigerated for 16 h and filtered to remove precipitate. The filtrate was acidified to pH 2 with 4M HCl, causing off-white solid to precipitate. The mixture was extracted twice with dichloromethane. The organic layer was then washed with brine, dried over Na2SO4, filtered and concentrated to an off-white solid (4.59 g, 72%). TLC $R_f$ 0.40 (15% methanol:dichloromethane).

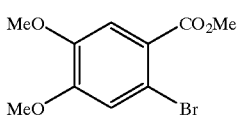

Step 2 A solution of K2CO3 (9.32 g, 67.5 mmol) in water (25 mL) was added to a suspension of acid from step 1(4.40 g, 16.9 mmol) in acetone (50 mL) and stirred for 30 min. Iodomethane (4.20 mL, 67.5 mmol) was added, and the biphasic mixture was stirred vigorously and heated at 75° C. for 16 h. Additional iodomethane (4.00 mL, 64.3 mmol) was added and heated for 4 h. The mixture was cooled to rt, concentrated in vacuo to a light yellow slurry, and partitioned between ethyl acetate and water. The water layer was washed with ethyl acetate, and the combined organic extracts were then washed with brine, dried over Na$_2$SO$_4$, filtered and concentrated to an pale yellow solid (4.89 g, >100% crude). This used without purification.

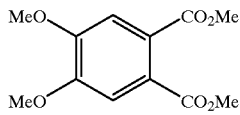

Step 3 An oven-dried, 3-necked round-bottomed flask was fitted with a septum, a condenser sealed with a septum, and a three-way stopcock. Ester from step 2 (4.80 g, 17.4 mmol) was dissolved in DMSO (35 mL) and reactants were added in the following order: Et$_3$N (7.30 mL, 52.3 mmol), Pd(OAc)$_2$ (392 mg, 1.74 mmol), 1,3-bis(diphenylphosphino)propane (DPPP) (720 mg, 1.74 mmol), and dry methanol (10.6 mL, 262 mmol). Carbon monoxide gas was then bubbled through the reaction mixture for 6 min and then the flask was heated to 65–70° C. under CO atmosphere for 1 h. The balloon was refilled and CO was bubbled into the mixture for 5 d. The reaction was still incomplete. The mixture was poured into ethyl acetate (300 mL), then washed with 10% HCl (twice), water, brine, dried over Na$_2$SO$_4$, filtered and concentrated to a green oil. Purification by flash chromatography (30% ethyl acetate:hexane) gave starting material (1.09 g, 23%) and dimethyl 4,5-dimethoxyphthalate (2.98 g, 67%) as a near colorless solid. TLC R$_f$ 0.38 (40% ethyl acetate:hexane).

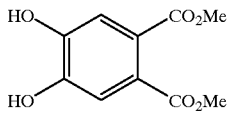

Step 4 A solution of diester from step 3 (1.95 g, 7.64 mmol) in 20 mL dichloromethane was cooled to –76° C. in a round-bottomed flask fitted with an air condenser. A 1.0M BBr$_3$ solution in dichloromethane (30.6 mL) was added dropwise over 10 min, and then stirred for 20 h, allowing to warm to ambient temperature. The mixture was poured into 200 mL ice water and then extracted with dichloromethane. The aqueous layer was concentrated to approximately 60 mL and lyophilized to an orange-yellow solid. The intermediate diacid was re-esterified by heating under reflux in methanol (65 mL) with conc. H$_2$SO$_4$ (0.1 mL) for 3 d. Solvent was removed in vacuo to give a yellow solid, which was dissolved in ethyl acetate and washed with water (twice), brine, dried over MgSO$_4$, filtered and concentrated to give dimethyl 4,5-dihydroxyphthalate (1.72 g, 99%) as a reddish oil that solidified upon standing. TLC R$_f$ 0.75 (15% methanol:dichloromethane).

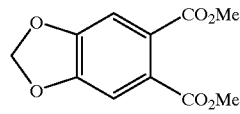

Step 5 To a solution of catechol from step 4 (1.72 g, 7.60 mmol) in DMF (6 mL) was added CsF (5.78 g, 38.0 mmol) to form a green suspension. After cooling to rt, dichloromethane (0.54 mL, 8.36 mmol) was added and then the mixture was heated to 110–115° C. for 90 min. The reaction had not gone to completion; additional dichloromethane (2 mL) was added and heating continued for 1 h. The reaction mixture was partitioned between diethyl ether and water. The aqueous layer was washed with ether (twice) and the combined organic layers were washed with water (twice), brine, dried over MgSO$_4$, filtered and concentrated to give dimethyl 4,5-methylenedioxyphthalate (1.39 g, 77%) as an orange oil that solidified upon standing. TLC R$_f$ 0.75 (50% ethyl acetate:hexane).

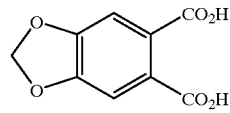

Step 6 A solution of LiOH•H$_2$O (3.00 g, 71.5 mmol) in 15 mL water was added to diester from step 5 (1.38 g, 5.80 mmol) in THF (30 mL) and stirred overnight. The mixture was concentrated to remove THF and rediluted in water. The basic solution was washed with ethyl acetate, acidified to pH 3 with conc. HCl, and lyophilized to give an orange solid. The solid was dissolved in methanol, acidified again with conc. HCl, and filtered to remove salt. The filtrate was concentrated in vacuo. Crude weight (5.8 g) indicated that salt was still present, so the solid was dissolved in acetone and filtered three times. The solvent was removed in vacuo to give 4,5-methylenedioxyphthalic acid (2.38 g, >100%) as a pale orange solid. TLC R$_f$ 0.10 (15% methanol: 85% dichloromethane).

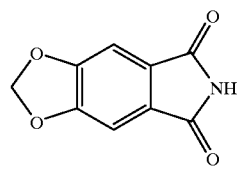

Step 7 The diacid from step 6 (1.66 g, 5.90 mmol) was dissolved in glacial acetic acid (16 mL), and urea (712 mg, 11.8 mmol) was added in one portion. This was heated under reflux to 150° C. for 3 h. The acetic acid was removed in vacuo and the residue was suspended in water and the solid was filtered and dried in vacuo to give 4,5-methylenedioxyphthalimide (214 mg, 19%) as a tan solid. TLC R$_f$ 0.55 (50% ethyl acetate:hexane).

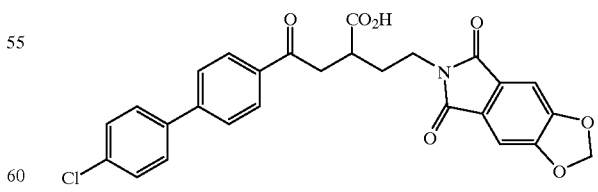

Example 419

Step 8—Preparation of Example 419. Steps 6–8 from Example 405 were followed to complete the synthesis of Example 419. MP 196–198° C.

EXAMPLE 420

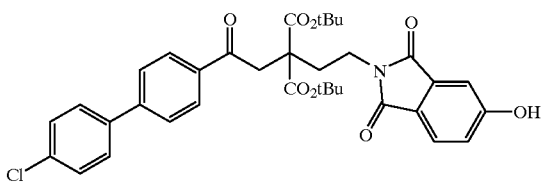

Step 1 A suspension of 10% Pd/C (40 mg, 20% w/w) in dioxane (4 mL) was purged with $H_2(g)$ for 45 min, then a solution of diester from Example 405, step 7 (200 mg, mmol) in dioxane (7 mL) was added via syringe. The suspension was stirred at rt for 3 d under $H_2$ atmosphere. The mixture was filtered through Celite, washed with ethyl acetate, and the filtrate was adsorbed onto silica. Purification by flash chromatography (1:1:3 ethyl acetate:dichloromethane:hexane) gave the disubstituted di-tert-butyl malonate (168 mg, 94%) as a colorless solid. TLC $R_f$ 0.30 (1:1:3 ethyl acetate:dichloromethane:hexane).

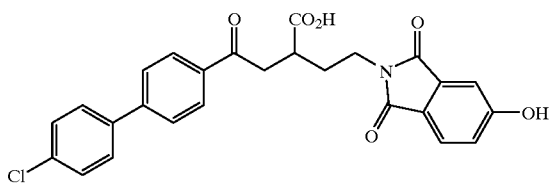

Example 420

Step 2—Preparation of Example 420. Example 420 was prepared from the product of step 1 above according to the procedure of Example 405, step 8. MP 211–215 (dec)° C.

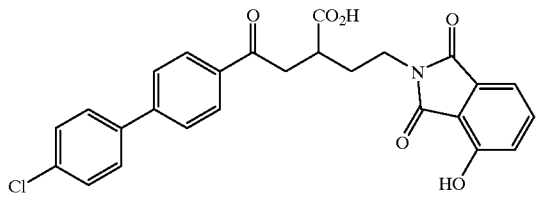

Example 421

EXAMPLE 421

Example 421 was prepared according to the procedure of Example 420. MP 201 (dec)° C.

EXAMPLE 422

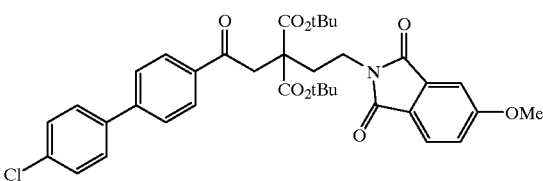

Step 1 A solution of the alcohol from Example 420, step 1 (94 mg, 0.15 mmol) in acetone (10 mL) was stirred with $Cs_2CO_3$ (145 mg, 0.44 mmol) for 30 min, then treated with iodomethane (0.25 mL, 4.0 mmol). The mixture was heated to 40° C. for 10 min, at which time the mixture changed from bright yellow to colorless. The mixture was concentrated, then partitioned between ethyl acetate and water. The water layer was washed with ethyl acetate, and the combined organic extracts were washed with brine, dried over $MgSO_4$, filtered and concentrated in vacuo to give the desired product (86 mg, 90%) as a pale yellow solid. TLC $R_f$ 0.60 (40%ethyl acetate:hexane)

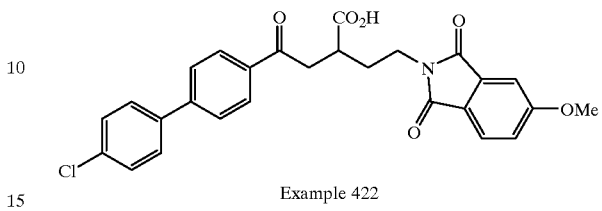

Example 422

Step 2—Preparation of Example 442. Example 422 was prepared from the product of step 1 above according to the procedure of Example 405, step 8. MP 63–67° C.

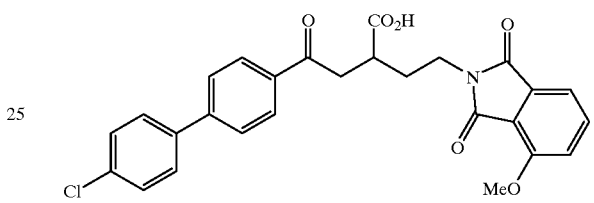

Example 423

EXAMPLE 423

Example 423 was prepared according to the procedure of Example 422. MP 186–190° C.

EXAMPLE 424

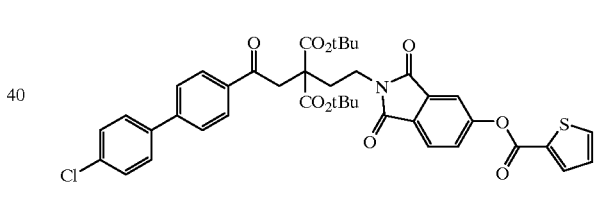

Step 1 A solution of the alcohol from Example 420 (100 mg, 0.16 mmol) and triethylamine (65 uL, 0.47 mmol) were added to methylene chloride (10 mL) and cooled to 0° C. 2-Thiophenecarbonyl chloride (33 uL, 0.32 mmol) was added and the mixture stirred 10 min. The solvent was removed in vacuo and the residue taken up in EtOAc, washed with water and dried over sodium sulfate. The solution was filtered and the solvent removed in vacuo to give a colorless powder (0.103 g, 90%). TLC $R_f$ 0.90 (15% EtOAc/85% Hexanes).

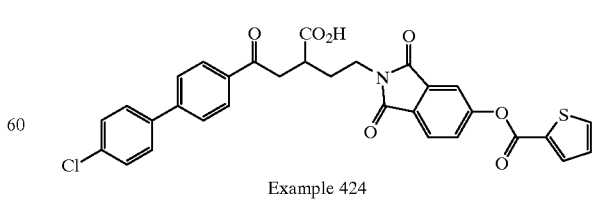

Example 424

Step 2—Preparation of Example 424. Example 424 was prepared from the product of step 1 above according to the procedure of Example 405, step 8. MP 181–182° C.

EXAMPLE 425

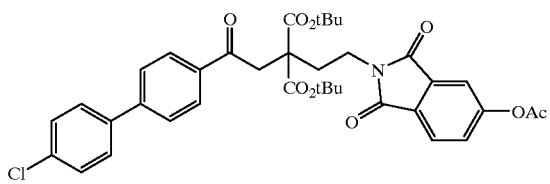

Step 1 A solution of alcohol from Example 420 (50 mg, 0.08 mmol) in pyridine (3 mL) was treated with acetic anhydride (15 mL, 0.16 mmol) and stirred at rt under argon for 3 d. Additional acetic anhydride was added (100 mL, 1.07 mmol) and stirred at rt for 2 h. The reaction mixture was partitioned between water and dichloromethane, and the aqueous phase was washed twice with dichloromethane. The combined organic layers were washed successively with water, sat. $CuSO_4$, and brine, dried over $MgSO_4$, filtered, and adsorbed onto silica. Purification by flash chromatography (40% ethyl acetate:hexane) gave the acetate (30 mg, 57%) as a colorless solid. TLC $R_f$ 0.55 (1:1:3 ethyl acetate:dichloromethane:hexane).

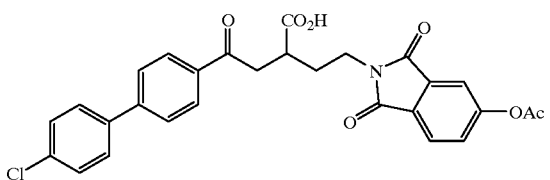

Example 425

Step 2—Preparation of Example 425. Example 425 was prepared from the product of step 1 above according to the procedure of Example 405, step 8. MP 176–178° C.

EXAMPLE 426

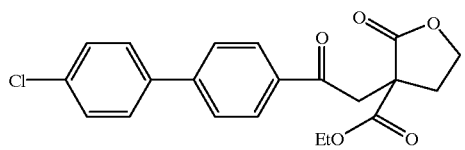

Step 1 Sodium iodide (1.5 g, 10 mmol) was added to 1-(2-bromoethanone)-4-(4-chlorophenyl)-benzene (Step 2 of Example 114, 3.09 g, 10 mmol) in DME (27 mL) under Ar and the solution was stirred for 15 min. In a seperate flask, tetrahydro-2-oxo-3-furancarboxylic acid ethyl ester (2.1 g, 11 mmol) was added to NaOEt (0.75 g, 11 mmol) in DME (10 mL) and mixed for 15 min. This solution was added to the sodium iodide solution via cannula and the combined mixture stirred 18 h at rt. The solvent was removed in vacuo and the residue dissolved in methylene chloride (200 mL) then washed with two 200 mL portions of water. The methylene chloride solution was dried over $MgSO_4$, filtered and the solvent removed in vacuo to give a crude solid. The resulting residue was recrystallized from ethyl acetate/hexanes to give the alkylated malonate (3.2 g, 76%). TLC $R_f$ 050 (40% EtOAc/60% Hexanes).

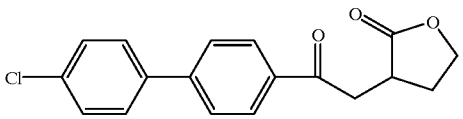

Step 2 A suspension of ethoxy biphenyl lactone from step 1 (11.0 g, 28 mmol) in glacial acetic acid (180 mL) and conc HCl (90 mL) was heated to reflux at which time the starting material dissolved and evolution of $CO_2$ was seen. After 4 h the reaction was cooled to rt, and the solvents removed in vacuo. The solid residue was dissolved in EtOAc then washed repeatedly with sat. $NaHCO_3$. The organic layer was then washed with brine and dried over $Na_2SO_4$. The solvent was removed in vacuo and the residue recrystallized from EtOAc/Hexane to give the lactone (7.8 g, 88%) as fine tan needles. MP 129–130°.

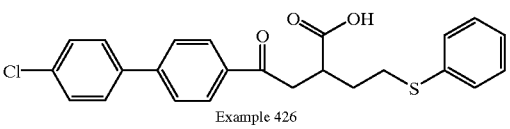

Example 426

Step 3—Preparation of Example 426. Sodium hydride (97%, 0.027 g, 3 mmol) was suspended in DMF (15 mL) and cooled to 0° C. tenzenethiol (0.29 mL, 2.86 mmol) was added dropwise, and the evolution of $H_2$ gas was noted. After stirring 10 min. at 0° C., the reaction was allowed to warm to rt. The lactone from step 2 (1.0 g, 3.18 mmol) was then added in portions, and the reaction heated slowly to 100° C. The solution became dark green in color. TLC after 3 h showed a new spot, and further heating did not result in any further consumption of the lactone The reaction was cooled to rt, then quenched with the addition of 10% HCl (10 mL). The reaction was then diluted with water and extracted with EtOAc. The combined EtOAc layers were washed with water, brine, and dried over $Na_2SO_4$. The solvent was removed in vacuo, and the residue purified via MPLC (90% EtOAc/Hexane), followed by recrystallization from hot $CHCl_3$/Hexane. Filtration of the solid gave the desired product (0.50 g, 37%) as tan needles. MP 179–181° C.

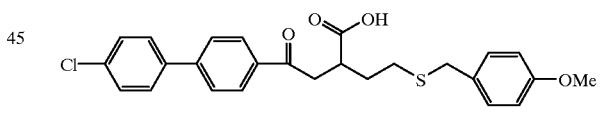

Example 427

EXAMPLE 427

Example 427 was prepared by the same method as Example 426 using the appropriate commercially available thiol in step 3. MP 138–140° C.

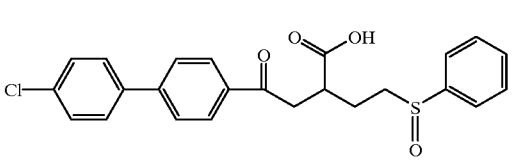

Example 428

EXAMPLE 428

A solution of Example 426 (0.05 g, 0.11 mmol) in $CH_2Cl_2$ (30 mL) was cooled to −78° C. m-CPBA (0,036 g, 0.17 immol based on 85% pure m-CPBA) was added in one portion and the reaction allowed to warm to −30° C. The reaction was stirred 2 h at −30° C. then the solvent was removed in vacuo. The residue was triturated in EtOAc, which dissolved the benzoic acid and remaining m-CPBA. The insoluble product was recovered by filtration, and dried in vacuo giving the desired product (0.03 g, 60%) as a white powder. MP 208° C. (dec).

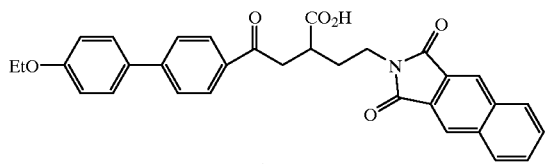

Example 429

EXAMPLE 429

To a round bottom flask equipped with a condenser was added 2,3-napthalene dicarboxirnide (1.0 g, 5.1 mmol) in absolute ethanol (150 mL). The mixture was gently refluxed (78° C.) until most of the solids were dissolved. The hot ethanol solution was decanted from any undissolved solids into an Erlenmeyer flask containing a prepared solution of potassium hydroxide (0.27 g, 5.1 mL) in water (0.27 mL) and absolute ethanol (0.80 mL). A white precipitate formed instantly. The mixture was stirred and cooled quickly to rt. Vacuum filtration yielded potassium-2,3-napthalene dicarboximide (0.88 g, 73%) as a white solid. The product was not analyzed directly used in the next step. To a round bottom flask equipped with a condenser was added potassium-2,3napthalene dicarboximide (0.47 g, 2.0 mmol) in anhydrous DMF (1.0 mL). The solution was heated to reflux (150° C.). Lactone from Example 426, step 2 (0.34 g, 1.0 mmol) in anhydrous DMF (1.0 mL) was added. The mixture was heated (150° C.) for 18 h and then cooled to rt. The solvent was removed in vacuo and the residue was partitioned between ethyl acetate (50 mL) and 1M HCl (10 mL). The phases were separated and the organic phase was washed with water (25 mL), dried (MgSO$_4$) and the solvent was removed in vacuo to afford a brown oil in which the excess potassium-2,3-napthalene dicarboximide was recrystallized from hexane-ethyl acetate. The mother liquor was concentrated to afford an orange solid which was purified on a silica gel column using 7.5% methanol-methylene chloride as the eluent to afford Example 429 (13 mg, 3%) as a white solid: MP 193–194° C.

Biological Protocols and in Vitro Test Data
Preparation of Gelatinase-B (92 kDa, MMP-9):

MMP-9 was isolated modifying the previously described procedures of Hibbs et al (J. Biol. Chem., 260 2493–2500, 1984) and Wilhelm et al (J. Biol. Chem., 264 17213–17221, 1989). Briefly, polymorphonuclear leukocytes (PMN) preparations were isolated as described above from 3 or more units of freshly drawn whole blood obtained from the New York Blood Center (N.Y., N.Y.). Cells were resuspended in phosphate buffered saline (PBS) containing 100 ng/ml phorbol myristate acetate (PMA) in the presence of 50 mM di-isopropylfluorophospate (DFP), 1 µg/ml leupeptin and aprotinin, and 1 mg/ml catalase for 1 hr at 37° C. Supernatants were collected by centrifugation (300×g) and the samples were frozen at −70° C. All chromatographic methods were performed at 4° C. Thawed samples were concentrated 5-fold using an Amicon chamber equipped with a YM-10 membrane. The concentrate was pressure dialyzed against 0.02M Tris-HCl, 0.1 M NaCl, 1 mM CaCl$_2$, 1 µM ZnCl$_2$, 0.001% Brij-35, 0.02% sodium azide (NaN$_3$), pH 7.5 and applied to DEAE ion exchange chromatography resin which was previously equilibrated with the same buffer at a flow rate of 0.4 ml/min. The column was extensively washed with the same buffer and gelatinase was eluted as 4 ml fractions from the column with 0.02M Tris-HCl, 0.5 M NaCl$_2$, 1 mM CaCl, 1 µM ZnCl$_2$, 0.001% Brij-35, 0.02% NaN$_3$, pH 7.5. Gelatinase containing fractions were observed by gelatin zymography (see below), loaded onto a gelatin agarose affinity resin and washed with the same buffer. Gelatinase activity was eluted at a flow rate of 1 ml/min from the column as 1 ml fractions with 0.02M Tris-HCl, 1 M NaCl, 1 mM CaCl$_2$, 1 µM ZnCl$_2$, 0.001% Brij-35, 0.02% NaN$_3$, pH 7.5 containing 10% dimethyl sulfoxide (DMSO). The fractions containing gelatinase activity were pooled and dialyzed against 0.005M Tris-HCl, 5 mM NaCl, 0.5 mM CaCl$_2$, 0.1 µM ZnCl$_2$, 0.001% Brij-35, pH 7.4. The protein content associated with material was determined with a micro-BCA assay (Pierce, Rockford, Ill.), lyophilized and reconstituted to a desired working concentration (100 µg/ml).

Thiopeptilide MMP-9 Inhibition Assay:

Progelatinase (10 µg/ml) isolated from human PMNs (described above) was activated with 1 mM 4-aminophenylmercuric acetate (APMA) in 50 mM Tris-HCl, 200 mM NaCl, 5 mM CaCl$_2$, 0.001% Brij-35, pH 7.6 at 37° C. for 16 hr. The activated enzyme was dialyzed against the above buffer to remove APMA. The thiopeptolide spectrophotometric (Weingarten, H., Feder, J., Anal. Biochem., 147, 437–440, 1985) substrate hydrolysis assay was modified to a micro-assay format. Spectrophotometric analysis of MMP-9 activity required a 1000-fold dilution of activated MMP-9 (10 ng/ml, 0.14 nM) in assay buffer comprised of 50 mM 4-(2-hydroxyethyl)1-piperazine ethane sulfonic acid (HEPES), 0.15 M NaCl, 10 mM CaCl$_2$, 0.001% Brij-35, pH 6.5 between 100 and 1000-fold for enzyme assays. Reaction mixtures for inhibitor studies contained 1 mM Ac-Pro-Leu-Gly-S-Leu-Leu-Gly-o-ethyl thiopeptolide substrate dissolved in HEPES assay buffer pH 6.5, along with 0.5 mM 5,5'-dithio-bis-(nitrobenzoic acid), drug concentrations ranging from 0.5 nM to 5 µM and activated enzyme (10–100 ng) in a total volume of 130 µl. The hydrolysis of substrate was monitored at 405 nm using an automated plate reader (Molecular Devices, Menlo Park, Calif.). Enzyme mediated substrate hydrolysis was corrected for non-enzymatic hydrolvsis of the substrate by the subtraction of values from control samples incubated in the absence of enzyme. Drug efficacy was reported as the percent inhibition of enzyme activity calculated as:

(Control Values−Treated Values)/Control Values×100

Active compounds with a demonstrated 30% inhibition of enzyme activity or greater were tested further at varying concentrations (0.5 nM–5 µM) and linear regression analysis of percent inhibition versus log drug concentration was used to obtain IC$_{50}$ values. Two way analysis of variance was used to determine significance between individual test groups.

Expression and Purification of Recombinant Truncated Prostromelysin (MMP-3):

Truncated Prostromelysin-257 was expressed in a soluble form in E. coli as described by Marcy et al., Biochemistry, 30, 6476–6483, 1991. Soluble truncated prostromelysin was purified by a modification of the monoclonal antibody affinity chromatography method described by Housley et al., J. Biol. Chem., 268, 4481–87, 1993.

Primary Thiopeptilide MMP-3 Inhibition Assay:

Enzyme: recombinant stromelysin expressed in *E. coli* and purified as described above. Truncated stromelysin was heat activated as described by Kokalitis et al., Biochem. J., 276, 217–221, 1991. The protocols for the assay of compounds as stromelysin inhibitors was the same as that used for MMP-9 except that the assay buffer was 50 mM MES, pH 6.5 containing 150 mM NaCl, 10 mM CaCl2, 0.005% Brij, and 1% DMSO. The enzyme concentration was 13 nM stromelysin. The substrate concentration was 658 micromolar ($\mu$M) and our drug concentrations were the same as with the MMP-9 assay.

Secondary P218 Quenched Fluorescence Assay for MMP-3 Inhibition:

This assay was originally described by Knight et al., FEBS Letters, 296, 263–266, 1992, for a related substrate. The assay is run continuously in a 3.0 ml cuvette using a Perkin-Elmer LS 50 B Spectrofluorimeter at 25° C. in a final volume of 2.0 mls. P218 substrate (10 mM) in 100% DMSO is diluted to a final concentration of 2.0 micromolar ($\mu$M) into assay buffer: 50 mM MES, pH 6.5 containing 150 mM NaCl, 10 mM CaCl2, 0.005% Brij-35, and 1%(v/v) DMSO. Test compounds(10 mM) in DMSO are diluted in assay buffer at an initial concentration of 10 to 100 micromolar. These are diluted to a final concentration in the assay from 10 nM to 1 $\mu$M depending upon their potency previously determined in primary thiopeptilide assay described above. The reaction is initiated by the addition of recombinant stromelysin (MMP-3) at a final concentration of 1.0 nM Upon peptide cleavage, the fluorescent MCA group was detected using an excitation wavelength of 328 nanometers and an emission wavelength of 393 nanometers. The assay is linear from 0.2 to 5 nM MMP-3 concentration and percent inhibition is calculated as described above for the primary thiopeptilide assay and $IC_{50}$ values are determined by a linear regression analysis of percent inhibition versus log drug concentration. The peptide sequence of the MCA substrate, hereinafter designated P218, is shown below:

MCA-Pro-Lys-Pro-Leu-Ala-Leu-DPA-Ala-Arg-NH$_2$ (SEQ ID NO: 1)

P218

Note that as the MCA group is a fluorescent tag, as explained in the paragraph immediately above, it is not part of the amino acid sequence of the peptide.

For MMP-3, this substrate has a $K_m$ of 16 $\mu$M at pH 6.5 and a kcat/$K_m$ value of 56,000M$^{-1}$sec$^{-1}$.

Secondary P218 Quenched Fluorescence Assay for MMP-2 Inhibition:

Gelatinase A (MMP-2) was prepared using a vaccinia expression system according to the method of R. Fridman, et al., *J. Biol. Chem.*, 267, 15398 (1992). Inhibition assays with MMP-2 were carried out as described for MMF-3 above using 0.2 nM final enzyme concentration and the P218 substrate. MMP-2 has a turnover number of 400,000 in this assay. Initial velocities (nM/sec.) never exceeded 5% of the total substrate in these experiments.

Biaryl Matrix Metalloprotease Inhibitors

Assay Data for Certain of the Invention and Reference Compounds:

All $IC_{50}$ values are expressed as nM. When "I=x %" is shown, x represent the % inhibition at 5 $\mu$M. When "x (n)" is shown, x is the average $IC_{50}$ value of n separate determinations.

| Ex. # | MMP-3 Thiopep. $IC_{50}$ | MMP-3 Fluorogenic $IC_{50}$ | MMP-9: Thiopep. $IC_{50}$ | MMP-2 Fluorogenic $IC_{50}$ |
|---|---|---|---|---|
| fenbufen |  | Inactive | I = 2% | 1,000 |
| 1 | 486 (7) | 805 (2) | 1,000 |  |
| 2 | 270 |  | 2,200 |  |
| 3 | I = 13% |  | I = 0% |  |
| 4 | 379 | 480 | 2,700 |  |
| 5 | I = 11% |  | I = 19% |  |
| 6 | 2,100 |  | I = 38% |  |
| 7 | 690 |  | 2,100 |  |
| 8 | I = 26% |  | I = 0% |  |
| 9 | I = 0% |  | I = 3% |  |
| 10 | I = 1% |  | I = 0% |  |
| 11 | I = 14% |  | I = 0% |  |
| 12 | I = 17% |  | I = 0% |  |
| 13 | I = 27% |  | I = 3% |  |
| 14 | 440 | 570 | 1,200 |  |
| 15 | 2,000 |  | I = 0% |  |
| 16 | 620 |  | 3,100 |  |
| 17 | I = 35% |  | I = 0% |  |
| 18 | I = 0.3% |  | I = 9% |  |
| 19 | 550 |  | 1,200 |  |
| 20 | I = 32% |  | I = 34% |  |
| 21 | 750 |  | 1,200 |  |
| 22 | 790 |  | 1,200 |  |
| 23 | I = 24% |  | I = 0% |  |
| 24 | I = 40% |  | I = 0% |  |
| 20 | 950 |  | I = 43% |  |
| 26 | 620 | 240 | 4,300 |  |
| 27 | I = 11% |  | I = 15% |  |
| 28 | 1 = 14% |  | I = 0% |  |
| 29 | I = 28% |  | I = 44% |  |
| 30 | I = 8% |  | I = 25% |  |
| 31 | I = 56% |  | I = 29% |  |
| 32 | I = 58% |  | 6,000 |  |
| 33 | 2,600 |  | 2,400 |  |
| 34 | 5,000 |  |  |  |
| 35 | I = 0% |  |  |  |
| 36 | I = 0% |  | I = 0% |  |
| 37 | I = 9% |  | I = 0% |  |
| 38 | 10,000 |  | I = 10% |  |
| 39 | I = 16% |  | I = 4% |  |
| 40 | 121 (4) |  | 50 |  |
| 41 | 118 (3) | 260 | 500 |  |
| 42 |  | 48 | 21 |  |
| 43 |  |  |  |  |
| 44 |  | 1,970 |  | 1,150 |
| 45 |  | 1 = 43% | 1 = 56% |  |
| 46 | 700 |  | 4,000 |  |
| 47 | 560 |  | I = 22% |  |
| 48 | I = 53% |  | 1 = 15% |  |
| 49 | 750 |  | I = 13% |  |
| 50 | 630 |  | 800 |  |
| 51 | 170 |  | 100 |  |
| 52 | 76(2) |  | 37 |  |
| 53 | 950 |  | 800 |  |
| 54 | 190 |  | 700 |  |
| 55 | 170 |  | 110 |  |
| 56 | 310 |  | 700 |  |
| 57 | I = 16% |  | I = 22% |  |
| 58 | 1,200 |  | 1,500 |  |
| 59 | I = 33% |  | 2,000 |  |
| 60 | 600 |  | 180 |  |
| 61 | I = 35% |  | I = 22% |  |
| 62 | 400 |  | 4,500 |  |
| 63 | 980 |  | 500 |  |
| 64 | 300 |  | I = 29% |  |
| 65 | 840 |  | I = 47% |  |
| 66 | I = 7% |  | I = 11% |  |
| 67 | 150 |  | 780 |  |
| 68 | 280 |  | 300 |  |
| 73 | 220 |  | 600 |  |
| 74 | 2,300 |  | I = 38% |  |
| 75 | 78 |  | 82 (2) |  |
| 76 | 1,000 |  | 1,800 |  |
| 77 | I = 24% |  | 1 = 7% |  |
| 78 | 310 |  | 1,200 |  |

| Ex. # | MMP-3 Thiopep. IC$_{50}$ | MMP-3 Fluorogenic IC$_{50}$ | MMP-9: Thiopep. IC$_{50}$ | MMP-2 Fluorogenic IC$_{50}$ |
|---|---|---|---|---|
| 79 | I = 12% | | I = 9% | |
| 80 | 470 | | 800 | |
| 81 | I = 30% | | I = 2% | |
| 82 | I = 23% | | I = 9% | |
| 83 | 720 | | 1,400 | |
| 84 | 150 | | 100 (2) | |
| 85 | 37 | | I = 44% (3) | |
| 88 | 168 (4) | | I = 30% | |
| 89 | 111 (4) | | 480 | |
| 90 | I = 36% | | I = 11% | |
| 91 | 174 | | 700 | |
| 92 | I = 60% | | I = 26% | |
| 114 | 244 (11) | 120 (3) | 285 (2) | 25 (2) |
| 115 | 1 = 39% | | I = 31% | |
| 116 | 145 (4) | 80 (2) | 190 | 28 (2) |
| 117 | 590 | | 3,800 | |
| 118 | 440 | | 2,200 | |
| 119 | 760 | | 1,800 | |
| 120 | 380 | | I = 60% | |
| 121 | 1,000 | | I = 45% | |
| 122 | 403 (2) | | | |
| 123 | I = 43% | | | |
| 124 | 180 (2) | | I = 28% | |
| 125 | 105 (2) | | 1,800 | |
| 126 | 600 (2) | | | |
| 130 | 230 | 1,200 | 2,900 | |
| 131 | 310 (2) | | 900 | |
| 132 | 112 (4) | | 2,600 (2) | |
| 133 | 640 | | 10,000 | |
| 135 | 2,800 (2) | | 2,800 | |
| 136 | 1,600 | | I = 50% (2) | |
| 142 | 310 (2) | | | |
| 178 | 150 | | 240 | |
| 179 | 160 (2) | | 200 | |
| 180 | 270 | | 360 | |
| 181 | 330 | | 290 | |
| 182 | I = 7% | | I = 17% | |
| 183 | 270 | | 710 | |
| 184 | 280 | | I = 41% | |
| 185 | 220 | | I = 31% | |
| 186 | 170 | | 383 (3) | |
| 187 | 757 | | 1,500 | |
| 188 | 151 | | 1,300 | |
| 189 | 530 | | 600 | |
| 190 | 227 | | 215 (2) | |
| 191 | 330 | | I = 62% | |
| 192 | 140 | | 510 | |
| 193 | 153 (3) | 150 (2) | 2,450 (2) | 40 (2) |
| 194 | 115 (2) | 62 | 750 | |
| 195 | I = 31% | | I = 20% | |
| 196 | 236 (12) | 180 (2) | 438 (5) | 20 (2) |
| 197 | 117 (2) | 92 | 197 (3) | 26 (2) |
| 198 | I = 23% | | I = 21% | |
| 199 | 170 | | 200 | |
| 200 | 640 | | 2,300 | |
| 201 | 340 | | 800 | |
| 202 | 250 | | 500 | |
| 203 | 247 (3) | | 1,200 | |
| 204 | 213 (3) | | 215 (2) | |
| 205 | 87 (3) | | 170 | |
| 206 | 950 (2) | | 417 (3) | |
| 207 | 180 (2) | | 290 (3) | |
| 208 | 140 (2) | | 1,050 (2) | |
| 209 | 340 | | 390 (2) | |
| 210 | 500 | | 205 (2) | |
| 211 | 440 | | 280 | |
| 212 | 650 | | 390 (2) | |
| 213 | 2,500 | | I = 41% | |
| 214 | 170 | | 2,200 | |
| 215 | 1.300 | | 1,200 | |
| 216 | 770 | | 590 | |
| 217 | 83 | | 245 (2) | |
| 218 | 170 | | 435 (2) | |
| 219 | 260 | | 600 | |
| 220 | 190 | | 950 | |
| 221 | 240 | | 2,400 | |
| 222 | 610 | | 1,800 | |
| 223 | 930 | | 580 | |
| 224 | 680 | | 550 | |
| 225 | 310 | | 550 | |
| 226 | 720 | | 255 (2) | |
| 227 | 220 | | 360 (2) | |
| 228 | 360 | | 800 | |
| 229 | 300 | | 900 | |
| 230 | 250 | | 550 | |
| 231 | 280 | | 820 | |
| 232 | 150 | | 200 (2) | |
| 233 | 339 (2) | | 4,800 | |
| 234 | 144 (2) | | 600 | |
| 235 | 1,600 | | | |
| 236 | 2,000 | | | |
| 237 | 2,000 | | | |
| 238 | 920 | | | |
| 239 | 490 | | I = 53% | |
| 240 | 96 (2) | | 300 (2) | |
| 241 | 195 (2) | | 340 (2) | |
| 242 | 490 | | I = 1,300 | |
| 243 | 360 | | 850 | |
| 244 | 79 (4) | 27 (1) | 600 | 7 (1) |
| 245 | I = 55% | | | |
| 246 | I = 14% | | | |
| 247 | I = 17% | | | |
| 248 | 830 | | | |
| 249 | 1,600 | | | |
| 250 | 125 (2) | | 800 | |
| 251 | 640 (3) | | 7,500 | |
| 252 | 293 (3) | | 2,900 | |
| 253 | I = 0% | | I = 21% | |
| 254 | 1 = 10% | | I = 27% | |
| 255 | 930 | | 2,000 | |
| 256 | 600 | | 3,000 | |
| 257 | 800 | | 2,100 | |
| 258 | 820 | | 2,100 | |
| 259 | 2,600 | | I = 37% | |
| 260 | 520 | | I = 16% | |
| 261 | 900 | | I = 20% | |
| 262 | 95 (2) | | 76 (2) | |
| 263 | I = 33% | | I = 21% | |
| 264 | I = 48% | | I = 31% | |
| 265 | 2,900 | | I = 42% | |
| 266 | 250 | | 650 | |
| 267 | 38 (3) | | 1.8 (2) | |
| 282 | I = 2% | | I = 0% | |
| 283 | 2,400 | | 7,000 | |
| 284 | I = 10% | | I = 1% | |
| 285 | 2,500 | | I = 21% | |
| 286 | I = 19% | | I = 0% | |
| 287 | I = 26% | | I = 3% | |
| 288 | I = 40% | | I = 46% | |
| 289 | 348 (4) | | 910 (2) | |
| 290 | I = 35% | | I = 15% | |
| 291 | 437 (3) | | 2,700 (3) | |
| 292 | I = 21% | | I = 12% | |
| 293 | I = 16% | | I = 0% | |
| 294 | 47 (8) | 14 (4) | 56 (5) | 4 (2) |
| 295 | 99 | | 600 | |
| 296 | 26 (10) | 12 (2) | 25 (4) | |
| 297 | | | 640 (3) | |
| 298 | 50 | | 850 | |
| 302 | | | | |
| 303 | 310 | | 1,400 | |
| 304 | 55 | | 42 (2) | |
| 305 | 470 | | 1,800 | |
| 306 | 150 | | 550 | |
| 307 | 33 | | 108 (2) | |
| 308 | | | | |
| 309 | 73 | | 62 (2) | |
| 310 | 80 | | 32 (2) | |
| 311 | 910 | | 700 | |
| 315 | 36 (4) | | | |

| Ex. # | MMP-3 Thiopep. IC$_{50}$ | MMP-3 Fluorogenic IC$_{50}$ | MMP-9: Thiopep. IC$_{50}$ | MMP-2 Fluorogenic IC$_{50}$ |
|---|---|---|---|---|
| 316 | 66 (4) | | | |
| 323 | 98 (2) | | | |
| 326 | 140 (2) | | | |
| 327 | I = 55% | | 12,000 | |
| 328 | I = 49% | | I = 45% | |
| 329 | I = 58% | | 8,000 | |
| 330 | I = 9% | | I = 16% | |
| 331 | I = 15% | | I = 18% | |
| 332 | I = 37% | | I = 41% | |
| 333 | I = 62% (2) | | I = 25% | |
| 334 | I = 42% | | 6,000 | |
| 335 | I = 55% | | 6,000 | |
| 336 | 1,400 | | 600 | |
| 337 | I = 20% | | I = 2% | |
| 335 | I = 24% | | 6,000 | |
| 339 | 1,700 | | 1,500 | |
| 340 | I = 4% | | I = 21% | |
| 341 | 2,400 | | 3,800 | |
| 342 | 360 | | 700 | |
| 343 | 500 | | 680 | |
| 344 | I = 11% | | I = 14% | |
| 345 | 5,000 | | I = 30% | |
| 346 | 6,000 | | I = 34% | |
| 347 | I = 12% | | I = 0% | |
| 348 | I = 31% | | I = 36% | |
| 349 | 550 | | 330 | |
| 350 | I = 4% | | I = 20% | |

Automated MMP Profiling Assay

This assay was run with a protocol analogous to that reported for MMP-3 inhibition using the synthetic peptide P218 and each of the three enzymes and measuring quenched fluorescence. This assay with each invention compound was run with the three enzymes MMP-3, MMP-9 and MMP-2 in parallel as adapted for a 96-well microtitre plate using a Hamilton AT® workstation.

Profiling Assay Data for Certain Compounds of the Invention

All IC$_{50}$ values are expressed as nM. When "I=x %" is shown, x represents the % inhibition at 5 $\mu$M.

| Ex. | MMP-3 Fluorogenic IC$_{50}$ | MMP-9 Fluorogenic IC$_{50}$ | MMP-2 Fluorogenic IC$_{50}$ |
|---|---|---|---|
| 69 | I = 0% | I = 0% | I = 0% |
| 70 | I = 44% | I = 7% | 1,750 |
| 71. | 1,160 | I = 24% | 969 |
| 72 | 409 | I = 22% | 90 |
| 85 | 80 | 1767 | 32 |
| 86 | 51 | 442 | 12.5 |
| 87 | I = 8% | I = 0% | I = 40% |
| 93 | 129 | >1,250 | 36 |
| 94 | 224 | 1,850 | 155 |
| 95 | 79 | 77 | 26 |
| 96 | 232 | >1,250 | 72 |
| 97 | 153 | 229 | 48 |
| 98 | 537 | >1,250 | 492 |
| 99 | 36 | 835 | 26 |
| 100 | 17 | 3,220 | 14 |
| 101 | I = 45% | I = 10% | 3,320 |
| 102 | 78 | 698 | 25 |
| 103 | 57 | I = 28% | 30 |
| 104 | 125 | I = 18% | 63 |
| 105 | 33 | I = 37% | 14 |
| 106 | 57 | 622 | 43 |
| 107 | 32 | I = 34% | 16 |
| 108 | I = 8% | I = 4% | I = 16% |
| 109 | 28 | 1,290 | 6.6 |
| 110 | 37 | I = 26% | 38 |
| 111 | 18 | 4,730 | 3.9 |
| 112 | 30 | 884 | 11 |
| 113 | 28 | 1,330 | 44 |
| 114 | 246 | 439 | 68 |
| 115 | >1,250 | >1,250 | 1,750 |
| 116 | 137 | 185 | 38 |
| 127 | 605 | 1,220 | 40 |
| 128 | 561 | 715 | 45 |
| 129 | 237 | 771 | 89 |
| 134 | 304 | 358 | 63 |
| 137 | >1,250 | 1,400 | 548 |
| 138 | 905 | I = 0% | 665 |
| 139 | 5,000 | 5,000 | 323 |
| 140 | 1,030 | >1,250 | 242 |
| 141 | <5,000 | I = % | 1,170 |
| 143 | 309 | 1,400 | 111 |
| 144 | 15 | 29 | 3.4 |
| 145 | 7.5 | 19 | 2.1 |
| 146 | 2,400 | 2,710 | 538 |
| 147 | 266 | 676 | 73 |
| 148 | 90 | 454 | 54 |
| 149 | 109 | 512 | 40 |
| 150 | 371 | 957 | 201 |
| 151 | 371 | 607 | 70 |
| 152 | 367 | 597 | 210 |
| 153 | 594 | 1,010 | 127 |
| 154 | 470 | 875 | 37 |
| 155 | 777 | >1,250 | 50 |
| 156 | 126 | 145 | 21 |
| 157 | 111 | 142 | 35 |
| 158 | 37 | <500 | 32 |
| 159 | 116 | >1,250 | 42 |
| 160 | 147 | 1,060 | 42 |
| 161 | 146 | 1,560 | 38 |
| 162 | 181 | I = 8% | 22 |
| 163 | 64 | I = 18% | 17 |
| 164 | 30 | 82 | 3.9 |
| 165 | 13 | 55 | 3.0 |
| 166 | 103 | 381 | 35 |
| 167 | I = 18% | I = 23% | I = 31% |
| 168 | 49 | 163 | 15 |
| 169 | 245 | 1,080 | 80 |
| 170 | 296 | 1,800 | 103 |
| 171 | 663 | 3,520 | 452 |
| 172 | 456 | 1,930 | 175 |
| 173 | 119 | 814 | 104 |
| 174 | 144 | 522 | 56 |
| 175 | 1 = 28% | I = 6% | 5,000 |
| 176 | 1 = 26% | I = 24% | 2,000 |
| 177 | 1 = 11% | I = 30% | 4,330 |
| 196 | 381 | 955 | 37 |
| 197 | 205 | 504 | 22 |
| 267 | 15 | 3.0 | 2.6 |
| 268 | 5.73 | 1.15 | 0.91 |
| 269 | 1,030 | 197 | 165 |
| 270 | 6.0 | 1.6 | 1.4 |
| 271 | 5.2 | 7.9 | 1.4 |
| 272 | 9.20 | 10.8 | 2.28 |
| 273 | 121 | 1.25 | 2.27 |
| 276 | 1262 | 275 | 39 |
| 279 | 402 | 286 | 67 |
| 280 | 146 | 66 | 29 |
| 294 | 158 | 176 | 11 |
| 296 | 144 | 111 | 6.4 |
| 297 | 5,730 | 2,370 | 2,070 |
| 299 | 58 | 531 | 52 |
| 300 | >1,250 | >1,250 | 2,500 |
| 301 | 130 | 290 | 18 |
| 312 | 180 | 871 | 60 |
| 313 | 3,330 | I = 20% | 2,780 |
| 314 | 399 | 555 | 13 |
| 317 | 75 | 808 | 37 |
| 318 | | | |

-continued

| Ex. | MMP-3 Fluorogenic IC$_{50}$ | MMP-9 Fluorogenic IC$_{50}$ | MMP-2 Fluorogenic IC$_{50}$ |
|---|---|---|---|
| 319 | 30 | 197 | 4.1 |
| 320 | I = 6% | I = 6% | I = 24% |
| 321 | | | |
| 322 | | | |
| 324 | 46 | 343 | 81 |
| 325 | I = 10% | I = 0% | 4,400 |
| 351 | 107 | 151 | 50 |
| 352 | 130 | 905 | 61 |
| 353 | 84 | 274 | 20 |
| 354 | 577 | 1,710 | 76 |
| 355 | 508 | 1,080 | 90 |
| 356 | I = 45% | I = 14% | 188 |
| 357 | I = 15% | I = 4% | I = 38% |
| 358 | I = 39% | I = 4% | 124 |
| 359 | 83 | I = 16% | 51 |
| 360 | 5.46 | 0.93 | 1.46 |
| 361 | 3.00 | 0.50 | 0.81 |
| 362 | 431 | 100 | 183 |
| 363 | 5,000 | I = 37% | <5,000 |
| 364 | 46 | 180 | 40 |
| 365 | 27 | 58 | 13 |
| 366 | 22 | 56 | 6.7 |
| 367 | 44 | 38 | 37 |
| 368 | 36 | 30 | 31 |
| 369 | 54 | 139 | 37 |
| 370 | 24 | 26 | 8.7 |
| 371 | 10 | 26 | 9.1 |
| 372 | 39 | 65 | 22 |
| 373 | 56 | 113 | 24 |
| 374 | 154 | 271 | 34 |
| 375 | 116 | 146 | 68 |
| 376 | 46 | 95 | 34 |
| 377 | 24 | 44 | 28 |
| 378 | 77 | 83 | 43 |
| 379 | 63 | 48 | 92 |
| 380 | 46 | 40 | 69 |
| 381 | 46 | 97 | 44 |
| 382 | 42 | 139 | 64 |
| 383 | 158 | 53 | 110 |
| 384 | 129 | 167 | 78 |
| 385 | 4.22 | 1.12 | 4.26 |
| 386 | 8.34 | 0.97 | 11.7 |
| 387 | 9.4 | 2.0 | 4.9 |
| 388 | 105 | 467 | 30 |
| 389 | 15 | 23 | 6.3 |
| 390 | 10 | 1.2 | 15 |
| 391 | 19 | 4.2 | 14 |
| 392 | 2.5 | | |
| 393 | I = 18% | I = 38% | 2,000 |
| 394 | I = 26% | 1 = 15% | 2,000 |
| 395 | 2,200 | I = 44% | 560 |
| 396 | 779 | 2,290 | 362 |
| 397 | 3,200 | I = 40% | 750 |
| 398 | | | |
| 399 | | | |
| 400 | | | |
| 401 | | | |
| 402 | | | |
| 403 | 17 | 5.7 | 6.4 |
| 404 | | | |
| 405 | 75 | 5.8 | 80 |
| 406 | 10.3 | 1.7 | 17 |
| 407 | 69 | 36 | 39 |
| 408 | | | |
| 409 | 12.3 | 1.9 | 30 |
| 410 | 104 | 44 | 80 |
| 411 | 116 | 213 | 27 |
| 412 | 84 | 41 | 10 |
| 413 | 39 | 109 | 10 |
| 414 | 37 | 15 | 79 |
| 415 | 12 | 1.2 | 34 |
| 416 | 9.5 | 2.5 | 23 |
| 417 | 32 | 12 | 3.7 |
| 418 | 305 | 89 | 420 |
| 419 | 6.7 | 0.85 | 31 |
| 420 | 14 | 1.7 | 5.1 |
| 421 | 12 | 1.7 | 0.75 |
| 422 | 8.4 | 1.6 | 14 |
| 423 | 19 | 6.1 | 15 |
| 424 | | | |
| 425 | 3.8 | 1.2 | 14 |
| 426 | 161 | 417 | 35 |
| 427 | 189 | 362 | 42 |
| 428 | 153 | 119 | 16 |
| 429 | 23 | 1.6 | 23 |
| 430 | I = 28% | I = 37% | 419 |
| 431 | 38 | 50 | 16 |
| 432 | 1,600 | >1,250 | 236 |
| 433 | 103 | 130 | 6.2 |
| 434 | 254 | 1,140 | 61 |
| 435 | 39 | 107 | 8.1 |
| 436 | 158 | 519 | 286 |
| 437 | 50 | 366 | 15 |
| 438 | | | |
| 439 | I = 0% | I = 3% | I = 24% |
| 440 | 58 | 380 | 43 |
| 441 | 38 | 149 | 27 |
| 442 | 2,760 | I = 40% | 962 |
| 443 | I = 20% | I = 16% | 4,610 |
| 444 | <5,000 | <5,000 | 43 |

It should be noted in the above tables that a biaryl portion is necessary for significant MMP inhibitory activity—see, for example, biphenyl example 1 in comparison to reference phenyl example 27 or biphenyl example 200 in comparison to reference phenyl example 253. It is also noted that reference phenoxyphenyl example 254 is only of very low potency. It is also demonstrated that, while a 4-substituent on ring A is not essential for potency, it does lead to significant improved potency—see low potency unsubstituted examples 13 and 135 in comparison to chlorine substituted examples 1 and 114. It is also clear that increased size of substituent $R^6$ on portion E leads to increased activity—see unsubstituted example 6 compared to methyl substituted example 25 compared to ethyl substituted example 117. This is also shown in a comparison of example 293 in which E represents a cyclopropane ring in comparison to much more active example 291 with a cyclobutane ring. Only minor activity, at best, is observed when the compound is neither substituted on biphenyl nor on portion E such as in reference compound Fenbufen (first entry of the table).

Inhibition of Tumor Metastases in in vivo Murine Models

The B16.F10 Melanoma Experimental Metastasis Model:

Six to eight week old male BDFl mice were injected in the tail vein with 1×10$^6$ B16.F10 melanoma cells. Animals were dosed with compounds intraperitoneally at −24 hrs, −3 hrs, +24 hrs and +48 hrs relative to the time of cell injection. Invention compounds were administered as a suspension in PEG400/tween80 (95:5 w/w) diluted to 4 mg/ml in phosphate buffered saline. Vehicle alone was administered to the control group in the same manner. On day 21 the animals were euthanized and the number of lung metastases was determined. Using the invention compounds of example 86, 116, 268, 296 or 299, the number of metastases was decreased between 38% and 49% as compared to the vehicle control In a second experiment animals were inoculated and dosed as in the experiment above. Compounds were administered orally as a suspension in the PEG400/tween80 vehicle at 40 mg/kg. The number of lung metastases was determined on day 21. The results are shown in FIG. 1. The number of metastases was decreased relative to the number observed in the zero control and vehicle treated groups.

The B16.F10 Melanoma Spontaneous Metastasis Model

Figure 2:
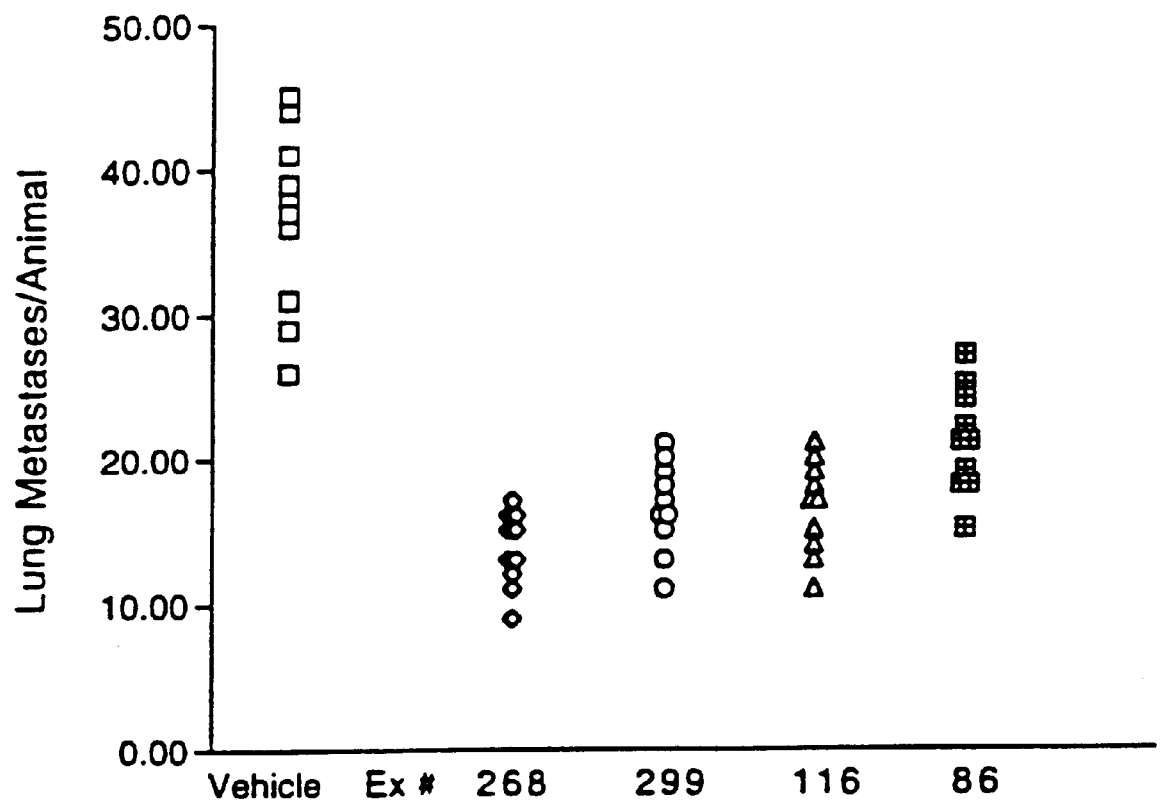
FIG. 2 is a graph which shows the inhibition of B16.F10 spontaneous metastasis in male BDF1 mice by invention compounds at 10 mg/kg (po)

Six to eight week old male BDF1 mice were inoculated inter-digitally in the right hind foot with $1 \times 10^6$ B16.F10 murine melanoma cells. On day 21 after inoculation the primary tumor mass was removed. The animals were dosed 1× daily with invention compounds beginning on day 23 after cell inoculation. Compounds were administered orally as a suspension of 10 mg/kg in PBS/PEG 400/tween 80. The animals were euthanized and the number of lung nodules determined on day 77. The results are shown in FIG. 2 The number of spontaneous metastases was reduced between 45% and 63% as compared to the vehicle control.

Figure 3:
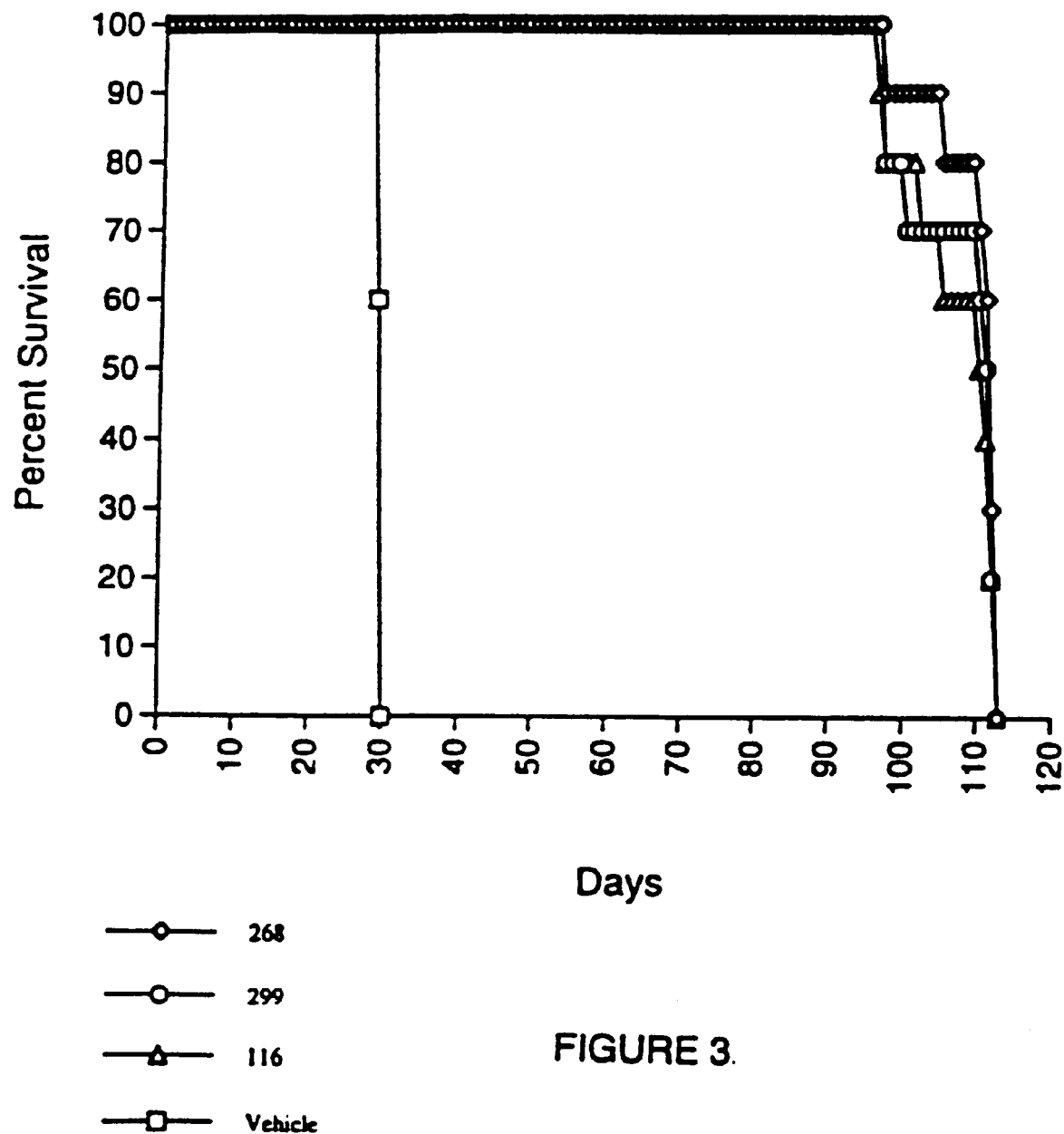
FIG. 3 is a graph which shows the inhibition of SKOV-3 ascites in female Balb/c nu/nu mice by invention compounds at 40 mg/kg (po).

Inhibition of Malignant Ascites in the Human Ovarian Carcinoma SKOV-3 Xenograph Model Intraperitoneal SKOV-3 Tumor Growth-Treatment with Invention Compounds Six to eight week old female Balb/c nu/nu mice were inoculated with $2 \times 10^5$ SKOV-3 human ovarian carcinoma cells intraperitoneally. Animals were dosed with invention compounds 1× daily from day 3 after inoculation until day 21. Compounds were administered as an oral suspension in the PEG/tween vehicle. The animals were monitored daily, the endpoint of the study is survival. The results are shown in FIG. 3. The animals treated with the invention compounds showed a 3.8-fold increase in survival compared to the vehicle control group.

Intraperitoneal SKOV-3 Tumor Growth-Treatment with Invention Compounds in Combination with Cisplatin Six to eight week old female Balb/c nu/nu mice were injected intraperitoneally with $1 \times 10^6$ SKOV-3 human ovarian carcinoma cells. Animals were treated once with 50 mg/m$^2$ Cisplatin on day 7 after inoculation. Invention compounds were administered at 20 mg/kg orally 1× daily from day 9 until death of the animal. The animals were monitored daily, and upon death tumor burden was determined and tissues were collected for histological examination.

At 20 mg/kg doses the invention compounds in combination with cisplatin increased the survival time >4.6 fold.

Inhibition of Cartilage Lesions in a Guinea Pig Model of Osteoarthritis

Osteoarthritis was surgically induced in the guinea pig left stifle by partial medial menisectomy according to a procedure reported by A. M. Bendele, "Progressive chronic osteoarthritis in femorotibial joints of partial medial menisectomized guinea pigs," *Vet. Pathol.* 1987 24, 444–448. Seven of the invention compounds were dissolved at 15 mg/ml in a vehicle of 10 mg/ml Tween 80, 190 mg/ml PEG and 0.44 mg/ml ethanolamine. This concentrate was diluted 1:1 with water before dosing (final concentration 7.5 mg/ml). On the 5th day before surgery, each animal received either a test compound plus vehicle or vehicle only administered by oral gavage each day at 15 mg/kg (2 ml/kg) up to surgery and then for four weeks post surgery (total 33 days of dosing). At the beginning of dosing and twice weekly thereafter the animals were weighed and the dose of the respective compounds or vehicles were calculated and adjusted if necessary. At the conclusion of the study the animals were euthanized by CO2 asphyxiation and their stifles removed, partially dissected and placed in 10% neutral buffered formalin. The extent of lesion development on the femoral head was measured by computer assisted surface area analysis.

Selected examples of the invention compounds caused inhibition of the lesion surface area in operated joints of those animals receiving compound as compared to those receiving vehicle only as follows:

| Example # | % Inhibition of Femoral Lesion Surface Area |
|---|---|
| 86 | 0 |
| 100 | 37.8 |
| 116 | 0 |
| 145 | 46.4 |
| 197 | 18* |
| 268 | 53 |
| 296 | 31 |
| 299 | 28 |

*Mean value of several separate experiments.

TABLE XXVIII

| EXAMPLE COMPOUND NUMBER: | Chemical Abstracts (CA) Index Name |
|---|---|
| 1: | [1,1'-Biphenyl]-4-butanoic acid, 4'-chloro-α-(2-methylpropyl)-γ-oxo- |
| 2: | [1,1'-Biphenyl]-4-butanoic acid, 4'-chloro-α-(2-methylpropyl)-γ-oxo-, (S)- |
| 3: | [1,1'-Biphenyl]-4-butanoic acid, 4'-chloro-α-(2-methylpropyl)-γ-oxo-, (R)- |
| 4: | [1,1'-Biphenyl]-4-butanoic acid, 4'-chloro-β-(2-methylpropyl)-γ-oxo-, (S)- |
| 5: | [1,1'-Biphenyl]-4-butanoic acid, 4'-chloro-β-(2-methylpropyl)-γ-oxo-, (R)- |
| 6: | [1,1'-Biphenyl]-4-butanoic acid, 4'-chloro-γ-oxo- |
| 7: | [1,1'-Biphenyl]-4-butanoic acid, 4'-bromo-γ-oxo- |
| 8: | [1,1'-Biphenyl]-4-butanoic acid, 4'-fluoro-γ-oxo- |
| 9: | [1,1'-Biphenyl]-4-butanoic acid, 2'-fluoro-γ-oxo- |
| 10: | [1,1'-Biphenyl]-4-butanoic acid, 2'-chloro-γ-oxo- |
| 11: | [1,1'-Biphenyl]-4-butanoic acid, 2',4'-difluoro-γ-oxo- |
| 12: | [1,1'-Biphenyl]-4-butanoic acid, 3'-chloro-γ-oxo- |
| 13: | [1,1'-Biphenyl]-4-butanoic acid, α-(2-methylpropyl)-γ-oxo- |
| 14: | [1,1'-Biphenyl]-4-butanoic acid, 4'-bromo-α-(2-methylpropyl)-γ-oxo- |
| 15: | [1,1'-Biphenyl]-4-butanoic acid, 4'-fluoro-α-(2-methylpropyl)-γ-oxo- |
| 16: | [1,1'-Biphenyl]-4-butanoic acid, 4'-ethyl-α-(2-methylpropyl)-γ-oxo- |
| 17: | [1,1'-Biphenyl]-4-butanoic acid, 2'-fluoro-α-(2-methylpropyl)-γ-oxo- |
| 18: | [1,1'-Biphenyl]-4-butanoic acid, 2'-chloro-α-(2-methylpropyl)-γ-oxo- |
| 19: | [1,1'-Biphenyl]-4-butanoic acid, 4'-methoxy-α-(2-methylpropyl)-γ-oxo- |
| 20: | [1,1'-Biphenyl]-4-butanoic acid, 2',4'-difluoro-α-(2-methylpropyl)-γ-oxo- |
| 21: | [1,1'-Biphenyl]-4-butanoic acid, 4'-methyl-α-(2-methylpropyl)-γ-oxo- |
| 22: | [1,1'-Biphenyl]-4-butanoic acid, α-(2-methylpropyl)-γ-oxo4'-pentyl- |
| 23: | [1,1'-Biphenyl]-4-butanoic acid, 4'-chloro-α-methylene-γ-oxo- |
| 24: | [1,1'-Biphenyl]-4-butanoic acid, 2'-chloro-α-methylene-γ-oxo- |
| 25: | [1,1'-Biphenyl]-4-butanoic acid, 4'-chloro-α-methyl-γ-oxo- |
| 26: | [1,1'-Biphenyl]-4-butanoic acid, 4'-chloro-γ-oxo-α-pentyl |
| 27: | Benzenebutanoic acid, 4-chloro-α-(2-methylpropyl)-γ-oxo- |

TABLE XXVIII-continued

| EXAMPLE COMPOUND NUMBER: | Chemical Abstracts (CA) Index Name |
|---|---|
| 28: | Benzenebutanoic acid, 4-methyl-α-methylene-γ-oxo- |
| 29: | 2-Butenoic acid, 4-(4-chloro[1,1-biphenyl]-4-yl)-4-oxo-,(E)- |
| 30: | 2-Butenoic acid, 4-[4-(4-chlorophenoxy)phenyl]-4-oxo-,(E)- |
| 31: | [1,1'-Biphenyl]-4-butanoic acid, 4'-hydroxy-α-(2-methylpropyl)-γ-oxo- |
| 32: | [1,1'-Biphenyl]-4-butanoic acid, 4'-chloro-β-methylene-γ-oxo- |
| 33: | [1,1'-Biphenyl]-4-butanoic acid, 4'-chloro-γ-hydroxy-α-(2-methylpropyl)- |
| 34: | [1,1'-Biphenyl]-4-butanoic acid, 4'-chloro-γ-hydroxy-α-(2-methylpropyl)- |
| 35: | 2(3H)-Furanone, 5-(4'-chloro[1,1'-biphenyl]-4-yl)dihydro-3-(2-methylpropyl)- |
| 36: | 2(3H)-Furanone, 5-(4'-chloro[1,1'-biphenyl]-4-yl)dihydro-3-(2-methylpropyl)- |
| 37: | Ethanone, 1-(4'-chloro[1,1'-biphenyl]-4-yl)- |
| 38: | [1,1'-Biphenyl]-4-butanoic acid, 4'-chloro-γhydroxy-α-methylene- |
| 39: | [1,1'-Biphenyl]-4-butanoic acid, 2'-fluoro-γhydroxy- |
| 40: | [1,1'-Biphenyl]-4-butanoic acid, 4'-iodo-γ-oxo-α-(3-phenylpropyl)- |
| 41: | [1,1'-Biphenyl]-4-butanoic acid, 4'-iodo-α-(2-methylpropyl)-γ-oxo- |
| 42: | [1,1'-Biphenyl]-4-butanoic acid, 4'-(3-ethoxy-3-oxo-1-propenyl)-γ-oxo-α-(3-phenylpropyl)-,(E)- |
| 43: | [1,1'-Biphenyl]-4-butanoic acid, 4'-(2-carboxyethenyl)-γ-oxo-α-(3-phenylpropyl)-,(E)- |
| 44: | [1,1'-Biphenyl]-4-butanoic acid, 4'-(3-ethoxy-3-oxopropyl)-α-(3-phenylpropyl)- |
| 45: | [1,1'-Biphenyl]-4-butanoic acid, 4'-(2-carboxyethyl)-α-(3-phenylpropyl)- |
| 46: | [1,1'-Biphenyl]-4-butanoic acid, 4'cyano-α-(2-methylpropyl)-γ-oxo- |
| 47: | [1,1'-Biphenyl]-4-butanoic acid, 4'-[[(1,1-dimethylethoxy)carbonyl]amino]-γ-oxo-α-(3-phenylpropyl)- |
| 48: | [1,1'-Biphenyl]-4-butanoic acid, 4'-(1,1-dimethylethyl)-γ-oxo-α-(3-phenylpropyl)- |
| 49: | [1,1'-Biphenyl]-4-butanoic acid, 4'-[[[(1,1-dimethylethoxy)carbonyl]amino]methyl]-γ-oxo-α-(3-phenylpropyl)- |
| 50: | [1,1]'-Biphenyl]-4-butanoic acid, 4'-(cyanomethyl)-γ-oxo-α-(3-phenylpropyl)- |
| 51: | [1,1'-Biphenyl]-4-butanoic acid, 4'-(methylthio)-γ-oxo-α-(3-phenylpropyl)- |
| 52: | [1,1'-Biphenyl]-4-butanoic acid, 4'-(2-chloroethoxy)-γ-oxo-α-(3-phenylpropyl)- |
| 53: | [1,1'-Biphenyl]-4-butanoic acid, 4'-(hydroxymethyl)-γ-oxo-α-(3-phenylpropyl)- |
| 54: | [1,1'-Biphenyl]-4-butanoic acid, 4'-(2-hydroxyethoxy)-γ-oxo-α-(3-phenylpropyl)- |
| 55: | [1,1'-Biphenyl]-4-butanoic acid, 4'-ethenyl-γ-oxo-α-(3-phenylpropyl)- |
| 56: | [1,1'-Biphenyl]-4-butanoic acid, 4'-cyano-γ-oxo-α-(3-phenylpropyl)- |
| 57: | [1,1'-Biphenyl]-4-butanoic acid, γ-oxo-α-(3-phenylpropyl)-4'-(1H-tetrazol-5-yl)- |
| 58: | [1,1'-Biphenyl]-4-butanoic acid, 4'-amino-γ-oxo-α-(3-phenylpropyl)- |
| 59: | [1,1'-Biphenyl]-4-butanoic acid, 4'-(aminomethyl)-γ-oxo-α-(3-phenylpropyl)- |
| 60: | [1,1'-Biphenyl]-4-butanoic acid, 4'-(dimethylamino)-γ-oxo-α-(3-phenylpropyl)- |
| 61: | 2-Pyridinebutanoic acid, 5-(4-ethylphenyl)-α-(2-methylpropyl)-γ-oxo- |
| 62: | [1,1'-Biphenyl]-4-butanoic acid, γ-oxo-α-(3-phenylpropyl)-4'-(trifluoromethyl)- |
| 63: | [1,1'-Biphenyl]-4-butanoic acid, 4'-nitro-γ-oxo-α-(3-phenylpropyl)- |
| 64: | [1,1'-Biphenyl]-4-butanoic acid, 3'4'-dichloro-α-(2-methylpropyl)-γ-oxo- |
| 65: | [1,1'-Biphenyl]-4-butanoic acid, 3',4'-dichloro-γ-oxo-α-(3-phenylpropyl)- |
| 66: | [1,1'-Biphenyl]-4-butanoic acid, 3',5'-dichloro-γ-oxo-α-(3-phenylpropyl)- |
| 67: | [1,1'-Biphenyl]-4-butanoic acid, 4'-(acetyloxy)-γ-oxo-α-(3-phenylpropyl)- |
| 68: | Benzenepentanoic acid, α-[2-[4-(5-chloro-2-thienyl)phenyl]-2-oxothyl]- |
| 69: | 2-Furancarboxylic acid, 5-[4-(3carboxy-1-oxo-6-phenylhexyl)phenyl]- |
| 70: | Benzenepentanoic acid, α-[2-oxo-2-[4-(3-pyridiyl)phenyl]ethyl]- |
| 71: | Benzenepentanoic acid, α-[2-oxo-2-[4-[6-(pentyloxy)-3-pyridinyl]phenyl]ethyl]- |
| 72: | [1,1'-Biphenyl]-4-butanoic acid, γ-oxo-4-'-(pentylthio)-α-(3-phenylpropyl)- |
| 73: | [1,1'-Biphenyl]-4-butanoic acid, 4'-methoxy-γ-oxo-α-(3-phenylpropyl)- |
| 74: | [1,1'-Biphenyl]-4-butanoic acid, 3'-chloro-4'-fluoro-γ-oxo-α-(3-phenylpropyl)- |
| 75: | [1,1'-Biphenyl]-4-butanoic acid, 4'-ethoxy-γ-oxo-α-(3-phenylpropyl)- |
| 76: | Benzenepentanoic acid, α-(2-oxo-2-[4-(3-thienyl)phenyl]ethyl]- |
| 77: | [1,1'-Biphenyl]-4-butanoic acid, 2',4'-dichloro-γ-oxo-α-(3-phenylpropyl)- |
| 78: | [1,1'-Biphenyl]-4-butanoic acid, 4'formyl-γ-oxo-α-(3-phenylpropyl)- |
| 79: | [1,1'-Biphenyl]-4-butanoic acid, γ-oxo-α-(3-phenylpropyl)-3',5'-bis(trifluoromethyl)- |
| 80: | Benzenepentanoic acid, α-[2-oxo-2-[4-(2-thienyl)phenyl]ethyl]- |
| 81: | [1,1'-Biphenyl]-4-butanoic acid, γ-oxo-α-(3-phenylpropyl)-3'-(trifluoromethyl)- |
| 82: | [1,1'-Biphenyl]-4-butanoic acid, 2'-formyl-γ-oxo-α-(3-phenylpropyl)- |
| 83: | [1,1'-Biphenyl]-4-butanoic acid, 4'-hydroxyγ-oxo-α-(3-phenylpropyl)- |
| 84: | [1,1'-Biphenyl]-4-butanoic acid, γ-oxo-α-(3-phenylpropyl)-4'-propoxy- |
| 85: | [1,1'-Biphenyl]-4-butanoic acid, γ-oxo-4'-(pentyloxy)-α-(3-phenylpropyl)- |
| 86: | [1,1'-Biphenyl]-4-butanoic acid, γ-oxo-4'-(pentyloxy)-α-(3-phenylpropyl)-,(S)- |
| 87: | [1,1'-Biphenyl]-4-butanoic acid, γ-oxo-4'-(pentyloxy)-α-(3-phenylpropyl)-,(R)- |
| 88: | [1,1'-Biphenyl]-4-butanoic acid, 4'-(hexyloxy)-γ-oxo-α-(3-phenylpropyl)- |

TABLE XXVIII-continued

| EXAMPLE COMPOUND NUMBER: | Chemical Abstracts (CA) Index Name |
|---|---|
| 89: | [1,1'-Biphenyl]-4-butanoic acid, 4'butoxy-γ-oxo-α-(3-phenylpropyl)- |
| 90: | [1,1'-Biphenyl]-4-butanoic acid, γ-oxo-4'-(3-phenylpropoxy)-α-(3-phenylpropyl)- |
| 91: | [1,1'-Biphenyl]-4-butanoic acid, 4'-(1-methylethoxy)-γ-oxo-α-(3-phenylpropyl)- |
| 92: | [1,1'-Biphenyl]-4-butanoic acid, 4'-(heptyloxy)-γ-oxo-α-(3-phenylpropyl)- |
| 93: | [1,1'-Biphenyl]-4-butanoic acid, 4'-(cyclohexylmethoxy)-γ-oxo-α-(3-phenylpropyl)- |
| 94: | [1,1'-Biphenyl]-4-butanoic acid, 4'-(2-methylpropoxy)-γ-oxo-α-(3-phenylpropyl)- |
| 95: | [1,1'-Biphenyl]-4-butanoic acid, γ-oxo-α-(3-phenylpropyl)-4'-(2-propenyloxy)- |
| 96: | [1,1'-Biphenyl]-4-butanoic acid, 4'-(3-methylbutoxy)-#xo-a-(3-phenylpropyl)- |
| 97: | [1,1'-Biphenyl]-4-butanoic acid, 4'-(cydopropylmethoxy)-γ-oxo-α-(3-phenylpropyl)- |
| 98: | [1,1'-Biphenyl]-4-butanoic acid, 4'-(1-ethylpropoxy)-γ-oxo-α-(3-phenylpropyl)- |
| 99: | [1,1'-Biphenyl]-4-butanoic acid, γ-oxo-4'-(phenylmethoxy)-α-(3-phenylpropyl)- |
| 100: | [1,1'-Biphenyl]-4-butanoic acid, γ-oxo-4'-(phenylmethoxy)-α-(3-phenylpropyl)-, (S)- |
| 101: | [1,1'-Biphenyl]-4-butanoic acid, γ-oxo-4'-(phenylmethoxy)-α-(3-phenylpropyl)-, (R)- |
| 102: | [1,1'-Biphenyl]-4-butanoic acid, γ-oxo-4'-(2-phenylethoxy)-α-(3-phenylpropyl)- |
| 103: | [1,1'-Biphenyl]-4-butanoic acid, 4'-[(4-methylphenyl)methoxy]-γ-oxo-α-(3-phenylpropyl)- |
| 104: | [1,1'-Biphenyl]-4-butanoic acid, γ-oxo-α-(3-phenylpropyl)-4'-[[4-(trifluoromethyl)phenyl]methoxy]- |
| 105: | [1,1'-Biphenyl]-4-butanoic acid, 4'-[(4-methoxyphenyl)methoxy]-γ-oxo-α-(3-phenylpropyl)- |
| 106: | [1,1'-Biphenyl]-4-butanoic acid, 4'-[(3-chlorophenyl)methoxy]-γ-oxo-α-(3-phenylpropyl)- |
| 107: | [1,1'-Biphenyl]-4-butanoic acid, 4'-[(4-fluorophenyl)methoxy]-γ-oxo-α-(3-phenylpropyl)- |
| 108: | [1,1'-Biphenyl]-4-butanoic acid, 4'-(decyloxy)-γ-oxo-α-(3-phenylpropyl)- |
| 109: | [1,1'-Biphenyl]-4-butanoic acid, γ-oxo-α-(3-phenylpropyl)4'-(3-pyridinylmethoxy)- |
| 110: | [1,1'-Biphenyl]-4-butanoic acid, γ-oxo-α-(3-phenylpropyl)4'-(2-pyridinylmethoxy)- |
| 111 | [1,1'-Biphenyl]-4-butanoic acid, γ-oxo-α-(3-phenylpropyl)4'-(4-pyridinylmethoxy)- |
| 112: | [1,1'-Biphenyl]-4-butanoic acid, 4'[[4-(aminocarbonyl)phenyl]methoxy]-γ-oxo-α-(3-phenylpropyl)- |
| 113: | [1,1'-Biphenyl]-4-butanoic acid, 4'-[(4-carboxyphenyl)methoxy]-γ-oxo-α-(3-phenylpropyl)- |
| 114: | [1,1'-Biphenyl]-4-butanoic acid, 4'-chloro-γ-oxo-α-(3-phenylpropyl)- |
| 115: | [1,1'-Biphenyl]-4-butanoic acid, 4'-chloro-γ-oxo-α-(3-phenylpropyl)-, (R)- |
| 116: | [1,1'-Biphenyl]-4-butanoic acid, 4'-chloro-γ-oxo-α-(3-phenylpropyl)-, (S)- |
| 117: | [1,1'-Biphenyl]-4-butanoic acid, 4'-chloro-α-ethyl-γ-oxo- |
| 118: | [1,1'-Biphenyl]-4-butanoic acid, 4'-chloro-γ-oxo-α-propyl- |
| 119: | [1,1'-Biphenyl]-4-butanoic acid, 4'-chloro-γ-oxo-α-2-propenyl- |
| 120: | [1,1'-Biphenyl]-4-butanoic acid, α-butyl-4'-chloro-γ-oxo- |
| 121: | [1,1'-Biphenyl]-4-butanoic acid, 4'-chloro-γ-oxo-α-2-propynyl- |
| 122: | [1,1'-Biphenyl]-4-butanoic acid, 4'-chloro-α-heptyl-γ-oxo- |
| 123: | [1,1'-Biphenyl]-4-butanoic acid, 4'-chloro-αdecyl-γ-oxo- |
| 124: | [1,1'-Biphenyl]-4-butanoic acid, 4'-nitro-γ-oxo-α-(2-phenylethyl)- |
| 125: | [1,1'-Biphenyl]-4-butanoic acid, 4'-cyano-γ-oxo-α-(2-phenylethyl)- |
| 126: | [1,1'-Biphenyl]-4-butanoic acid, 4'-chloro-α-[2-(2-iodophenyl)ethyl]-γ-oxo- |
| 127: | [1,1'-Biphenyl]-4-butanoic acid, 4'-chloro-α-[2-(3-iodophenyl)ethyl]-γ-oxo- |
| 128: | [1,1'-Biphenyl]-4-butanoic acid, 4'-chloro-α-[2-(4-iodophenyl)ethyl]-γ-oxo- |
| 129: | [1,1'-Biphenyl]-4-butanoic acid, 4'-chloro-α-[2-(3,5-dimethoxyphenyl)ethyl]-γ-oxo- |
| 130: | [1,1'-Biphenyl]-4-butanoic acid, 4'-chloro-γ-oxo-α-phenyl- |
| 131: | [1,1'-Biphenyl]-4-butanoic acid, 4'-chloro-γ-oxo-α-(phenylmethyl)- |
| 132: | [1,1'-Biphenyl]-4-butanoic acid, 4'-chloro-γ-oxo-α-(2-phenylethyl)- |
| 133: | [1,1'-Biphenyl]-4-butanoic acid, 4'-chloro-γ-oxo-α-[(trimethylsilyl)methyl]- |
| 134: | [1,1'-Biphenyl]-4-butanoic acid, 4'bromo-γ-oxo-α-(3-phenylpropyl)- |
| 135: | [1,1'-Biphenyl]-4-butanoic acid, γ-oxo-α-(3-phenylpropyl)- |
| 136: | [1,1'-Biphenyl]-4-butanoic acid, 4'amino-γ-oxo-α-(2-phenylethyl)- |
| 137: | [1,1'-Biphenyl]-4-butanoic acid, γ-oxo-α-(2-phenylethyl)-4'-[[(phenylmethoxy)carbonyl)amino]- |
| 138: | [1,1'Biphenyl]-4-butanoic acid, 4'-[[(1,1-dimethylethoxy)carbonyl]amino]-γ-oxo-α-(2-phenyl-ethyl) |
| 139: | [1,1'-Biphenyl]-4-butanoic acid, 4'(acetylamino)γ-oxo-α-(2-phenylethyl)- |
| 140: | [1,1'-Biphenyl]-4-butanoic acid, γ-oxo-4'-](1-oxopentyl)amino]-α-(2-phenylethyl)- |
| 141: | [1,1'-Biphenyl]-4-butanoic acid, 4'-[(3,3-dimethyl-1-oxobutyl)amino]-γ-oxo-α-(2-phenylethyl)- |
| 142: | [1,1'-Biphenyl]-4-butanoic acid, 4'-chloro-α-[2-(2-(methoxycarbonyl)phenyl]ethyl]-γ-oxo- |
| 143: | [1,1'-Biphenyl]-4-butanoic acid, α-[2-(2-carboxyphenyl)ethyl]-4'-chloro-γ-oxo- |
| 144: | [1,1'-Biphenyl]-4-butanoic acid, 4'-chloro-α-[2-[2-[(diethylamino)carbonyl]phenyl]ethyl]-γ-oxo- |

TABLE XXVIII-continued

| EXAMPLE COMPOUND NUMBER: | Chemical Abstracts (CA) Index Name |
|---|---|
| 145: | [1,1'-Biphenyl]-4-butanoic acid, 4'-chloro-α-[2-[3-[(diethylamino)carbonyl]phenyl]ethyl]-γ-oxo-, (S)- |
| 146: | [1,1'-Biphenyl]-4-butanoic acid, 4'-chloro-α-[2-[3-[(diethylamino)carbonyl]phenyl]ethyl]-γ-oxo-, (R)- |
| 147: | [1,1'-Biphenyl]-4-butanoic acid, α-]2-]2-[(butylamino)carbonyl]phenyl]ethyl]-4'-chloro-γ-oxo- |
| 148: | [1,1'-Biphenyl]-4-butanoic acid, α-[2-(3-carboxyphenyl)ethyl]-4'-chloro-γ-oxo- |
| 149: | [1,1'-Biphenyl]-4-butanoic acid, 4'-chloro-α-[2-[3-[(diethylamino)carbonyl]phenyl]ethyl]-γ-oxo- |
| 150: | [1,1'-Biphenyl]-4-butanoic acid, α-[2-[3-[(butylamino)carbonyl]phenyl]ethyl]-4'-chloro-γ-oxo- |
| 151: | [1,1'-Biphenyl]-4-butanoic acid, 4'-chloro-α-[2-[4-[(diethylamino)carbonyl]phenyl]ethyl]-γ-oxo- |
| 152: | [1,1'-Biphenyl]-4-butanoic acid, α-[2-[4-[(butylamino)carbonyl]phenyl]ethyl]-4'-chloro-γ-oxo- |
| 153: | [1,1'-Biphenyl]-4-butanoic acid, α-[2-(4-carboxyphenyl)ethyl]-4'-chloro-γ-oxo- |
| 154: | [1,1'-Biphenyl]-4-butanoic acid, 4'-methoxy-γ-oxo-α-(2-phenylethyl)- |
| 155: | [1,1'-Biphenyl]-4-butanoic acid, 4'-hydroxy-γ-oxo-α-(2-phenylethyl)- |
| 156: | [1,1'-Biphenyl]-4-butanoic acid, 4'-ethoxy-γ-oxo-α-(2-phenylethyl)- |
| 157: | [1,1'-Biphenyl]-4-butanoic acid, γ-oxo-α-(2-phenylethyl)-4'-propoxy- |
| 158: | [1,1'-Biphenyl]-4-butanoic acid, γ-oxo-4'-(pentyloxy)-α-(2-phenylethyl)- |
| 159: | [1,1'-Biphenyl]-4-butanoic acid, 4'-(hexyloxy)-γ-oxo-α-(2-phenylethyl)- |
| 160: | [1,1'-Biphenyl]-4-butanoic acid, 4'-butoxy-γ-oxo-α-(2-phenylethyl)- |
| 161: | [1,1'-Biphenyl]-4-butanoic acid, γ-oxo-α-(2-phenylethyl)-4'-(phenylmethoxy)- |
| 162: | [1,1'-Biphenyl]-4-butanoic acid, α-[2-(3-iodophenyl)ethyl]-γ-oxo-4'-(pentyloxy)- |
| 163: | [1,1'-Biphenyl]-4-butanoic acid, α-[2-(3-iodophenyl)ethyl]-γ-oxo-4'-(phenylmethoxy)- |
| 164: | [1,1'-Biphenyl]-4-butanoic acid, α-[2-[3-[(diethylamino)carbonyl]phenyl]ethyl]-γ-oxo-4'-(pentyloxy)- |
| 165: | [1,1'-Biphenyl]-4-butanoic acid, α-[2-[3-[(diethylamino)carbonyl]phenyl]ethyl]-γ-oxo-4'-(phenylmethoxy)- |
| 166: | 1,2-Pyrrolidinedicarboxylic acid, 3-[(4'-chloro[1,1'-biphenyl]-4-yl)carbonyl]-,1-(phenylmethyl) ester, (2S-trans)- |
| 167: | 1,2-Pyrrolidinedicarboxylic acid, 3-[(4'-chloro[1,1'-biphenyl]-4-yl)carbonyl]-,1-(phenylmethyl) ester, (2'R-trans)- |
| 168: | L-Proline, 3-[(4'-chloro[1,1'-biphenyl]-4-yl)carbonyl]-1-[[(phenylmethyl)amino]carbonyl]-, trans- |
| 169: | L-Proline, 3-[(4'-chloro[1,1'-biphenyl]-4-yl)carbonyl]-1-(1-oxo-3-phenylpropyl)-, trans- |
| 170: | L-Proline, 3-[(4'-chloro[1,1'-biphenyl]-4-yl)carbonyl]-1-(phenyl-acetyl)-, trans- |
| 171: | L-Proline, 3-[(4'-chloro[1,1'-biphenyl]-4-yl)carbonyl]-1-(3,3-dimethyl-1-oxobutyl)-, trans- |
| 172: | 1,2-Pyrrolidinedicarboxylic acid, 3-[(4'-chloro[1,1'-biphenyl]-4-yl)carbonyl]-,1-(2-methylpropyl) ester, (2S-trans)- |
| 173: | L-Proline, 3-[(4'-chloro[1,1'-biphenyl]-4-yl)carbonyl]-1-[(phenylamino)carbonyl]-,trans- |
| 174: | 1,3-Pyrrolidinedicarboxylic acid, 4-[(4'-chloro[1,1'-biphenyl]-4-yl)carbonyl]-,1-(phenylmethyl) ester, trans- |
| 175: | 3-Pyrrolidinecarboxylic acid, 4-[(4'-chloro[1,1'-biphenyl]-4-yl)carbonyl]-1-(phenylmethyl)-, trans- |
| 176: | Bicyclo[2.2.1]hept-5-ene-2-carboxylic acid, 3-[(4'Chloro]1,1'-biphenyl]-4-yl)carbonyl]-, (2-endo,3-exo)- |
| 177: | Bicyclo[2.2.1]hept-5-ene-2-carboxylic acid, 3-[(4'-chloro[1,1'-biphenyl]-4-yl)carbonyl]-, (2-exo,3-endo)- |
| 178: | [1,1'-Biphenyl]-4-butanoic acid, 4'-bromo-γ-oxo-α-(3-phenylpropyl)-, (S)- |
| 179: | [1,1'-Biphenyl]-4-butanoic acid, 4'-chloro-γ-oxo-α-(4-phenylbutyl)- |
| 180: | [1,1'-Biphenyl]-4-butanoic acid, 4'-chloro-γ-oxo-α-(5-phenylpentyl)- |
| 181: | [1,1'-Biphenyl]-4-butanoic acid, 4'-chloro-γ-oxo-α-(6-phenylhexyl)- |
| 182: | [1,1'-Biphenyl]-4-butanoic acid, α-([1,1'-biphenyl]-4-ylmethyl)4'-chloro-γ-oxo- |
| 183: | [1,1'-Biphenyl]-4-butanoic acid, 4'-chloro-γ-oxo-α-(3-phenyl-2-propenyl)-, (E)- |
| 184: | [1,1'-Biphenyl]-4-butanoic acid, 4'-chloro-α[3-(4-methylphenyl)propyl]-γ-oxo- |
| 185: | [1,1'-Biphenyl]-4-butanoic acid, 4'chloro-α-[3-(4-chlorophenyl)propyl]-γ-oxo- |
| 186: | [1,1'-Biphenyl]-4-butanoic acid, 4'-chloro-α-[3-(4-methoxyphenyl)propyl]-γ-oxo- |
| 187: | [1,1'-Biphenyl]-4-butanoic acid, 4'-chloro-α[2-(4-methoxyphenyl)ethyl]-γ-oxo- |
| 188: | [1,1'-Biphenyl]-4-butanoic acid, 4'-chloro-α-[2-(3-methoxyphenyl)ethyl]-γ-oxo- |
| 189: | [1,1'-Biphenyl]-4-butanoic acid, 4'-chloro-γ-oxo-α(3-phenyl-2-propynyl)- |
| 190: | [1,1'-Biphenyl]-4-butanoic acid, 4'-chloro-γ-oxo-α-[2-(phenylmethoxy)ethyl]- |
| 191: | [1,1'-Biphenyl]-4-butanoic acid, 4'-chloro-α-[(2-methoxyethoxy)methyl]-γ-oxo- |
| 192: | [1,1'-Biphenyl]-4-butanoic acid, 4'-chloro-γ-oxo-α-[(phenylmethoxy)methyl]- |
| 193: | [1,1'-Biphenyl]-4-butanoic acid, 4'-chloro-α-[[(2,2-dimethyl-1-oxopropyl)thio]methyl]-γ-oxo- |
| 194: | [1,1'-Biphenyl]-4-butanoic acid, 4'-chloro-α-[[(2,2-ditmthyl-1-oxopropyl)thio]methyl]-γ-oxo- |
| 195: | [1,1'-Biphenyl]-4-butanoic acid, 4'-chloro-α-[[(2,2-dimethyl-1-oxopropyl)thio]methyl]-γ-oxo- |
| 196: | [1,1'-Biphenyl]-4-butanoic acid, 4'-chloro-γ-oxo-α-[(phenylthio)methyl]- |
| 197: | [1,1'-Biphenyl]-4-butanoic acid, 4'-chloro-γ-oxo-α-[(phenylthio)methyl]-, (S)- |
| 198: | [1,1'-Biphenyl]-4-butanoic acid, 4'-chloro-γ-oxo-α-[(phenylthio)methyl]-, (R)- |

TABLE XXVIII-continued

| EXAMPLE COMPOUND NUMBER: | Chemical Abstracts (CA) Index Name |
|---|---|
| 199: | [1,1'-Biphenyl]-4-butanoic acid, 4'-chloro-γ-oxo-α-[(2-thienylthio)methyl]- |
| 200: | [1,1'-Biphenyl]4-butanoic acid, α-[(acetylthio)methyl]-4'-chloro-γ-oxo- |
| 201: | [1,1'-Biphenyl]-4-butanoic acid, 4'-chloro-α-[[[(4-methoxyphenyl)methyl]thio]methyl]-γ-oxo- |
| 202: | [1,1'-Biphenyl]-4-butanoic acid, α-[benzoylthio]methyl]-4'-chloro-γ-oxo- |
| 203: | [1,1'-Biphenyl]-4-butanoic acid, 4'-chloro-γ-oxo-α-[[(phenylmethyl)thio]methyl]- |
| 204: | [1,1'-Biphenyl]-4-butanoic acid, 4'-chloro-α-[[(4-hydroxyphenyl)thio]methyl]-γ-oxo- |
| 205: | [1,1'-Biphenyl]-4-butanoic acid, 4'-chloro-γ-oxo-α-[[(2-phenylethyl)thio]methyl]- |
| 206: | [1,1'-Biphenyl]-4-butanoic acid, 4'-chloro-α-[[(4-methoxyphenyl)thio]methyl]-γ-oxo- |
| 207: | [1,1'-Biphenyl]-4-butanoic acid, 4'-chloro-γ-oxo-α-[[(3-phenylpropyl)thio]methyl]- |
| 208: | [1,1'-Biphenyl]-4-butanoic acid, 4'-chloro-α-[[(4-fluorophenyl)thio]methyl]-γ-oxo- |
| 209: | [1,1'-Biphenyl]-4-butanoic acid, 4'-chloro-α-[[(4-chlorophenyl)thio]methyl]-γ-oxo- |
| 210: | [1,1'-Biphenyl]-4-butanoic acid, α[[(4-bromophenyl)thio]methyl]-4'-chloro-γ-oxo- |
| 211: | [1,1'-Biphenyl]-4-butanoic acid, 4'-chloro-α-[[(4-methylphenyl)thio]methyl]-γ-oxo- |
| 212: | [1,1'-Biphenyl]-4-butanoic acid, 4'-chloro-α-[[(4-ethylphenyl)thio]methyl]-γ-oxo- |
| 213: | [1,1'-Biphenyl]-4-butanoic acid, 4'-chloro-α-[[[4-(1,1-dimethylethyl)phenyl]thio]methyl]-γ-oxo- |
| 214: | [1,1'-Biphenyl]-4-butanoic acid, 4'-chloro-α-[(cyclohexylthio)methyl]-γ-oxo- |
| 215: | [1,1'-Biphenyl]-4-butanoic acid, 4'-chloro-α[[(3,4-dimethoxyphenyl)thio]methyl]-γ-oxo- |
| 216: | [1,1'-Biphenyl]-4-butanoic acid, 4'-chloro-α-[[(3,4-dichlorophenyl)thio]methyl]-γ-oxo- |
| 217: | [1,1'-Biphenyl]-4-butanoic acid, 4'-chloro-α-[[[2-(hydroxymethyl)phenyl]thio]methyl]-γ-oxo- |
| 218: | [1,1'-Biphenyl]-4-butanoic acid, 4'-chloro-α-[[(2-fluorophenyl)thio]methyl]-γ-oxo- |
| 219: | [1,1'-Biphenyl]-4-butanoic acid, α-[[(2-bromophenyl)thio]methyl]-4'-chloro-γ-oxo- |
| 220: | [1,1'-Biphenyl]-4-butanoic acid, 4'-chloro-α-[[(2-ethylphenyl)thio]methyl]-γ-oxo- |
| 221: | [1,1'-Biphenyl]-4-butanoic acid, 4'-chloro-α-[[[2-(1-methylethyl)phenyl]thio]methyl]-γ-oxo- |
| 222: | [1,1'-Biphenyl]-4-butanoic acid, 4'-chloro-γ-oxo-α[(4-pyridinylthio)methyl]- |
| 223: | [1,1'-Biphenyl]-4-butanoic acid, α-[[[4-(acetylamino)phenyl]thio]methyl]-4'-chloro-γ-oxo- |
| 224: | [1,1'-Biphenyl]-4-butanoic acid, 4'chloro-α-[[(4-nitrophenyl)thio]methyl]-γ-oxo- |
| 225: | [1,1'-Biphenyl]-4-butanoic acid, α-[[[4-(2-carboxyethyl)phenyl]thio]methyl]-4'-chloro-γ-oxo- |
| 226: | [1,1'-Biphenyl]-4-butanoic acid, 4'-chloro-α-[(2-naphthalenylthio)methyl]-γ-oxo- |
| 227: | [1,1'-Biphenyl]-4-butanoic acid, 4'-chloro-α-[(1-naphthalenylthio)methyl]-γ-oxo- |
| 228: | [1,1'-Biphenyl]-4-butanoic acid, α-[[(3-bromophenyl)thio]methyl]-4'-chloro-γ-oxo- |
| 229: | [1,1'-Biphenyl]-4-butanoic acid, 4'-chloro-α-[[(2-methoxyphenyl)thio]methyl]-γ-oxo- |
| 230: | [1,1'-Biphenyl]-4-butanoic acid, 4'-chloro-α-[[(2-chlorophenyl)thio]methyl]-γ-oxo- |
| 231: | [1,1'-Biphenyl]-4-butanoic acid, 4'-chloro-α-[[(3-methylphenyl)thio]methyl)-γ-oxo- |
| 232: | [1,1'-Biphenyl]-4-butanoic acid, 4'-chloro-α-[[(2-methylphenyl)thio]methyl]-γ-oxo- |
| 233: | [1,1'-Biphenyl]-4-butanoic acid, α[[(2-carboxyphenyl)thio]methyl]-4'-chloro-γ-oxo- |
| 234: | [1,1'-Biphenyl]-4-butanoic acid, 4'-chloro-α-[[(3-methoxyphenyl)thio]methyl]-γ-oxo- |
| 235: | [1,1'-Biphenyl]-4-butanoic acid, 4'-chloro-α-[[(3,5-dimethylphenyl)thio]methyl]-γ-oxo- |
| 236: | [1,1'-Biphenyl]-4-butanoic acid, 4'-chloro-γ-oxo-α-[[[3-(trifluoromethyl)phenyl]thio]methyl]- |
| 237: | [1,1'-Biphenyl]-4-butanoic acid, 4'-chloro-α-[[[4-(methoxycabonyl)phenyl]thio]methyl]-γ-oxo- |
| 238: | [1,1'-Biphenyl]-4-butanoic acid, α-[[[4-(carboxymethyl)phenyl]thio]methyl]-4'-chloro-γ-oxo- |
| 239: | [1,1'-Biphenyl]-4-butanoic acid, 4'-chloro-α-[[(1-methylethyl)thio]methyl]-γ-oxo- |
| 240: | [1,1'-Biphenyl]-4-butanoic acid, 4'chloro-α-[[(2-hydroxyphenyl)thio]methyl]-γ-oxo- |
| 241: | [1,1'-Biphenyl]-4-butanoic acid, 4'chloro-γ-oxo-α-[(8-quinolinylthio)methyl]- |
| 242: | [1,1'-Biphenyl]-4-butanoic acid, 4'-chloro-α-[[(3-chlorophenyl)thio]methyl]-γ-oxo- |
| 243: | [1,1'-Biphenyl]-4-butanoic acid, 4'-chloro-α-[[(3-fluorophenyl)thio]methyl]-γ-oxo- |
| 244: | [1,1'-Biphenyl]-4-butanoic acid, 4'-chloro-α-[[[2-(methoxycarbonyl)phenyl]thio]methyl]-γ-oxo- |
| 245: | [1,1'-Biphenyl]-4-butanoic acid, 4'-chloro-α-methyl-γ-oxo-α-(phenylthio)- |
| 246: | [1,1'-Biphenyl]-4-butanoic acid, 4'-chloro-γ-oxo-α-[(phenylsulfinyl)methyl]-,stereoisomer |
| 247: | [1,1'-Biphenyl]-4-butanoic acid, 4'-chloro-γ-oxo-α-[(phenylsulfinyl)methyl]-,stereoisomer |
| 248: | [1,1'-Biphenyl]-4-butanoic acid, 4'-chloro-γ-oxo-α-[(phenylsulfinyl)methyl]-,stereoisomer |

TABLE XXVIII-continued

| EXAMPLE COMPOUND NUMBER: | Chemical Abstracts (CA) Index Name |
|---|---|
| 249: | [1,1'-Biphenyl]-4-butanoic acid, 4'-chloro-γ-oxo-α-[(phenylsulfinyl)methyl]-,stereoisomer |
| 250: | [1,1'-Biphenyl]-4-butanoic acid, 4'-chloro-α-[[[2-[(methylamino)carbonyl]phenyl]thio]methyl]-γ-oxo- |
| 251: | [1,1'-Biphenyl]-4-butanoic acid, 4'-chloro-γ-oxo-α-(phenylthio)- |
| 252: | [1,1'-Biphenyl]-4-butanoic acid, 4'-chloro-γ-oxo-α-[(phenylmethyl)thio]- |
| 253: | Benzenebutanoic acid, α-[(acetylthio)methyl]-4-methyl-γ-oxo- |
| 254: | Benzenebutanoic acid, α-(acetylthio)-4-(4-chlorophenoxy)-γ-oxo- |
| 255: | [1,1'-Biphenyl]-4-butanoic acid, 4'-chloro-γ-oxo-β-[(2-thienylthio)methyl]- |
| 256: | [1,1'-Biphenyl]-4-butanoic acid, 4'-chloro-β-[[(2,2-dimethyl-1-oxopropyl)thio]methyl]-γ-oxo- |
| 257: | [1,1'-Biphenyl]-4-butanoic acid, 4'-chloro-γ-oxo-β-[(phenylthio)methyl]- |
| 258: | [1,1'-Biphenyl]-4-butanoic acid, β-[(acetylthio)methyl]-4'-chloro-γ-oxo- |
| 259: | 1-Piperazineacetic acid, α-[2-(4'-chloro[1,1'-biphenyl]-4-yl)-2-oxoethyl]-4-methyl-, monohydrochloride |
| 260: | [1,1'-Biphenyl]-4-butanoic acid, 4'-chloro-α-[(diphenylmethyl)amino]-γ-oxo-, hydrochloride |
| 261: | 4-Morpholineacetic acid, α-[2-(4'-chloro[1,1'-biphenyl]-4-yl)-2-oxoethyl]-3,5-dimethyl-, hydrochloride |
| 262: | 2H-Isoindole-2-pentanoic acid, α-[2-(4'-chloro[1,1'-biphenyl]-4-yl)-2-oxoethyl]-1,3-dihydro-1,3-dioxo- |
| 263: | [1,1'-Biphenyl]-4-butanoic acid, 4'-chloro-α-[2-(dimethylamino)ethyl]-γ-oxo-,hydrochloride |
| 264: | [1,1'-Biphenyl]-4-butanoic acid, 4'-chloro-α-[2-(diethylamino)ethyl]-γ-oxo-,hydrochloride |
| 265: | [1,1'-Biphenyl]-4-butanoic acid, 4'-chloro-α-[3-(diethylamino)propyl]-γ-oxo-,trifluoroacetate |
| 266: | [1,1'-Biphenyl]-4-butanoic acid, 4'-chloro-α-[3-(methylthio)propyl]-γ-oxo- |
| 267: | 2H-Isoindol-2-butanoic acid, α-[2-(4'-chloro[1,1'-biphenyl]-4-yl)-2-oxoethyl]-1,3-dihydro-1,3-dioxo- |
| 268: | 2H-Isoindole-2-butanoic acid, α-[2-(4'-chloro[1,1'-biphenyl]-4-yl)-2-oxoethyl]-1,3-dihydro-1,3-dioxo-, (S)- |
| 269: | 2H-Isoindole-2-butanoic acid, α-[2-(4'-chloro[1,1'-biphenyl]-4-yl)-2-oxoethyl]-1,3-dihydro-1,3-dioxo-, (R)- |
| 270: | 2H-Isoindole-2-butanoic acid, α-[2-(4'-bromo[1,1'-biphenyl]-4-yl)-2-oxoethyl]-1,3-dihydro-1,3-dioxo- |
| 271: | 2H-Isoindole-2-butanoic acid, 1,3-dihydro-1,3-dioxo-α-[2-oxo-2-[4'-(phenylmethoxy)[1,1'-biphenyl]-4-yl]ethyl]- |
| 272: | 2H-Isoindole-2-butanoic acid, 1,3-dihydro-1,3-dioxo-α-[2-oxo-2-[4'-(pentyloxy)[1,1'-biphenyl]-4-yl)ethyl]- |
| 273: | 2H-Isoindole-2-butanoic acid, α-[2-(4'-ethoxy [1,1'-biphenyl]-4-yl)-2-oxoethyl]-1,3-dihydro-1,3-dioxo- |
| 276: | 2H-Isoindole-2-propanoic acid, α-[2-(4'-chloro[1,1'-biphenyl]-4-yl)-2-oxoethyl]-1,3-dihydro-1,3-dioxo- |
| 279: | [1,1'-Biphenyl]-4-butanoic acid, α-[2-[(2-carboxybenzoyl)amino]ethyl]-4'-chloro-γ-oxo- |
| 280: | [1,1'-Biphenyl]-4-butanoic acid, α-[2-[(2-carboxybenzoyl)amino]ethyl]-4'-chloro-γ-oxo- |
| 282: | [1,1'-Biphenyl]-4-butanoic acid, 4'-chloro-α,α-dimethyl-γ-oxo- |
| 283: | [1,1'-Biphenyl]-4-butanoic acid, 4'-chloro-α,β-dimethyl-γ-oxo-, (R*,R*)- |
| 284: | [1,1'-Biphenyl]-4-butanoic acid, 4'-chloro-α,β-dimethyl-γ-oxo-, (R*,S*)- |
| 285: | Cyclohexanecarboxylic acid, 2-[(4'-chloro[1,1'-biphenyl]-4-yl)carbonyl]-, trans- |
| 286: | Cyclohexanecarboxylic acid, 2-[('-chloro[1,1'-biphenyl]-4-yl)carbonyl]-, cis- |
| 287: | Benzoic acid, 2-[(4'-chloro[1,1'-biphenyl]-4-yl)carbonyl]- |
| 288: | Cyclopentanecarboxylic acid, 2-[(4'-chloro[1,1'-biphenyl]-4-yl)carbonyl]-, cis- |
| 289: | Cyclopentanecarboxylic acid, 2-[(4'-chloro[1,1'-biphenyl]-4-yl)carbonyl]-, trans- |
| 290: | Cyclobutanecarboxylic acid, 2-[(4'-chloro[1,1'-biphenyl]-4-yl)carbonyl]-, cis- |
| 291: | Cyclobutanecarboxylic acid, 2-[(4'-chloro[1,1'-biphenyl]-4-yl)carbonyl]-, trans- |
| 292: | Cyclopropanecarboxylic acid, 2-[(4'-chloro[1,1'-biphenyl]-4-yl)carbonyl]-, cis- |
| 293: | Cyclopropanecarboxylic acid, 2-[(4'-chloro[1,1'-biphenyl]-4-yl)carbonyl]-, trans- |
| 294: | Cyclopentanecarboxylic acid, 2-[(4'-chloro[1,1'-biphenyl]-4-yl)carbonyl]-5-(phenylthio)-, (1α,2β,5β)- |
| 295: | Cyclopentanecarboxylic acid, 2-[(4'-chloro[1,1'-biphenyl]-4-yl)carbonyl]-5-(phenylthio)-, (1α,2β,5α)- |
| 296: | Cyclopentanecarboxylic acid, 2-[(4'-chloro[1,1'-biphenyl]-4-yl)carbonyl]-5-(phenylthio)-,[1S-(1α,2β,5β)]- |
| 297: | Cyclopentanecarboxylic acid, 2-[(4'-chloro[1,1'-biphenyl]-4-yl)carbonyl]-5-(phenylthio)-, [1R-(1α,2β,5β,)]- |
| 298: | Benzoic acid, 2-[[2-carboxy-3-[(4'-chloro[1,1'-biphenyl]-4-yl)carbonyl]cyclopentyl]thio]-, 1-methyl ester, (1α, 2α,3β)- |
| 299: | Benzoic acid, 2-[[2-carboxy-3-[(4'-chloro[1,1'-biphenyl]-4-yl)carbonyl]cyclopentyl]thio]-, 1-methyl ester, [1S-(1α,2α,3β)]- |
| 300: | Benzoic acid, 2-[[2-carboxy-3-[(4'-chloro[1,1'-biphenyl]-4-yl)carbonyl]cyclopentyl]thio]-, 1-methyl ester, [1R-(1α,2α,3β)]- |
| 301: | Benzoic acid, 2-[[2-carboxy-3-[(4'-chloro[1,1'-biphenyl]-4-yl)carbonyl]cyclopentyl]thio]-, [1S-(1α,2α,3β)]- |
| 302: | Cyclopentanecarboxylic acid, 2-[(4'-chloro[1,1'-biphenyl]-4-yl)carbonyl]-5-[(4-fluorophenyl)thio]-, (α,2α,5α)- |
| 303: | Cyclopentanecarboxylic acid, 2-[(4'-chloro[1,1'-biphenyl]-4-yl)carbonyl]-5-[(4-fluorophenyl)thio]-, (1α,2β,5α)- |
| 304: | Cyclopentanecarboxylic acid, 2-[(4'-chloro[1,1'-biphenyl]-4-yl)carbonyl]-5-[(2-methylphenyl)thio]-, (1α,2β,5β)- |
| 305: | Cyclopentanecarboxylic acid, 2-[(4'-chloro[1,1'-biphenyl]-4-yl)carbonyl]-5-[(2-methylphenyl)thio]-, (1α,2α,5α)- |

TABLE XXVIII-continued

| EXAMPLE COMPOUND NUMBER: | Chemical Abstracts (CA) Index Name |
|---|---|
| 306: | Cyclopentanecarboxylic acid, 2-[(4'-chloro[1,1'-biphenyl]-4-yl)carbonyl]-5-[(2-methylphenyl)thio]-, (1α,2β,5α)- |
| 307: | Benzoic acid, 2-[[2-carboxy-3-[(4'-chloro[1,1'-biphenyl]-4-yl)carbonyl]cyclopentyl]thio]-, 1-methyl ester, (1α,2β,3α)- |
| 308: | Benzoic acid, 2-[[2-carboxy-3-[(4'-chloro[1,1'-biphenyl]-4-yl)carbonyl]cyclopentyl]thio]-, 1-methyl ester, (1α,2α,3α)- |
| 309: | Cyclopentanecarboxylic acid, 2-[(4'-chloro[1,1'-biphenyl]-4-yl)carbonyl]-5-[(4-fluorophenyl)thio]-, (1α,2β,5β)- |
| 310: | Cyclopentanecarboxylic acid, 2-[(4'-chloro[1,1'-biphenyl]-4-yl)carbonyl]-5-[(4-chlorophenyl)thio]-, (1α,2β,5β)- |
| 311: | Cyclopentanecarboxylic acid, 2-[(4'-chloro[1,1'-biphenyl]-4-yl)carbonyl]-5-[(4-chlorophenyl)thio]-, (1α,2β,5α)- |
| 312: | Cyclopentanecarboxylic acid, 2-[(49'-chloro[1,1'-biphenyl]-4-yl)carbonyl]-5-(phenylthio)-, (1α,2β,5α)- |
| 313: | Cyclopentanecarboxylic acid, 2-[(4'-chloro[1,1'-biphenyl]-4-yl)carbonyl]-5-(phenylthio)-, (1α,2β,5α)- |
| 314: | [1,1'-Biphenyl]-4-butanoic acid, 4'-chloro-γ-oxo-α-[(phenylsulfonyl)methyl]-, (S) |
| 315: | Cyclopentanecarboxylic acid, 2-[(4'-ethoxy[1,1'-biphenyl]-4-yl)carbonyl]-5-(phenylthio)-, (1α,2β,5β)- |
| 316: | Cyclopentanecarboxylic acid, 2-[(4'-ethoxy[1,1'-biphenyl]-4-yl)carbonyl]-5-(phenylthio)-, (1α,2β,5α)- |
| 317: | Cyclopentanecarboxylic acid, 2-[[4'-(pentyloxy)[1,1'-biphenyl]-4-yl]carbonyl]-5-(phenylthio)-, (1α,2β,5α- |
| 318: | Cyclopentanecarboxylic acid, 2-[[4'-(pentyloxy)[1,1'-biphenyl]-4-yl]carbonyl]-5-(phenylthio)-, (1α,2β,5β)- |
| 319: | Cyclopentanecarboxylic acid, 2-[[4'-(pentyloxy)[1,1'-biphenyl]-4-yl]carbonyl]-5-(phenylthio)-, (1α,2β,5β)-(+)- |
| 320: | Cyclopentanecarboxylic acid, 2-[[4'-(pentyloxy)[1,1'-biphenyl]-4-yl]carbonyl]-5-(phenylthio)-, (1α,2β,5β)-(_31)- |
| 321: | Cyclopentanecarboxylic acid, 2-[[4'-(pentyloxy)[1,1'-biphenyl]-4-yl]carbonyl]-5-(phenylthio)-, (1α,2β,5α)-(+)- |
| 322: | Cyclopentanecarboxylic acid, 2-[[4'-(pentyloxy)[1,1'-biphenyl]-4-yl]carbonyl]-5-(phenylthio)-, (1α,2β,5α)-(−)- |
| 323: | Cyclopentanecarboxylic acid, 2-[(4'-ethoxy[1,1'-biphenyl]-4-yl)carbonyl]-5-(phenylmethyl)-, (1α,2β,5β)- |
| 324: | Cyclopentanecarboxylic acid, 2-[[4'-(pentyloxy)[1,1'-biphenyl]-4-yl]carbonyl]-5-(phenylmethyl)-, [1S-(1α,2β,5β)]- |
| 325: | Cyclopentanecarboxylic acid, 2-[[4'-(pentyloxy)[1,1'-biphenyl]-4-yl]carbonyl]-5-(phenylmethyl)-, [1R-(1α,2β5β)]- |
| 326: | Cyclopentanecarboxylic acid, 2-[(4'-chloro[1,1'-biphenyl]-4-yl)carbonyl]-5-(phenylmethyl)-, (1α,2β,5β)- |
| 327: | 3-Cyclohexene-1-carboxylic acid, 6-[(4'-chloro[1,1'-biphenyl]-4-yl)carbonyl]-3,4-dimethyl-, trans- |
| 328: | 3-Cyclohexene-1-carboxylic acid, 6-[(4'-chloro[1,1'-biphenyl]-4-yl)carbonyl]-,trans- |
| 329: | 3-Cyclohexene-1-carboxylic acid, 6-[(4'-chloro[1,1'-biphenyl]-4-yl)carbonyl]-3-methyl-, trans- |
| 330: | Bicyclo[2.2.2]oct-5-ene-2-carboxylic acid, 3-[(4'-chloro[1,1'-biphenyl]-4-yl)carbonyl]-, (2R*,3R*)- |
| 331: | Bicyclo[2.2.2]octane-2-carboxylic acid, 3-[(4'-chloro[1,1'-biphenyl]-4-yl)carbonyl]-, trans- |
| 332: | [1,1'-Biphenyl]-4-pentanoic acid, 4'-chloro-β-methyl-δ-oxo- |
| 333: | [1,1'-Biphenyl]-4-pentanoic acid, 4'-chloro-δ-oxo- |
| 334: | [1,1'-Biphenyl]-4-pentanoic acid, 4'-chloro-β,β-dimethyl-δ-oxo- |
| 335: | [1,1'-Biphenyl]-4-pentanoic acid, 4'-chloro-β-ethyl-β-methyl-δ-oxo- |
| 336: | Cyclopentaneacetic acid, 1-[2-(4'-chloro[1,1'-biphenyl]-4-yl)-2-oxoethyl]- |
| 337: | [1,1'-Biphenyl]-4-pentanoic acid, 4'-chloro-α,α-dimethyl-δ-oxo- |
| 338: | [1,1'-Biphenyl]-4-pentanoic acid, 4'chloro-α-(2-methylpropyl)-δ-oxo- |
| 339: | Cyclohexaneacetic acid, 1-[2-(4'-chloro[1,1'-biphenyl]-4-yl)-2-oxoethyl]- |
| 340: | Cyclopentanepropanoic acid, 1-[(4'-chloro[1,1'-biphenyl]-4-yl)carbonyl]- |
| 341: | [1,1'-Biphenyl]-4-pentanoic acid, 4'-chloro-δ-oxo-α-(3-phenylpropyl)- |
| 342: | [1,1'-Biphenyl]-4-pentanoic acid, 4'-chloro-γ-(2-methylpropyl)-δ-oxo- |
| 343: | [1,1'-Biphenyl]-4-pentanoic acid, 4'-chloro-δ-oxo-γ-(3-phenylpropyl)- |
| 344: | 1-Hexanone, 1-(4'-bromo[1,1'-biphenyl]-4-yl)-6-phenyl-3-(1H-tetrazol-5-yl)- |
| 345: | Phosphonic acid, [1-[2-(4'-bromo[1,1'-biphenyl]-4-yl)-2-oxoethyl]-4-phenylbutyl]- |
| 346: | 2-Pyrrolidinecarboxamide, 1-[2-[2-(4'-chloro[1,1'-biphenyl]-4-yl)-2-oxoethyl]-4-methyl-1-oxopentyl]-N-methyl-, (2S)- |
| 347: | Benzenebutanoic acid, 4-(2-methyl-4-oxazolyl)-α-(2-methylpropyl)-γ-oxo- |
| 348: | Benzenebutanoic acid, α-(2-methylpropyl)-4-(2-methyl-4-thiazolyl)-γ-oxo- |
| 349: | 2-Thiophenebutanoic acid, 5-(4-chlorophenyl)-γ-oxo-α-(3-phenylpropyl)- |
| 350: | 2-Furanbutanoic acid, 5-(4-chlorophenyl)-γ-oxo-α-(3-phenylpropyl)- |
| 351: | [1,1'-Biphenyl]-4-butanoic acid, 4'ethynyl-γ-oxo-α-(3-phenylpropyl)- |
| 352: | [1,1'-Biphenyl]-4-butanoic acid, 4'-(1-hexynyl)-γ-oxo-α-(3-phenylpropyl)- |
| 353: | [1,1'-Biphenyl]-4-butanoic acid, 4'-(3-methoxy-1-propenyl)-γ-oxo-α-(3-phenylpropyl)-, (E)- |
| 354: | [1,1'-Biphenyl]-4-butanoic acid, 4'-(3-methoxy-1-propenyl)-γ-oxo-α-(3-phenylpropyl)-, (Z)- |
| 355: | [1,1'-Biphenyl]-4-butanoic acid, 4'-(3-methoxypropyl)-γ-oxo-α-(3-phenylpropyl)- |
| 356: | [1,1'-Biphenyl]-4-butanoic acid, 4'-(1-hexenyl)-γ-oxo-α-(3-phenylpropyl)-, (Z)- |
| 357: | [1,1'-Biphenyl]-4-butanoic acid, 4'-hexyl-α-(3-phenylpropyl)- |
| 358: | [1,1'-Biphenyl]-4-butanoic acid, γ-oxo-4'-(2-phenylethenyl)-α-(3-phenylpropyl)-, (Z)- |
| 359: | [1,1'-Biphenyl]-4-butanoic acid, γ-oxo-4'-(2-phenylethyl)-α-(3-phenylpropyl)- |

TABLE XXVIII-continued

| EXAMPLE COMPOUND NUMBER: | Chemical Abstracts (CA) Index Name |
|---|---|
| 360: | Cyclopentanecarboxylic acid, 2-[(4'-chloro[1,1'-biphenyl]-4-yl)carbonyl]-5-[(1,3-dihydro-1,3-dioxo-2H-isoindol-2-yl)methyl]-, (1α,2β,5β)- |
| 361: | Cyclopentanecarboxylic acid, 2- [(4'-chloro[1,1'-biphenyl]-4-yl)carbonyl]-5-[(1,3-dihydro-1,3-dioxo-2H-isoindol-2-yl)methyl)-, [1S-(1α,2β,5β)]- |
| 362: | Cyclopentanecarboxylic acid, 2-[(4'-chloro[(1,1'-biphenyl]-4-yl)carbonyl]-5-[(1,3-dihydro-1,3-dioxo-2H-isoindol-2-yl)methyl]-, [1R-(1α,2β,5β)]- |
| 363: | Cyclopentanecarboxylic acid, 2-[(4'-chloro[1,1'-biphenyl[-4-yl)carbonyl]-5-[2-(4-methylphenyl)ethenyl]-, [1α,2β,5β(E))]- |
| 364: | Cyclopentanecarboxylic acid, 2-[(4'-chloro[1,1'-biphenyl]-4-yl)carbonyl]-5-[(methoxymethoxy)methyl]-, (1α,2β,5β)- |
| 365: | Cyclopentanecarboxylic acid, 2-[(4'-chloro[1,1'-biphenyl]-4-yl)carbonyl]-5-[(phenylmethoxy)methyl]-, (1α,2β,5β)- |
| 366: | Cyclopentanecarboxylic acid, 2-[(4'-chloro[1,1'-biphenyl]-4-yl)carbonyl]-5-(phenoxyrnethyl)-, (1α,2β,5β) |
| 367: | Cyclopentanecarboxylic acid, 2-(benzoyloxy)methyl]-5-[(4'-chloro[1,1'-biphenyl]-4-yl)carbonyl]-, (1α,2β,5β)- |
| 368: | 1,2-Benzenedicarboxylic acid, 1-[[2-carboxy-3-[(4'-chloro[1,1'-biphenyl]-4-yl)carbonyl]cyclopentyl]methyl]2-methyl ester, (1α, 2β,3α)- |
| 369: | Cyclopentanecarboxylic acid, 2-[(4'-chloro[1,1'-biphenyl]-4-yl)carbonyl]-5-[(2-thienylthio)methyl]-, (1α2β5β)- |
| 370: | Cyclopentanecarboxylic acid, 2-[(benzoylamino)methyl]-5-[(4'-chloro[1,1'-biphenyl]-4-yl)carbonyl]-, (1α,2β,5β)- |
| 371: | Cyclopentanecarboxylic acid, 2-[(4'-chloro[1,1'-biphenyl]-4-yl)carbonyl]-5-[[(2-methoxyethoxy)methoxy]methyl]-, (1α,2β,5β)- |
| 372: | Cyclopentanecarboxylic acid, 2-[(4'-chloro[1,1'-biphenyl]-4-yl)carbonyl]-5-[[(phenylmethyl)thio]methyl]-, (1α,2β,5β)- |
| 373: | Cyclopentanecarboxylic acid, 2-[(4'-chloro[1,1'-biphenyl]-4-yl)carbonyl]-5-[(phenylthio)methyl]-, (1α,2β,5β)- |
| 374: | Cyclopentanecarboxylic acid, 2-[(4'-chloro[1,1'-biphenyl]-4-yl)carbonyl]-5-[(propylthio)methyl]-, (1α,2β,5β)- |
| 375: | Cyclopentanecarboxylic acid, 2-[(2-benzothiazolylthio)methyl]-5-[(4'-chloro[1,1'-biphenyl]-4-yl)carbonyl]-, (1α,2β,5β)- |
| 376: | Benzoic acid, 2-[[[2-carboxy-3-[(4'-chloro[1,1'-biphenyl]-4-yl)carbonyl]cyclopentyl]methyl]thio]-, 1-methyl ester, (1α,2β,3α)- |
| 377: | Cyclopentanecarboxylic acid, 2-[(4'-chloro[1,1'-biphenyl]-4-yl)carbonyl]-5-[[[(phenylmethoxy)carbonyl]amino]]methyl]-, (1α2β5β)- |
| 378: | Benzoic acid, 2-methyl-,[2-carboxy-3-[(4'-chloro[1,1'-biphenyl]-4-yl)carbonyl]cyclopentyl]methyl ester, (1α,2β,3α)- |
| 379: | Benzoic acid, 3-methyl-, [2-carboxy-3-[(4'-chloro[1,1'-biphenyl]-4-yl)carbonyl]cyclopentyl]methyl ester, (1α,2β,3α)- |
| 380: | Benzoic acid, 4-methyl-, [2-carboxy-3-[(4'-chloro[1,1'-biphenyl]-4-yl)carbonyl]cyclopentyl]methyl ester, (1α,2β,3α)- |
| 381: | Benzoic acid, 2-methoxy-, [2-carboxy-3-[(4'-chloro[1,1'-biphenyl]-4-yl)carbonyl]cyclopentyl]methyl ester, (1α,2β,3α)- |
| 382: | Benzoic acid, 3-methoxy-, [2-carboxy-3-[(4'-chloro[1,1'-biphenyl]-4-yl)carbonyl]cyclopentyl]methyl ester, (1α,2β,3α)- |
| 383: | Benzoic acid, 4-methoxy-, [2-carboxy-3-[(4'-chloro[1,1'-biphenyl]-4-yl)carbonyl]cyclopentyl]methyl ester, (1α,2β,3α)- |
| 384: | Cyclopentanecarboxylic acid, 2-[(2-benzoxazolylthio)methyl]-5-[(4'-chloro[1,1'-biphenyl]-4-yl)carbonyl]-, (1α,2β,5β)- |
| 385: | Cyclopentanecarboxylic acid, 2-[(4'-chloro[1,1'-biphenyl]-4-yl)carbonyl]-5-[(1,3-digydro-4-nitro-1,3-dioxo-2H-isoindol-2-yl)methyl]-, (1α,2β,5β)- |
| 386: | Cyclopentanecarboxylic acid, 2-[(4'-chloro[1,1'-biphenyl]-4-yl)carbonyl]-5-[(1,3-dihydro-5-nitro-1,3-dioxo-2H-isoindol-2-yl)methyl]-, (1α,2β,5β)- |
| 387: | Cyclopentanecarboxylic acid, 2-[(4'-chloro[1,1'-biphenyl]-4-yl)carbonyl]-5-[(1,3-dihydro-1,3-dioxo-2H-benz[ƒ]isoindol-2-yl)methyl]-, (1α,2β,5β)- |
| 388: | Cyclopentanecarboxylic acid, 2-[(4'-chloro[1,1'-biphenyl]-4-yl)carbonyl]-5-[(4-chlorophenoxy)methyl]-, (1α,2β,5β)- |
| 389: | Cyclopentanecarboxylic acid, 2-[(4'-chloro[1,1'-biphenyl]-4-yl)carbonyl]-5-[[(1,3-dihydro-1,3-dioxo-2H-isoindol-2-yl)-oxy]methyl]-, (1α,2β,5β)- |
| 390: | Cyclopentanecarboxylic acid, 2-[(4'-chloro[1,1'-biphenyl]-4-yl)carbonyl]-5-[(5-chloro-1,3-dihydro-6-nitro-1,3-dioxo-2H-isoindol-2-yl) methyl]-, (1α,2β,5β)- |
| 391: | Cyclopentanecarboxylic acid, 2-[(4'-chloro[1,1'-biphenyl]-4-yl)carbonyl]-5-[(5,6-dichloro-1,3-dihydro-1,3-dioxo-2H-isoindol-2-yl)methyl]-, (1α,2β,5β)- |
| 392: | Cyclopentanecarboxylic acid, 2-[(4-amino-1,3-dihydro-1,3-dioxo-2H-isoindol-2-yl)methyl]-5-[(4'-chloro[1,1'1-biphenyl]-4-yl)carbonyl]-, (1α,2β,5β)- |
| 393: | Cyclobutanecarboxylic acid, 2-(acetyloxy)-4-[(4'-chloro[1,1'-biphenyl]-4-yl)carbonyl]-, (1α,2α,4α- |
| 394: | Cyclobutanecarboxylic acid, 2-(acetyloxy)-4-[(4'-chloro[1,1'-biphenyl]-4-yl)carbonyl]-, (1α,2β,4α)- |
| 395: | Cyclobutanecarboxylic acid, 2-(acetyloxy)-4-[(4'-chloro[1,1'-biphenyl]-4-yl)carbonyl]-, (1α,2α,4β)- |
| 396: | Cyclobutanecarboxylic acid, 2-(acetyloxy)-4-[(4'-chloroz[1,1'-biphenyl]-4-yl)carbonyl]-, (1α,2β,4β)- |
| 397: | Cyclobutanecarboxylic acid, 2-[(acetyloxy)methyl]-4-[(4'-chloro[1,1'-biphenyl]-4-yl)carbonyl]-, (1α,2β,4α)- |
| 398: | Cyclobutanecarboxylic acid, 2-[(acetyloxy)methyl]-4-[(4'-chloro[1,1'-biphenyl]-4-yl)carbonyl]-, (1α,2β,4β)- |
| 399: | Cyclobutanecarboxylic acid, 2-[(acetyloxy)methyl]-4-[(4'-chloro[1,1'-biphenyl]-4-yl)carbonyl]-, (1α,2β,4β)- |
| 400: | Cyclobutanecarboxylic acid, 2-[(4'-chloro[1,1'-biphenyl]-4-yl)carbonyl]-4-(hydroxymethyl)-, (1α,2β,4β)- |
| 401: | Cyclobutanecarboxylic acid, 2-[(acetyloxy)methyl]-4-[(4'-chloro[1,1'-biphenyl]-4-yl)carbonyl]-, (1α,2α,4β)- |
| 402: | Cyclobutanecarboxylic acid, 2-[(4'-chloro[1,1'-biphenyl]-4-yl)carbonyl]-4-[(1,3-dihydro-1,3-dioxo-2H-isoindol-2-yl)methyl]-, (1α,2β,4β)- |
| 403: | 3-Furancarboxylic acid, 4-[(4'-chloro[1,1'-biphenyl]-4-yl) carbonyl]-2-[(1,3-dihydro-1,3-dioxo-2H-isoindol-2-yl)methyl] tetrahydro-, (2α,3β,4α)- |

TABLE XXVIII-continued

| EXAMPLE COMPOUND NUMBER: | Chemical Abstracts (CA) Index Name |
|---|---|
| 404: | [1,1'-Biphenyl]-4-butanoic acid, 4'-chloro-α-[2-[[2-(methoxycarbonyl)benzoyl]amino]ethyl]-γ-oxo- |
| 405: | 2H-Isoindole-2-butanoic acid, α-[2-(4'-chloro[1,1'-biphenyl]-4-yl)-2-oxoethyl]-1,3-dihydro-1,3-dioxo-5-(phenylmethoxy)- |
| 406: | 2H-Isoindol-2-butanoic acid, α-[2-(4'-chloro[1,1'-biphenyl]-4-yl)-2-oxoethyl]-1,3-dihydro-1,3-dioxo-5-propoxy- |
| 407: | 2H-Isoindole-2-butanoic acid, α-(2-(4'-chloro[1,1'-biphenyl]-4-yl)-2-oxoethyl]-1,3-dihydro-1,3-dioxo-4-(phenylmethoxy)- |
| 408: | 2H-Isoindole-2-butanoic acid, 5-amino-α-[2-(4'-chloro[1,1'-biphenyl]-4-yl)-2-oxoethyl]-1,3-dihydro-1,3-dioxo- |
| 409: | 2H-Benz[f]isoindole-2-butanoic acid, α-[2-(4'-chloro[1,1'-biphenyl]-4-yl)-2-oxoethyl]-1,3-dihydro-1,3-dioxo- |
| 410: | 1H-Benz[de]isoquinoline-2(3H)-butanoic acid, α-[2-(4'-chloro[1,1'-biphenyl]-4-yl)-2-oxoethyl]-1,3-dioxo- |
| 411: | 1 Pyrrolidinebutanoic acid, α-[2-(4'-chloro[1,1'-biphenyl]-4-yl)-2-oxoethyl]-2,5-dioxo- |
| 412: | 1 Pyrrolidinebutanoic acid, α-[2-(4'-ethoxy[1,1'-biphenyl]-4-yl)-2-oxoethyl]-2,3-dioxo- |
| 413: | 2H-Isoindole-2-butanoic acid, α-[2-(4'-chloro[1,1'-biphenyl]-4-yl)-2-oxoethyl]-1,3,3a,4,7,7a-hexahydro-1,3-dioxo-,cis- |
| 414: | 2H-Isoindole-2-butanoic acid, α-[2-(4'-chloro[1,1'biphenyl]-4-yl)-2-oxoethyl]-5-(1,1-dimethylethyl)-1,3-dihydro-1,3-dioxo- |
| 415: | 2H-Isindole-2-butanoic acid, 5,6-dichloro-α-[2-(4'-chloro[1,1'-biphenyl]-4-yl)-2-oxoethyl]-1,3-dihydro-1,3-dioxo- |
| 416: | 2H-Isoindole-2-butanoic acid, α-[2-(4'-chloro[1,1'-biphenyl]-4-yl)-2-oxoethyl]-1,3-dihydro-5-methyl-1,3-dioxo- |
| 417: | 2H-Pyrrolo:3,4-clpyridine-2-butanoic acid, α-[2-(4'-chloro[1,1'-biphenyl]-4-yl)-2-oxoethyl]-1,3-dihydro-1,3-dioxo- |
| 418: | 1H-Benz[de]isoquinoline-2(3H)-butanoic acid, 6-bromo-α-[2-(4'-chloro[1,1'-biphenyl]-4-yl)-2-oxoethyl]-1,3-dioxo- |
| 419: | 6H-1,3-Dioxolo[4,5-f]isoindole-6-butanoic acid, α-[2-(4'-chloro[1,1'-biphenyl]-4-yl)-2-oxoethyl]-5,7-dihydro-5,7-dioxo- |
| 420: | 2H-Isoindole-2-butanoic acid, α-[2-(4'-chloro[1,1'-biphenyl]-4-yl)-2-oxoethyl]-1,3-dihydro-5-hydroxy-1,3-dioxo- |
| 421: | 2H-Isoindole-2-butanoic acid, α-[2-(4'-chloro[1,1'-biphenyl]-4-yl)-2-oxoethyl]-1,3-dihydro-4-hydroxy-1,3-dioxo- |
| 422: | 2H-Isoindole-2-butanoic acid, α-[2-(4'-chloro[1,1'-biphenyl]-4-yl)-2-oxoethyl]-1,3-dihydro-5-methoxy-1,3-dioxo- |
| 423: | 2H-Isoindole-2-butanoic acid, α-[2-(4'-chloro[1,1'-biphenyl]-4-yl-2-oxoethyl]-1,3-dihydro-4-methoxy-1,3-dioxo- |
| 424: | 2H-Isoindole-2-butanoic acid, α-[2-(4'-chloro[1,1'-biphenyl]-4-yl)-2-oxoethyl]-1,3-dihydro-1,3-dioxo--5-[(2-thienylcarbonyl)oxy]- |
| 425: | 2H-Isoindole-2-butanoic acid, 5-(acetyloxy)-α-[2-(4'-chloro[1,1'-biphenyl]-4-yl)-2-oxoethyl]1,3-dihydro-1,3-dioxo- |
| 426: | [1,1'-Biphenyl]-4-butanoic acid, 4'-chloro-γ-oxo-α-[2-(phenylthio)ethyl]- |
| 427: | [1,1'-Bipheny]-4-butanoic acid, 4'-chloro-α-[2-[[(4-methoxyphenyl)methyl]thio]ethyl]-γ-oxo- |
| 428: | [1,1'-Biphenyl]-4-butanoic acid, 4'-chloro-γ-oxo-α-[2-(phenylsulfinyl)ethyl]- |
| 429: | 2H-Benz[f]isoindole-2-butanoic acid, α-(2-(4'-ethoxy[1,1'-biphenyl]-4-yl)-2-oxoethyl]-1,3-dihydro-1,3-dioxo- |
| 430: | [1,1'-Biphenyl]-4-butanoic acid, α-(acetylamino)-4'-chloro-γ-oxo- |
| 431: | 2H-Isoindole-2-hexanoic acid, α-[2-(4'-chloro[1,1'-biphenyl]-4-yl)-2-oxoethyl]-1,3-dihydro-1,3-dioxo- |
| 432: | [1,1'-Biphenyl]-4-butanoic acid, 4'-chloro-α-[[[3-(methoxycarbonyl)phenyl]thio]methyl]-γ-oxo- |
| 433: | [1,1'-Biphenyl]-4-butanoic acid, 4'-chloro-α-[[(2,6-dimethylphenyl)thio]methyl]-γ-oxo- |
| 434: | [1,1'-Biphenyl]-4-butanoic acid, 4'-chloro-α-[[[4-chloro-2-(methoxycarbonyl)phenyl]thio]methyl]-γ-oxo- |
| 435: | [1,1'-Biphenyl]-4-butanoic acid, 4'-chloro-α-[[[3-[(diethylamino)carbonyl]phenyl]thio]methyl]-γ-oxo- |
| 436: | [1,1'-Biphenyl]-4-butanoic acid, 4'-chloro-α-[[[2-[(dimethylamino)carbonyl]phenyl]thio]methyl]-γ-oxo- |
| 437: | [1,1'-Biphenyl]-4-butanoic acid, 4'-chloro-α-[[[3-[(dimethylamino)carbonyl]phenyl]thio]methyl]-γ-oxo- |
| 438: | Bicydo[2.2.1]hept-5-ene-2-carboxylic acid, 3-[[4'-(pentyloxy)[1,1'-biphenyl]-4-yl]carbonyl]-, (2-endo,3-exo)- |
| 439: | 1 Cyclopentene-1-carboxylic acid, 5-[(4'-chloro[1,1'-biphenyl]-4-yl)carbonyl]- |
| 440: | Cyclopentanecarboxylic acid, 2-[(4'-chloro[1,1'-biphenyl]-4-yl)carbonyl]-5-[(phenylmethyl)thiol-, (1α,2β5α)- |
| 441: | Cyclopentanecarboxylic acid, 2-[(4'-chloro[1,1'-biphenyl]-4-yl)carbonyl]-5-[(phenylmethyl)thiol, (1α,2β,5β)- |
| 442: | 1-Cydopentene-1-carboxylic acid, 5-[[4'-(pentyloxy)[1,1'-biphenyl]-4-yl]carbonyl]- |
| 443: | 1-Cydopentene-1-carboxylic acid, 5-[[4'-(hexyloxy)[1,1'-biphenyl]-4-yl]carbonyl]- |
| 444: | [1,1'-Biphenyl]-4-butanoic acid, 4'-hydroxy-γ-oxo-α-[(phenylthio)methyl]- |

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

What is claimed is:

1. Compounds having matrix metalloprotease inhibitory activity and the generalized formula:

(T)<sub>x</sub>A—B—C—D—E—G wherein (a) (T)<sub>x</sub>A represents a substituted or unsubstituted phenol group; and each T represents a substituent group, independently selected from the group consisting of:
the halogens —F, —Cl, —Br, and —I;
alkyl of 1–10 carbons;
haloalkyl of 1–10 carbons;
alkenyl of 2–10 carbons;
alkynyl of 2–10 carbons;

—(CH$_2$)$_p$Q, wherein
p is 0 or an integer 1–4, and
alkenyl-Q, wherein
said alkenyl moiety comprises 2–4 carbons; and
Q is selected from the group consisting of aryl of 6–10 carbons, heteroaryl comprising 4–9 carbons and at least one N, O, or S heteroatom, —CN, —CHO, —NO$_2$, —CO$_2$R$^2$, —OCOR$^2$, —SOR$^3$, —SO$_2$R$^3$, —CON(R$^2$)$_2$, —SO$_2$N(R$^2$)$_2$, —C(O)R$^2$, —N(R$^2$)$_2$, —N(R$^2$)COR$^2$, —N(R$^2$)CO$_2$R$^3$, —N(R$^2$)CON(R$^2$)$_2$, —CHN$_4$, —OR$^4$, and —SR$^4$;
wherein
R$^2$ represents H;
alkyl of 1–6 carbons;
aryl of 6–10 carbons;
heteroaryl comprising 4–9 carbons and at least one N, O, or S heteroatom; or
arylalkyl in which the aryl portion contains 6–10 carbons and the alkyl portion contains 1–4 carbons; or
heteroaryl-alkyl in which the heteroaryl portion comprises 4–9 carbons and at least one N, O, or S heteroatom and the alkyl portion contains 1–4 carbons;
R$^3$ represents alkyl of 1–4 carbons;
aryl of 6–10 carbons;
heteroaryl comprising 4–9 carbons and at least one N, O, or S heteroatom; or
arylalkyl in which the aryl portion contains 6–10 carbons and the alkyl portion contains 1–4 carbons; or
heteroaryl-alkyl in which the heteroaryl portion comprises 4–9 carbons and at least one N, O, or S heteroatom and the alkyl portion contains 1–4 carbons;
R$^4$ represents H;
alkyl of 1–12 carbons;
aryl of 6–10 carbons;
heteroaryl comprising 4–9 carbons and at least one N, O, or S heteroatom;
arylalkyl in which the aryl portion contains 6–10 carbons and the alkyl portion contains 1–4 carbons;
heteroaryl-alkyl in which the heteroaryl portion comprises 4–9 carbons and at least one N, O, or S heteroatom and the alkyl portion contains 1–4 carbons;
alkenyl of 2–12 carbons;
alkynyl of 2–12 carbons;
—(C$_q$H$_{2q}$O)$_r$R$^5$ wherein q is 1–3; r is 1–3; and R$^5$ is H provided q is greater than 1, or alkyl of 1–4 carbons, or phenyl;
—(CH$_2$)$_s$X wherein s is 2–3 and X is halogen; or
—C(O)R$^2$;
and with the proviso that unsaturation in a moiety which is attached to Q or which is part of Q is separated from any N, O, or S of Q by at least one carbon atom, and
x is 0, 1, or 2;
(b) B represents an aromatic or heteroaromatic ring selected from the group consisting of:

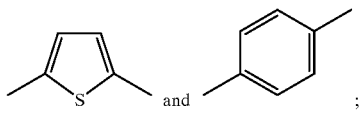

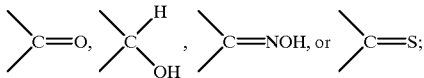

(c) D represents $$\begin{matrix}\diagdown\\\diagup\end{matrix}C=O, \quad \begin{matrix}\diagdown\\\diagup\end{matrix}C\begin{matrix}H\\OH\end{matrix}, \quad \begin{matrix}\diagdown\\\diagup\end{matrix}C=NOH, \text{ or } \begin{matrix}\diagdown\\\diagup\end{matrix}C=S;$$

(d) E represents a chain of 3 carbon atoms bearing m substituents R$^6$, wherein said R$^6$ groups are independent substituents, or constitute spiro or nonspiro rings in which a) two groups R$^6$ are joined, and taken together with the chain atom(s) to which said two R$^6$ group(s) are attached, and any intervening chain atoms, constitute a 3–7 membered ring, or b) one group R$^6$ is joined to the chain on which said one group R$^6$ resides, and taken together with the chain atom(s) to which said R$^6$ group is attached, and any intervening chain atoms, constitutes a 3–7 membered ring; and wherein
m is an integer of 1–3;
the number of carbons in the totality of R$^6$ groups is at least two;
each group R$^6$ is independently selected from the group consisting of;
alkyl of 1–10 carbons, provided that if said A unit is phenyl, said B unit is phenylene, mn is 1, n is 2, and said alkyl group is located on the alpha carbon relative to said D unit, then x is 1 or 2;
aryl of 6–10 carbons, provided that if said A unit is phenyl, said B unit is phenylene, said aryl group is phenyl, n is 2, and m is 1 or 2, then x is 1 or 2;
heteroaryl comprising 4–9 carbons and at least one N, O, or S heteroatom;
arylalkyl wherein the aryl portion contains 6–10 carbons and the alkyl portion contains 1–8 carbons;
heteroaryl-alkyl wherein the heteroaryl portion comprises 4–9 carbons and at least one N, O, or S heteroatom, and the alkyl portion contains 1–8 carbons;
alkenyl of 2–10 carbons;
aryl-alkenyl wherein the aryl portion contains 6–10 carbons and the alkenyl portion contains 2–5 carbons;
heteroaryl-alkenyl wherein the heteroaryl portion comprises 4–9 carbons and at least one N, O, or S heteroatom and the alkenyl portion contains 2–5 carbons;
alkynyl of 2–10 carbons;
aryl-alkynyl wherein the aryl portion contains 6–10 carbons and the alkynyl portion contains 2–5 carbons;
heteroaryl-alkynyl wherein the heteroaryl portion comprises 4–9 carbons and at least one N, O, or S heteroatom and the alkynyl portion contains 2–5 carbons;
—(CH$_2$)$_t$R$^7$ wherein
t is 0 or an integer of 1–5; and R⁷ is selected from the group consisting of

[chemical structures: phthalimide, naphthalimide, naphthalimide-fused variant, —N(R²)—R², pyrrolidinone, succinimide, maleimide, substituted succinimide with R², indole with R¹, piperidine/morpholine with (R¹)ᵤ and Y, —N(R²)—C(O)—OR³, —N(R²)—C(O)—R², —N(R²)—C(O)—N(R²)—R²]

and corresponding heteroaryl moieties in which the aryl portion of an aryl-containing R⁷ group comprises 4–9 carbons and at least one N, O, or S heteroatom; wherein
   Y represents O or S;
   $R^1$ represents H or alkyl of 1–3 carbons, and $R^2$, and $R^3$ are as defined above; and
   u is 0, 1, or 2; and
   —$(CH_2)_v ZR^8$ wherein
      v is 0 or an integer of 1 to 4; and
      Z represents

[chemical structures: —S—, —S(O)—, —S(O)₂—, or —O—]

$R^8$ is selected from the group consisting of:
   alkyl of 1 to 12 carbons;
   aryl of 6 to 10 carbons;
   heteroaryl comprising 4–9 carbons and at least one N, O, or S heteroatom;
   arylalkyl wherein the aryl portion contains 6 to 12 carbons and the alkyl portion contains 1 to 4 carbons;
   heteroaryl-alkyl wherein the aryl portion comprises 4–9 carbons and at least one N, O, or S heteroatom and the alkyl portion contains 1–4 carbons;
   —$C(O)R^9$ wherein $R^9$ represents alkyl of 2–6 carbons, aryl of 6–10 carbons, heteroaryl comprising 4–9 carbons and at least one N, O, or S heteroatom, or arylalkyl in which the aryl portion contains 6–10 carbons or is heteroaryl comprising 4–9 carbons and at least one N, O, or S heteroatom, and the alkyl portion contains 1–4 carbons;
   and with the provisos that
      when $R^8$ is —$C(O)R^9$, Z is S or O; and
      when Z is O, $R^8$ may also be —$(C_qH_{2q}O)_rR^5$ wherein q, r, and $R^5$ are as defined above; and
   —$(CH_2)_w SiR^{10}_3$ wherein
      w is an integer of 1 to 3; and
      $R^{10}$ represents alkyl of 1 to 2 carbons;
and with the proviso that
aryl or heteroaryl portions of any of said T or $R^6$ groups optionally may bear up to two substituents selected from the group consisting of —$(CH_2)_y C(R^{11}(R^{12})$OH, —$(CH_2)_y OR^{11}$, —$(CH_2)_y SR^{11}$, —$(CH_2)_y S(O)R^{11}$, —$(CH_2)_y S(O)_2 R^{11}$, —$(CH_2)_y SO_2 N(R^{11})_2$, —$(CH_2)_y N(R^{11})_2$, —$(CH_2)_y N(R^{11})COR^{12}$, —$OC(R^{11})_2 O$— in which both oxygen atoms are connected to the aryl ring, —$(CH_2)_y COR^{11}$, —$(CH_2)_y CON(R^{11})_2$, —$(CH_2)_y CO_2 R^{11}$, —$(CH_2)_y OCOR^{11}$, -halogen, —CHO, —$CF_3$, —$NO_2$, —CN, and —$R^{12}$,
wherein
   y is 0–4;
   $R^{11}$ represents H or alkyl of 1–4 carbons; and
   $R^{12}$ represents alkyl of 1–4 carbons, and
(e) G represents —M,

[chemical structures: —C(O)—N—CH(proline-like ring)—M, or —C(O)—N(H)—CH($R^{13}$)—M]

wherein
M represents —$CO_2H$, —$CON(R^{11})_2$, or —$CO_2R^{12}$; and
$R^{13}$ represents any of the side chains of the 19 non-cyclic naturally occurring amino acids;
and pharmaceutically acceptable salts thereof.

2. A compound of claim 1 wherein at least one of the units B, T, and $R^6$ comprises a heteroaromatic ring.

3. A compound of claim 2 wherein the B unit comprises a thiophene ring.

4. A compound of claim 2 wherein said D unit is a carbonyl group.

5. A compound of claim 2 wherein in said E unit, m is 1.

6. A compound of claim 2 wherein said G unit is —$CO_2H$.

7. A compound of claim 1 wherein

B is p-phenylene; and aryl portions of aryl-containing T and $R^6$ moieties contain only carbon in the rings.

8. A compound of claim 7 wherein said D unit is a carbonyl group.

9. A compound of claim 7 wherein in said E unit, m is 1.

10. A compound of claim 7 wherein said G unit is —CO$_2$H.

11. A compound of claim 7 wherein
m is 1; and
R$^6$ is an independent substituent.

12. A compound of claim 7 wherein
m is 2 or 3; and
when m is 2, both groups R$^6$ are independent substituents, or together constitute a spiro ring, or one group R$^6$ is an independent substituent and the other constitutes a spiro ring; and
when m is 3, two groups R$^6$ are independent substituents and one group R$^6$ constitutes a ring, or two groups R6 constitute a ring and one group R6 is an independent substituent, or three groups R6 are independent substituents.

13. A compound of claim 7 wherein
m is 1 or 2; and
when m is 1, the group R$^6$ constitutes a nonspiro ring;
when m is 2, both groups R$^6$ together constitute a nonspiro ring or one group R6 is an independent substituent and the other constitutes a nonspiro ring.

14. A composition having matrix metalloprotease inhibitory activity, comprising a compound of claim 1 and a pharmaceutically acceptable carrier.

15. A method of treating a mammal to achieve an effect, wherein the effect is: alleviation of osteoarthritis, rheumatoid arthritis, septic arthritis, periodontal disease, corneal ulceration, proteinuria, aneurysmal aortic disease, dystrophobic epidermolysis bullosa, conditions leading to inflantmatory responses, osteopenias mediated by MMP activity, tempero mandibular joint disease, or demyelating diseases of the nervous system; retardation of tumor metastasis or degenerative cartilage loss following traumatic joint injury; reduction of coronary thrombosis from atherosclerotic plaque rupture; or improved birth control; the method comprising administering an amount of a compound of claim 1 which is effective to inhibit the activity of at least one matrix metalloprotease in said mammal, thereby to achieve said effect.

16. The method of claim 15 wherein the effect is alleviation of osteoarthritis.

17. The method of claim 15 wherein the effect is retardation of tumor metastasis.

18. A compound of claim 1, wherein said compound is one of the following listed materials:

| Example No. | Name |
|---|---|
| 332: | [1,1'-Biphenyl]-4-pentanoic acid, 4'-chloro-β-methyl-δ-oxo- |
| 333: | [1,1,'-Biphenyl]-4-pentanoic acid, 4'-chloro-β-oxo- |
| 334: | [1,1'-Binhenyl]-4-pentanoic acid, 4'-chloro-β,β-dimethyl-δ-oxo- |
| 335: | [1,1'-Biphenyl]-4-pentanoic acid, 4'-chloro-β-ethyl-β-methyl-δ-oxo- |
| 336: | Cyclopentaneacetic acid, 1-[2-(4'-chloro[1,1'-biphenyl]-4-yl)-2-oxoethyl]- |
| 337: | [1,1'-Biphenyl]-4-pentanoic acid, 4'-chloroα,α-dimethyl-δ-oxo- |
| 338 | [1,1'-Biphenyl]-4-pentanoic acid, 4'-chloro-α-(2-methylpropyl)-δ-oxo- |
| 339: | Cyclohexaneacetic acid, 1-[2-(4'-chloro[1,1'-biphenyl]-4-yl)-2-oxoetyl]- |
| 340: | Cyclopentanepropanoic acid, 1-[(4'-chloro[1,1'-biphenyl]-4-yl)carbonyl]- |
| 341: | [1,1'-Biphenyl]-4-pentanoic acid, 4'-chloro-δ-oxo-α-(3-phenylpropyl)- |
| 342: | [1,1'-Biphenyl]-4-pentanoic acid, 4'-chloroγ-(2-methylpropyl)-δ-oxo- |
| 343: | [1,1'-Biphenyl]-4-pentanoic acid, 4'-chloro-δ-oxo-γ-(3-phenylpropyl)-. |

* * * * *